(12) United States Patent
Plasterk et al.

(10) Patent No.: US 8,895,720 B2
(45) Date of Patent: Nov. 25, 2014

(54) NUCLEIC ACID MOLECULES AND COLLECTIONS THEREOF, THEIR APPLICATION AND MODIFICATION

(71) Applicant: Koninklijke Nederlandse Akademie van Wetenschappen, Amsterdam (NL)

(72) Inventors: Ronald H. A. Plasterk, Bussum (NL); Eugene Berezikov, Vleuten (NL); Edwin Pieter Cuppen, Utrecht (NL)

(73) Assignee: Koninklijke Nederlandse Akademie van Wetenschappen, Amsterdam (NL)

( * ) Notice: Subject to any disclaimer, the term of this patent is extended or adjusted under 35 U.S.C. 154(b) by 0 days.

(21) Appl. No.: 13/722,643

(22) Filed: Dec. 20, 2012

(65) Prior Publication Data

US 2013/0178387 A1    Jul. 11, 2013

Related U.S. Application Data

(62) Division of application No. 12/087,649, filed as application No. PCT/NL2007/000012 on Jan. 10, 2007, now Pat. No. 8,362,230.

(51) Int. Cl.
  *C07H 21/04*  (2006.01)
  *C12N 15/113* (2010.01)
  *C12Q 1/68*   (2006.01)

(52) U.S. Cl.
  CPC ........ *C12N 15/113* (2013.01); *C12Q 2600/158* (2013.01); *C12N 2310/141* (2013.01); *C12Q 2600/178* (2013.01); *C12N 2320/10* (2013.01); *C12Q 1/6886* (2013.01)
  USPC ....................................................... 536/24.5

(58) Field of Classification Search
  USPC ....................................................... 536/24.5
  See application file for complete search history.

(56) References Cited

U.S. PATENT DOCUMENTS

2007/0050146 A1* 3/2007 Bentwich et al. ............... 702/19
2010/0273255 A1* 10/2010 Tuschl et al. .................. 435/325

FOREIGN PATENT DOCUMENTS

WO    WO2006119266 A2 * 11/2006

* cited by examiner

*Primary Examiner* — Brian Whiteman
(74) *Attorney, Agent, or Firm* — Morgan, Lewis & Bockius LLP

(57) ABSTRACT

The invention provides a method for characterising a sample comprising nucleic acid derived from a cell. The method comprises determining whether a sample comprises at least a minimal sequence of at least one new microRNA (miRNA) according to the invention or a mammalian ortholog thereof and characterizing the sample on the basis of the presence or absence of the miRNA. The invention further provides nucleic acid molecules and collections thereof and their use in therapeutic and diagnostic applications. The invention furthermore provides a method for identifying a miRNA molecule or a precursor molecule thereof.

9 Claims, 558 Drawing Sheets

FIG. 1B

FIG 1B Con't.

FIG. 1B Cont'd.

FIG 1B Con't.

FIG. 1B Con't.

FIG. 1B Con't.

FIG 1B Con't.

FIG. 1B Con't.

FIG. 1B Con't.

FIG 1B Con't.

FIG. 1B Cont.

FIG 1B Con't.

FIG 1B Con't.

FIG 1B Con't.

FIG. 1B Con't.

FIG 1B Cont'l.

FIG. 1B Con't.

FIG. 1B Con't.

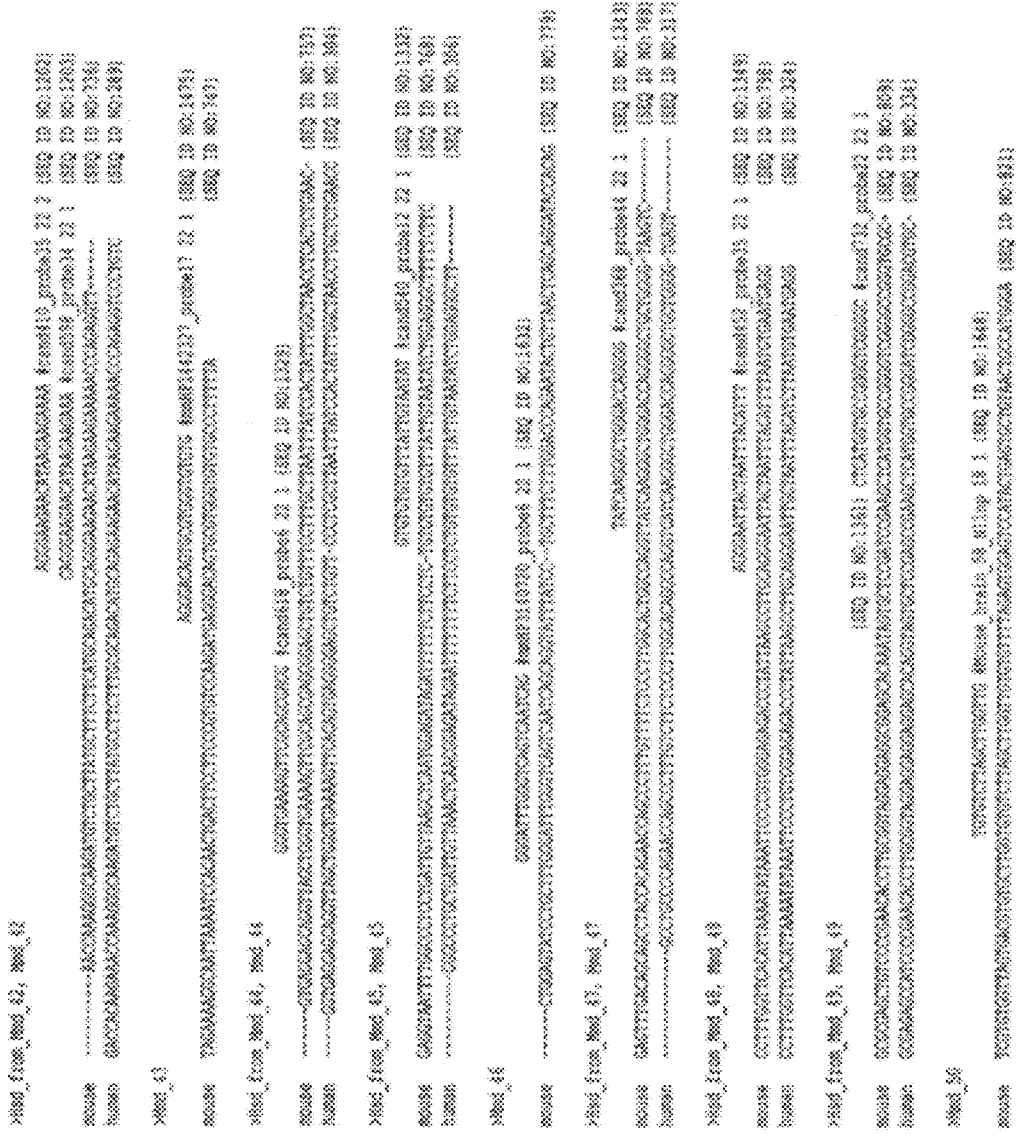
FIG 1B Con't.

FIG. 1B Con't.

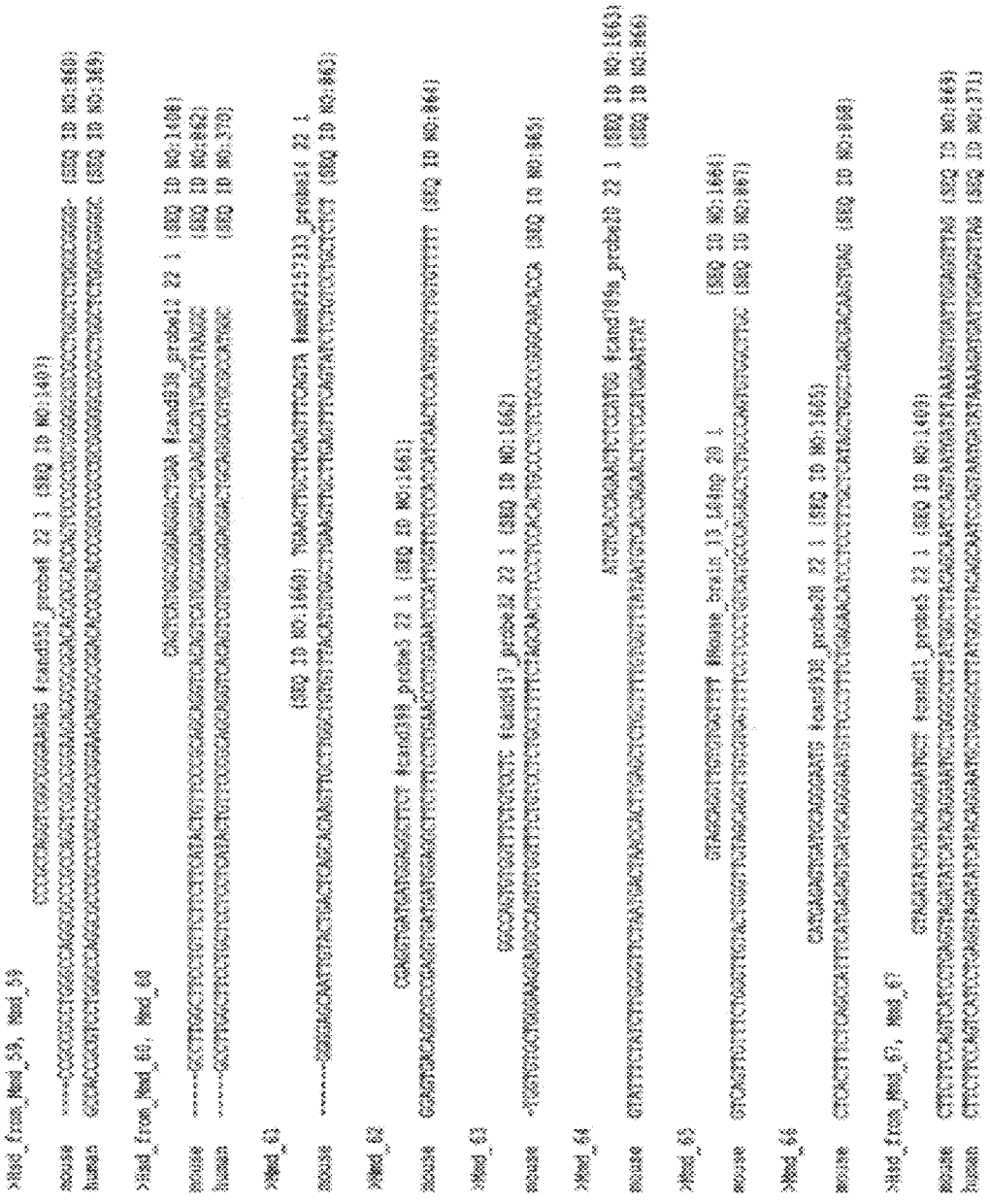
FIG. 1B Con't.

FIG. 1B Cont.

FIG. 1B Con't.

FIG. 1B Con't.

FIG. 1B Con't.

FIG 1B Con't.

FIG. 1B Con't.

FIG 1B Con't.

FIG. 1B Con't.

FIG. 1B Con't.

FIG. 1B Con't.

FIG. 1B Con't.

FIG. 1B Cont'l.

FIG 1B Con't.

FIG. 1B Con't.

FIG. 1B Con't.

FIG. 1B Con't.

FIG. 1B Con't.

FIG. 1B Cont'd.

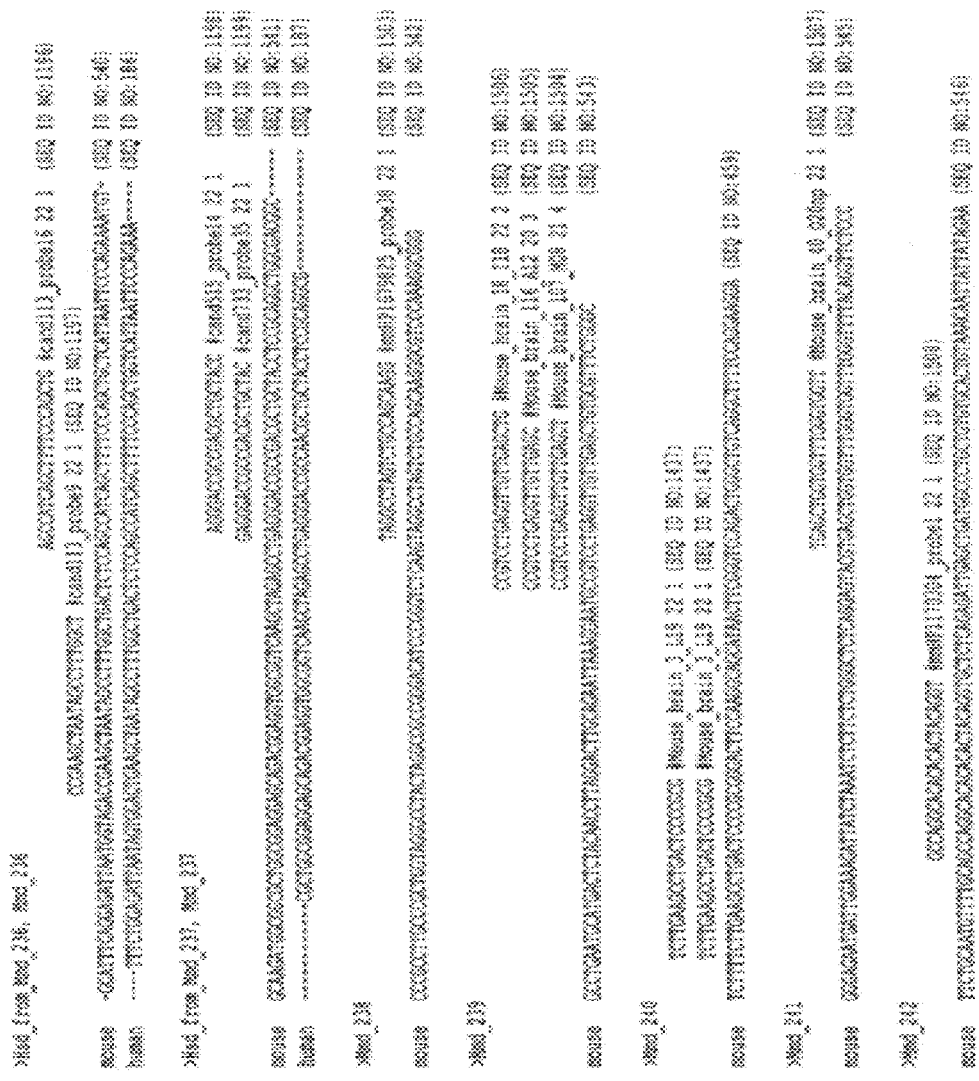
FIG. 1B Con't.

FIG. 1B Con't.

FIG. 1B Cont.

FIG. 1B Con't.

FIG. 1B Con't.

FIG. 1B Con't.

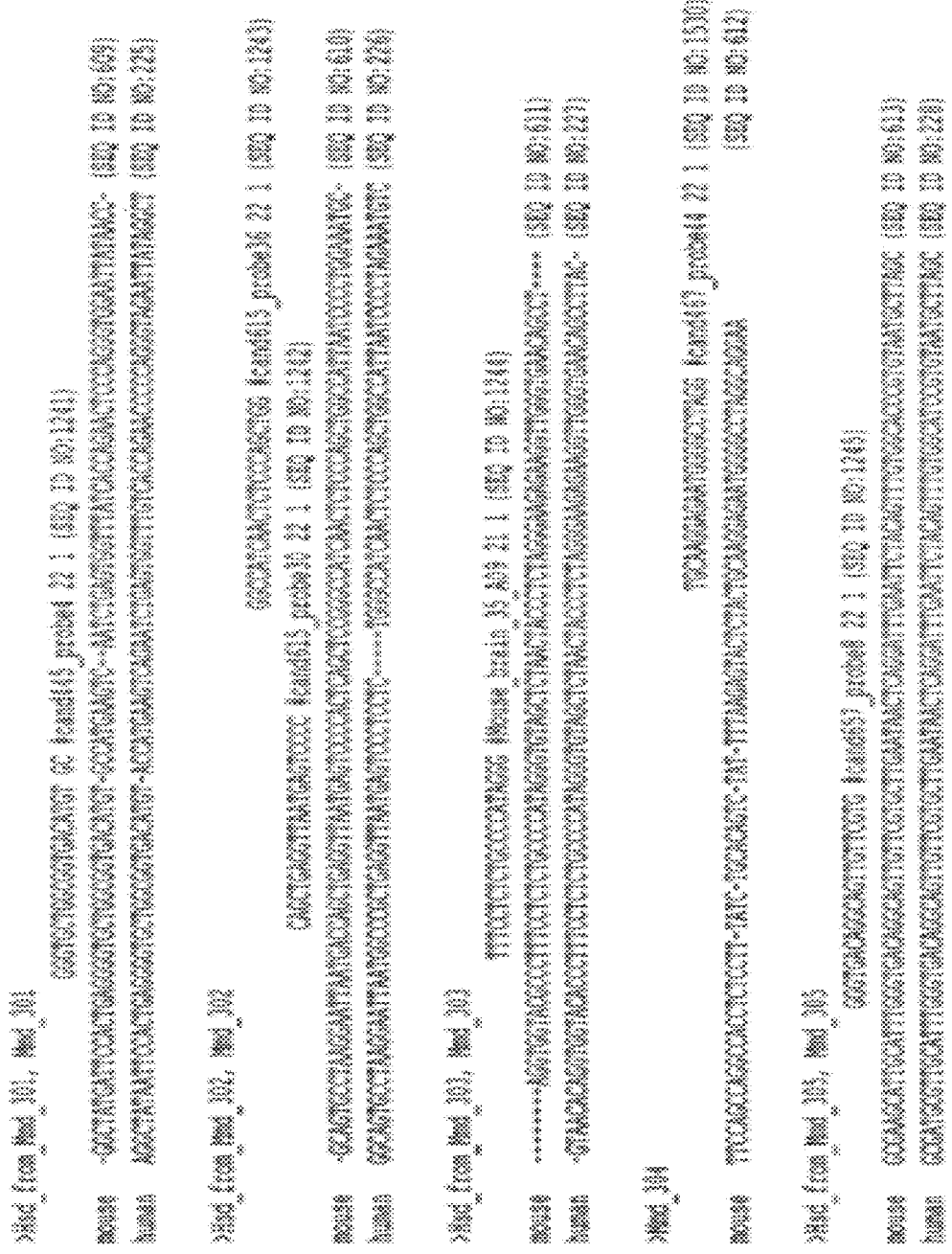

FIG 1B Con't.

FIG. 1B Con't.

FIG 1B Con't.

FIG. 1B Con't.

FIG. 1B Cont.

FIG. 1B Con't.

FIG. 1B Cont.

FIG. 1B Con't.

FIG. 1B Con't.

FIG 1B Con't.

FIG 1B Con't.

FIG. 1B Con't.

FIG. 1B Con't.

FIG 1B Con't.

FIG 1B Con't.

FIG. 1B Con't.

FIG. 1B Cont'd.

FIG 1B Con't.

FIG. 1B Cont'.

FIG. 1B Con't.

FIG. 1B Con't.

FIG 1B Cont'd.

FIG. 1B Con't.

FIG. 1B Cont.

FIG. 1B Con't.

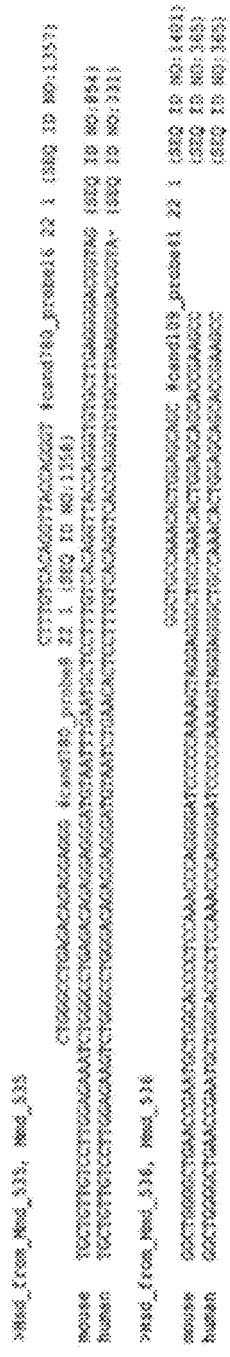
FIG. 1B Con't.

FIG 1C Con't.

FIG. 1C Con't.

FIG. 1C Con't.

FIG. 1C Con't.

FIG. 1C Cont.

FIG. 1C Con't.

FIG. 1C Con't.

FIG. 1C Con't.

FIG. 1C Com't.

FIG. 1C Con't.

FIG. 1C Cont'd.

FIG 1C Con't.

```
>MM_242
mouse    AATGATGGAGGTGCAGGCGTTTCCTGGGATTAATGACCAGCTGGGAGGAGAACCAGTGGCCCTCGGCTCTCCCTCCAGCCAGCCATTAACTCCAAGCAAATGTCTTTGCTGAGGTCGTT- (SEQ ID NO:4377)
human    AATGATGGAGGTGCAGGCATTTCCTGAGGATTAATGACCAGCTGGGAGGAGAACCAGTGGCCCTTGGCTCTGCCTCCCAGCCAGCCATTAATTCTAAGGAAATGTCTTTGCTGAGGTCCTT- (SEQ ID NO:2032)
chimp    --TGATGGAGATGCAGGCATTTCCTGAGGATTAATGACCAGCTGGGAGGAGAACCAGTGGCCCTTGGCCTCTGCCTCCCAGCCAGCCATTAATTCTAAGGAAATGTCTTTGCTGAGGTCCTTA (SEQ ID NO:8122)
macaque  -ATGATGGAGGTGCAGGCATTTCCTAGGATTAATGACCAGCTGGGAGGAGAACCAGTGGCCCTTGGCCTCTGCCTCCTCGCCTCCCAGCCAGCCATTAATTCTAAGGAAATGTCTTTGCTGAGGTCGT-- (SEQ ID NO:5310)

>MM_244
mouse    GCGTCCCCGTGGCTGCGCG #Mouse_libl_27868_19_1 (SEQ ID NO:10088)
         cggcggggcggggACCCACGGGGGCGCGTCCCGTGCGGCGCCCCCCGCTGCGGCATCCCGGGCGCGGCGCGCGTTCCCGTTGGTCTTGGCCTTCCCGTG (SEQ ID NO:4378)

>MM_245
mouse    TGATTTGGTTGTTTGGGT #Mouse_libl_1032_18_1 (SEQ ID NO:10089)
         TTCTTGTTTGATTTGGTTGTTTGGTTGTTTATGGTGTCCTGGATGTTCCTCATGTTTGAAGATGTCTAGGATGCTTTGGGAAACCTTGGCACTTGAGAGTTCACTCAAGAA (SEQ ID NO:4379)

>MM_246
mouse    TCTTGAAGCCTGACTCCCCGCG #Mouse_libl_13896_22_1 (SEQ ID NO:1437)
         TTTCCCTTTTCTTTTCTTGAAGCCTGACTCCCCGCGGGACTTCCAAGCCAGCAAGCTTCCAAGCAGCATAACTTCGGGTCAGACTGGGCTGTCAGGCTTTTCCAGGAACGATCCAGGAA (SEQ ID NO:4380)

>MM_247
mouse    TCTTGAAGCCTGACTCCCCGCG #Mouse_libl_13896_22_1 (SEQ ID NO:1437)
         TTTCCCTTTTCTTTTCTTGAAGCCTGACTCCCCGCGGGACTTCCAAGCAGCATAACTTCGGGTCAGACTGGGCTGTCAGGCTTTTCCAGGAACGATCCAGGAA (SEQ ID NO:4381)

>MM_248
mouse    TCTTGAAGCCTGACTCCCCGCG #Mouse_libl_13896_22_1 (SEQ ID NO:1437)
         TTCCCTTTTTCTTTTCTTGAAGCCTGACTCCCCGCGGGACTTCCAAGCAGCATAACTTCGGGTCAGACTGGGCTGTCAGGCTTTTCCAGGAACGATCCAGGAA (SEQ ID NO:4320)

>MM_249
mouse    TCTTGAAGCCTGACTCCCCGCG #Mouse_libl_13896_22_1 (SEQ ID NO:1437)
         TTTCCCTTTTTCTTTTCTTGAAGCCTGACTCCCCGCGGGACTTCCAAGCAGCATAATTCGGGTCAGACTGGGCTGTCAGGCTTTTCCAGGAACGATCCAGGAA (SEQ ID NO:4382)

>MM_250
mouse    TCTTGAAGCCTGACTCCCCGCG #Mouse_libl_13896_22_1 (SEQ ID NO:1437)
         TTCCCTTTTTCTTTTCTTGAAGCCTGACTCCCCGCGGGACTTCCCGGGACTTCCAAGCAGCATAACTTCGGGTCCAGACTGGGCTGTCAGGCTTTCCAGGAAGGATCCAGGAA (SEQ ID NO:4320)

>MM_251
mouse    CCAGGTGCTGGTGGAAATAGAG #Mouse_libRAKE_cand854_probe3_22_1 (SEQ ID NO:1287)
         ---CTTCCTGCTAAGAGGCTGCCAGGTGCTGGTGGAAATAGAGGCCCAAGAGGCTGGAGAGCAGCTGGCAGGCAGCTGTCCACCAGATGATGTAAGGCCAGCATGCCTCGAGGAAG (SEQ ID NO:4383)
human    CTGCAGGCAGTAGGAGCCTGCCAAGTGCTGGTGGAAGTAGAGGCCCGAAAAGGCCTGGAGCAGCTCGCAGGGAGCAGCCGTCCAGGGAGCCGGTCGGCAGCCGTGAGGTAGGCAGGACGGCCACGG------ (SEQ ID NO:2033)

>MM_252
mouse    CGGCACCCTTCAAGTCCTGAA #Mouse_libl_20768_21_1 (SEQ ID NO:1521)
         CGCCCATTCGGGACTGGAGGGATGGGCTTCAAGTCCTGAACACCG (SEQ ID NO:4384)

>MM_253
         (SEQ ID NO:10090) AGGGACATCACACCTAGAGAAC #Mouse_libRAKE_mmHP773617_probe40_22_1 (SEQ ID NO:4385)
mouse    GGACCATGCCCCAGTGCCCATCAAGAGGGACATTAGGCTCTCGATTGCCCTCATGTTATGCAGAACAGAGGGACATCACACCTAGAGACCCTCCAGCTGATCTCCTAGGCTTGGCT (SEQ ID NO:4385)

>MM_254
mouse    GGCACTGGCCAAGCCAAAGTCA #Mouse_libRAKE_cand273_probe11_22_1 (SEQ ID NO:1570)
         ------TCAGGCAGTTCGCTCCACCTTCTTCCTCCGGCACTGGCCAAGCCAAAGTCAGTGATGATGCAATCTTGGAGTCAGTCAGTAAAGGAGATTCTCAGGCTTGA (SEQ ID NO:4386)
```

FIG. 1C Con't.

FIG. 1C Cont'.

FIG. 1C Con't.

FIG. 1C Con't.

FIG. 1C Con't.

FIG. 1C Con't.

FIG. 1C Con't.

FIG 1C Con't.

FIG. 1C Con't.

FIG. 1C Cont'L.

FIG. 1C Con't.

FIG. 1C Con't.

FIG. 1C Cont.

FIG. 1C Con't.

FIG. 1C Con't.

FIG. 1C Con't.

FIG. 1C Con't.

FIG 1C Con't.

FIG. 1C Con't.

FIG. 1C Con't.

FIG. 1C Cont.

FIG 1C Con't.

FIG 1C Con't.

FIG. 1C Cont.

FIG. 1C Con't.

FIG 1C Con't.

```
chimp      TACACGGCAGGGTCTGAGCCTCGCCCCTGTGTCCCGAGTCACGGCAGGGTCTGAGCCTCGGCCCGTGTCTCGGCCCGTGTCTCCGAGTGCACGGCAGGGTC (SEQ ID NO:12352) AGGGTCTCAGCCTCGGCCG #Chimp_lib1_122252 19 1
                                                                                                      (SEQ ID NO:12352) AGGGTCTCAGCCTCGGCCG #Chimp_lib1_122252 19 1
                                                                                                      (SEQ ID NO:12352) AGGGTCTCAGCCTCGGCCG #Chimp_lib1_122252 19 1
                                                                                                      (SEQ ID NO:12352) AGGGTCTCAGCCTCGGCCG #Chimp_lib1_122252 19 1
                                                                                                      (SEQ ID NO:12352) AGGGTCTCAGCCTCGGCCG #Chimp_lib1_122252 19 1
                                                                                                      (SEQ ID NO:7551)

>PT_332 chimp      GGCTCGGCCCGTGTCTGTCTCCCTGAGTGCACGGCAGGGTCTGAGCCTCGGCCCGTGTCTGTGTGAGTGCACGGCAGGGTCTCAGCCTCGGCCCGTGTGTCTGTGTGAGTACACGGCAGGGTC (SEQ ID NO:7552)
human      ------CCCGTGTCTGTCTGTGAGTACACGGCAGGGTCTCAGCCTCGGCCCGTGTCTCAGCCTCGGCCCGTGTGT--CCTCGAGTACACATCAGG--- (SEQ ID NO:3456)

>PT_333

TGAAAGCTGCCATGGCCCTGG #Chimp_lib1_45322 21 2 (SEQ ID NO:12354)
                       TGAAAGCTGCCATGGCCCTGGAG #Chimp_lib1_76879 23 1 (SEQ ID NO:12355)
                                                      GATCTTCATGCCCTGGGTCTGCC #Chimp_lib1_139004 24 1 (SEQ ID NO:12353)
chimp      GTGGGGTAAAACCCCAGACGCCATGGCCCTGCAGAAAAAGCTGAACCAGGCCCTTTGGATCTTCATGCCCTGGGTCTGCCCACAC (SEQ ID NO:7553)
human      GTGGGGTAAAACCCCAGACGCCATGGCCCATGGCCCTGCAGAAAAAGCTGAACCAGGCCCTTTGGATCTTCATGCCCTGGGTCTGCCCACAC (SEQ ID NO:2095)
macaque    GTGGGGTAAAACCCTGGATGCCATGAAAGCCCTGAGCGCCATGGCCCTTGGCCTTGGCCTTGGGCCTTGGGGTCTGCCCACAC (SEQ ID NO:5457)
mouse      --TGGGGTAAAACCAGGAGCATGGAAGCTGCCTTGGCCCTGAGAAGAACCTGAACCAGGCCCTCTGCATGCCCTGGGTCTGCCCGCA- (SEQ ID NO:4881)

>PT_334, HS_292

ACCCTATCAATATTGTCTCTG #Chimp_lib1_30730 21 1 (SEQ ID NO:12358)
                                          TAGTGCAATATTGCTTATAGG #Chimp_lib1_17904 22 1 (SEQ ID NO:1076)
                                          TAGTGCAATATTGCTTATAGGGTT #Human_lib9_9447 24 1 (SEQ ID NO:9053)
                                          TAGTGCAATATTGCTTATAGGGTTT #Human_lib9_6603 25 1 (SEQ ID NO:1078)
                                          TAGTGCAATATTGCTTATAGGGT #Chimp_lib1_86690 23 1 (SEQ ID NO:1077)
                                          TAGTGCAATATTGCTTATA #Chimp_lib1_182382 19 1 (SEQ ID NO:12357)
                                          AGTGCAATATTGCTTACAGG #Chimp_lib1_110260 20 1 (SEQ ID NO:12356)
                                          GTGCAATATTGCTTACAGG #Human_lib9_5201 20 1 (SEQ ID NO:9054)
chimp      TCTGTTTATCACCAGATCCTAGAACCCTATCAATATTGTCTCTGCTCTGTGTAAATAGTTCTGAGTAGTGCAATATTGCTTATAGGGTTTGGGTTTGGGTGTTTGGAAAGAACAATGGGCAGG (SEQ ID NO:1871)
human      -CTGTTTATCACCAGATCCTAGAACCCTATCAATATTGTCTCTGCTCTGTGTAAATAGTTCTGAGTAGTGCAATATTGCTTATAGGGTTTGGGTTTGGGTGTTTGGAAAGAACAATGGGCAG- (SEQ ID NO:1872)
macaque    --TGTTTATCACCAGATCCTAGAACCCTATCAATATTGTCTCTGCTCTGTGTAAATAGTTCTGACTAGTGCAATATTGCTTATAGGGTTTAGGGTTTGGGTGTTTGGGAAGAACA------- (SEQ ID NO:5004)

>PT_338

CAGGGGCTGGCAGTGAGATGGT #Chimp_lib1_70612 22 3 (SEQ ID NO:11306)
                       CATTTCCCTGCCATTCCCTTGG #Chimp_lib1_159176 22 1 (SEQ ID NO:11304)
                                          CCAGGGCTGGCAGTGAATGG #Chimp_lib1_67942 21 1 (SEQ ID NO:11305)
chimp      TGAGTCCAGTGGCCTCGGCTCGTCCATTCCCTTGGCTCCATTCCCTTGGCTTCAATTTACTCCCAGGGCTGCAGTGGGCTGCAGTGGGTCAAGGCTCACACCTTCA (SEQ ID NO:7556)
human      ------GTGGCTCTGGTCGTCGGTCCATTCCCTGGCTCCATTCCCTTGGCTTCAATTTACTCCCAGGGCTGCAGTGGGCTGCAGTGGGTCAAGGCTCAC------- (SEQ ID NO:3457)
macaque    TGAGTCCGGTGGCTCTGGTCGTCGGTCCATTCCCTGGCTCCATTCCCTTGGCTTCAATTTACTCCCAGGGCTGCAGTGGGCTGCAGTGGGTCAAGGCTCACACCTTCA (SEQ ID NO:5458)

>PT_339

TTCCTCTCTGATGACTTCCTGTT #Chimp_lib1_52270 21 2 (SEQ ID NO:12363)
                       TTCCTCTCTGATGACTTCCTGT #Chimp_lib1_23587 20 1 (SEQ ID NO:12361)
                       TTCCTCTCTGATGACTTCCTG #Chimp_lib1_45097 19 1 (SEQ ID NO:12362)
chimp      TCAGTGAGTTCCAAGCTGGGATTGAGAAGGGAGGACCAGTGAAGGACCCGGAGGTTATACTTCCTCTGTTAGTGCCACGTGTCTGGCCACTGA (SEQ ID NO:7557)
human      TCAGTGAGTTCCAAGCTGGGATTGAGAAGGGAGGACCAGTGAAGGACCCGGAGGTTATACTTCCTCTGTTAGTGCCACGTGTCTGGCCACTGA (SEQ ID NO:3458)
macaque    TCAGTGAGTTCCAGGCTGGGATTGGAGAAGGGAGGAGACTGGAGACTGGAGGTTATACTTCCTCTGTTAGTGCCACGTGTCTGGGCCACTGA (SEQ ID NO:5459)

>PT_340

GTACATGATGACAACTGCCTCC #Chimp_lib1_85762 22 1 (SEQ ID NO:12367)
```

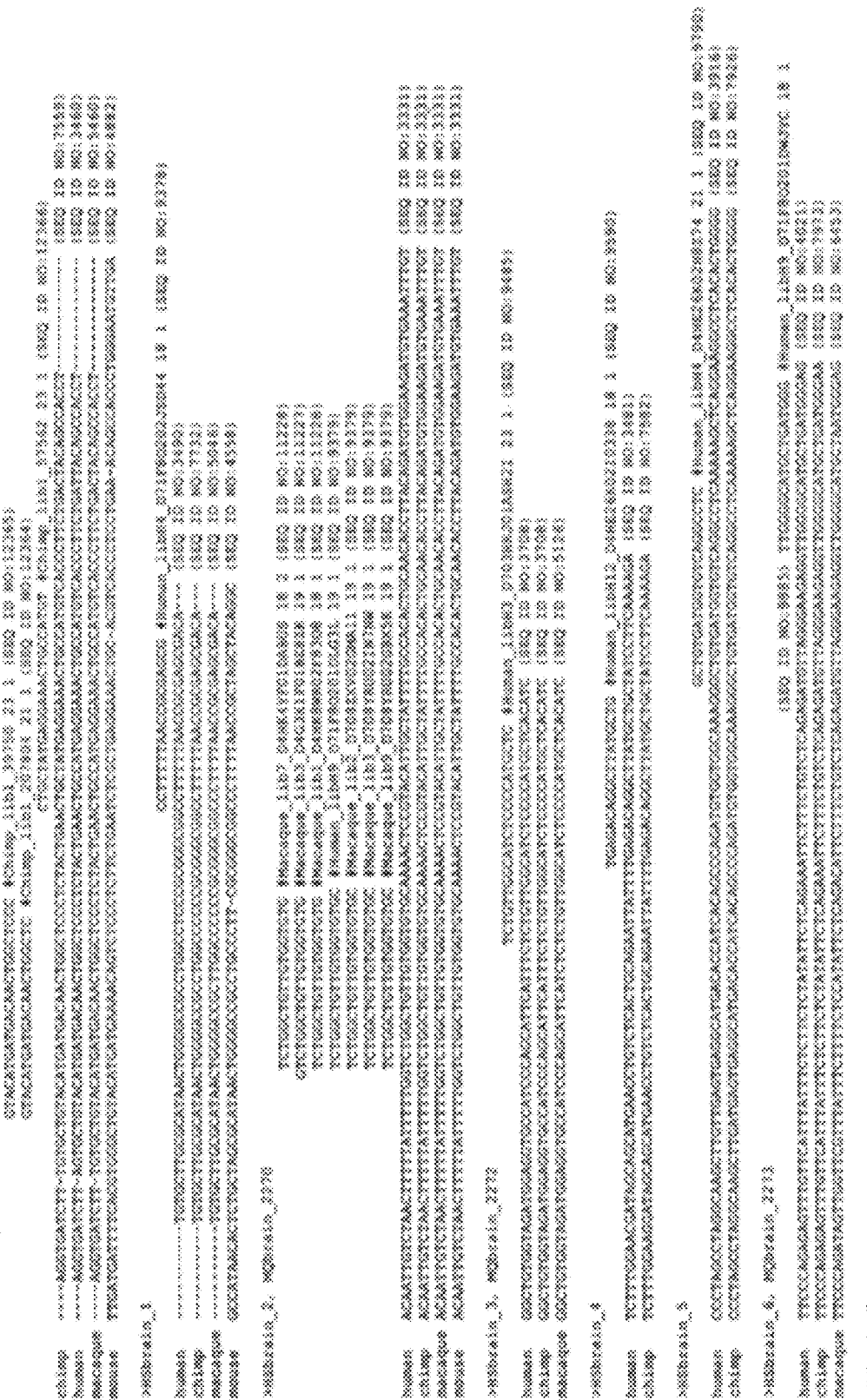

FIG. 1C Cont'd.

FIG. 1C Con't.

FIG. 1C Cont'L.

FIG. 1C Con't.

FIG 1C Con't.

FIG. 1C Cont'L.

FIG. 1C Con't.

FIG. 1C Con't.

FIG. 1C Cont.

FIG. 1C Con't.

FIG. 1C Con't.

FIG. 1C Con't.

FIG 1C Con't.

FIG 1C Con't.

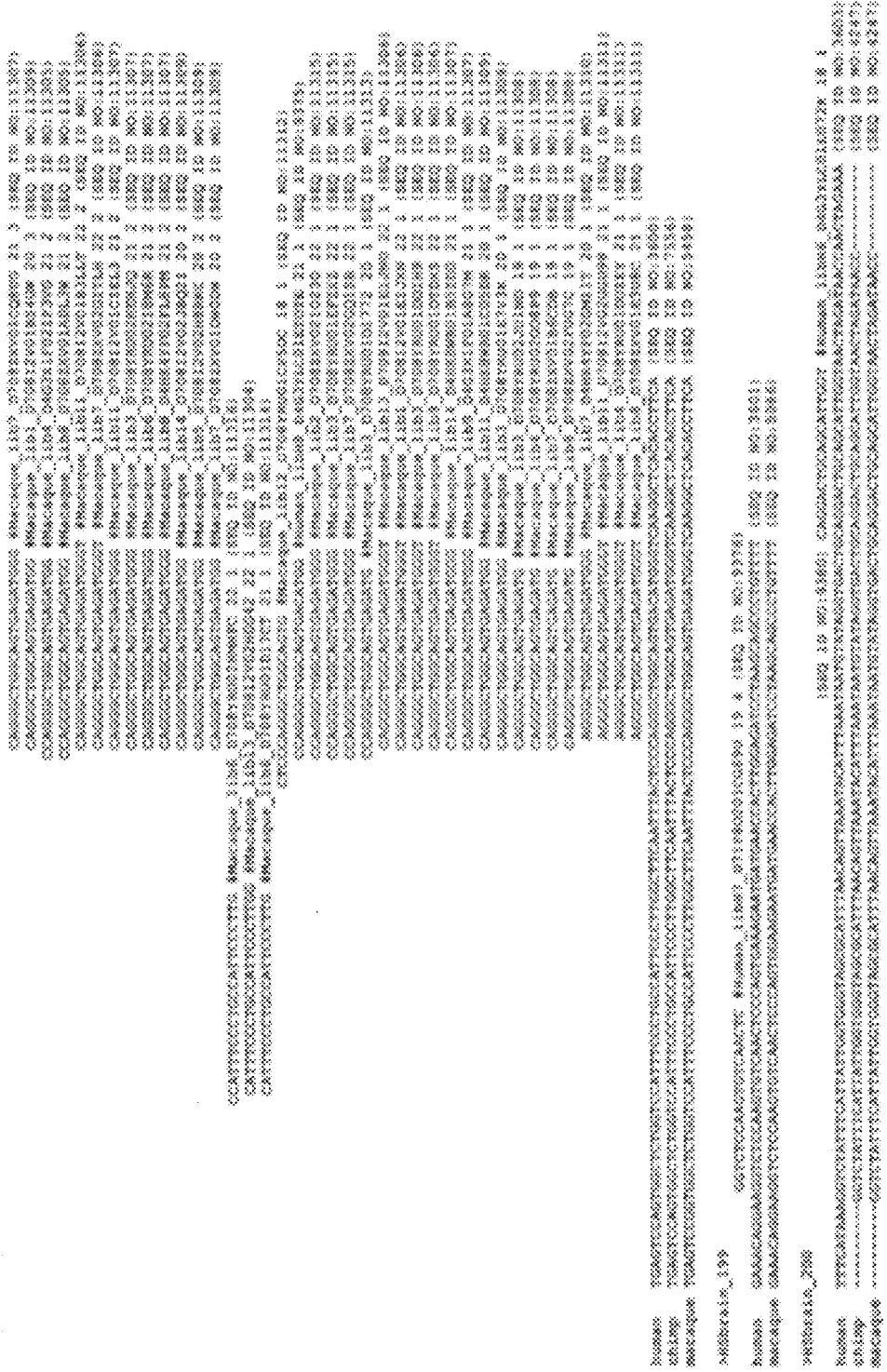
FIG 1C Con't.

FIG. 1C Con't.

FIG. 1C Con't.

FIG. 1C Con't.

FIG. 1C Cont.

FIG 1C Con't.

FIG. 1C Cont'd.

FIG. 1C Con't.

FIG. 1C Con't.

FIG. 1C Con't.

FIG. 1C Con't.

FIG. 1C Cont.

FIG 1C Con't.

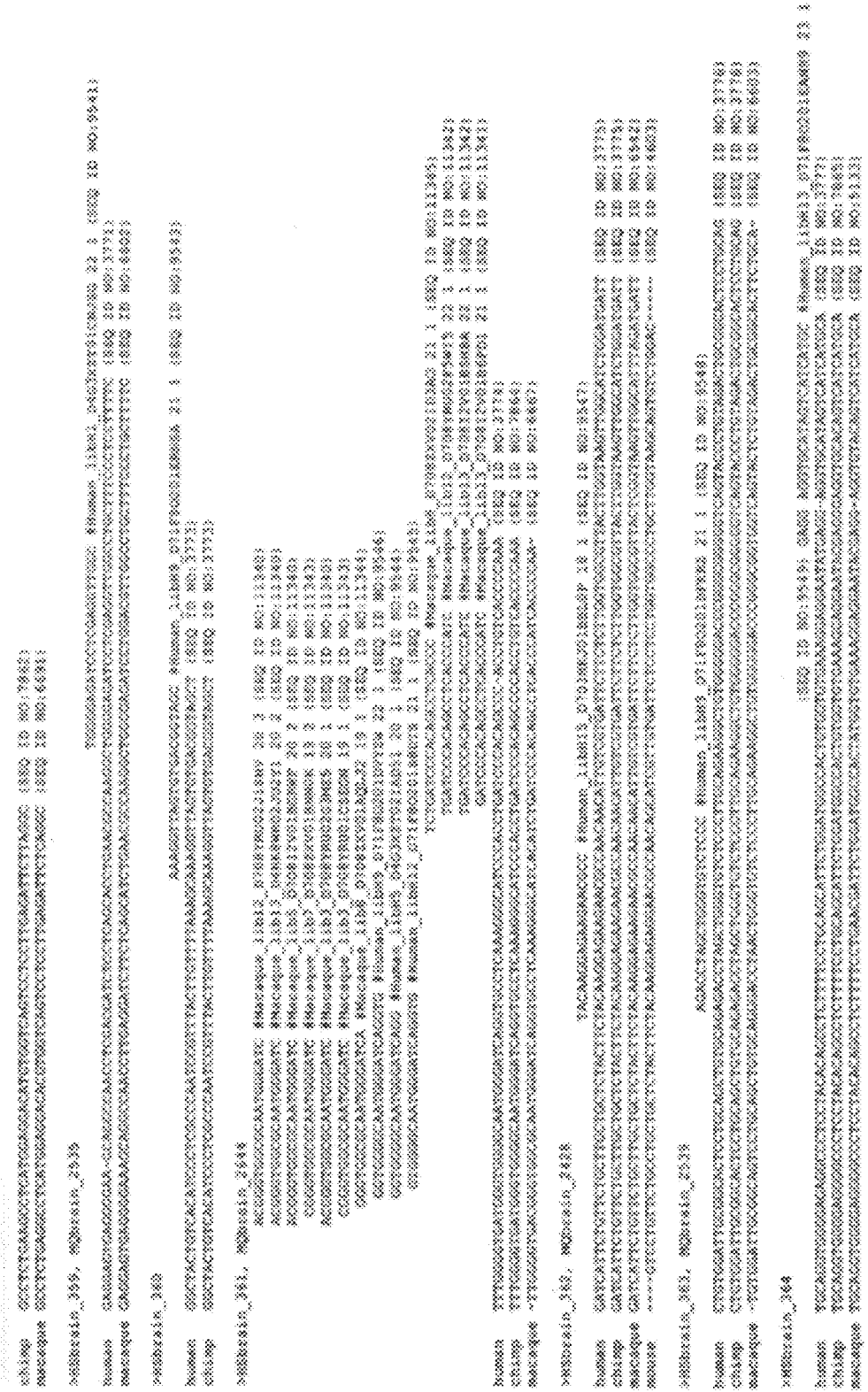

FIG. 1C Con't.

FIG 1CC Con't.

FIG 1C Con't.

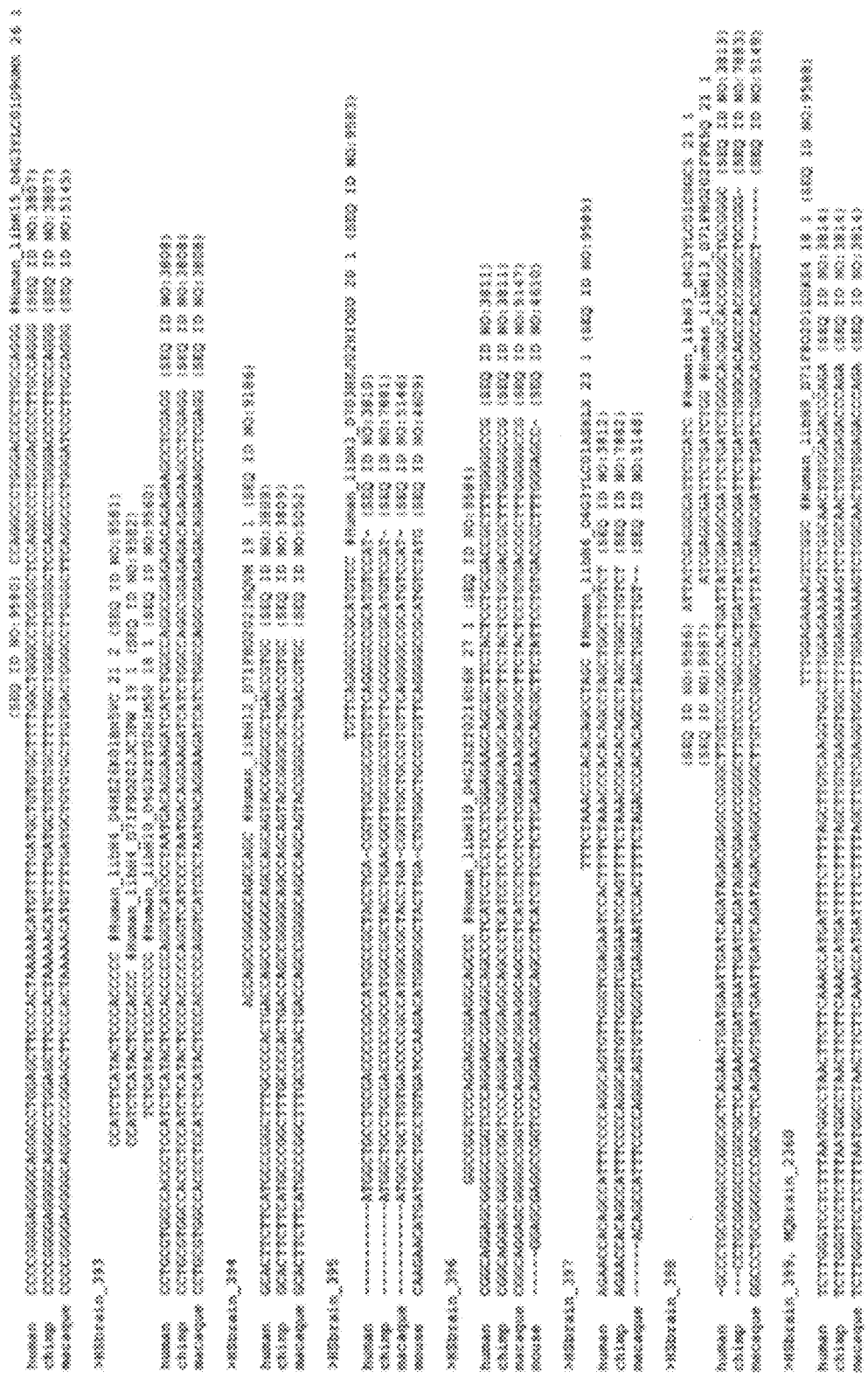
FIG. 1C Con't.

FIG. 1C Con't.

FIG. 1C Con't.

FIG. 1C Con't.

FIG. 1C Con't.

FIG. 1C Cont'l.

FIG. 1C Con't.

FIG. 1C Con't.

FIG. 1C Con't.

FIG. 1C Cont.

FIG. 1C Con't.

FIG 1C Con't.

FIG 1C Con't.

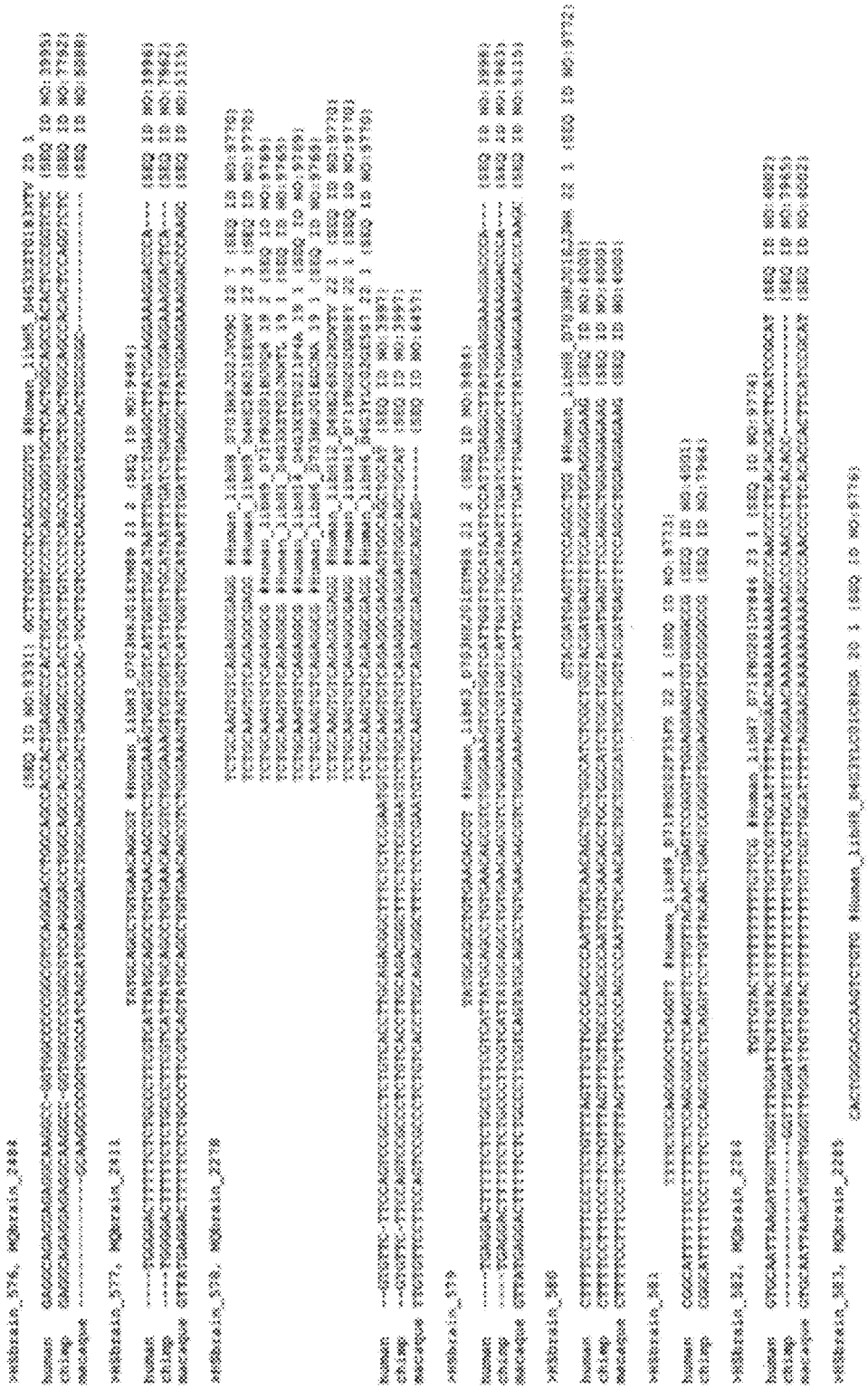
FIG. 1C Con't.

FIG. 1C Cont'd.

FIG. 1C Con't.

FIG. 1C Con't.

FIG. 1C Con't.

FIG. 1C Con't.

FIG 1C Con't.

FIG. 1C Con't.

FIG 1C Con't.

FIG 1C Con't.

FIG 1C Con't.

FIG. 1C-Con't.

FIG 1C Con't.

FIG 1C Con't.

FIG 1CC con't.

FIG 1C Con't.

FIG 1C Cont'L.

FIG. 1C Con't.

FIG. 1C Con't.

FIG 1C Cont.

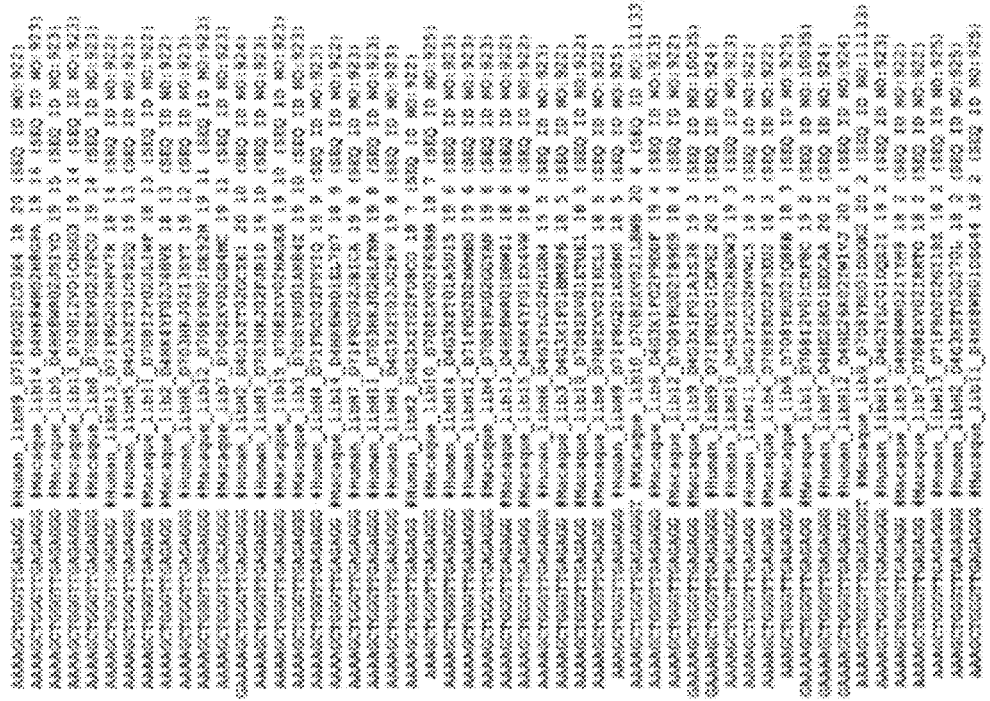
FIG 1C Con't.

FIG 1C Con't.

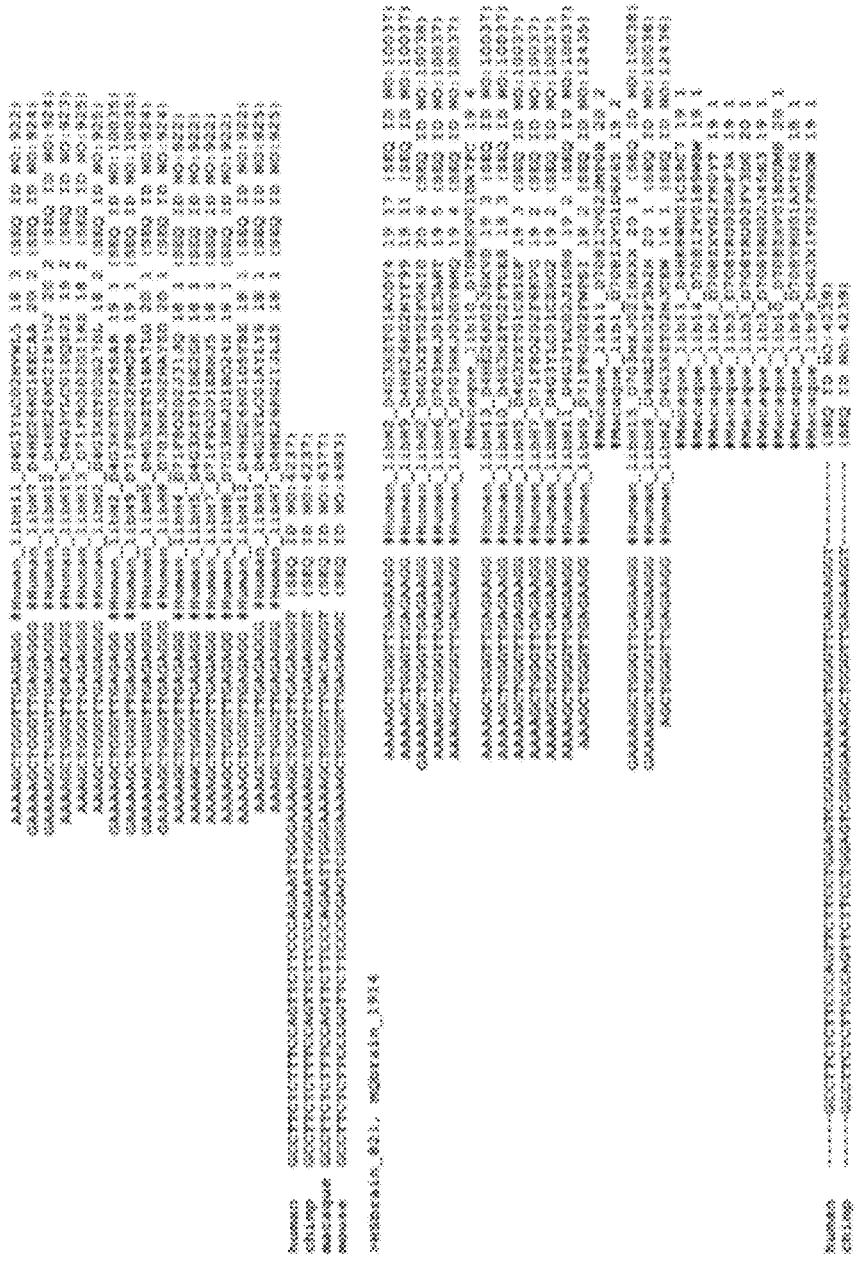
FIG 1C Con't.

FIG. 1C Con't.

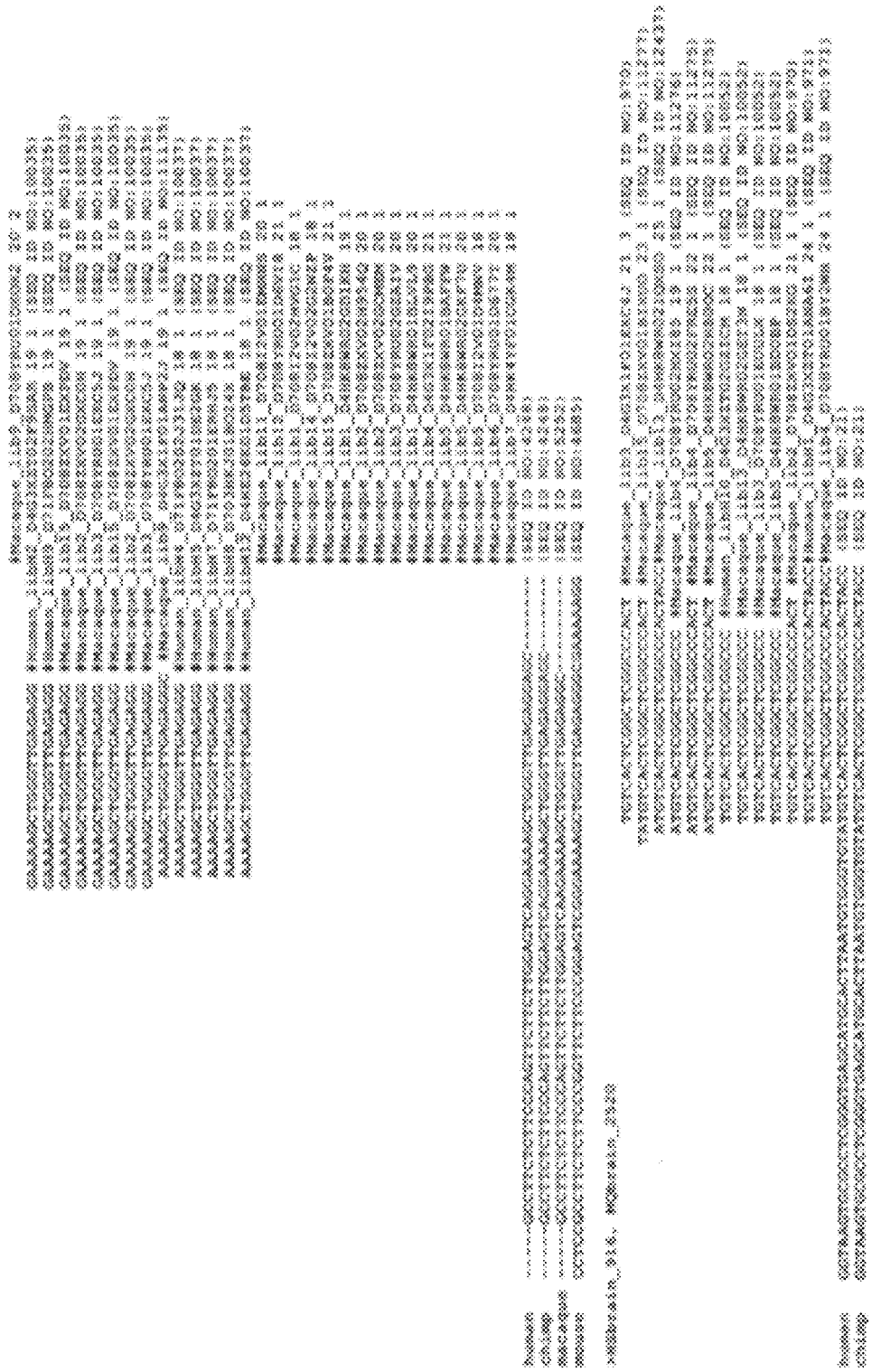
FIG. 1C Con't.

FIG. 1C Con't.

FIG 1C Com't

FIG 1C Con't.

FIG 1CC Con't.

FIG 1C Con't.

FIG. 1C Cont.

FIG. 1CC Con't.

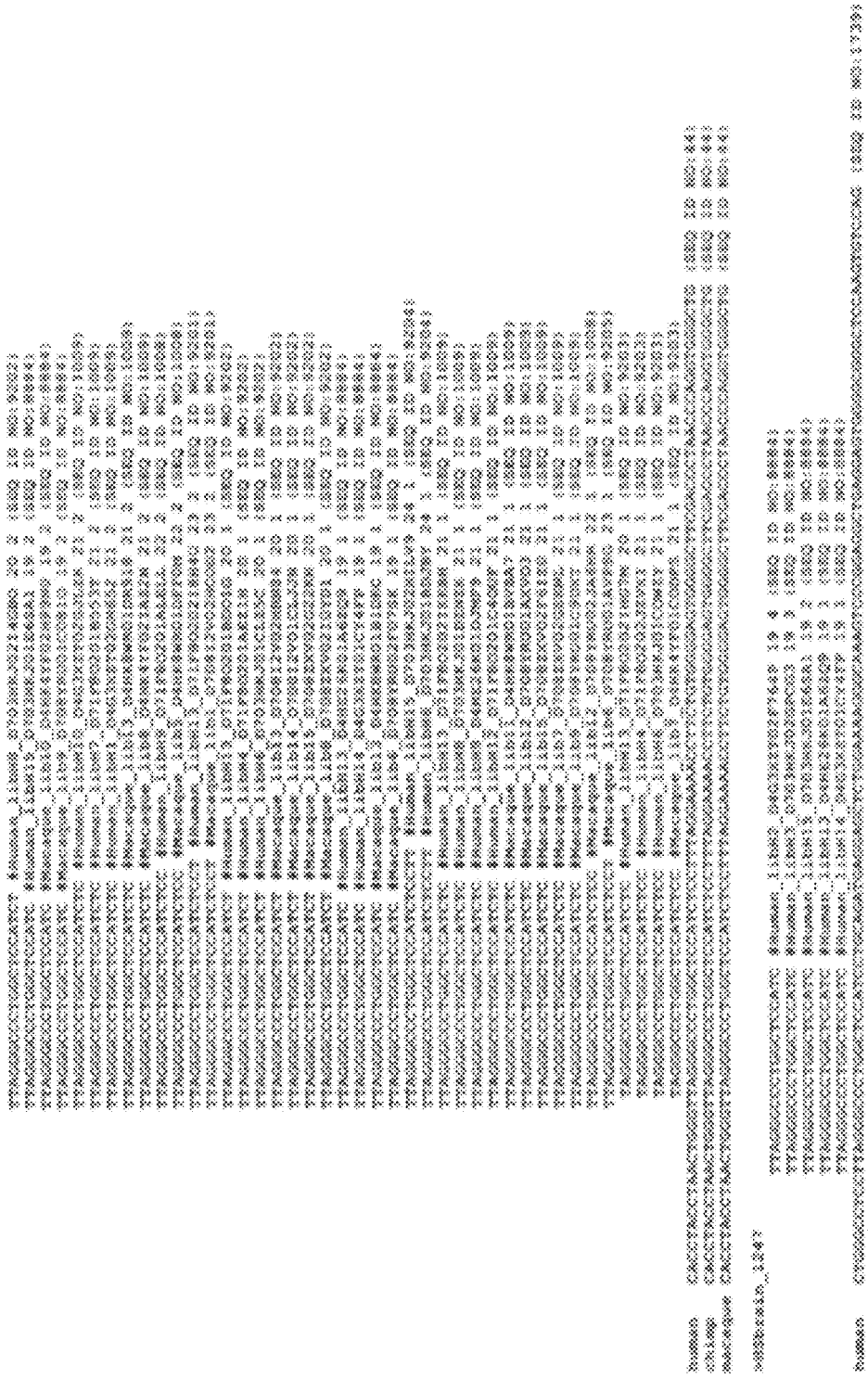
FIG 1C Con't.

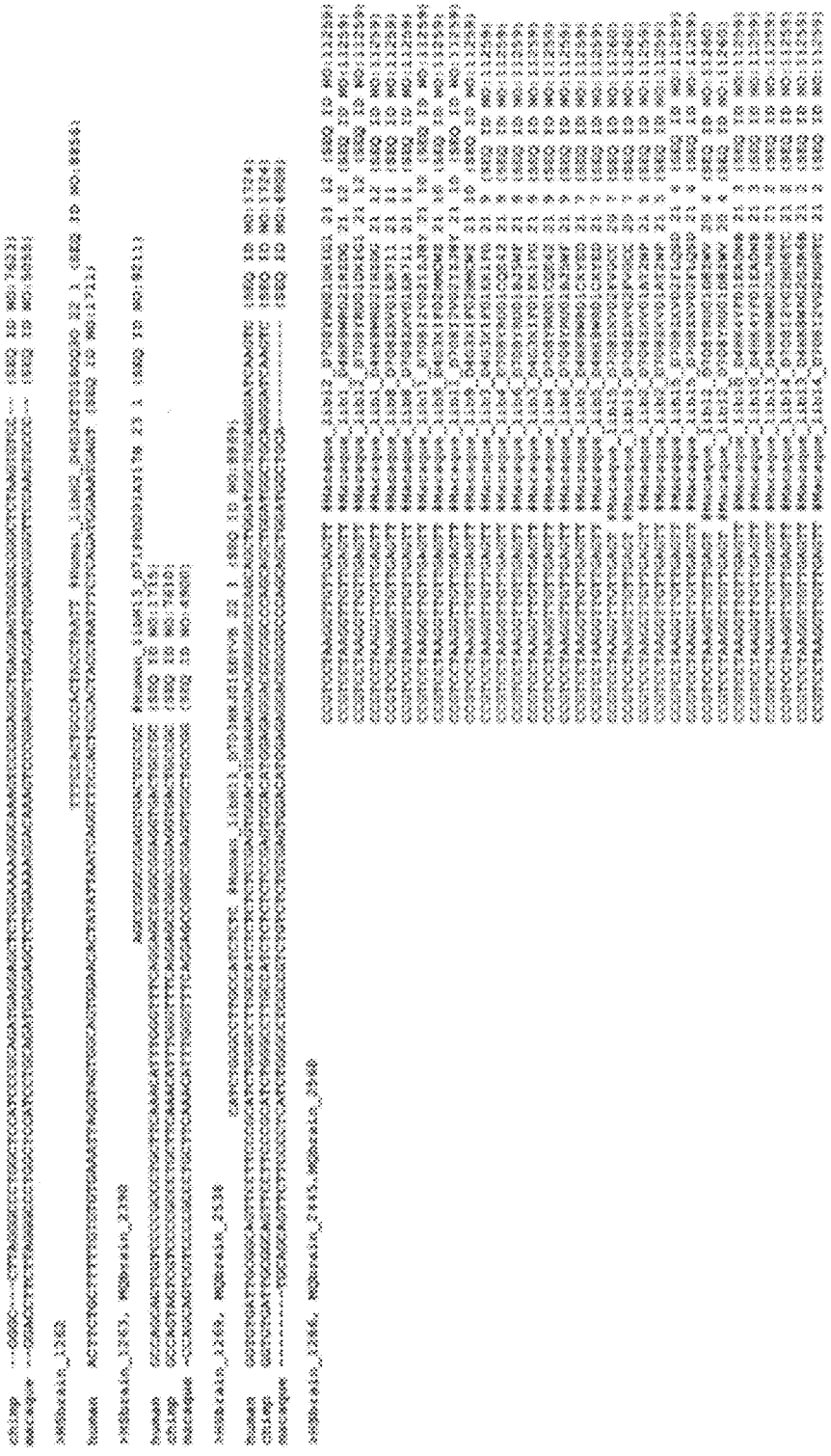
FIG 1C Con't.

FIG. 1C Con't.

FIG. 1C Con't.

FIG. 1C Cont'L.

FIG. 1C Con't.

FIG. 1C Con't.

FIG. 1C Con't.

FIG 1C Con't.

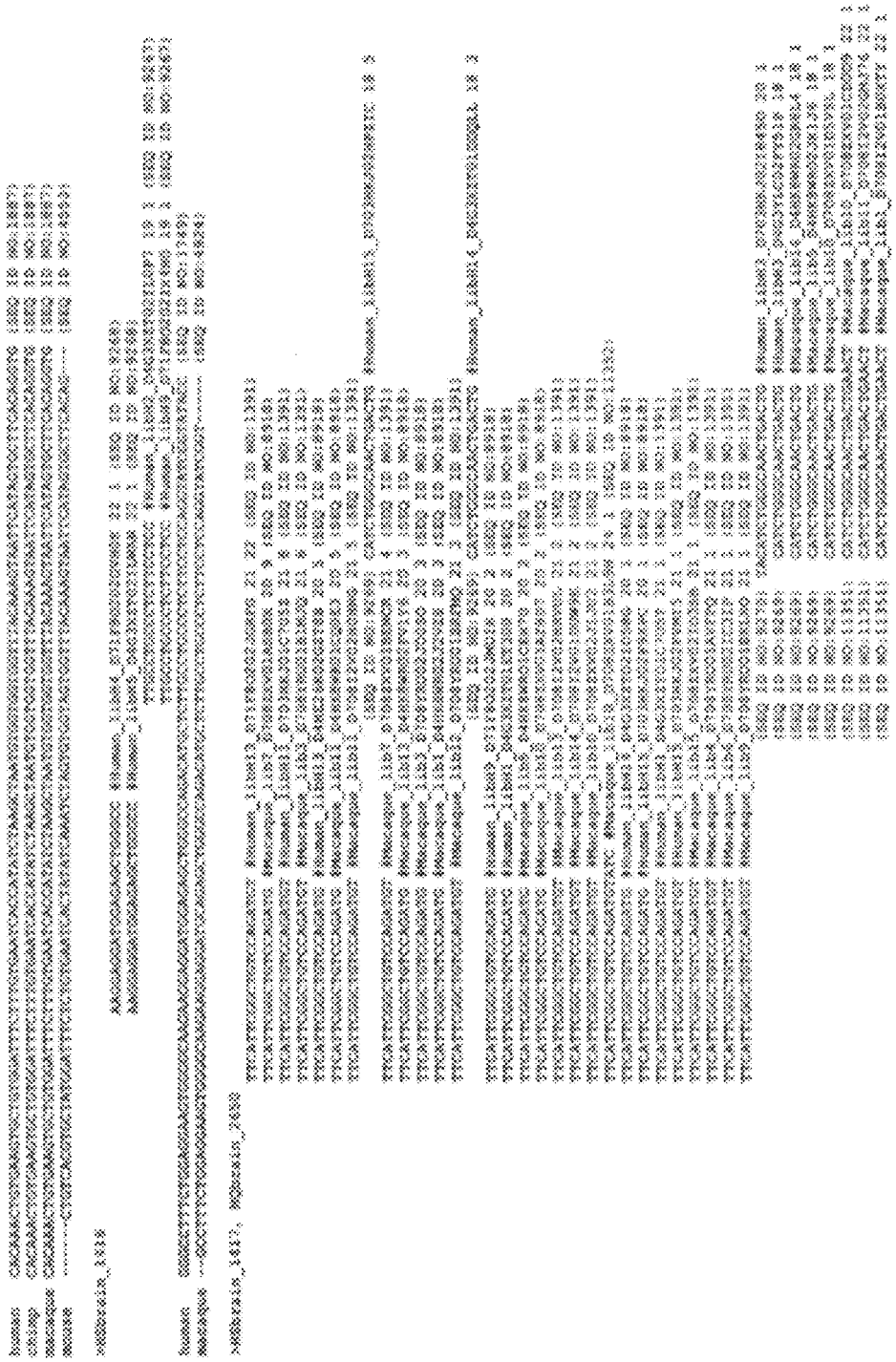
FIG. 1C Con't.

FIG 1C Con't.

FIG 1C Con't.

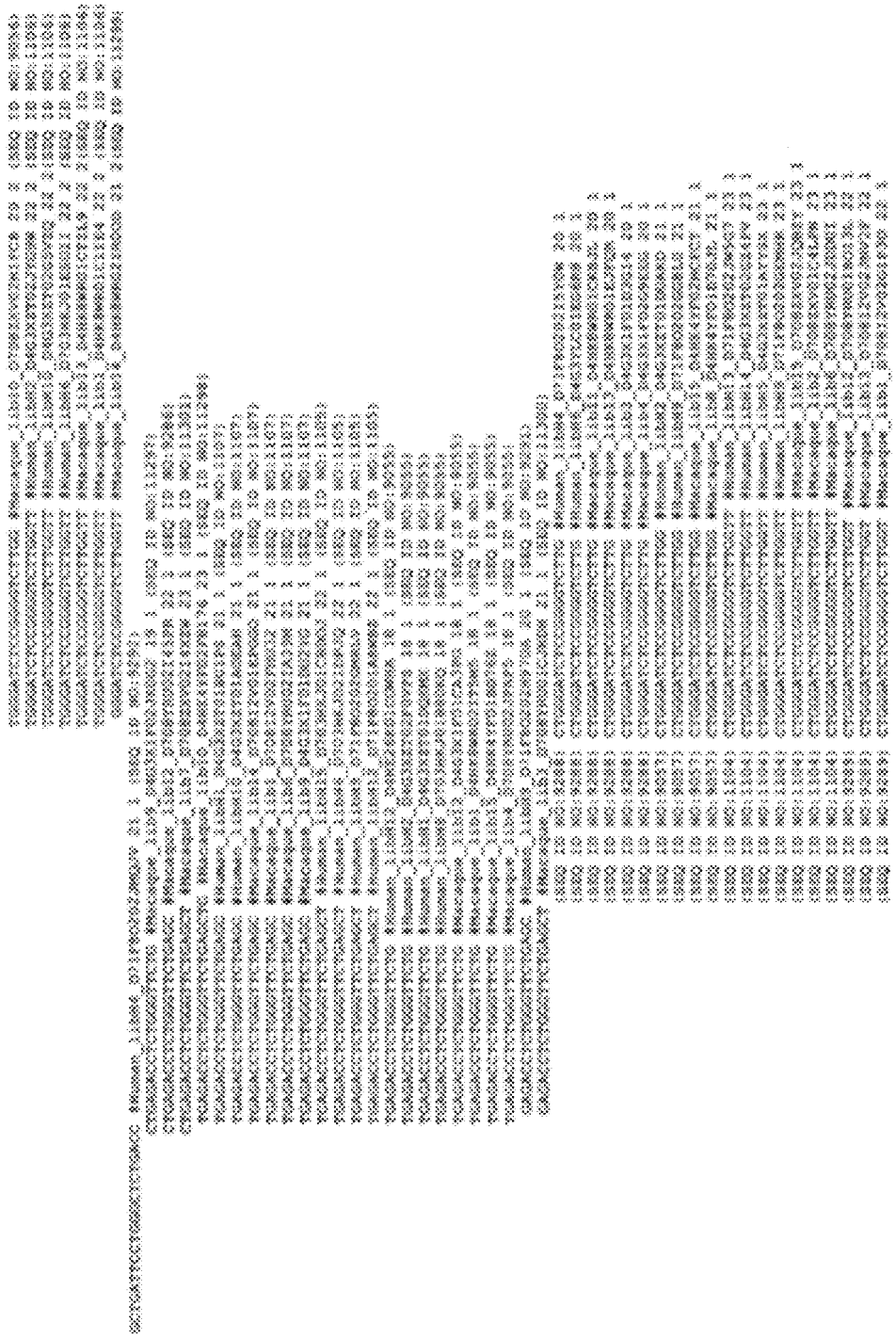
FIG 1C Con't.

FIG 1C Con't.

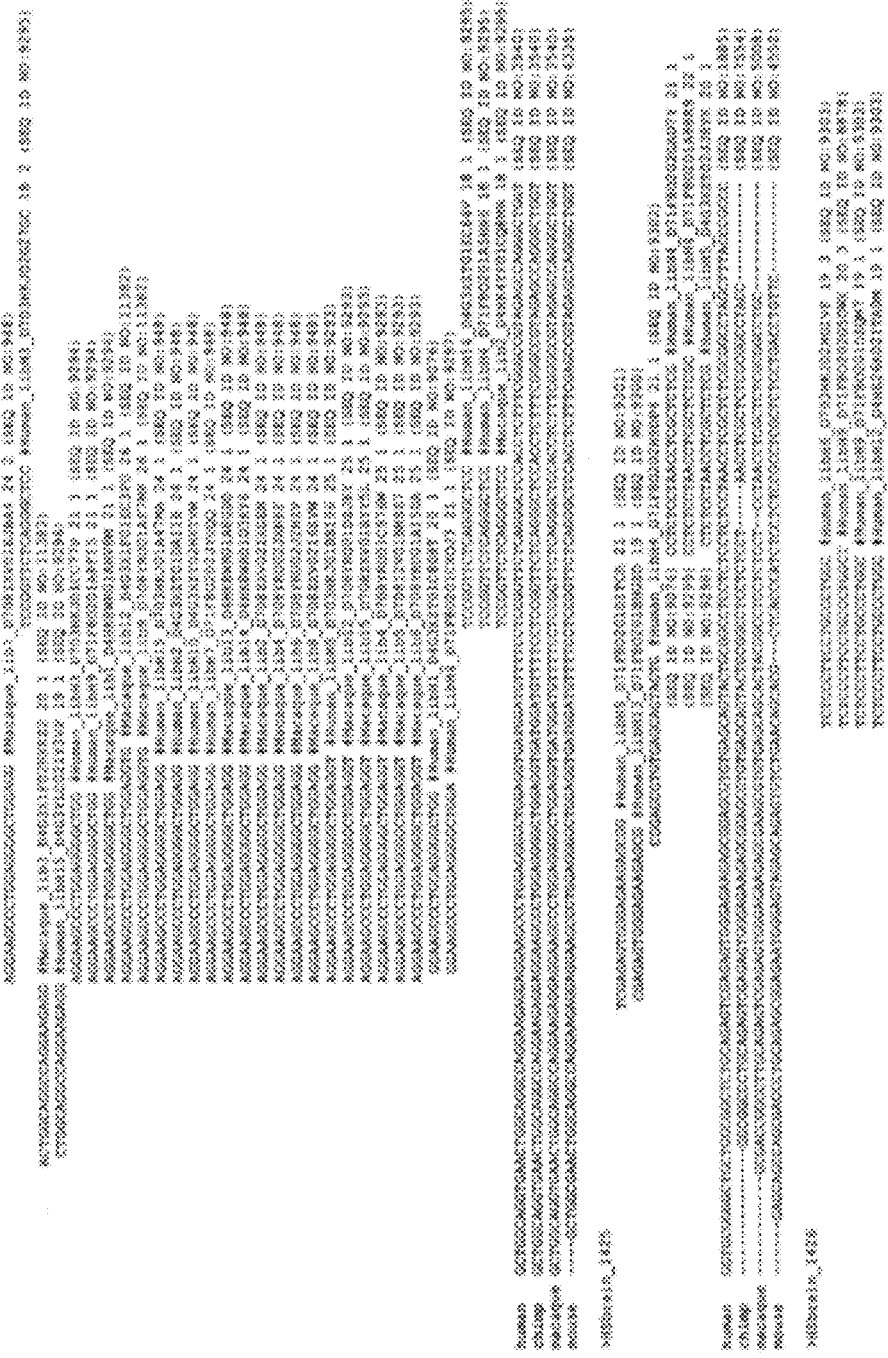
FIG. 1C Cont'l.

FIG. 1C Cont'l.

FIG 1C Con't.

FIG. 1C Con't.

FIG 1C Con't.

```
macaque CTGTTGGGAGGCTGAGGGAAGTCAACTTCCCCTCTACCTCCTCCATTCCAGACAG (SEQ ID NO:5483)

>MQbrain_11
                                                                             (SEQ ID NO:10305) AAGGGAGGAGGAGGGTGATGG #Macaque_lib9_D708YRU01A8322 19 1
macaque TGTTAGTAGGGCTGCTCACTCTC--ATCTCTCCTTATGTCTGAGATTCTGGCCTTCCTGTCTTAGGGAGGTCCATTATTTTACACTAAAGGGAGGAAGGGTGATGGAGAATTGTTGACA----(SEQ ID NO:5586)
human   -GTTAGTAGGGCAGTCACTCTCATCTCACCTTATGTCTGAGATTCTGGCCTTCCTATGCTTTCCTATGCTTTGGGGAGGTCCATTATTTTTACACTAAAGGGGAGAAGGGTGATGGAGAATTGTTGAC-----(SEQ ID NO:2175)
chimp   --------GGGCAGTCACTCTCTCATCTCTCTATGTCTGAGATTCTGGCCCTTCCTATGTCTTGGGGAGGTCCATTATTTTTACACTAAAGGGAGGAGGGGTGATGGAGAATTGTTGACACGCTT(SEQ ID NO:8206)

>MQbrain_12
macaque      TCAGTGCTTAGGCCTGGGGTCCAGCCTGG  #Macaque_lib5_D708I2V02F8NY5 29 1 (SEQ ID NO:10411)
macaque TGCTTGCAGTTCAGTGCTTAGGCCTTAGGCCTGGGGTCCAGCCTGGCTCCAGGTGGAGCTGCTCCAGGTGTGTGCTGTGTCACCAAGCTTACAGCA (SEQ ID NO:5686)

>MQbrain_13
macaque      TCGAGGGAAAGTCCTGCTG  #Macaque_lib4_D4G3X1F02HBVAE 21 1 (SEQ ID NO:10517)
macaque GGGAGAGCCCTCGAGGGAAAGGTCCTGCTGAGGTGTCTTGCAAGGCATCCACAGCCAGGCCGGCTCCCTTGTCCAGGCC (SEQ ID NO:5784)
human   GGCAGAGCCCTCGAGGGAAAGGTCCTGAGCTCTGCTGAGCTCCCTTGCAAGGCCCCACAGCCCCACAGCCTCCCTTGTGCCAGGCC (SEQ ID NO:8286)

>MQbrain_14
                                     (SEQ ID NO:10619) AGTGAAGGTGGTGCTGCTG #Macaque_lib11_D4HK8WR01CNFF0 21 1
macaque GGTGGGGGCCTTCCCTGCAGGCAGGGGCGGGGCCATCCCAACGCCCTTTGCGGCGGCAGTGAAGGTGGGAGTGGAAGGTGGTGCTGCTGTTCCCCAGTGTCGGGAAGATGGGCGCCGCC (SEQ ID NO:5883)
human   GGTGGGCATTCCCTGCAGCAAGGGCGGGGCCACCCACCCACCCAACGCCCTTCTGCGGCCAAGTAGGTTGGGAGTGGAAGGTGGTGCTGCTGCTGCTGCTGTCGGGGAGATGGGCGCCGCC (SEQ ID NO:2380)
chimp   -GTGGGGCATTCCCTGCAGCAAGGGCGGGGCCACCCACCCAACGCCCTCGCGGCCAAGTAGGTTGGGAGTGGAAGGTGGTGCTGCTGCTGCCAGTGTCGGGAAGATGGGCGCCGC- (SEQ ID NO:8330)

>MQbrain_15
                   GAATGCTGGACTGAGGCC #Macaque_lib14_D70BI2V01DX10G 19 1 (SEQ ID NO:10724)
macaque CCACCCAATCAAGGAGTGAAGGAGGAATGCTGGACTGAGGCCCTGAGCCAGATGGCCAAGAGGGTGACAGCTTCCTTCCTGTGTATACTCCGTCCAGTTCCTTGAGAAAAA-TGG (SEQ ID NO:5984)
human   ----CCAATCAAGGAAGGAGGAATGCTGGACTGGACTGGAGCCCTGAGCCAGATGGCCAGAGAGGGTGACAGCTTCCTTCCTGTGTACTCGTCCAGTTCCTTAGAAAAAATGG (SEQ ID NO:2450)
chimp   ----CCAATCAAGGAAGGAAGGAGGAATGCTGGACTGGACTGGAGCCCTGAGCCAGATGGCCAGAGAGGGTGACAGCTTCCTTCCTGTGTACTCGTCCAGTTCCTTAGAAAAAATGG (SEQ ID NO:2450)

>MQbrain_16
        GCTGCCGGTCCCCGAGGTCCTGG  #Macaque_lib15_D708XV02IKDRJ 22 1 (SEQ ID NO:10832)
macaque CGCTGCCGGTCCCCGAGGTCCTGGCCTGCCCTGCGGGGCCCGGCC (SEQ ID NO:6087)
human   CGCTGTCGGTCCCCGAGGTCCCCGAGCTGCCCTGCGGGGCCCCGGCC (SEQ ID NO:2520)

>MQbrain_17
                    ATTCGGCTACGATCACCAGG #Macaque_lib13_D4HK8WR01CWV8A 20 2 (SEQ ID NO:10950)
                    TTCCGCTACGATCACCAGGGT #Macaque_lib13_D708I2V02JWPDG 21 1 (SEQ ID NO:10951)
macaque ACAAATAAGAGCTGTCTCAATAAATGATTCGGCTACGATCACCAGGGTATGTCGTAGTTAAAAGCCCTGGTGATGGTAGCTGAATAATTATTGAGACAAGCTTAGGT (SEQ ID NO:6189)
human   ----TAAGAGCTGCTCTCAATAAATGATTCAGCTACGATCACCAGGGCATATCATAGCTGAAAGCCCTGGTGATGGTAGCTGAATAATTATTGAGACAATCTTA--- (SEQ ID NO:2603)

>MQbrain_18
                           (SEQ ID NO:10734) TCTGCGATGGCTGGTTTTG #Macaque_lib15_D4HK4YF02IITPB 18 1
macaque TCATGTCGTAAAATTGACTTCATAGTTATTGGGTTAGGGAGGTCGGGAAGAGATAATCTTTCTGATTACCTGTTTTGTCGATGGCTGGTTTTGAGGTTTAAACCTGACTTGA (SEQ ID NO:6283)
human   TCATGTCATAAAATGACTTCATAGTTATTGGGTTAGGGAGGTGGAGAGAGATAATCTTTTCATTA--TGTTTGTCTGATGGCTGGTTTGAGGTTTAAACCTGACTTGA (SEQ ID NO:2528)
chimp   TCATGTCATAAAATGACTTCATAGTTATTGGGTTAGGGAGGTGGAGAAGAGATAATCTTTTCATTA--TGTTTTGACTGATGGCTGGTTTTGAGGTTCAAACCTGACTTGA (SEQ ID NO:8400)

>MQbrain_19
                CTGCGTCAGCTACCGGAGGGAGCCACGTGGTGCTGAGCGTAGAGGGCACAGGGCTCGGACCAGGTCGGCCAATGACGGTGACTGGCACCA #Macaque_lib15_D70BZXV02IFGK8 21 1 (SEQ ID NO:6370)
macaque TGGTGCTCAGCTACCGGAGGGAGCCACGTGGTGCTGAGCGTAGAGGGCACAGGGCTCGGACCAGGTCGGCCAATGACGGTGACTGGCACCA (SEQ ID NO:11170)

>MQbrain_20
```

FIG 1C Cont.

FIG. 1C Con't.

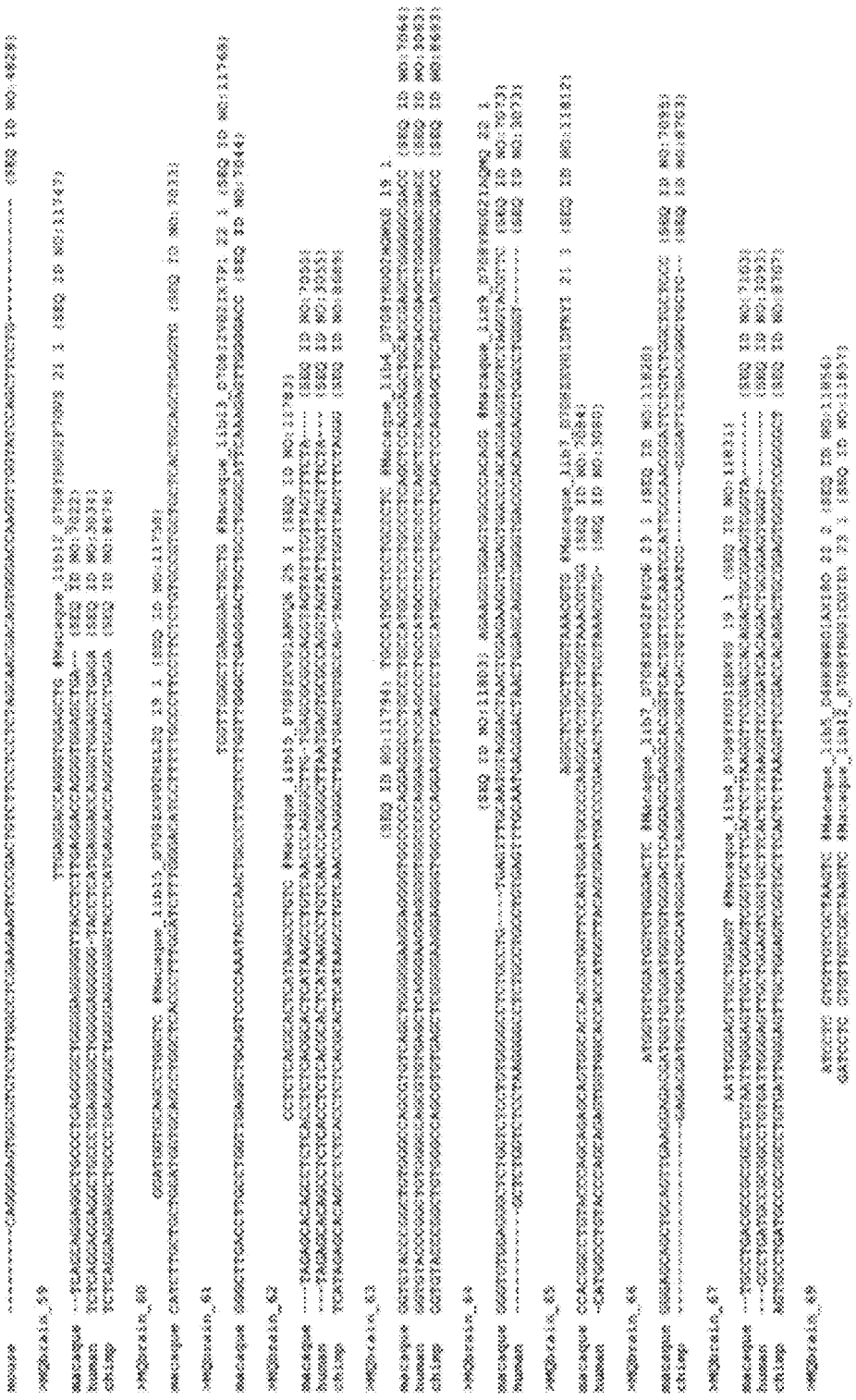

FIG 1C Con't.

FIG. 1C Cont'L.

FIG. 1C Con't.

FIG. 1C Cont'd.

FIG. 1C Con't.

FIG. 1C Cont.

FIG. 1C Con't.

FIG. 1C Con't.

FIG. 1C Con't.

FIG 1C Cont'd.

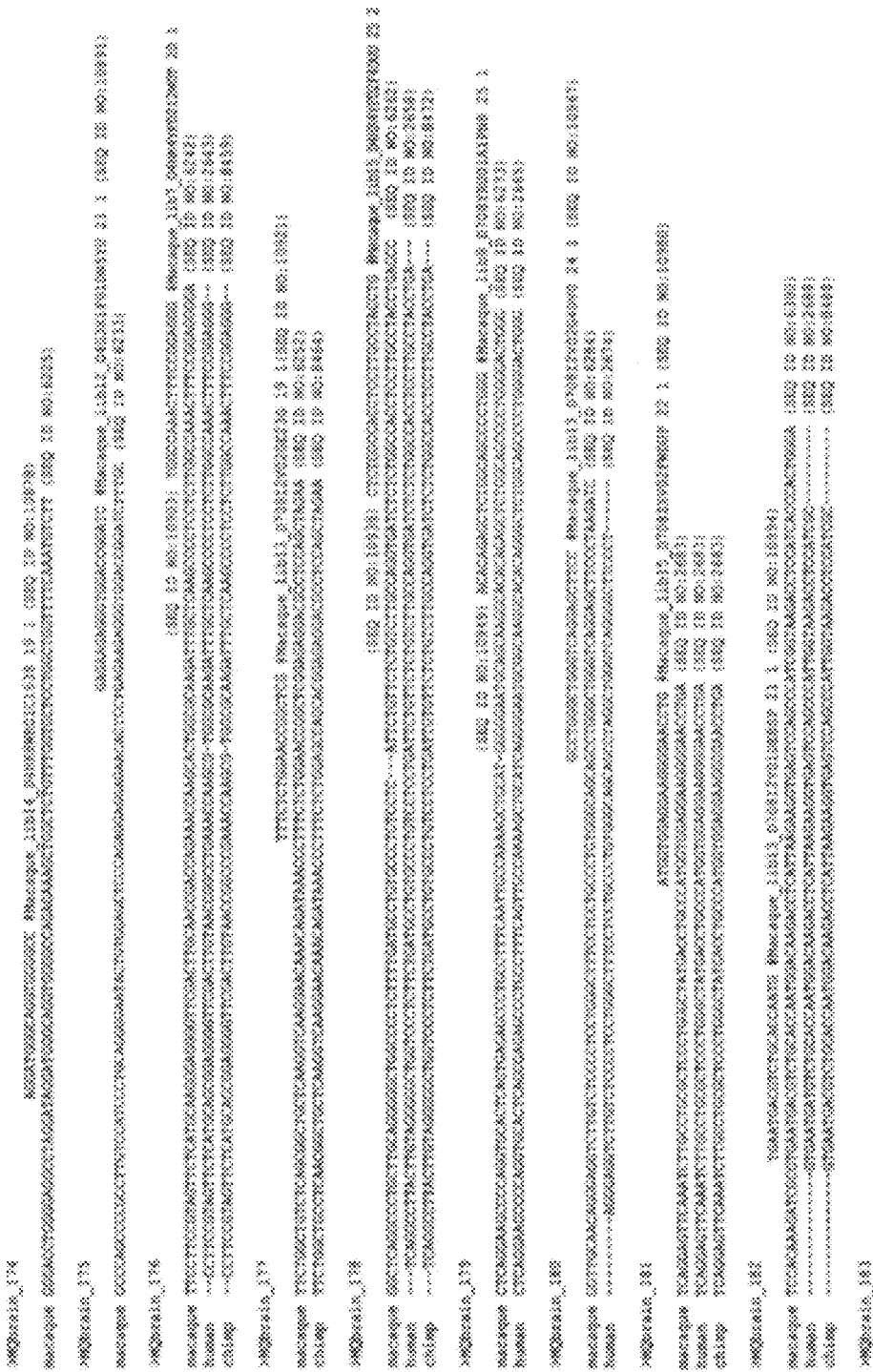
FIG 1C Con't.

FIG. 1C Con't.

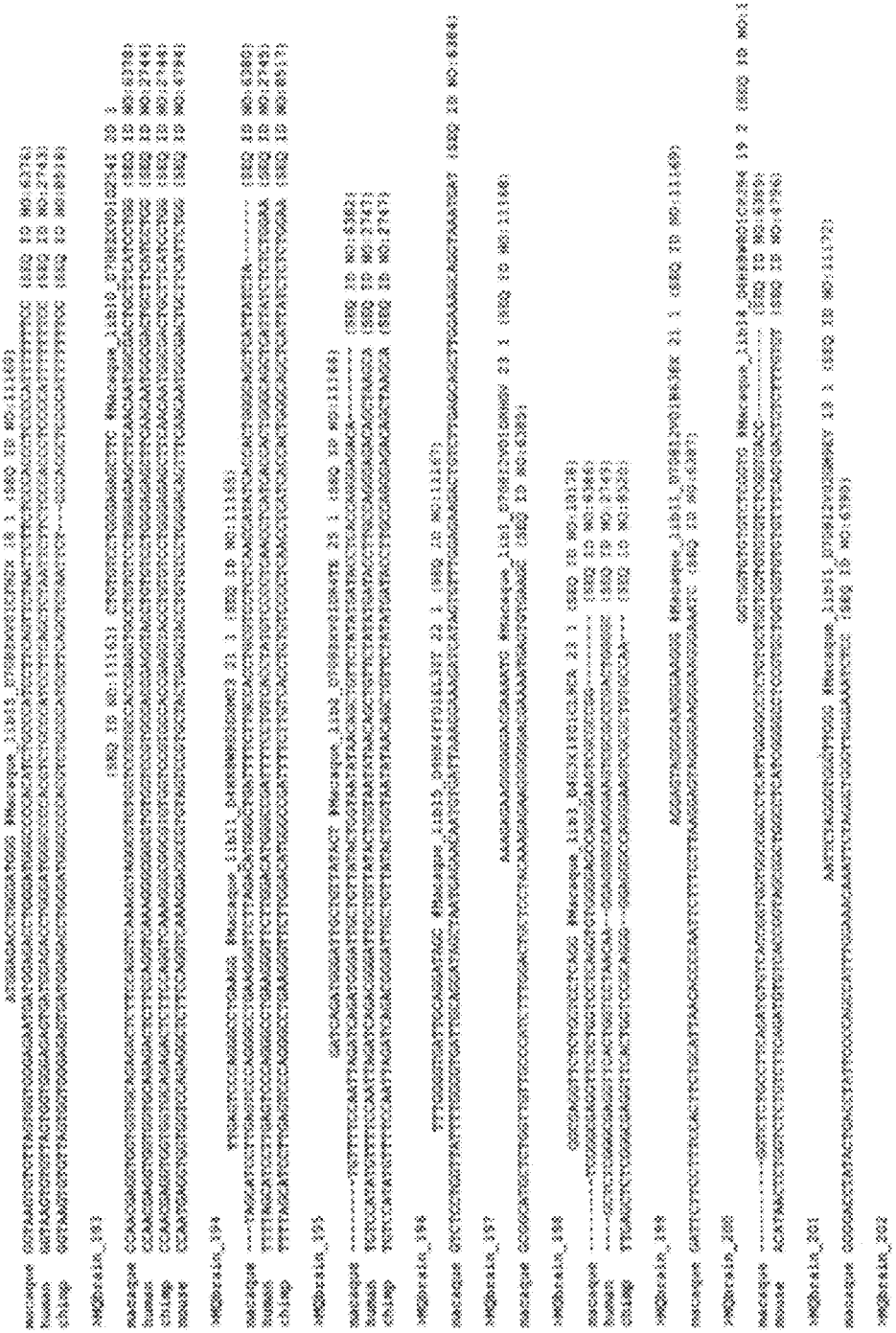
FIG. 1C Con't.

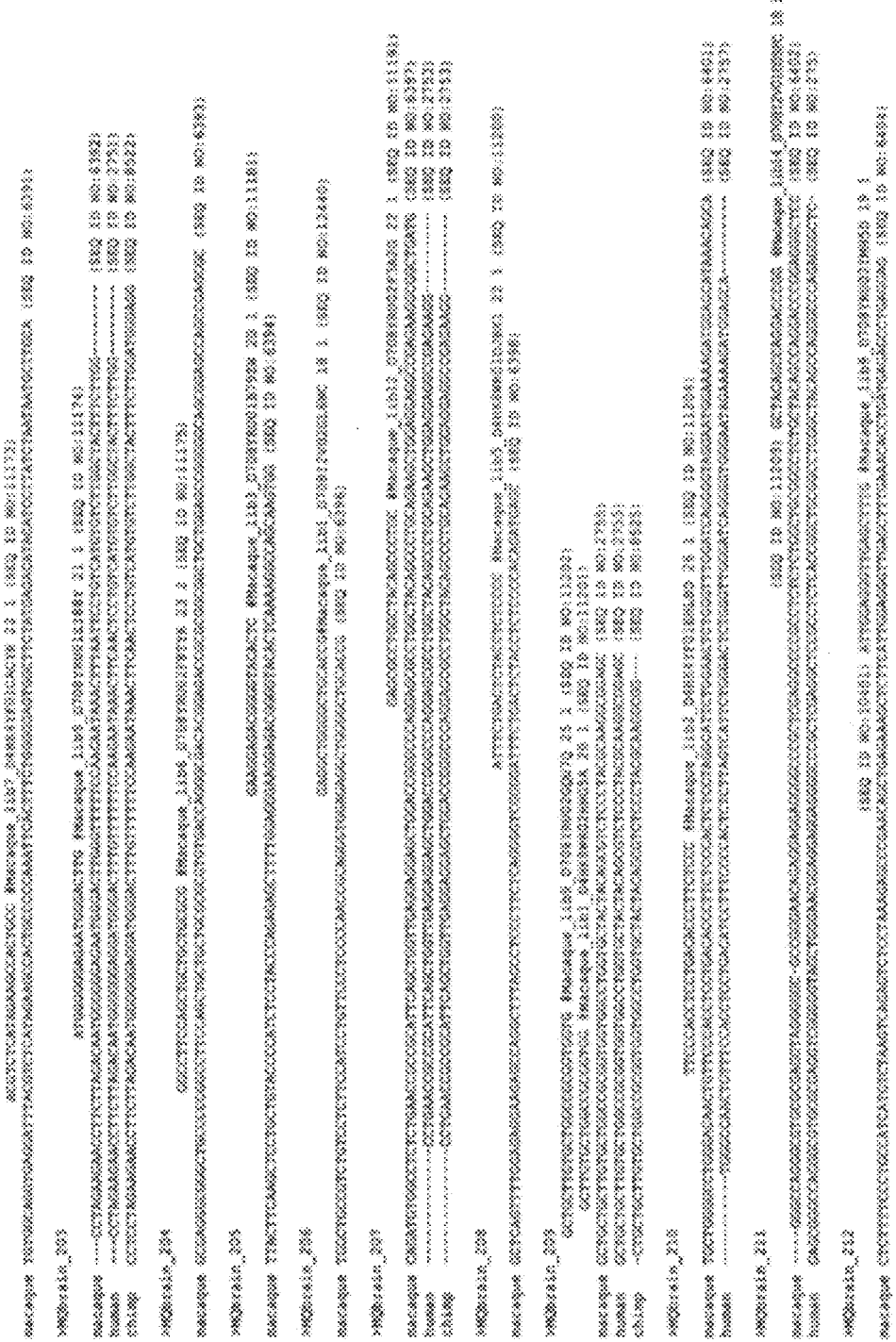
FIG 1C Con't.

FIG. 1C Con't.

FIG. 1C Con't.

FIG 1C Con't.

FIG. 1C Con't.

FIG 1C Con't.

```
chimp      TGTTGTTCAAAGTTATATTACTGGCCAGAATGGAAATTATAGGAACTAGCTATGTATGAAATTCCATGTTTCCATCCATTGTGCCAGGTTTGTATTCCCTTAAGATGGCA (SEQ ID NO:2824)

>MQbrain_299
                                                          CCATCCCTACCCATGCTGCC #Macaque_lib14_D4HK8WR02HWA9G_21_1 (SEQ ID NO:10228)
macaque    ATTAAATTGGTTCCAATATGGAAAGAAATGTTGTGTGTCCCTTCAGGCACCTGCAACCCCATCCCTACCCATGCTGCCTTCAAACCTTGTTTGAT (SEQ ID NO:5601)
chimp      ------TTGGTTCCAGTATGGGAAAGGAATGTTGTGTATGGTCCCATCGGCACCTGCAACCCTCAACCCTCCAACCCCATCCCTATGCCATGCTGTCTTCAA-------- (SEQ ID NO:8215)

>MQbrain_300
                                     TTGGTCGTGGACGTGGTCAGC #Macaque_lib15_D708ZXV02F2ZIM_21_1 (SEQ ID NO:10307)
macaque    GAGCCAAGGTTGAGGCTGCCTCAACAACCAAATTCAGTAAGAGGCAGAGATTTGGTCGTGGACGTGGTCAGCCACCTC   (SEQ ID NO:6725)
human      ------GGCTGAGGCTGTGTCAACAACCAAATTCCAGTAAGAGGCAGAGATTTGGTTGTGGATGTGGTCAGCC------  (SEQ ID NO:2826)
chimp      ------GGCTGAGGCTGCCTCAACAACCAAATTCCAGTAAGAGGCAGAGATTTGGTCGTGGATGTGGTCAGCC------  (SEQ ID NO:8564)

>MQbrain_301
                                 GCCGGGAGGCCATGGGGTG #Macaque_lib9_D4G3X1F01A4M0G_18_1 (SEQ ID NO:11432)
macaque    TCTCACCATAGCTCTGCGCCCTTGGCTTCTGCCTGCCGGAGGCCATGGGGTGGATACAGGGTGGGA (SEQ ID NO:6726)
human      -CCCACCAGCTCTGCCCCTCCTCAGCTTCCTGCCTGCCGAGAGGCCCATGGGATGGCAGGGTGGG- (SEQ ID NO:2827)

>MQbrain_302
           TTAGGGTTGGAGGGAGGCTC #Macaque_lib12_D708YRU01CY3WN_20_2 (SEQ ID NO:11433)
macaque    GGATGCTTAGGGTTGGAGGGAGGCTCAGAGAGTGCAAATGTTCCTCTTGACCCACCTCCCATCC (SEQ ID NO:6727)

>MQbrain_303
           GTGGAGGGGTCCGGCAGGTC #Macaque_lib9_D4G3X1F01ASP09_20_1 (SEQ ID NO:11434)
macaque    CTCTCCTCTGCAGGGAGTCAGTGGAGGGGTCCGGCAGGTCAGGGGTCTCCCGTTCCTCCTCCGTTCCTGGTTCAGACAGCGGCAAGG (SEQ ID NO:6728)
human      CTCTCCTCTGCAGGGAGTCAGTGGAGGGGTCCGGCAGGTCAGGGGGTCTCCCGTCCCGTTCCTGCCTTCCTGGTTCACGGACACGGCAAGGG (SEQ ID NO:2828)
chimp      CTCTCCTCTGCAGGGAGTCAGTGGAGGGGTCCGGCAGGTCAGGGGGTCTCCCGTTCCCGTCCCGTTCCTGGTTCACGGACACGGCAAGGG (SEQ ID NO:2828)

>MQbrain_304
                                     GGCTGGTCCTTGCTGGGTG #Macaque_lib15_D708ZXV02JKCKL_19_1 (SEQ ID NO:11435)
macaque    GCAAAGCATTTGTAGAAATAATTAATAGTACTACTCATGCATCAGTTTATGAGGCTGGTCCTTGCTGGGTGCTATATTTAGATCCAACTCTTTGT (SEQ ID NO:2829)
human      GCAAAGCATTTGTAGAAATAATTAATAGTACTCATGCATCAGTTTATGAGGCTGGTCCTTGCTGGGTGCTATATTAGATCAACTCTTTGT (SEQ ID NO:2829)
chimp      GCAAAGCATTTGTAGAAATAATTAATAGTACTCATGCATCAGTTTATGAGGCTGGTCCTTGCTGGGTGCTATATTGAGATCAACTCTTTGT (SEQ ID NO:2829)

>MQbrain_305
              AGGGCAAAGCT      ATGTGACTTC #Macaque_lib13_D708I2V02HG7PX_21_1 (SEQ ID NO:11436)
macaque    -GCTTCCCAC--AGTCA--GCATAGAAGTGGGCAACCTAAGGCCAAAGCT---ATGTGACTTCTTGGGC-- (SEQ ID NO:6729)
mouse      CTCGACCAACTGGACATGCATGTCTGTGGCCAAACTAAGGCCAAATGCAGTGCATGGGTGG (SEQ ID NO:4808)

>MQbrain_306
           TTGCTGCCGTGCTGACTT #Macaque_lib13_D708I2V02HONKK_19_1 (SEQ ID NO:11437)
macaque    AGTTTGCTGCCGTGCCGTGCTGACTTTGGGGTTTTCTTTTTAGAGCCTGTCCCATTGCAGCTTCAGATGCTGCCAAGATGCAGCTGCCAAGGTTAGGCCTGGGAGGAGGAGGAGGGGTTCGGCTCCGGCAGAGTCT (SEQ ID NO:6730)

>MQbrain_307
                CTTGACCCCTGCCAGGCTG #Macaque_lib15_D708ZXV02GJQ7R_20_1 (SEQ ID NO:11438)
macaque    GGGACTTTATTTGCCCTTGACCCCTGCCAGGCTGCTCAGTGGGTAGATAGGAGAATCCTGCTTCATCTGCCTCCTCCACCTTCTAGGCCAGGTGGCAGGAGGCAAACAAGCCT (SEQ ID NO:6731)

>MQbrain_308
           GGAAATGAGAAGAAGGATGGG #Macaque_lib9_D708YRU02GHBK7_18_1 (SEQ ID NO:11439)
macaque    ATGCTAAGGAAATGAGAAGAAGGATGGGAGTAAAAAGGAGGAGTAAAAGAGGACAAGCCCCGATGCTCTTTTATCAGTTCCCCCCCTTCCTCCTCCTCCTCCTCCTCCTCCTCCTCTCAT (SEQ ID NO:6732)
human      ------AGGAAATAAGAAGGATGGGAGGAGTAAAAGAAGAGACGAAAAAGAGGAGCAAGCCCCCGATGTCTGTTTATCAGCTCCCCC---TCTCTCCTCTCCT---------- (SEQ ID NO:2830)
```

FIG.1C Cont.

FIG. 1C Con't.

FIG. 1C Cont.

FIG. 1C Con't.

FIG 1C Con't.

FIG 1C Cont'L

FIG. 1C Con't.

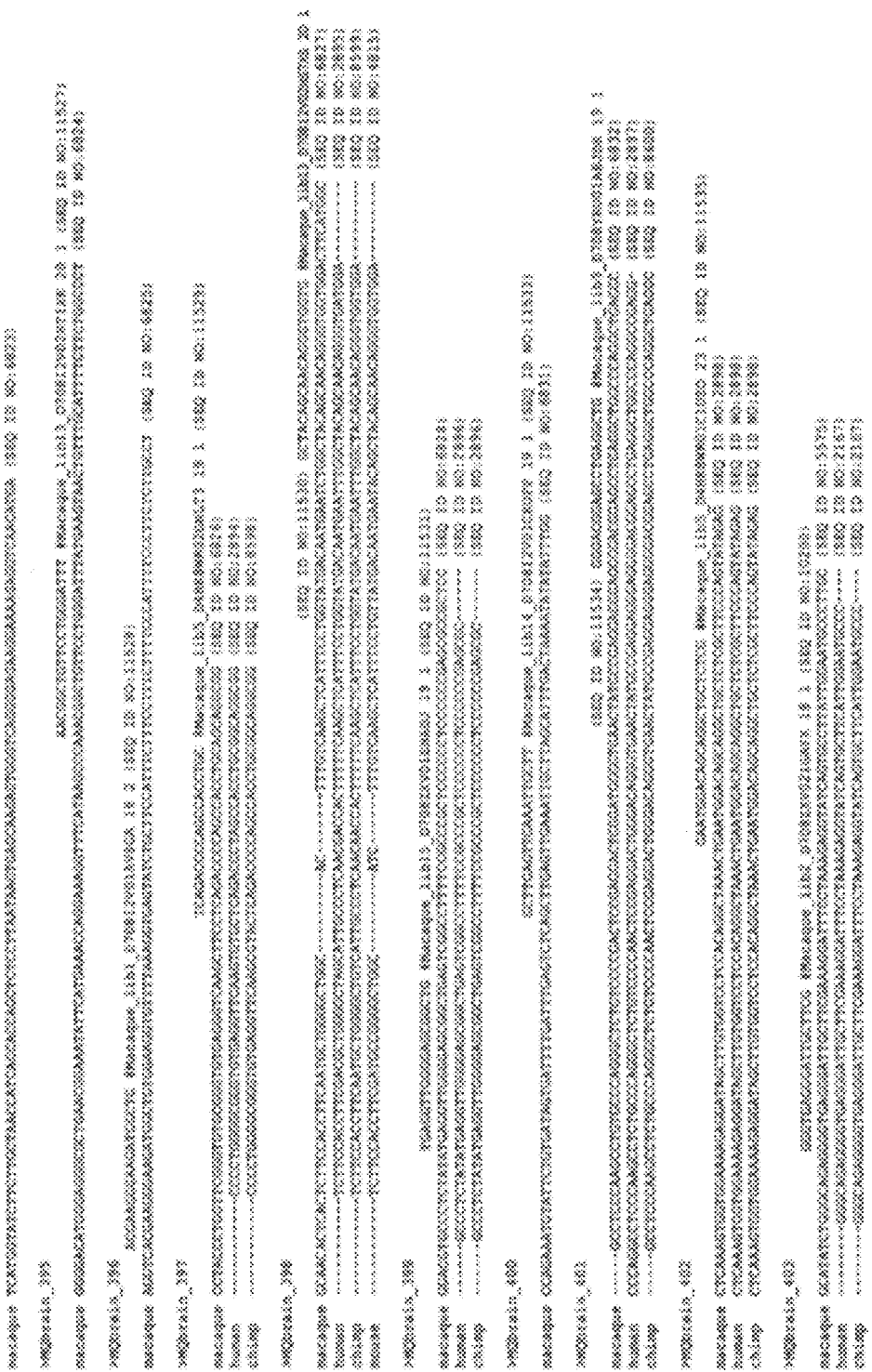
FIG. 1C Con't.

FIG. 1C Cont.

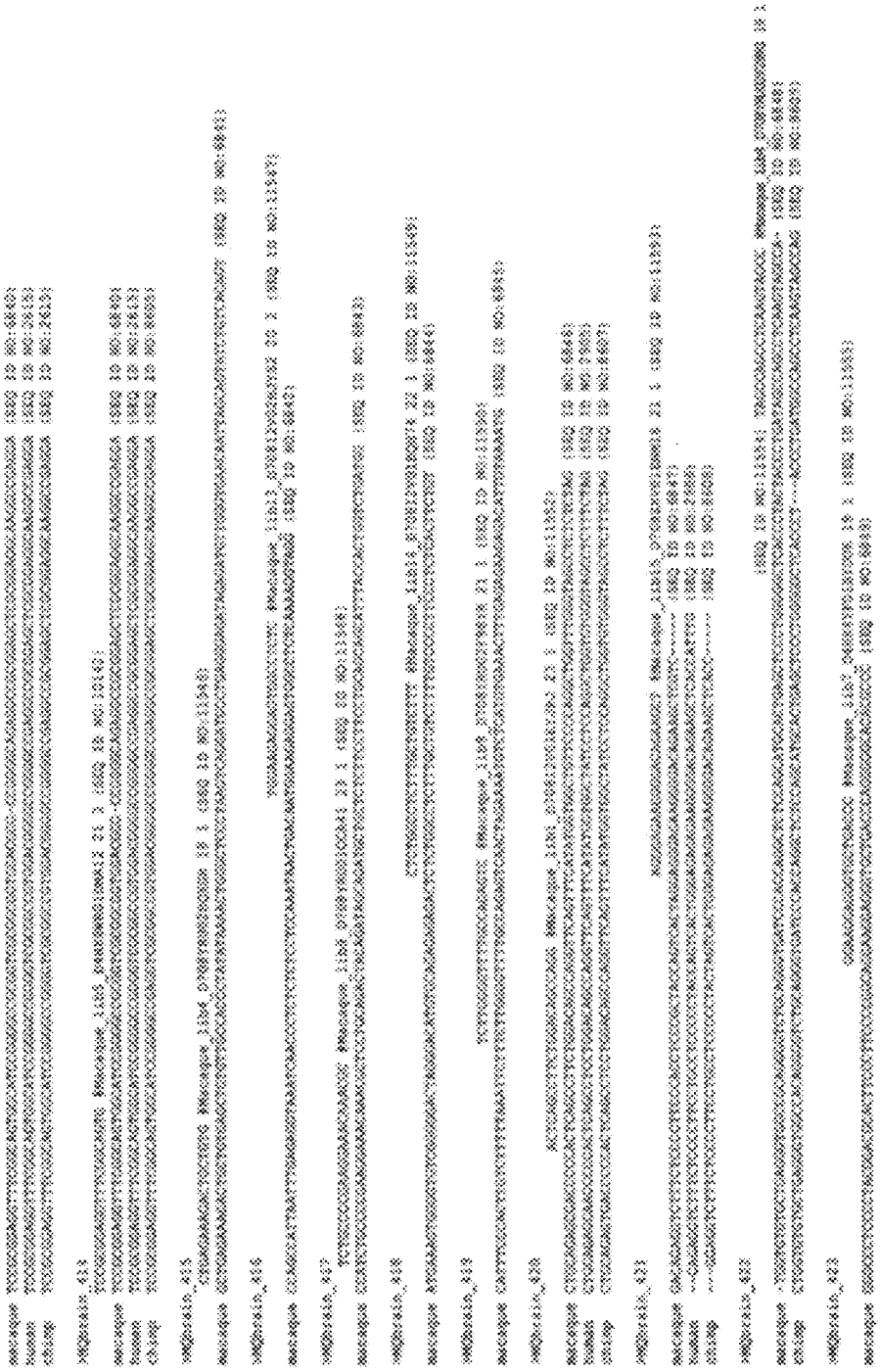
FIG. 1C Con't.

FIG. 1C Con't.

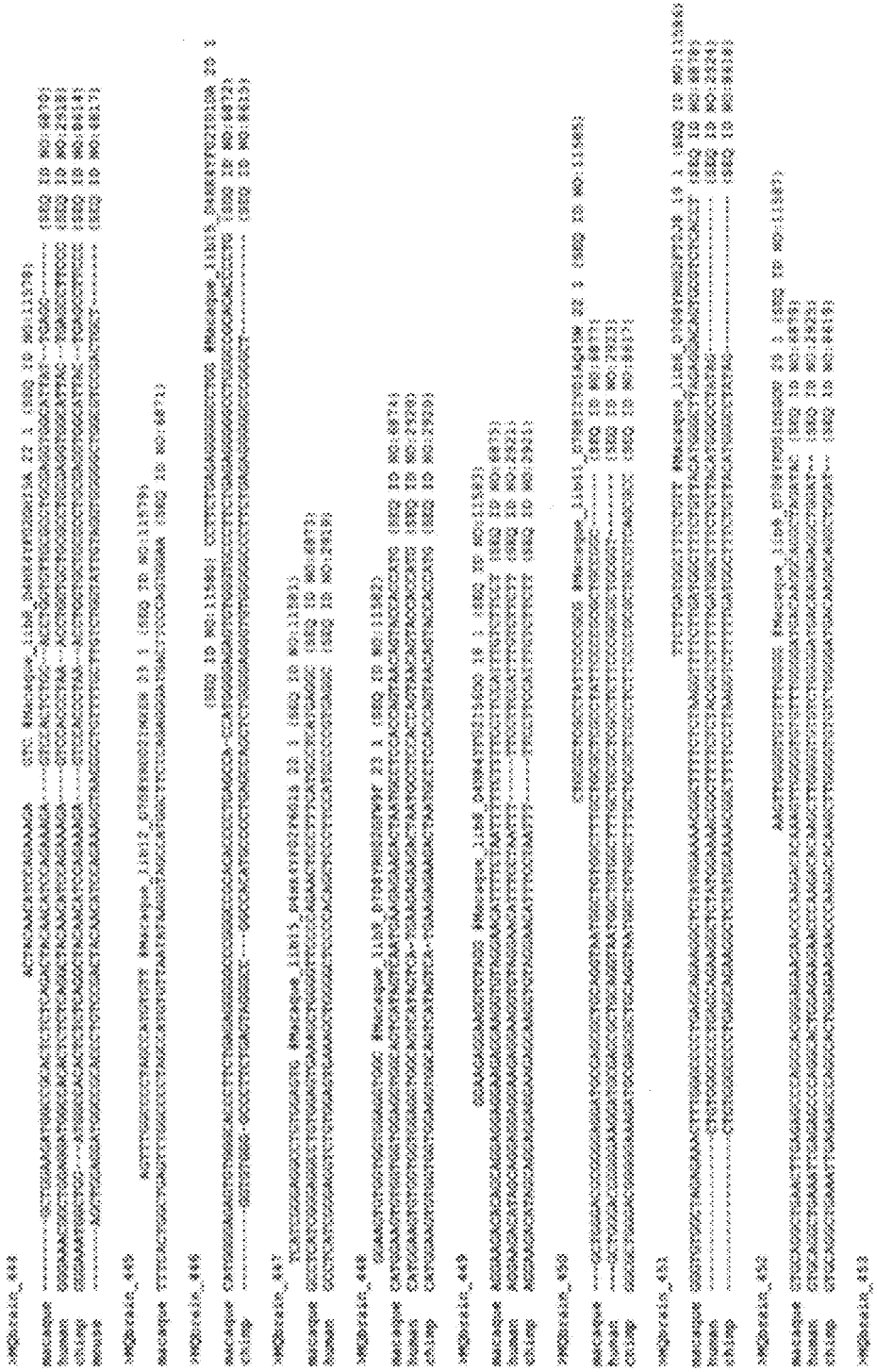
FIG. 1C Con't.

FIG. 1C Cont'l.

FIG. 1C Con't.

FIG 1C Con't.

FIG. 1C Con't.

FIG. 1C Cont'L.

FIG. 1C Con't.

FIG. 1C Con't.

FIG. 1C Cont'.

FIG. 1C Con't.

FIG 1C Con't.

FIG 1C Con't.

FIG. 1C Cont'd.

FIG. 1C Com't.

FIG. 1C Con't.

FIG. 1C Con't.

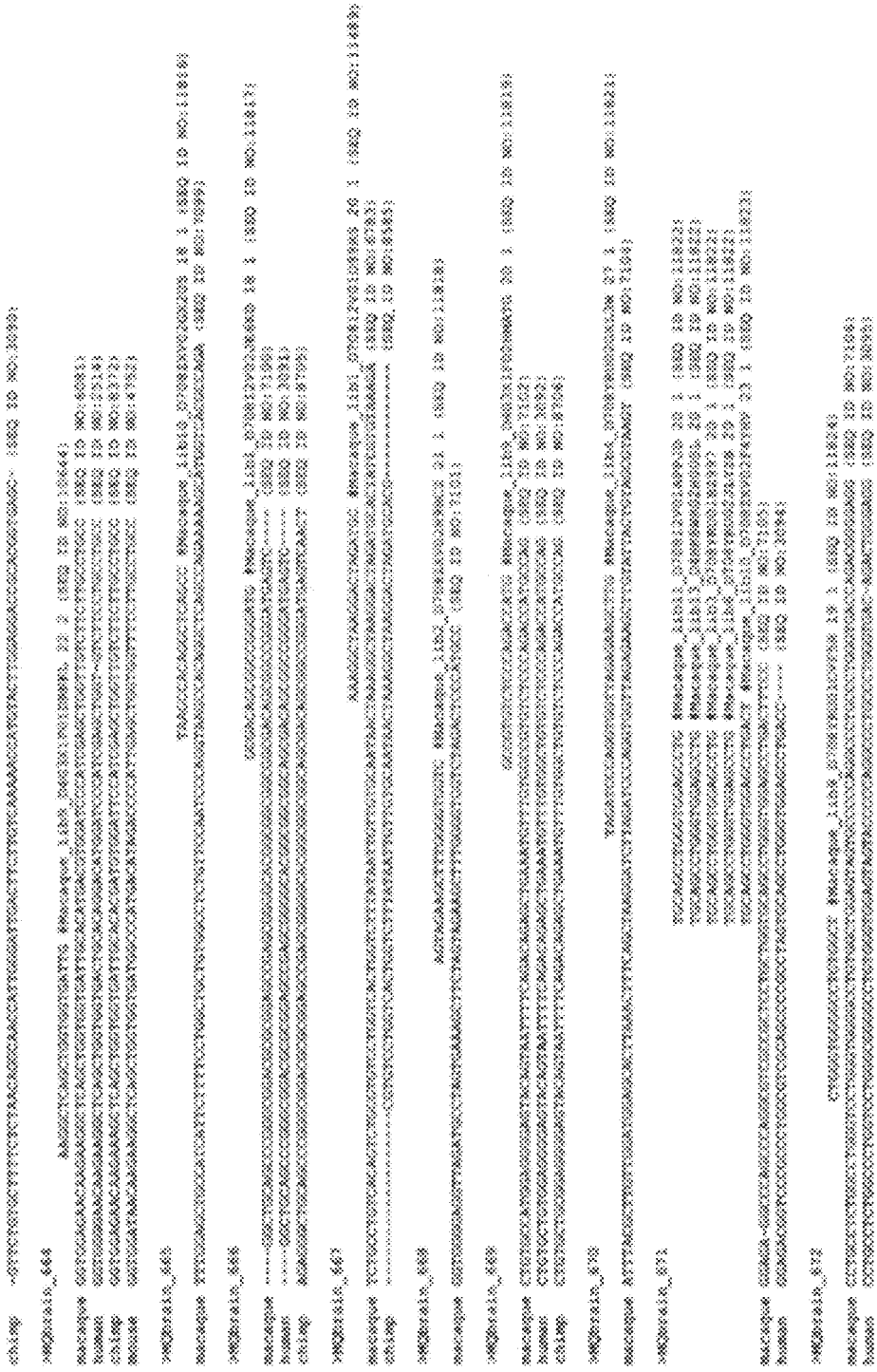
FIG. 1C Con't.

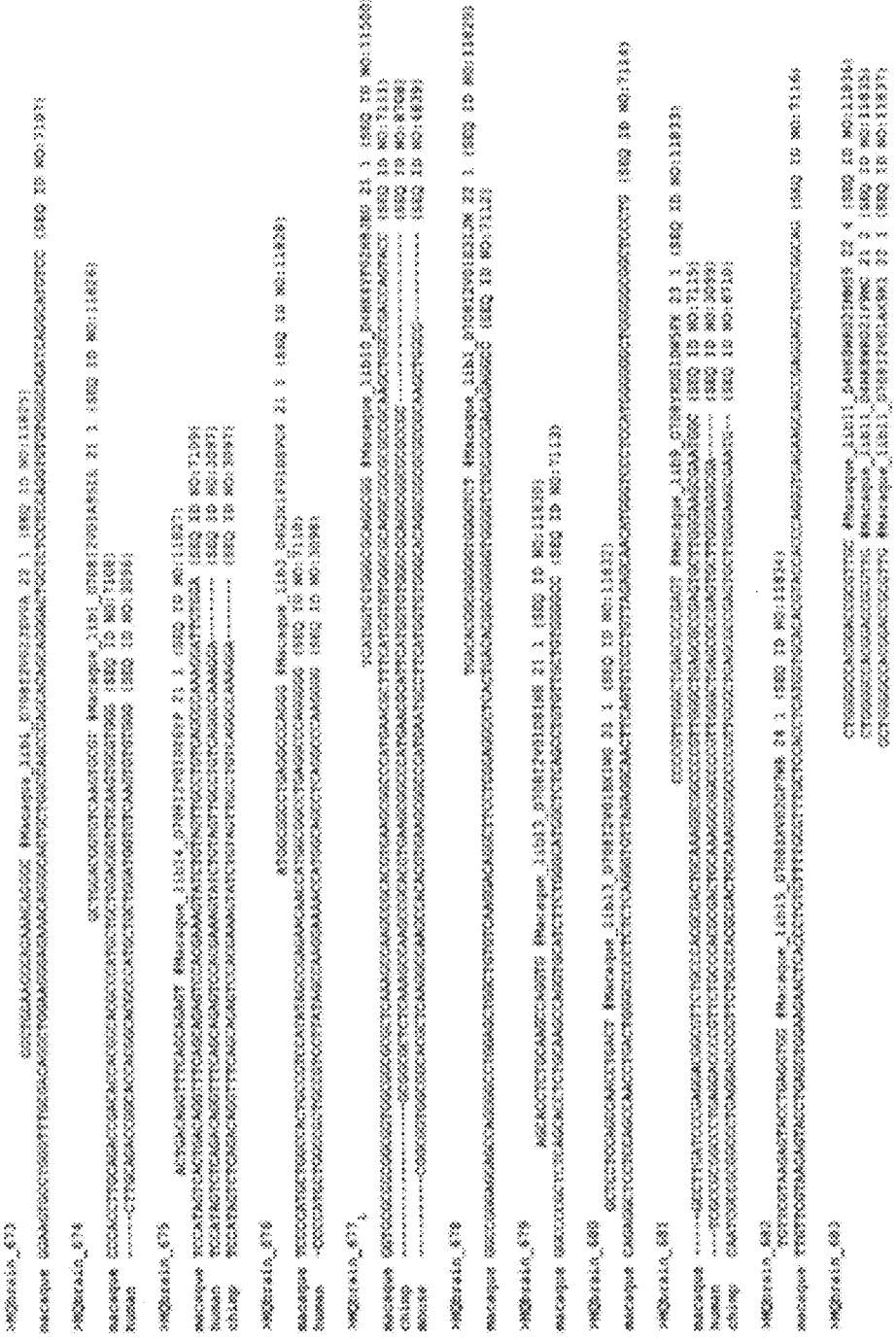
FIG. 1C Con't.

FIG 1C Con't.

FIG. 1C Cont.

FIG 1C Con't.

FIG 1C Con't.

FIG. 1C Con't.

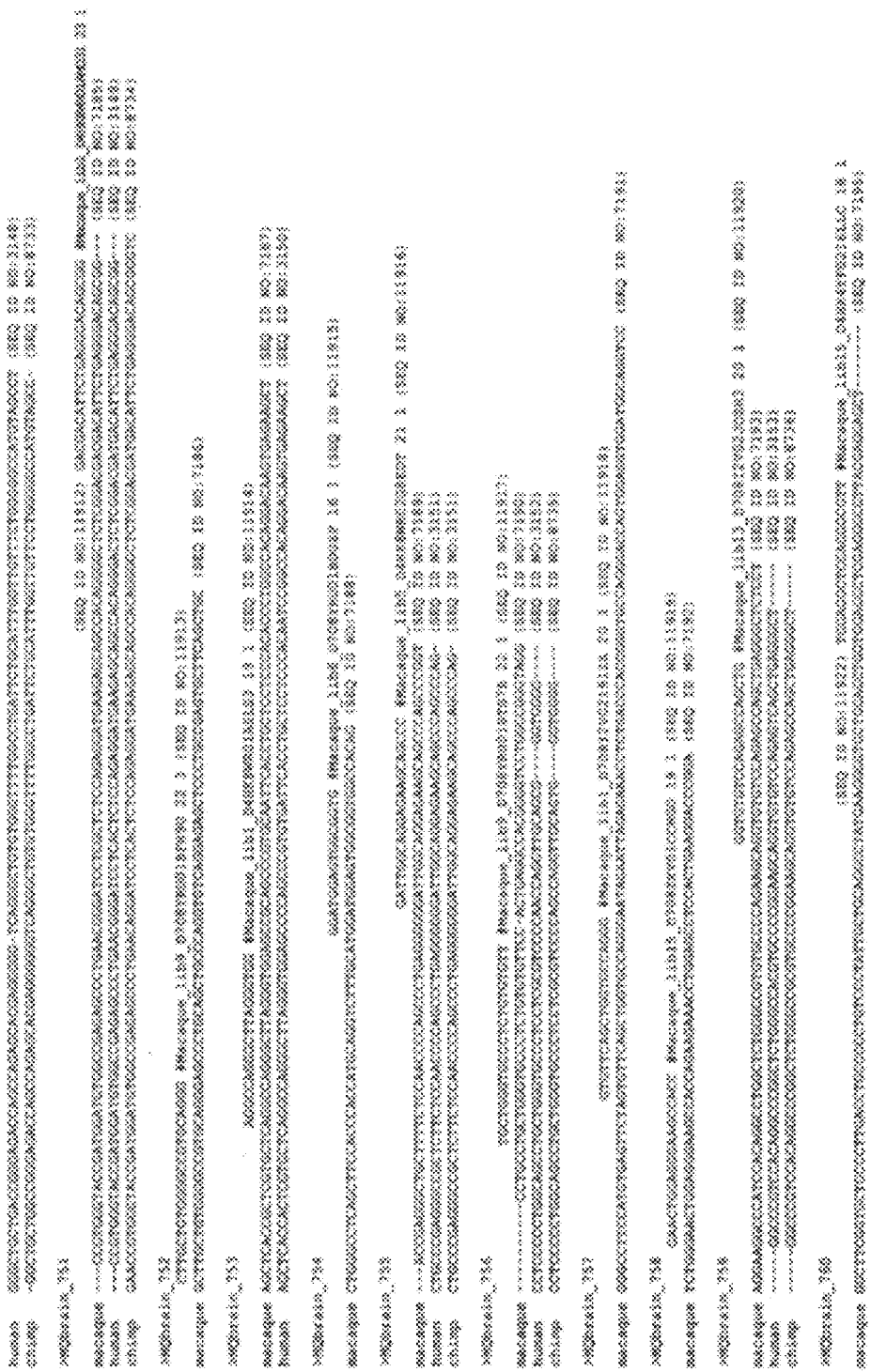

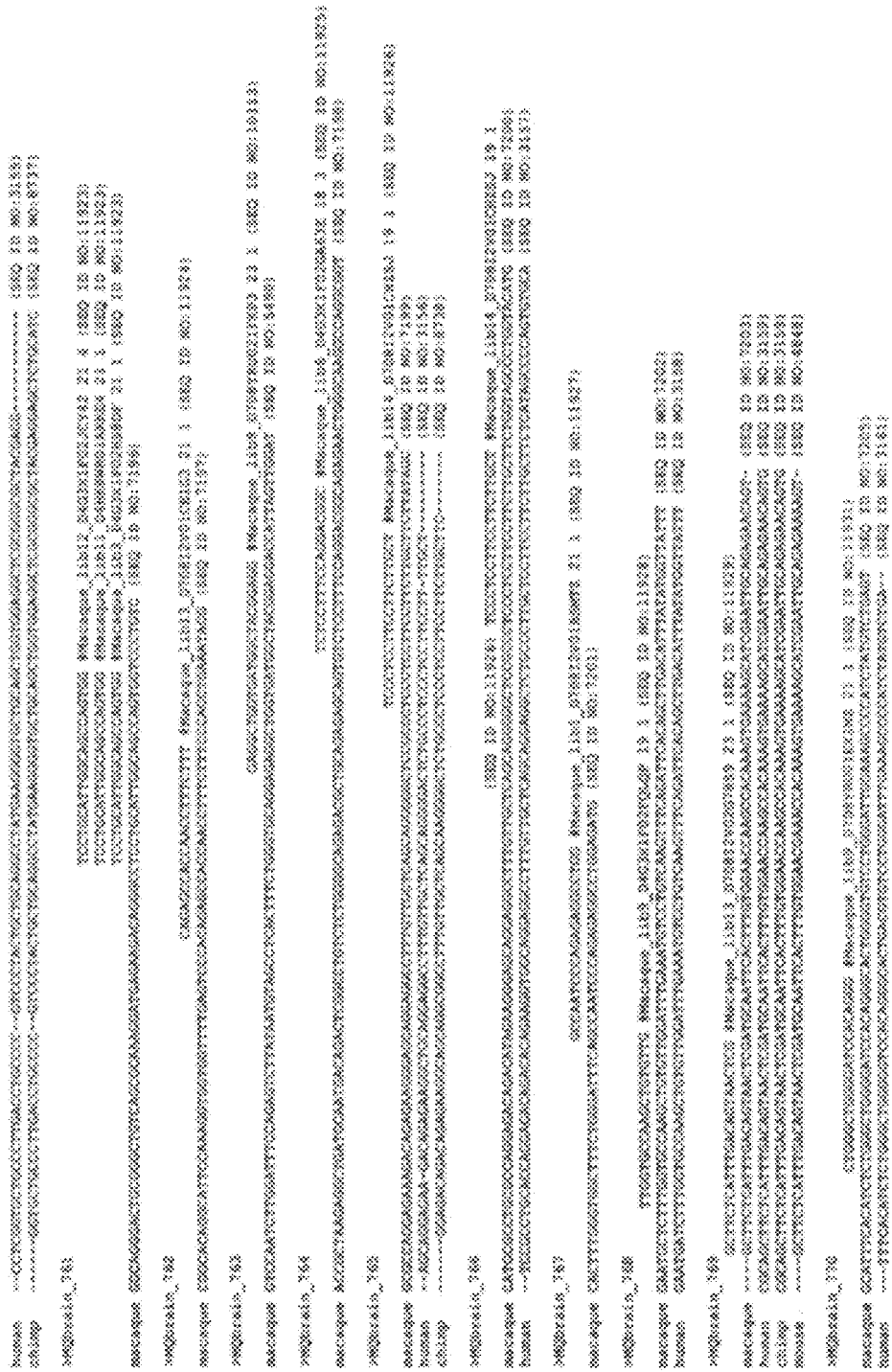
FIG. 1C Con't.

FIG. 1C Con't.

FIG. 1C Cont'd.

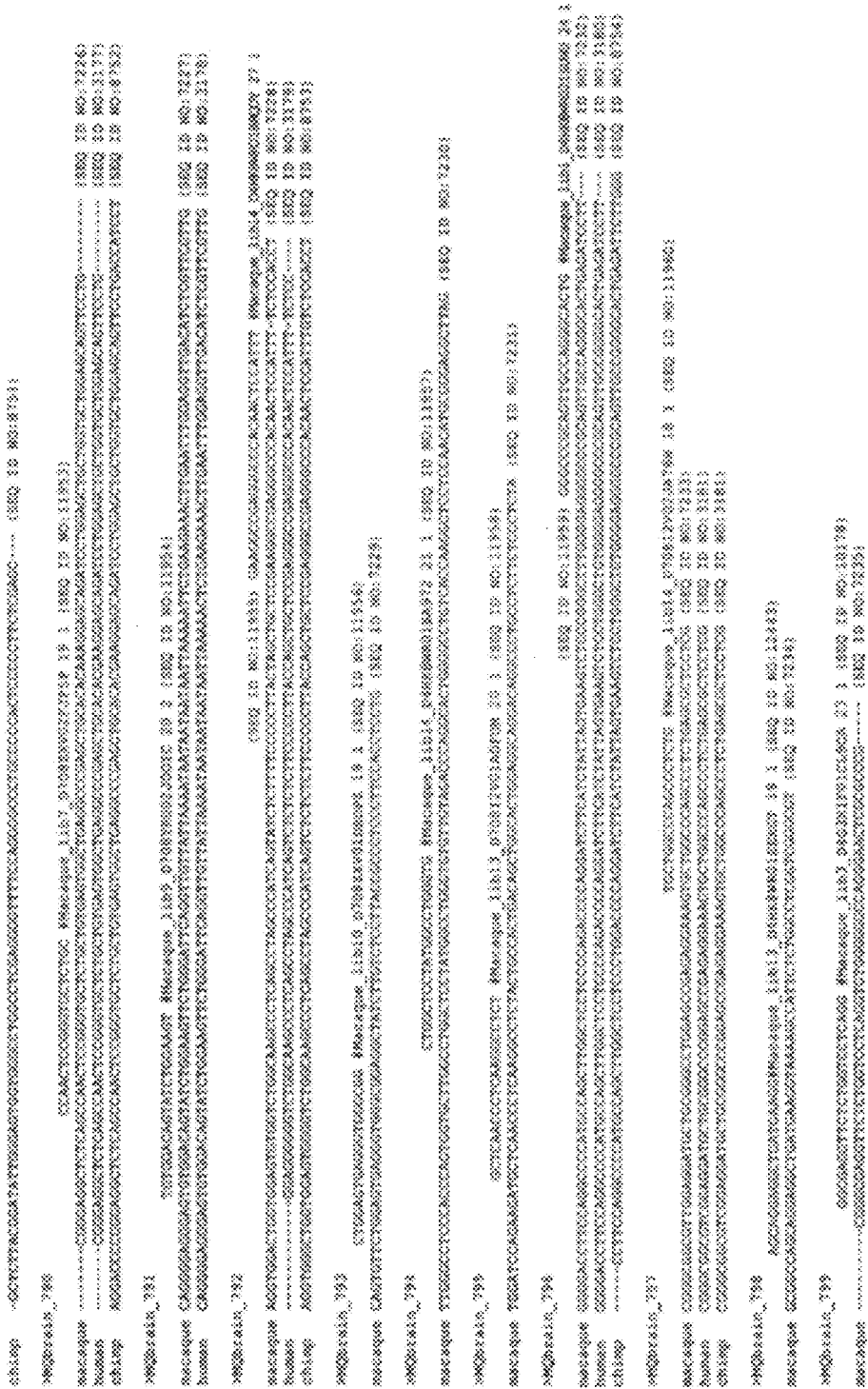

FIG. 1C Cont'd.

FIG. 1C Con't.

FIG. 1C Con't.

FIG. 1C Cont'd.

FIG. 1C Con't.

FIG. 1C Com't.

FIG. 1C Con't.

FIG. 1C Con't.

FIG 1C Com't.

FIG. 1C Con't.

FIG. 1C Con't.

FIG. 1C Con't.

FIG 1C Cont'd.

FIG. 1C Con't.

FIG. 1C Cont'.

FIG 1C Con't.

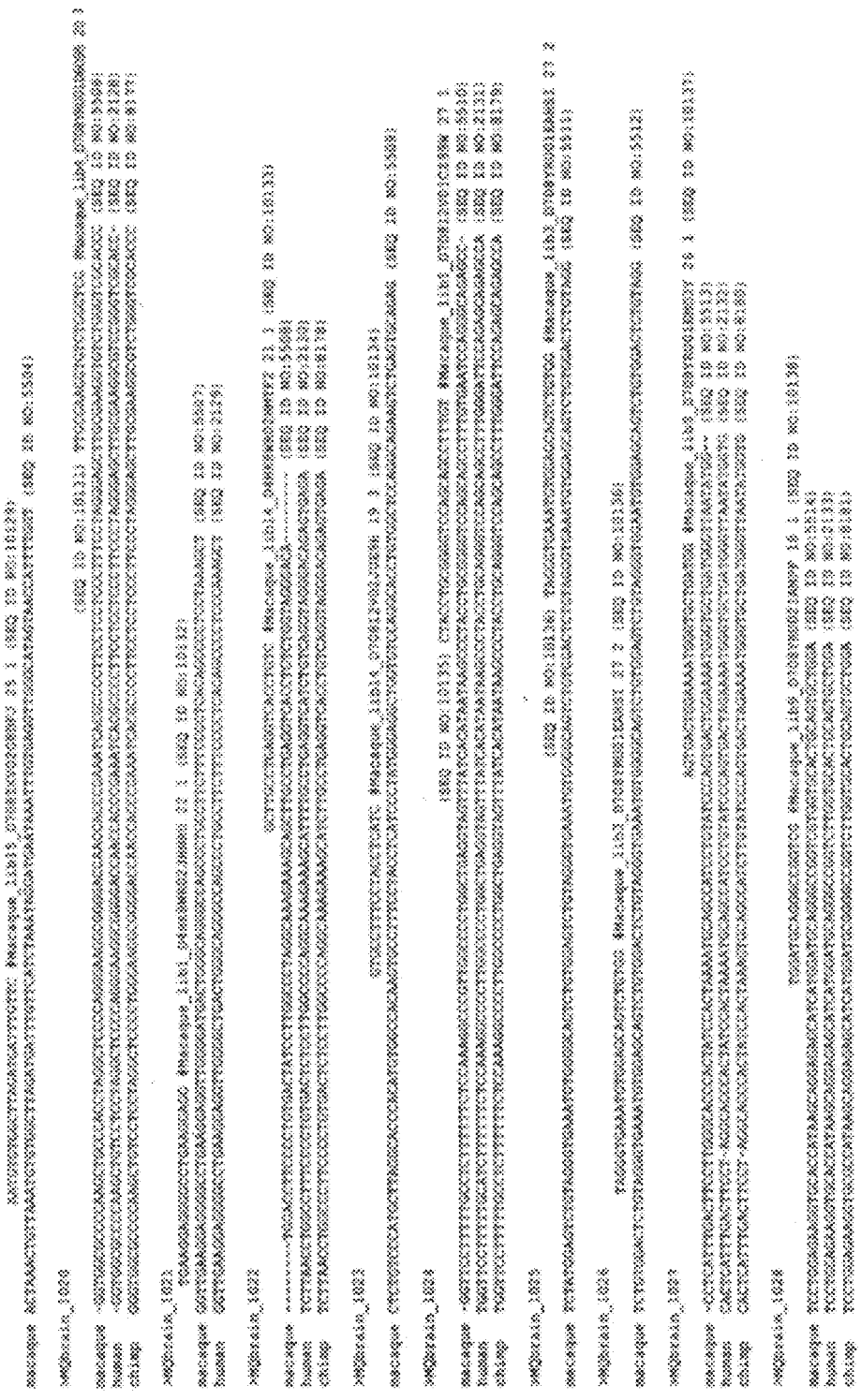
FIG 1C Con't.

FIG 1C Cont'.

FIG 1C Con't.

FIG 1C Con't.

FIG. 1C Cont'.

FIG. 1C Con't.

FIG. 1C Con't.

FIG. 1C Con't.

FIG. 1C Con't.

FIG. 1C Con't.

FIG. 1C Con't.

FIG. 1C Cont.

FIG. 1C Con't.

FIG 1C Com't

FIG 1C Con't.

FIG. 1C Cont.

FIG. 1C Con't.

FIG. 1C Con't.

FIG 1C Con't.

FIG 1C Con't.

FIG. 1C Con't.

FIG 1C Con't.

FIG. 1C Cont'd.

FIG. 1C Con't.

FIG. 1C Con't.

FIG 1C Cont.

FIG. 1C Con't.

FIG. 1C Con't.

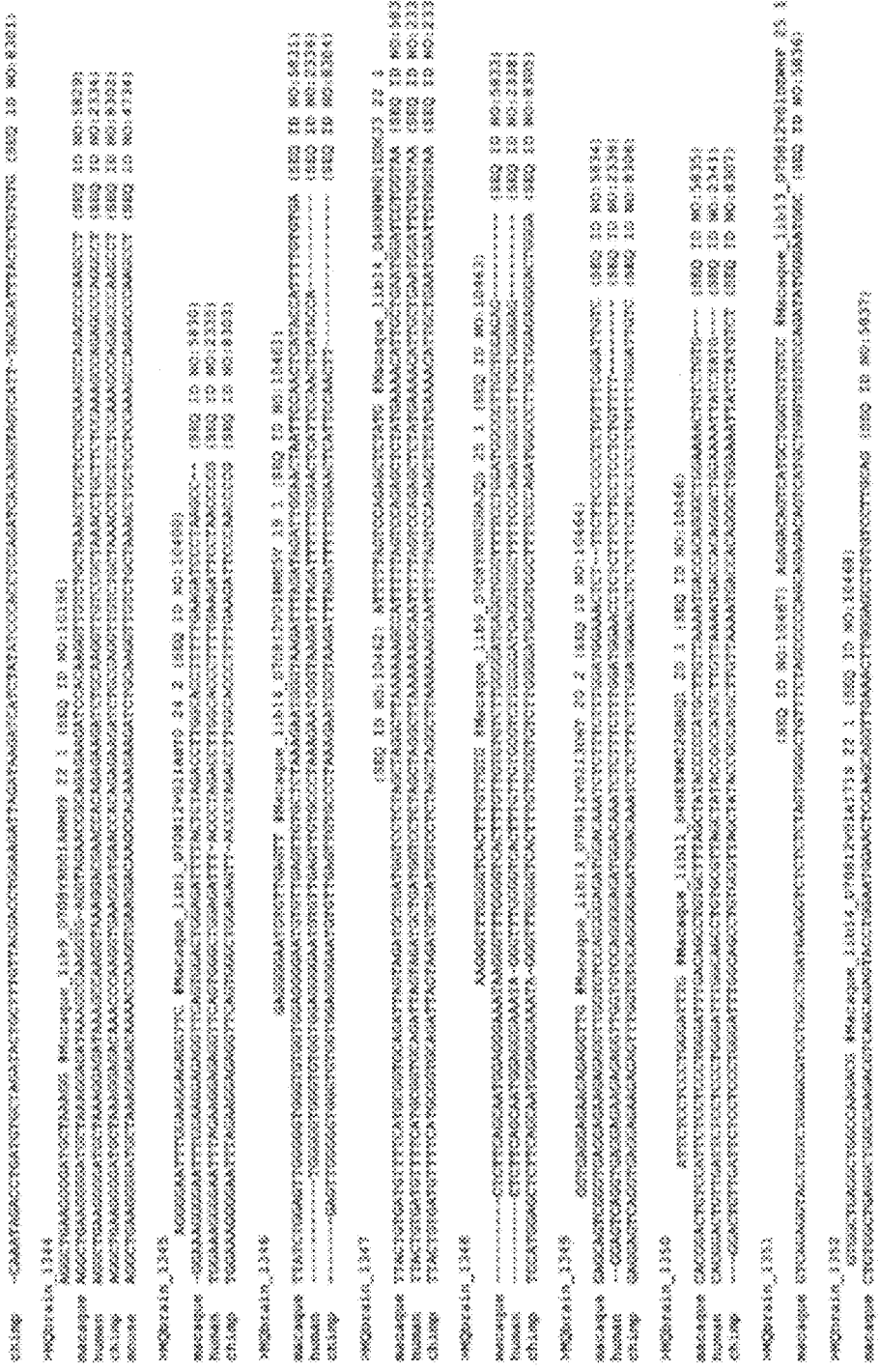
FIG 1C Con't.

FIG 1C Cont'L.

FIG. 1C Con't.

FIG. 1C Cont'd.

FIG. 1C Con't.

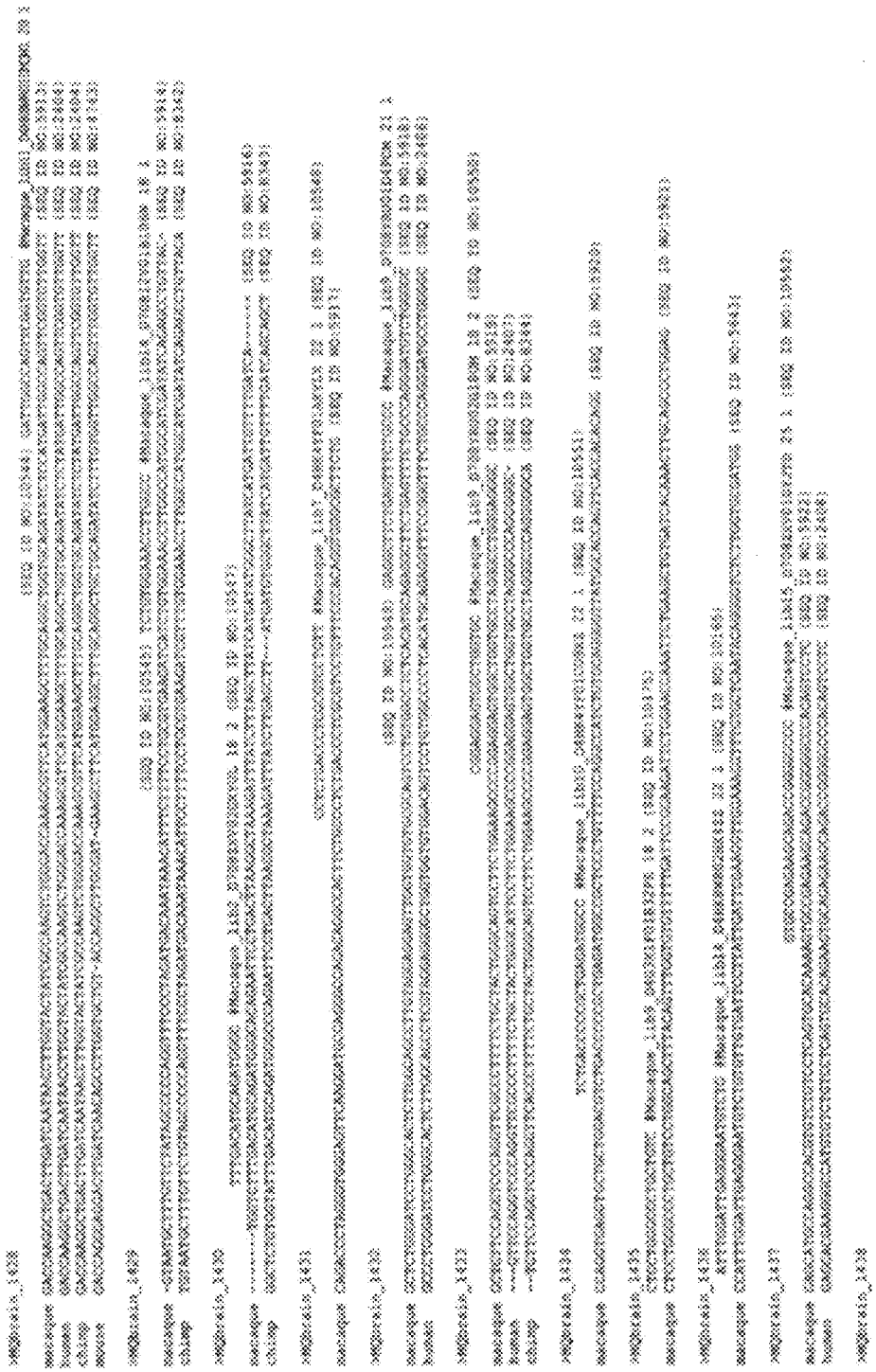
FIG. 1C Cont'L

FIG. 1C Con't.

FIG 1C Con't.

FIG. 1C Com't.

FIG 1C Con't.

FIG 1C Con't.

FIG. 1C Con't.

FIG. 1C Con't.

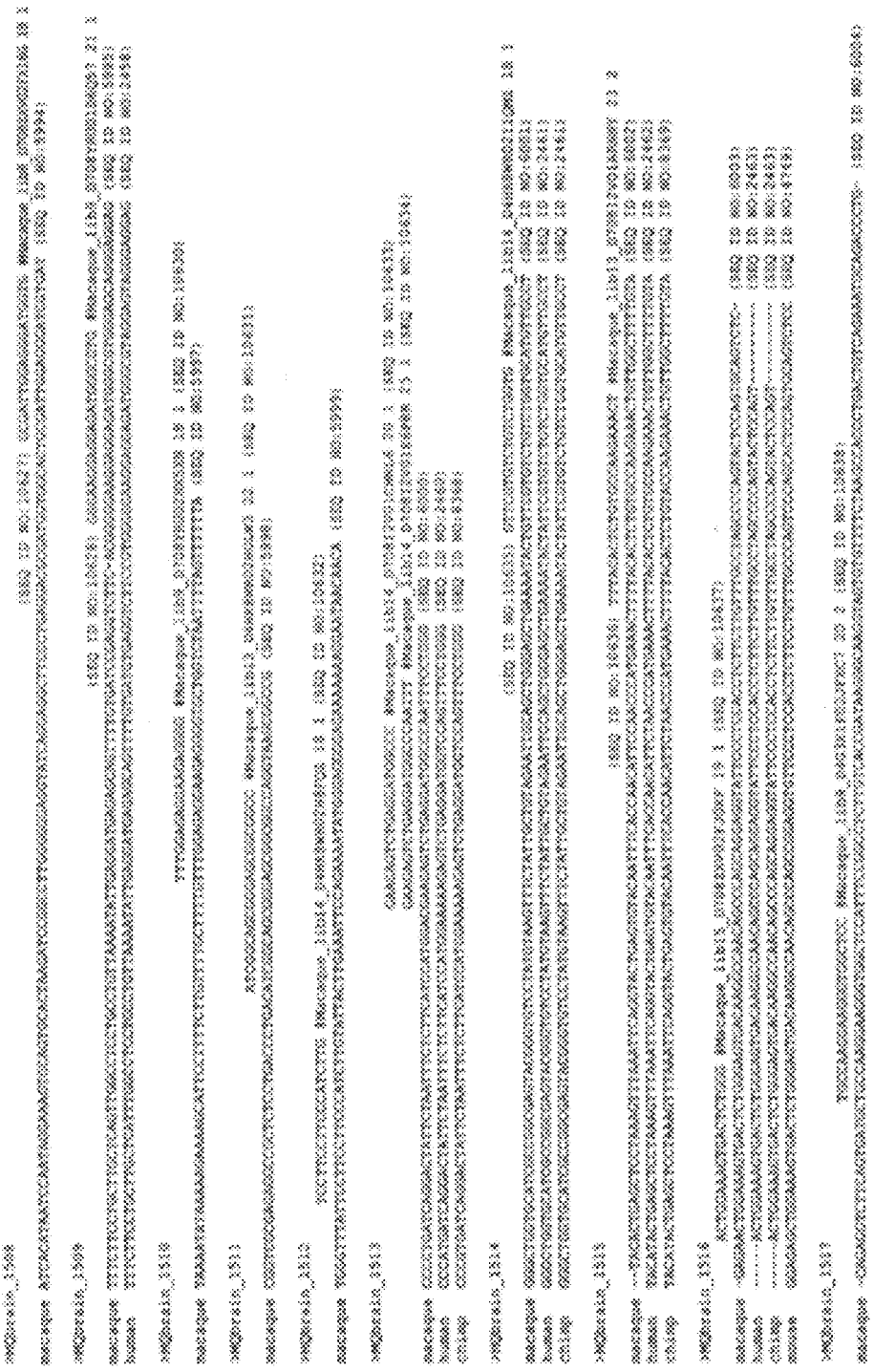
FIG 1C Com't.

FIG. 1C Com't.

FIG. 1C Con't.

FIG 1C Con't.

FIG. 1C Cont.

FIG 1C Con't.

FIG. 1C Cont'd.

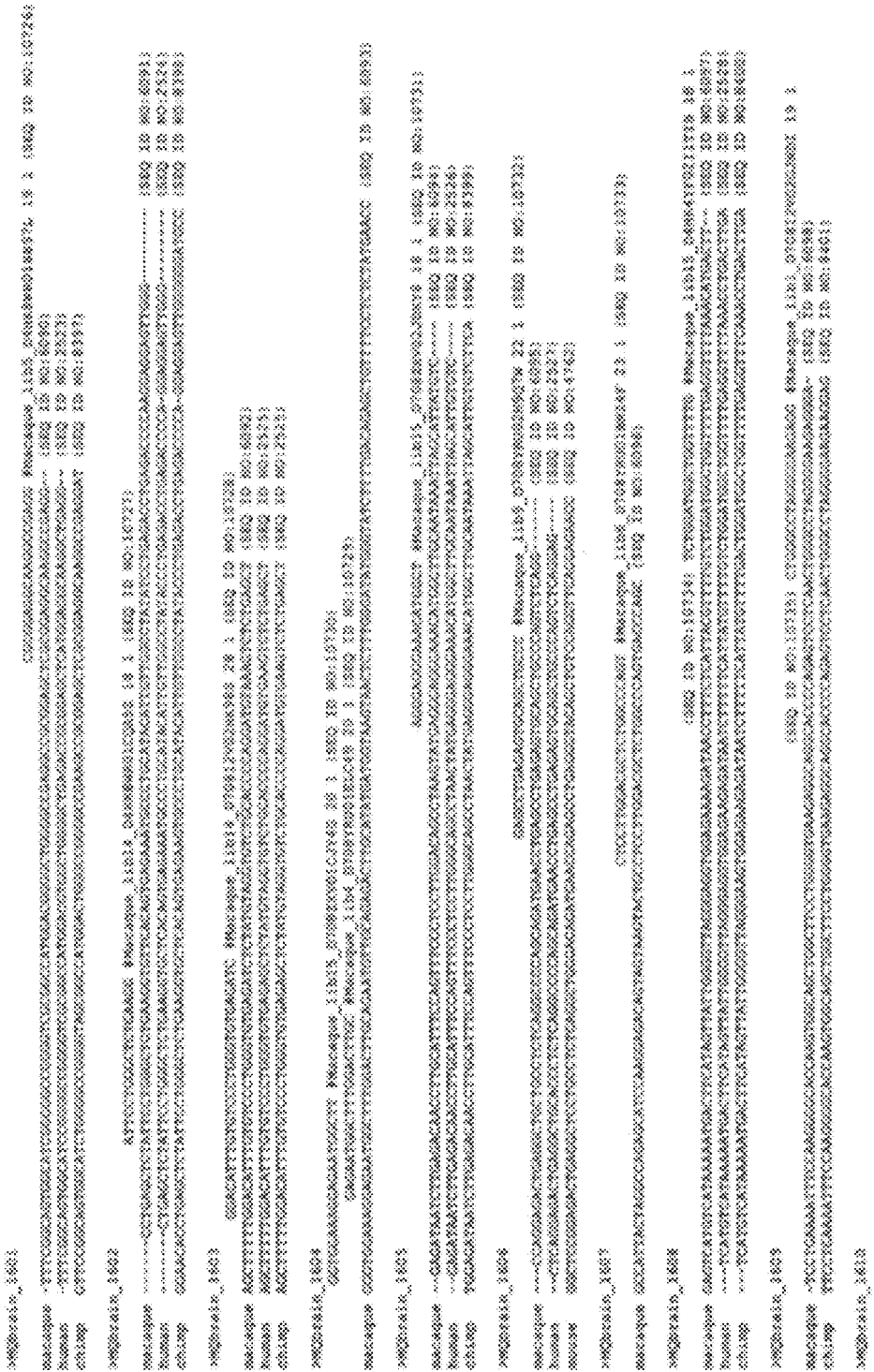
FIG 1C Con't.

FIG. 1C Con't.

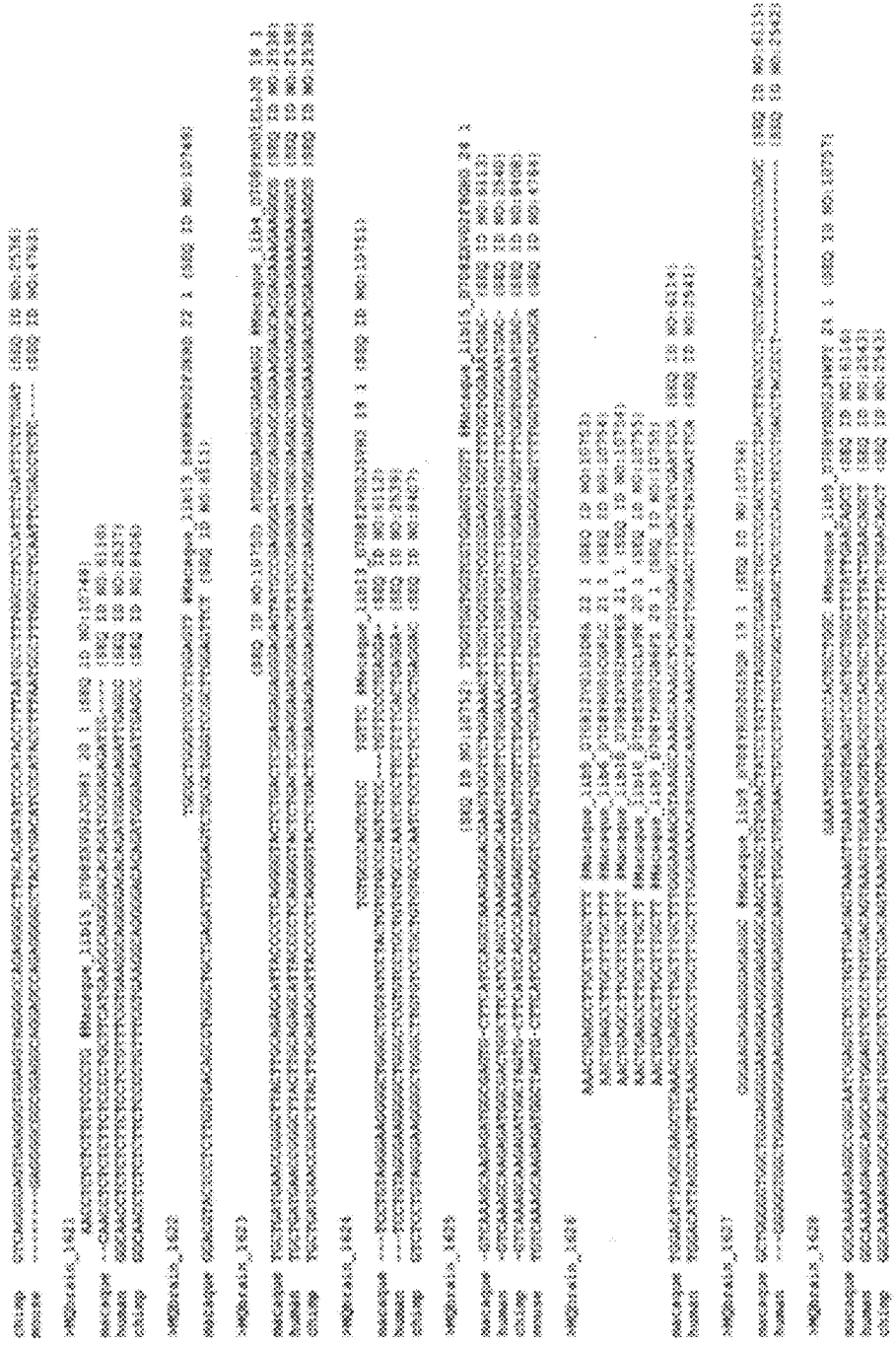
FIG 1C Con't.

FIG 1CC Cont.

FIG 1C Con't.

FIG. 1C Con't.

FIG. 1C Cont'd.

FIG. 1C Con't.

FIG. 1C-Con't.

FIG. 1C Cont.

FIG. 1C Con't.

FIG. 1C Cont.

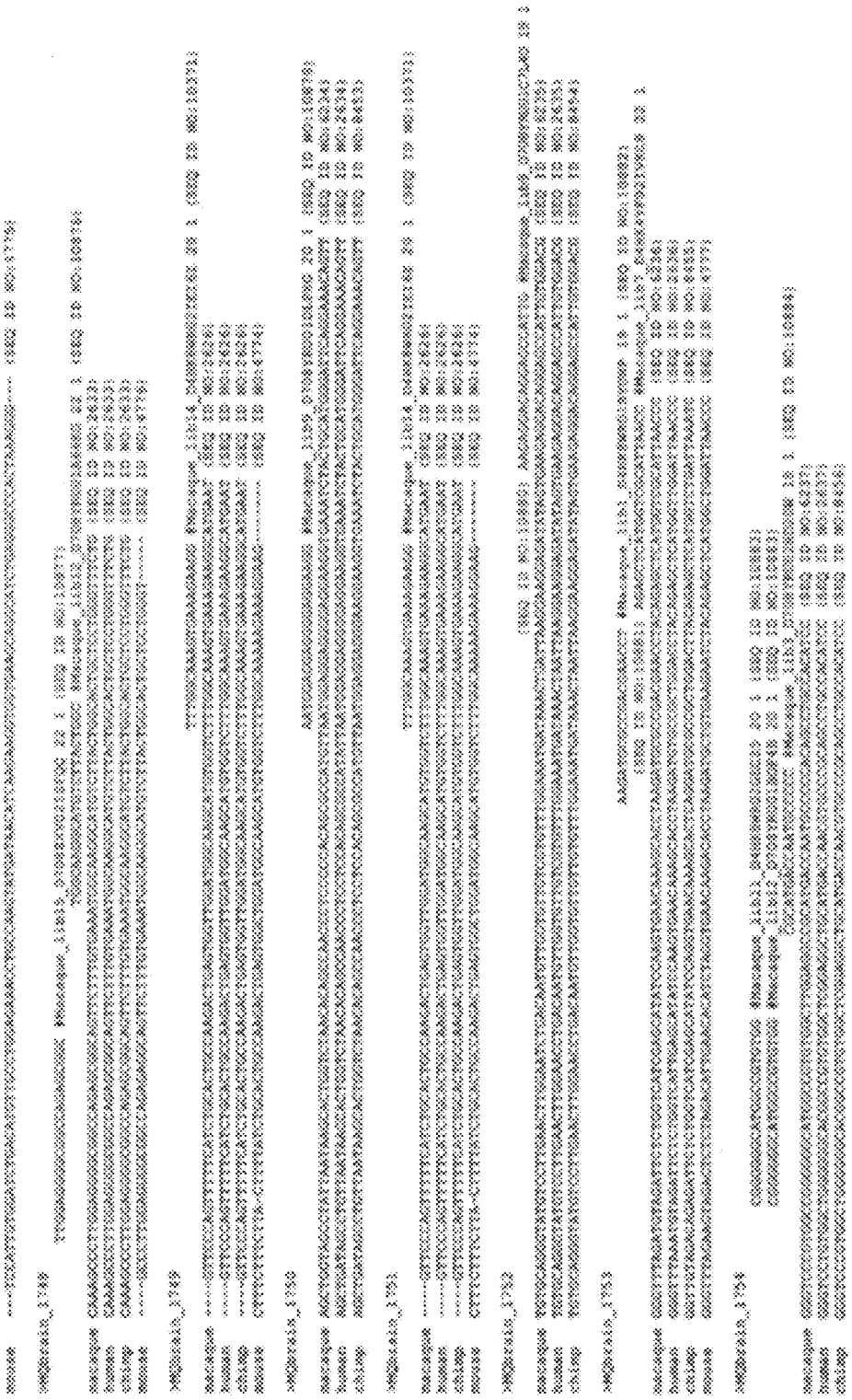
FIG 1C Con't.

FIG. 1C Con't.

FIG 1C Con't.

FIG. 1C Con't.

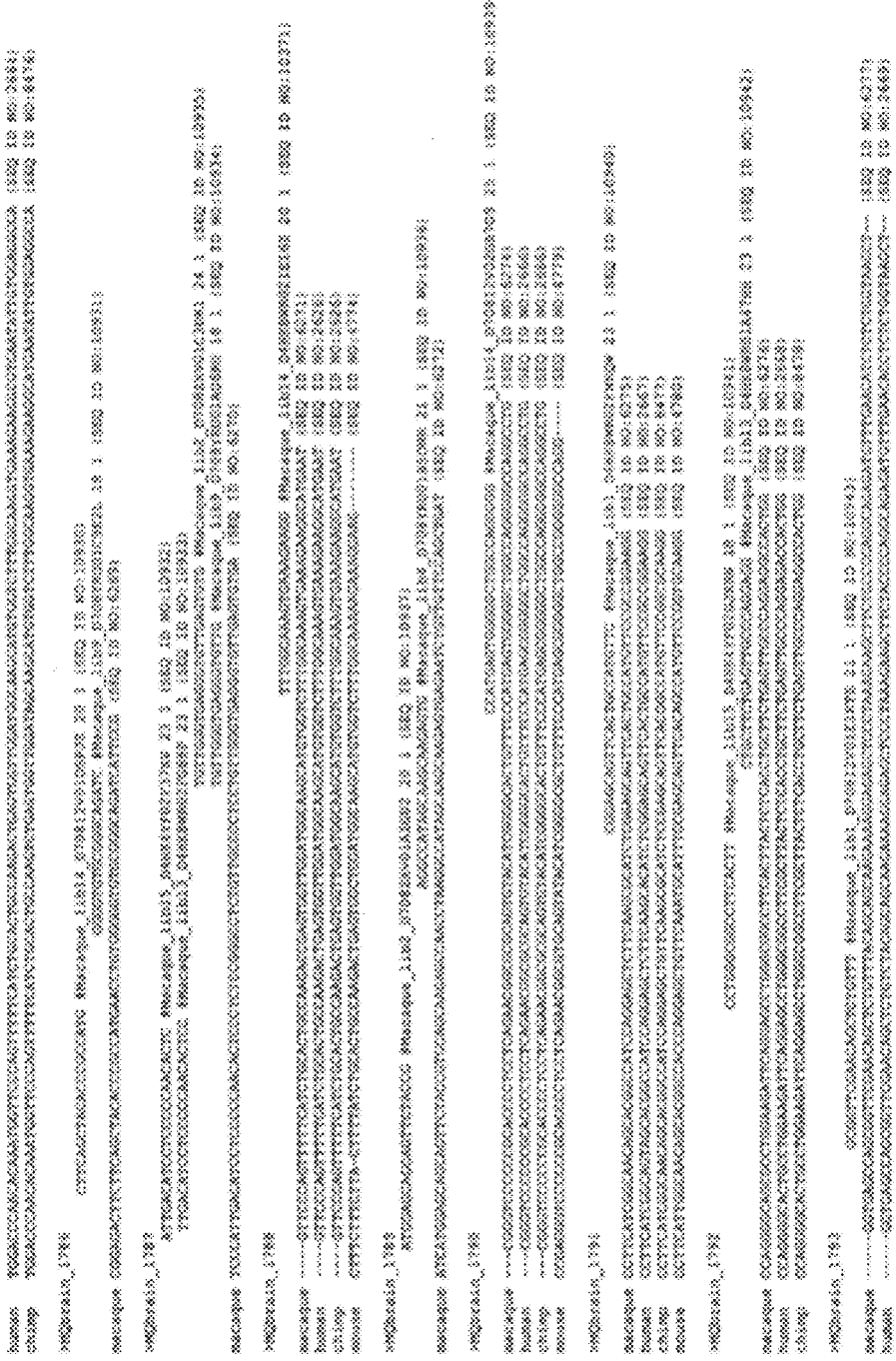
FIG 1C Con't.

FIG. 1C Cont.

FIG. 1C Con't.

FIG 1C Cont'd.

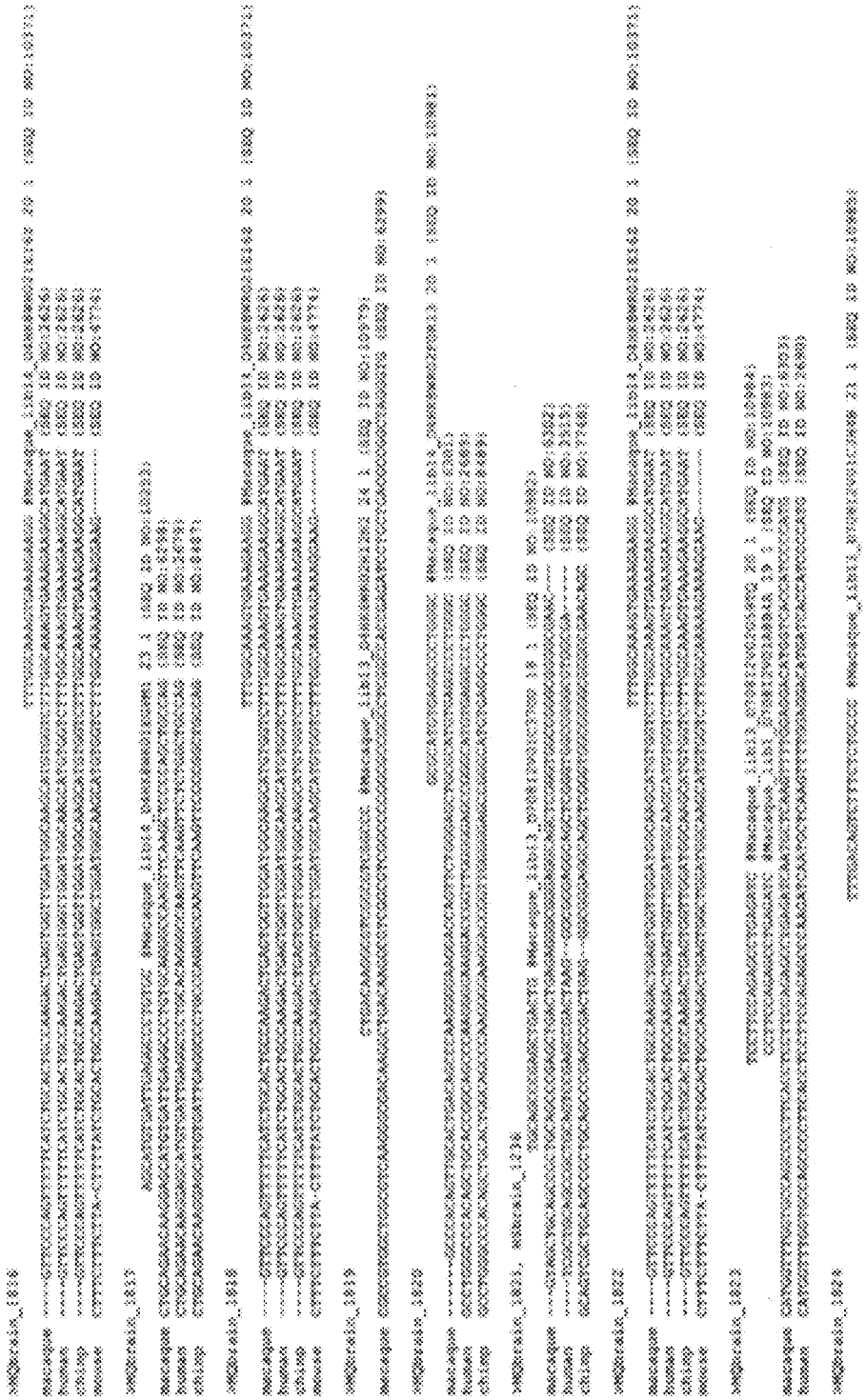
FIG. 1C Com't.

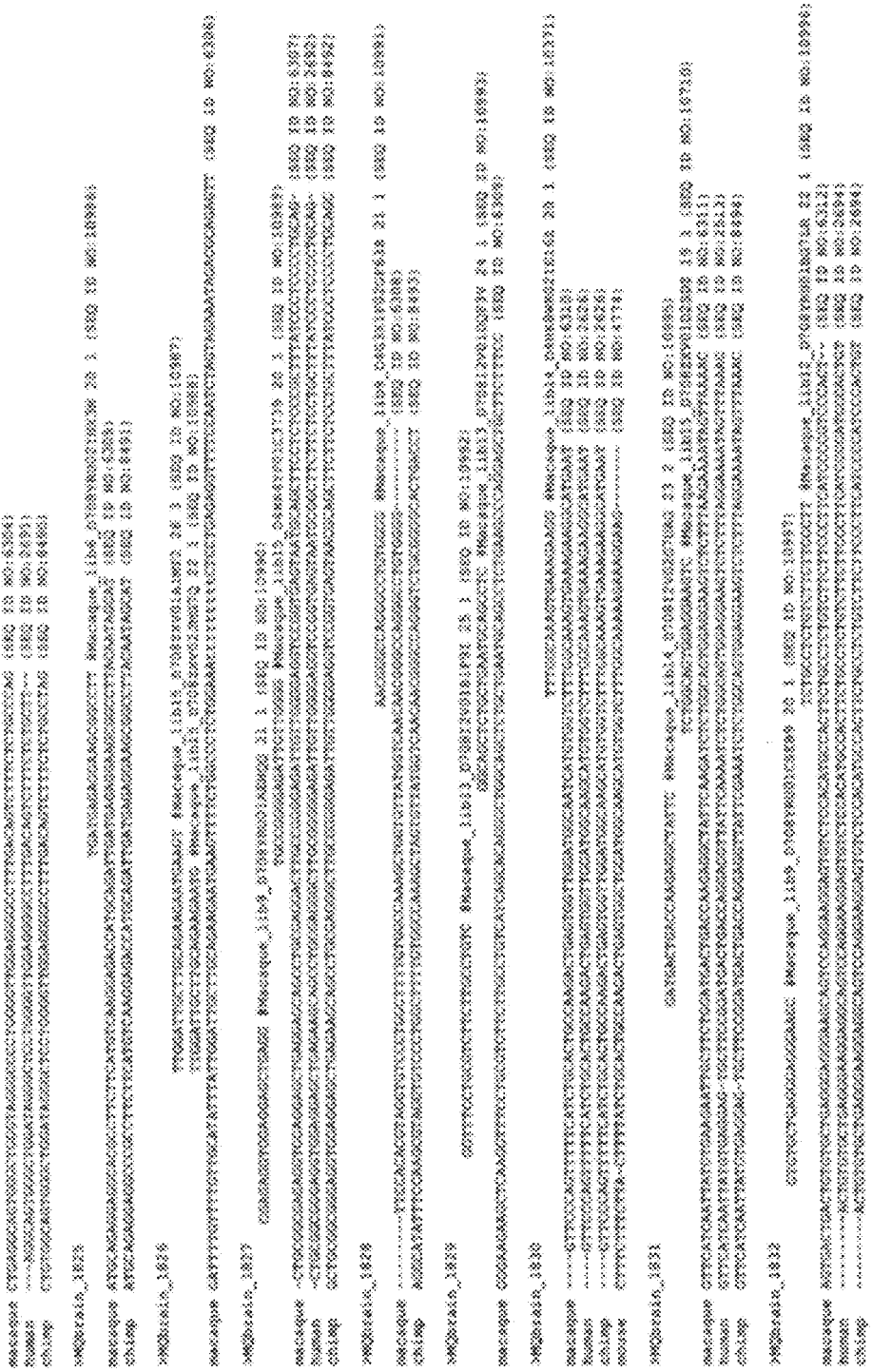

FIG. 1C Con't.

FIG 1C Con't.

FIG. 1C Con't.

FIG. 1C Con't.

FIG. 1C Cont.

FIG 1C Con't.

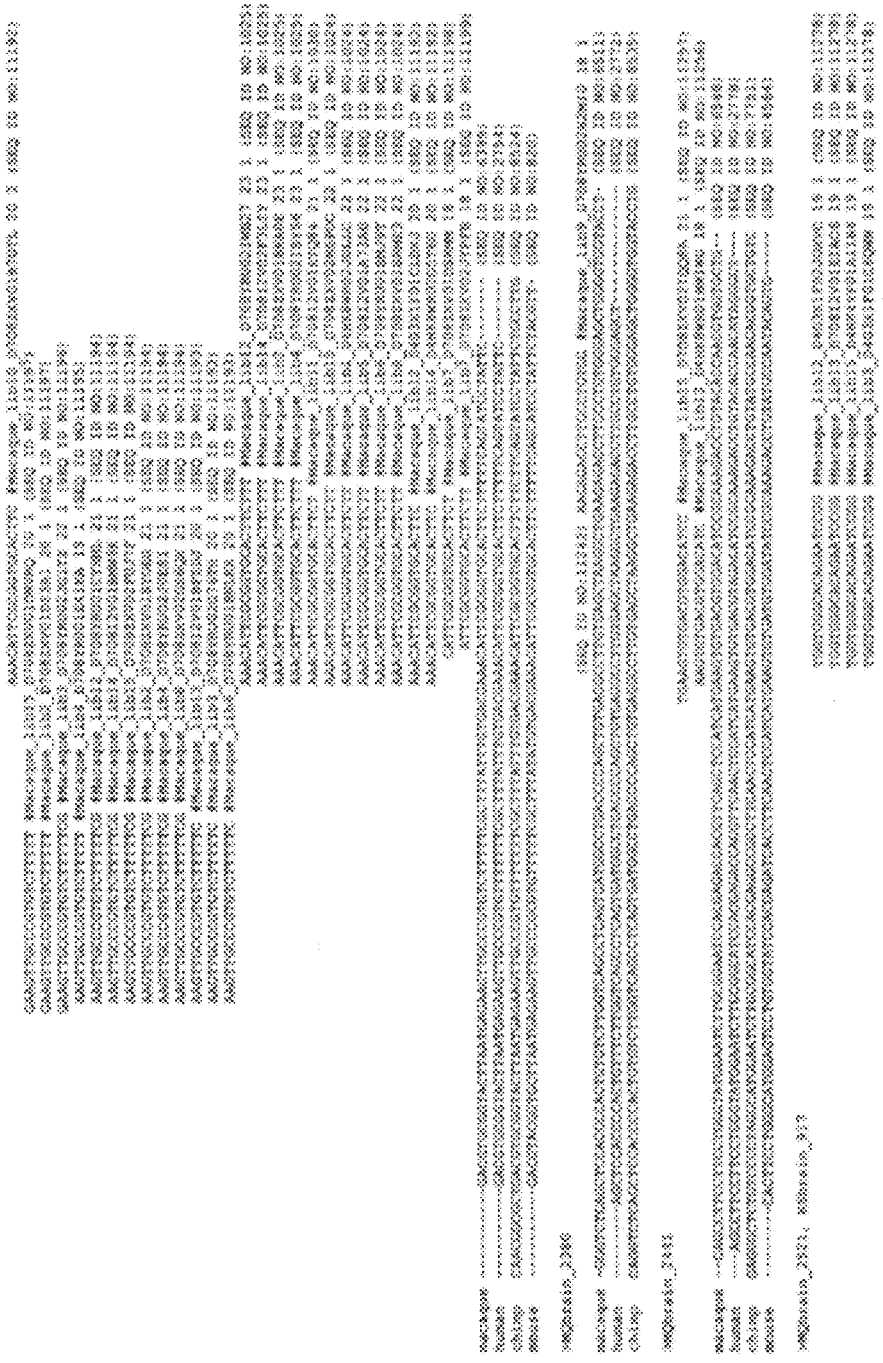
FIG. 1C Con't.

```
Mmd_2
cand360 probe20                    1  2  3  4  5  6  7  8  9  10 11 12 13 14 15 16 17 18 19 20 21 22    (SEQ ID NO:501)
GAAGAAATCCTACTCGGGTGGATATAATACAACCTGCTAAGTGTTCTAGCACTTAGCAGGTTGTATTATCATTGTCCGAGGTTATGGCTCTCGTC
...(((...(((((((..(..((((((((((((((((((((((.....))))))))))))))))))))..).)))))).....))...)))...

Mmd_3
cand234 probe26                    23 24 25 26 27 28 29 30 31 32 33 34 35 36 37 38 39 40 41 42 43 44   (SEQ ID NO:606)
TTGGCAGACTGGGAAATCTCTGCAGGCAAATGTGATGTCACTGAAGAAACCACACACTTACCTGTAGAGATTCTTCAGTCTGACAA
.((.(((((((((...(((((((((((.((.((((...((......))).....))))).)).)))))))))))...))))))))).).

Mmd_5
cand210 probe14                    1  2  3  4  5  6  7  8  9  10 11 12 13 14 15 16 17 18 19 20 21 22    (SEQ ID NO:820)
GACGTACGGTGCTTAATGAGAAGTTGCCCGCGTGTTTTTCGCTTTATATGTGACGAAACATTCGCGGTGCACTTCTTTTTCAGCATCCTATTCTACGTT
(((((.(((((((..((.((((((((.(((((((((((((((((......))))))))))..))))).)).))))))))))).)).)))))).....)))))

Mmd_6
cand347 probe29                    23 24 25 26 27 28 29 30 31 32 33 34 35 36 37 38 39 40 41 42 43 44   (SEQ ID NO:861)
AGATTTGCTTTTTCTCTTCCATGCCTTGAGTGTAGGACCGTTGACATCTTAATTACCCTCCCACACCCAAGGCTTGCAGGAGAGCAAGCCTTCT
(((...((((.(((((((((..((.(((((.((((....((.....)).)))).)))))))..)))))))).))).))))..)))

Mmd_7
cand355 probe41                    23 24 25 26 27 28 29 30 31 32 33 34 35 36 37 38 39 40 41 42 43 44   (SEQ ID NO:872)
GCTATGTACTGCACAACCCTAGGAGGGGGTGCCATTCACATAGAGTATAATTGAATGGCGCCACTAGGGTTGTGCAGTGTACAGC
(((.(((((((((....(((((((((((((....((......)).....))))))))).))))))))).)))

Mmd_9
cand212 probe16                    1  2  3  4  5  6  7  8  9  10 11 12 13 14 15 16 17 18 19 20 21 22    (SEQ ID NO:894)
GAGCTTTGGTACTTGGAGAGTGGTTATCCCTGTCCTCTTCGCTTCACTCATGCCGAATCGTACAGGGTCATCCACTTTTTCAGTATCAAGTGCGC
..((((((((((((..((((((((((....(((((.(..((((.........).))))..)..))))))....)))))))))..))))))))).))..

Mmd_11
cand254 probe17                    1  2  3  4  5  6  7  8  9  10 11 12 13 14 15 16 17 18 19 20 21 22    (SEQ ID NO:403)
GTGCTCTTGTGGCCCATGAAATCAAGCTTGGGTGAGACCTGGTGCAGAACAGGAAGGCGACCCATACTTGGTTTCAGTGGCTGCAAGAATGACTGCAT
(((((((((..(((..(((((((((((..((((((...((((....))))....).))))))..))).))))))))..)))..(((((......))))

Mmd_13
cand43 probe5                      1  2  3  4  5  6  7  8  9  10 11 12 13 14 15 16 17 18 19 20 21 22    (SEQ ID NO:425)
TGGCAGGCCAGGAAGAGGAGGAAGCCCTGGAGGGGCTGGAGGTGATGGATGTTTTCCTCCGGTTCTCAGGGCTCCACCTCTTTCGAGCCGTAGAGCCA
.(((.(((..((((((((...(((..(((((((((((((..((((...)))..)))))))))))))..)))))))))).)))...)))...

Mmd_14
cand972 probe5                     1  2  3  4  5  6  7  8  9  10 11 12 13 14 15 16 17 18 19 20 21 22    (SEQ ID NO:436)
GGATCTCAGACGTCTCGGGGATCATCATGTCACGAGATACCACTGTGCCCTTGTGACAGATTGATAACTGAAAGGTCTGGGAGCC
(((.(((((((.(..(((((....(((((....((((...((((...)))..)))))).)))))..)))..))))))))))).))

Mmd_15
cand371 probe3                     1  2  3  4  5  6  7  8  9  10 11 12 13 14 15 16 17 18 19 20 21 22    (SEQ ID NO:447)
TGGGGACTGCCCTCAAGGAGCTTACAATCTAGCTGGGGGTAGATGACTTGCACTTGAACACAACTAGACTGTGAGCTTCTAGAGGGCAGGGGCCTTA
((((.((((((((((((((.((((((.(((...((......))...)).)))))).))))))))))))))).))))....))))

Mmd_16
cand213 probe4                     1  2  3  4  5  6  7  8  9  10 11 12 13 14 15 16 17 18 19 20 21 22    (SEQ ID NO:458)
GCTACTGTTTCATACTTGAGGAGAAATTATCCTTGGTGTGTTGGCTCTTTTGGATGAATCATACAAGGATAATTTCTTTTTGAGTATCAAATACTGC
((...((((.(((((.((((((((((((((.(((((((..((....)).)).)))))).)))))))))))..))))).))))..))

Mmd_17
cand216 probe21                    1  2  3  4  5  6  7  8  9  10 11 12 13 14 15 16 17 18 19 20 21 22    (SEQ ID NO:468)
GGTAAGTGTGCCTCGGGTGAGCATGCACTTAATGTAGGTGTATGTCACTCGGCTCGGCCCACTACC
((((.((((.(((((((((((((...))))))))))))))...))).))))
```

FIG. 2: Con't.

```
Mmd_19                             23 24 25 26 27 28 29 30 31 32 33 34 35 36 37 38 39 40 41 42 43 44        (SEQ ID NO:490)
cand623 probe27
GGGCCCCCGCAACTGCTGCTACCGCCGGCCCCCGAGCTTTGAGGTTTCCACCCATGGCCGGGCCTCCTCCGGGCCGGCAGCAGCCGCCGAACAGCTC
(((((..(..((((....(((((((((((((.(((.((.(((....))))).))))))).......)))))))))))))).)).)....))))

Mmd_20                             1  2  3  4  5  6  7  8  9 10 11 12 13 14 15 16 17 18 19 20 21 22        (SEQ ID NO:502)
cand601 probe3
GGTGAGTCTCCTCAGGTGCTCATGTGGGAGAGATTAGCCTGTGTTTATAAGCTGGTCTGTTCATTAAGCGCCTGCTGGAGTGGAACC
(((....(((((.(((((((((...(((((((..(((((((((..(((....)))))))))))..)))))))))..)))))....)))

Mmd_21                             1  2  3  4  5  6  7  8  9 10 11 12 13 14 15 16 17 18 19 20 21 22        (SEQ ID NO:513)
mmHP533267 probe20
GTGTGTCTCATTTCTGAGCCTTTATATACCCTCCCATATTGAGCAATGCTGTGGTGGGAGGTTAAGGATGAAGGCCTCAGGAGGCTAAAGC
....((((((((....((((((((((((.((.((((((((((..((.(((....))).)).)....)))))))))).))...)).))))))))......

Mmd_22                             1  2  3  4  5  6  7  8  9 10 11 12 13 14 15 16 17 18 19 20 21 22        (SEQ ID NO:524)
cand472 probe7
GTATTTGAGGTTTAGGAAGGCGTGATAATGAGGCTGTGAAGATTCATGGCCTCTTTTCTATGGCTTAATTTAGGCTCTATATCAAATAT
(((((((((((((((....(((.(((((.((.(.(((((((((....))))))))).))).)).))))....)))...)))))))))))))

Mmd_23                             1  2  3  4  5  6  7  8  9 10 11 12 13 14 15 16 17 18 19 20 21 22        (SEQ ID NO:533)
cand644 probe15
CATTCTTTCAGTGTTGAAACAATCTCTACTGAACCAAGCTCCAAAGCGAGTTCACTGGAGTTTGTTTCAGTATTGCAGGAGTG
(((((((.((((((((((((.(((((.(((((((....))).))))))).))))).)))))).)))))))

Mmd_24                             23 24 25 26 27 28 29 30 31 32 33 34 35 36 37 38 39 40 41 42 43 44        (SEQ ID NO:544)
cand174 probe40
TTCTCAACAGTGATGTGATATGTGATTTCCCCTTCCAAGCCATGGTGCAGTTTCATCGGCACCATGGCCAAGAGGGCTCCATCTTGGTAAGAGAA
.((((..((((.((......(((((.(((((((((((.(((((((((.(......)))))))))))))))..)))))...)))))))))))))).

Mmd_26                             1  2  3  4  5  6  7  8  9 10 11 12 13 14 15 16 17 18 19 20 21 22        (SEQ ID NO:199)
cand65 probe6
CTCTGCTTCACCTTTCTTTTAGCAAAGATGAGGATTTCTACCTTCAACATACATTGTTGGTCTTGTCTTCTGTTTTTGTTAGGAGGGACAGCAGTG
..(((((.....(..(((((((((((((((((((...(((((....)))))....)))))-.)))))))))))))))...)-)))))..

Mmd_27                             1  2  3  4  5  6  7  8  9 10 11 12 13 14 15 16 17 18 19 20 21 22        (SEQ ID NO:573)
mmHP744986 probe7
GGGGAATTTCTGGCCACAATTTGTAACACTAAAAGGCTCCCCAAAGGGAGGGGGTGCAAAATGATACAAATTGGGTACAAAGGATAGCCACT
..((..((((.(((.(((((((((..((.((((.......))))..))....)))))))))....)))...))...

Mmd_28                             1  2  3  4  5  6  7  8  9 10 11 12 13 14 15 16 17 18 19 20 21 22        (SEQ ID NO:584)
cand386 probe17
TGAATGGCTTTGCTCCTTTTCTGCATCACTTCCATCAGCGCACCCACAATTCCTGAAGTGGGTGCGGGTGTTGGTGGTGTGGACTCTTGGCCATCA
.(((.((((..(.((((.((((....(((((((((((.((((.......))))))))))))))..))))..))))..).))))))).

Mmd_31                             1  2  3  4  5  6  7  8  9 10 11 12 13 14 15 16 17 18 19 20 21 22        (SEQ ID NO:617)
mmHP2052196 probe5
AGCTGTGTCATCAATAGAAGCTCAGGGCCTTAGGGAACTGGAGGGCACTTCTGACCCACTGCTCTCACTCTTTGGCTCTACTTCTGACAATGACTTGCT
(((...((((...(((((((.((((((..((((......(((((((.......))))))).))))..)))))).)))))))...))))..)))

Mmd_32                             23 24 25 26 27 28 29 30 31 32 33 34 35 36 37 38 39 40 41 42 43 44        (SEQ ID NO:627)
cand756 probe40
AAGCTGACGCTACCCATCCCCTCCACGTGCCCCGAGCCCTTTGCCCGCCTACTGGAGGGTGAGCCAGGGCCCTGTGGAGAGGGTAGGCTCAGCTT
(((((((((.(((((.....((((((((.(.((...(.(((.((....)).)))).)))).))))))))..))))))).)))))))

Mmd_33                             1  2  3  4  5  6  7  8  9 10 11 12 13 14 15 16 17 18 19 20 21 22        (SEQ ID NO:638)
cand162 probe18
GCTGTGAGGTCAGAATCCTGTGCTTACGACACCTCGGTCTGTTGCCATGAAACAGGGGCGGATTAAGGCTGGAGCGCAGGGATCAGGCCCCTCCGC
(((.((..((((((.(((.((((((((((...((((((((.(.((....)))))))))))....)))...))))))))))).).))))).).))
```

FIG. 2: Con't.

Mmd_35 cand684 probe15 (SEQ ID NO:660)
```
                        1  2  3  4  5  6  7  8  9 10 11 12 13 14 15 16 17 18 19 20 21 22
GGGCTTGGCCTGGCTCTGCTGGGACACTTCACACTTTTGCCATTTTTGGCCAGAAGGCTCTCCCTGCTAGCCGGGCTCTGTTC
((((..(((((((((((...((.((((.........(((((((((....))).))))))....))))).).)))))))))..))))
```

Mmd_36 cand566 probe27 (SEQ ID NO:671)
```
                        23 24 25 26 27 28 29 30 31 32 33 34 35 36 37 38 39 40 41 42 43 44
GCTGATATACAGCATTTGGCAGGATTCCTTGCTAGCATTTGGTAATAATTCCATACCAAATGCTAGGGAGAAACCCACCCAAATGGAACCGCTTCAAGC
((((((........(((((((..((.(.(((.((((((((((((.........))))))))))))).))).))..)))))))).))).)))
```

Mmd_37 mmHP200260 probe14 (SEQ ID NO:682)
```
                        1  2  3  4  5  6  7  8  9 10 11 12 13 14 15 16 17 18 19 20 21 22
CCTTCTGGAATTTGCTTGTGGCGCTGTTTATTACCTACCAGGCATTTTGCTGAAGGTGCAATTTGCAGAGCCATTAATGGCAATGAAGTTCCAGCGGG
(((.(((((((((((((..((((((((((...((((((....(((.....))).(.))))))..))..)))).))))))....)))))....))))))).)))
```

Mmd_39 cand184 probe5 (SEQ ID NO:273)
```
                        1  2  3  4  5  6  7  8  9 10 11 12 13 14 15 16 17 18 19 20 21 22
CAGCTCAGAATGTGGTAGGAGCTATCAGAACTTAGTGATCAAGTGAAGTCGTAGTTACTAATTTCTGATGCTCTTCCCCTGCAGAAGAGAGCTG
((((((....(((((.(((((((((.(((((((((....(......).)))))))))).))))))))))).))..))).....))))))
```

Mmd_40 cand519 probe11 (SEQ ID NO:714)
```
                        1  2  3  4  5  6  7  8  9 10 11 12 13 14 15 16 17 18 19 20 21 22
GACGGCTCAGAAGTCCATGGAGCTGTGGGCCAGGTAGTCCTTGCGGCCAATGTTGCTGACCTGCTTGGTCTGCATAGCTTCAAGTTTGGGGCAGTC
((..((((.(((.((((((((((((((((((((((((((((...(......)))))))).)).)))))))))))..)))))).)))).)))
```

Mmd_41 cand98 probe29 (SEQ ID NO:725)
```
                        23 24 25 26 27 28 29 30 31 32 33 34 35 36 37 38 39 40 41 42 43 44
ATCAGTTTGTGTGCATTTGCAGGAACTTGTGAGTCTCCTATTGAAAATAGACAGGAGACTGACAAGTTCCCGGGAACACCCACAAATCTTCCTACTGGT
(((((((((((.(...(((.((.(((((((.(((((((..((.....))..))))))).)))))))).)))).).).))..)))))))))
```

Mmd_44 cand618 probe6 (SEQ ID NO:757)
```
                        1  2  3  4  5  6  7  8  9 10 11 12 13 14 15 16 17 18 19 20 21 22
GTGAGGAGCAGGTTAGCTGGGTGAAAAGTTCGCAGCGAGGGGAGCTGTCTGTTTCCTTTGCTTAATTTATCCACTATTTGGCTAACCTCACTCTGAAC
((..((((.(((((((((...(((((.(((((....(((((((((((.....)))))))))))))).))))).))....)))))))..)))..))
```

Mmd_45 cand540 probe12 (SEQ ID NO:768)
```
                        1  2  3  4  5  6  7  8  9 10 11 12 13 14 15 16 17 18 19 20 21 22
GAGGTAATTTTGGCCCTCCTGATTGTTAAGCTCAATGGAGATAGATTTTTTCTTCCTCTGTGTGTGTGTTTATTGTAATATCTGGAGGGCTTTTTCTTC
((((.......(((((((((((..(((..(((((....(((......)))....)).)))))........))).))))))))....))))
```

Mmd_46 mmHP3140720 probe6 (SEQ ID NO:779)
```
                        1  2  3  4  5  6  7  8  9 10 11 12 13 14 15 16 17 18 19 20 21 22
CTGGAGTATCCTGCTTTGGGATTTGGGTCAGTCAATCAGCAGGTATTTATCCTGCTTTCTTTGGACCCAGAATACTGTTAACTCAGCAGGATACCACAG
(((.(((((((((...(((((........((((......(((((....))))))))).......).)...))))))))).))
```

Mmd_47 cand368 probe44 (SEQ ID NO:788)
```
                        23 24 25 26 27 28 29 30 31 32 33 34 35 36 37 38 39 40 41 42 43 44
GAGTTTGACAGCAGCCTACCACAGAACCAGCCCTTTGTTTTCTCCCTTGGCACTGGCCAGGTTATCAAGGGCTGGGACCAGGGGCTGCTGGGGTAAGTC
(((((...(((((((((...((((((((((.((........((((((.....))))..)).))))))))))...))))))))))....)).)))
```

Mmd_48 cand452 probe35 (SEQ ID NO:798)
```
                        23 24 25 26 27 28 29 30 31 32 33 34 35 36 37 38 39 40 41 42 43 44
CCTTTGGTTCACATTAAAATATAAAATTCCCCGTGGGAGAGACCCTATTAAGCCTTGCAGGGAATTACTAATTTACATTTTAATGTGAATGAGG
(((((...((((((((..(((.(((((((...((.........))...)...)))).......))))).))))))))))))))))
```

Mmd_49 cand732 probe22 (SEQ ID NO:809)
```
                        1  2  3  4  5  6  7  8  9 10 11 12 13 14 15 16 17 18 19 20 21 22
GCGCGAGCTGTCCCCGAACACCTTGCGGTAGGAGGAGGCGGAGCACAAATAGTGCTCCGATCCGAAGCTCATGGTGCCGGGGTCGGGGCCGGGTGCGC
((((..(((.((((..(((.(((.(((.((.((((((((((....)))))))..))..))..)).).)).))).)))..))))..)))))
```

FIG 2: Con't.

```
Mmd_52
cand922 probe21                1  2  3  4  5  6  7  8  9 10 11 12 13 14 15 16 17 18 19 20 21 22    (SEQ ID NO:355)
CCAGCAGCAGCTTCAGGCCGACAGCTTCAAAGCTAAGCAGATGGAAAACCACCAGCTTATTAAGGAGGCTGTAGAAATGAAGTCTGTCATGG
(((...(((((((((.....(((((((.....(((((-(-(((.....))).).)))))....)))))))).....)))))).))))...)))

Mmd_53
mmHP3172562 probe11            1  2  3  4  5  6  7  8  9 10 11 12 13 14 15 16 17 18 19 20 21 22    (SEQ ID NO:848)
ATGACGTAAACTCTAGTTCATATTTGAGTGTCAAAAGTTGGAGTTTGACATATTCCAAAATGTCACTCAAGATGGAGTTTGGGTTAT
(((((.(((((((((........(((((((((.(((.....(((((((........)))))))..)).)))))))))..))))))))).)))))

Mmd_56
cand266 probe12                1  2  3  4  5  6  7  8  9 10 11 12 13 14 15 16 17 18 19 20 21 22    (SEQ ID NO:857)
GACCAAGGTCTTTGGTCTTGGAGGAAGGTGTGCTGCTGGAGGAAGCCACGGAGGCTGGGCTGGTGGGGGCATCTTTCTTCAGACCACGGGCTTTGTC
...((((((((.(((((((.(((((((((((-(.-(.....(((......))).)...)..).-.).))))))))))))))).))))))..

Mmd_57
mmHP1485966 probe13            1  2  3  4  5  6  7  8  9 10 11 12 13 14 15 16 17 18 19 20 21 22    (SEQ ID NO:858)
TGGGAAGGGCATTGCTTATTTTGTATGCTTCTGGGTTGATTTTGGAAGTGATCTGTGACCCAGAAACGCAAAGGACAGTGTGGGCTGCCTTTCATCA
...((((((((....(((((.((((.((((((((((((((((.....))).....)).)))))))))..)))..))))).))))))))))....

Mmd_58
cand712 probe10                1  2  3  4  5  6  7  8  9 10 11 12 13 14 15 16 17 18 19 20 21 22    (SEQ ID NO:859)
GCACCCGAACGAGGGGTTGACCAAAGCAGCCATGATGGCAATGTCCGAACGTATGAAGACCGGTTGTCATCTGGTCTGCAGCCCAGCCCCGAGC
....((...(..(((((((.((((((.((((.(((.((((.....)))))..)..)))))))))))...))....

Mmd_59
cand552 probe8                 1  2  3  4  5  6  7  8  9 10 11 12 13 14 15 16 17 18 19 20 21 22    (SEQ ID NO:860)
CCGCCGCCTGGGCCAGGCGCCCGCCAGGTCGCGGGAAGAGGCGCGGACACGCGCACCAGTCCCGCCGCGGGGGCGCGCCTGGCTCTGGGCGGGG
((.(((((((..((((((((((((((.((..(.((((((((...((((((....)))))..)).).)))))))).).))).)))))

Mmd_60
cand838 probe12                1  2  3  4  5  6  7  8  9 10 11 12 13 14 15 16 17 18 19 20 21 22    (SEQ ID NO:862)
GCCTTGGCTTCCTGTTCTTCTTCATACTGTTCCCGCAGCAGGTCACAGTCATGGCGGGAGGACTGAAGAGCATGAGCTAAGGC
((((((((((..((((((((.....(((((((.((.......))....))))))).)..)).)))))))).))))))))

Mmd_61
mmHP2157333 probe14            1  2  3  4  5  6  7  8  9 10 11 12 13 14 15 16 17 18 19 20 21 22    (SEQ ID NO:863)
GGGGAGCAATTGTACTGACTCAGCACAAGTTGCTTGGCTGTGTTTACATGTGTGGCTTGAAGTTGCTTGAGTTTCAGTATCTCTGTCCTGCTCTCT
((((((((((.(((((((((((((((...(.((..........)).).-)))))....)))).)))).-.)))))))....))..)))))))))

Mmd_62
cand398 probe5                 1  2  3  4  5  6  7  8  9 10 11 12 13 14 15 16 17 18 19 20 21 22    (SEQ ID NO:864)
GGAGTGACAGGCGCCGAGGTGATGATGGAGGCTTCTTTCCTCGAACCCTGGAAATCCATTGGTTGTCCATCATCAACTCCATGGTGCTTGTGTTTTT
.....(((((((((((..(((((((((...(((((........)))))..)).))))))))))).......)))))))).......

Mmd_63
cand457 probe32               23 24 25 26 27 28 29 30 31 32 33 34 35 36 37 38 39 40 41 42 43 44    (SEQ ID NO:865)
TGGTGTGCTGGGAAGGAGGCCAGTGTGGTTTCTGTCCTCTGCCTTTTCTAGCAACTTCCCTCCACACTGCCCTCTCTGCCCGGGCAACACCA
.(((((((((((.((((((.((((((((.....((.....((((....))))........))))))))).)))).))..)))..))))).

Mmd_64
cand789a probe20               1  2  3  4  5  6  7  8  9 10 11 12 13 14 15 16 17 18 19 20 21 22    (SEQ ID NO:866)
GTATTTCTATCTTGGGGTTCTAATGACTAACCACTTGAGCTCTGCTTTTGTGGTTTATAATGTCACCAGAACTCTCCATGGAATTAT
(((-((((((...(((((((..((((.((((((..(((((...))))..)))))).......)))).-.))))))))..)))))))).))

Mmd_66
cand938 probe28               23 24 25 26 27 28 29 30 31 32 33 34 35 36 37 38 39 40 41 42 43 44    (SEQ ID NO:868)
CTCACTTTCTCAGCCATTTCATGAGAGTGATGCAGGGAATGTTCCCTTTCTGAGAACATCCTCCTTTGCTCATAGCTGGCTAGACGACAAGTGAG
(((((((((((.....((.(((.(..((((.((((((.(......).)))))))..))).)).)).))..)).).)).))))))))
```

FIG. 2: Con't.

```
Mmd_68                      1  2  3  4  5  6  7  8  9 10 11 12 13 14 15 16 17 18 19 20 21 22    (SEQ ID NO:870)
cand586 probe2
CGCCCTGTTTAAAGGAAGAAGTTTGTTCTGTTGTAAACAGTGATGGGAACTGTTTGCTTTGGATGGGCTTGGTCCTTATGAGCCAAAGAGCG
(((.(((((((((((((..(((((...(((....((((((((((.......)))))))))))..))))..)))))..)))))..))))))))...)).))))

Mmd_69                      1  2  3  4  5  6  7  8  9 10 11 12 13 14 15 16 17 18 19 20 21 22    (SEQ ID NO:871)
cand632 probe11
GAGGGGGGAGTTCTCTCAGGAAGAAGCCAGGTGAAACTCAAAGGGTCCAAAGAAGGCTTCGCTTTGAGTTTCTTTCTGGTTCTGTTTGAACCTGACACTC
((((...((.((((....(((.........((((((((((((((((.(.((......)).....)..))))))))))...))))))))))...)..))))

Mmd_70                                                 23 24 25 26 27 28 29 30 31 32 33 34 35 36 37 38 39 40 41 42 43 44   (SEQ ID NO:873)
cand200 probe39
GATTAATTCTACATGCGCCTAATTAGACCCACAATTGGCTAATTGCATCCACAATTAGCCAATTGCAGGCCCAATTGGCCACTTGTCCCATAATT
..............(((.((((((((((.(.(((.(((((((((((((((((......))))))))))))))))).)).)..))))))))))....

Mmd_71                                                 23 24 25 26 27 28 29 30 31 32 33 34 35 36 37 38 39 40 41 42 43 44   (SEQ ID NO:874)
cand402 probe35
CACTGTAACAACGTTTTCCTTCTGACTGATTACATTACATATTGCTATTAGTGAGCATCAGAGTGTAGTGCAATCAGTCAGGGGAAAATGAGTG
...........((((((((((.(((((((((((((((((..(((((.......))))....)))))))))).))))))))))))))))))....

Mmd_73                                                 23 24 25 26 27 28 29 30 31 32 33 34 35 36 37 38 39 40 41 42 43 44   (SEQ ID NO:876)
cand715 probe23
GGGCTATGGAGCCGCCACACATCTTGCAGCAGACACTGATGATGAGGGGCTGCGGCTCGCCC
(((((...((.(((((.(((.(((((((...(((......))).-))))))).-))))))))..))...))))

Mmd_74                                                 23 24 25 26 27 28 29 30 31 32 33 34 35 36 37 38 39 40 41 42 43 44   (SEQ ID NO:877)
cand734 probe31
CATGCCCTGATATTTGTGTTGGGATAATTACCATCTCTCAGGCCTCACTCGGTGGCAAGATGAGATGAAAACCCATAAAACACCACTCAGGGCTGTG
...((((((....(((..((((((((((.((.(((((((((((..(((((.(.......).)))))..))..)).)))))))......)))...........)))))))))....

Mmd_75                      1  2  3  4  5  6  7  8  9 10 11 12 13 14 15 16 17 18 19 20 21 22    (SEQ ID NO:878)
cand656 probe13
GGGAAAAAAAAAAGGCAGACACTGTGTTTGATGCCAATAATGGTTGCCAGTGGCACCGAGGTTGGCATCAGACCCTCTTTGTCTAGCTGCTGAATGCCT
(((..........(((((((((..(.(((((((((((((((..((((.(((...)))))))..))))))))))))))))...).))))..)))..........)))

Mmd_76                      1  2  3  4  5  6  7  8  9 10 11 12 13 14 15 16 17 18 19 20 21 22    (SEQ ID NO:879)
cand645 probe3
AGGCAGCAATTTGTGTCAGATTTCAATCTATTTAAGGGAAAAACCAATGAAGTCTGGTTGAAAAATGGAGAGTAAATTGCTGTCT
((((((((((((((.((.(((((((((((((..((((((...((....))..))))))...))))))...))))))))))))))))

Mmd_77                      1  2  3  4  5  6  7  8  9 10 11 12 13 14 15 16 17 18 19 20 21 22    (SEQ ID NO:880)
cand483 probe21
TCTCCAAACTGTTATTTAAAGCAGGGTTTCGCAAGGCTCAGCGAGCCTGCACCAATTTTAATTGTGTTTTTAAAACTCAGGATGGAGA
(((((((..(((......(((((..((((((((..(((((((...))))))...)))......)))).)))))).........)))..))))))

Mmd_80                      1  2  3  4  5  6  7  8  9 10 11 12 13 14 15 16 17 18 19 20 21 22    (SEQ ID NO:884)
cand261 probe12
GGACAGTGTGTTGATGTTTATTGGTGTCTCTTTTCTCTTCTAGGGCCAGCAGAGAGAAGAGACTCCATCTTCCAGAGGTTGCCACTGTCT
(((((((((...((......(((((((((((((.(((((.((......)).))))))))))))))).))......))......))))))))))))

Mmd_81                                                 23 24 25 26 27 28 29 30 31 32 33 34 35 36 37 38 39 40 41 42 43 44   (SEQ ID NO:885)
cand28 probe40
TTCCTTTAACTCTCAGCTTCTATTTAAAAAGCTAAATTTGGGAGCCTGTCGATGCTCCCAATTCAGACATTTTAAATAGGAACTGAAAGTCAGGAA
.(((((...(((.(((((((((((((((((((.(((....((((((((........))))))))...)).).)))))))))))))...)))).))))).

Mmd_82                      1  2  3  4  5  6  7  8  9 10 11 12 13 14 15 16 17 18 19 20 21 22    (SEQ ID NO:886)
cand896 probe6
GGTCCATCTTTGGGCCAAGATACGTAGTCGCCAACAGTGAGTTGGCGACTGTATTTTCGAGTCCTGGCGCAAAGCAAGATC
(((((....(((.(((((((.((((((((((((((((((.......)))))))).........)).)).)))).))))))...))))
```

FIG. 2: Con't.

```
Mmd_84
cand6 probe6                   1  2  3  4  5  6  7  8  9 10 11 12 13 14 15 16 17 18 19 20 21 22     (SEQ ID NO:888)
GGTGTGAAAGGGTAGGAGAGATGCTGGGGGTGGGGGTGCTTGTGTTTTAGACCCCCAATATTATCCCAGTGTCCCCTGCCTTCCTTCTTCC
((...(((((((((((((.(.(((((((((((..(((((((.((.......))))))))))......))))))))))))))))..)))..))

Mmd_85
cand59 probe28                23 24 25 26 27 28 29 30 31 32 33 34 35 36 37 38 39 40 41 42 43 44     (SEQ ID NO:889)
CAGGCCACTCCATCTGTTCAAACATAATGCTCCAAAGCAAGGAATATGTTCCAAACCAAAGAGCATGATATTTGACAGATGGAGATGCCCATACGCCTG
(((((((((((((((((((.((((..(((.(((((.......(((....))))..........))))).))).(((((((((((((..)))........)))))

Mmd_87
mmHP1815876 probe21            1  2  3  4  5  6  7  8  9 10 11 12 13 14 15 16 17 18 19 20 21 22     (SEQ ID NO:891)
GGCAGTCTGGGAGTGATGTCCCTGTGTCATTAGTGATATGATGGCAATCAACAGTCCAATGTCCCTCTTGATGGCACTTTGGACATGACCCTAGTGGCT
(((((...(((((((..((.((((((.((((((.((((......)))..)))))))))))))..)...))))....))))))))))...)))))..)))

Mmd_88
cand279 probe13                1  2  3  4  5  6  7  8  9 10 11 12 13 14 15 16 17 18 19 20 21 22     (SEQ ID NO:892)
AGCCTAACACTCCGCGGGAGTTTCCATGGCGACCGAAGCCGGGACCGCGCGGCCTGGCAGCGTTGCCATGGAGACAACTCCGGAGCTGGGGCT
(((((....(((((..((..((((((((((((.(..(((((((.((....)))))))))..))))))))))))))..)).)))))...)))))

Mmd_90
cand363 probe7                 1  2  3  4  5  6  7  8  9 10 11 12 13 14 15 16 17 18 19 20 21 22     (SEQ ID NO:895)
GGGATCACCGCCTCCATTTAGGTGTCAATTGTGTAAATTTCCAGCTGTTGCTCATCTCAACAGCTGGAGTTCAATATGCTCAGGGCGTATCTGGAGGCCCC
((.......(((((..((..(((((...((((((((((((((.......)))))))))))))....))))....)))))..)))))))))

Mmd_91
cand629 probe16                1  2  3  4  5  6  7  8  9 10 11 12 13 14 15 16 17 18 19 20 21 22     (SEQ ID NO:896)
GCAGCAGGTAGCTCTGTCTGCTGTCTCTTTAGATAAAATGTATGTCTGGCACGGAGGGAACAGCTGAGAACTACCTGTTGT
(((((((((((((..(((....(((((....))))).))).))).)))))).))).)).))...))))))

Mmd_92
mmHP2160056 probe22            1  2  3  4  5  6  7  8  9 10 11 12 13 14 15 16 17 18 19 20 21 22     (SEQ ID NO:897)
CTTTGAGTGAGGGTACCCATGCTGAAGGTATTCATGATGCGGTCAGGATATTCTTCTCTGATCTTGCTGATGAGCAGGGTGCCCATGCCAGAG
(((((.(((.(((((((...(.(((((....(((((((((.......)).))))))....).)))))..)))).))..)..))))).))))

Mmd_93
cand331 probe6                 1  2  3  4  5  6  7  8  9 10 11 12 13 14 15 16 17 18 19 20 21 22     (SEQ ID NO:898)
TTGTAGTTGACTAAACAGCGTCTGGTAGACGCAGATGGCATCATTAATCCGAGCGCTTTCTACATCTACCTGACCGCTTGGGTCAGCAACGA
((((.((((((((....((((((.((((.(.((((.((((((......))))).))))..))).)).))))....))))))).))))

Mmd_94
cand696 probe8                 1  2  3  4  5  6  7  8  9 10 11 12 13 14 15 16 17 18 19 20 21 22     (SEQ ID NO:899)
CTTCTGTAGATTGTGGACAAAGCCTTAGAAGAGCCAAAGTATAGCTCGCTGTATGCTCAGCTATGTCTGCGATTGGCAGAAG
(((((((.(((((((..(((((.(((..(((((((.....))..)))).)))..)).))))...)))))..))))))))

Mmd_95
cand584 probe24               23 24 25 26 27 28 29 30 31 32 33 34 35 36 37 38 39 40 41 42 43 44     (SEQ ID NO:900)
GTTCGAGGAGACACTATCAAAGTTAAGGCAGGGGAGCCAGTTAACATCCCTGCAGACGTGACCGGCCTCCCCATGCCTAAGATTGAGTGGTCCAAGAAT
(((((..(((..(((..((((((((((.((((((..((((....))))...))..))))..)))))....))..).))))).)))..)))

Mmd_97
cand68 probe2                  1  2  3  4  5  6  7  8  9 10 11 12 13 14 15 16 17 18 19 20 21 22     (SEQ ID NO:902)
AGCTTTCTCCAACTGTAACAATCTCCACTTCACTGTCAGTTGAGGTAACATTAATTTCTTCATTGGCAGTGACCTGGGGAGTGAAGGAGGCT
(((((((((.((.........((((((..(((((((((((((.((((.((........)))))))))))))))))).))))))))))))))

Mmd_98
cand482 probe12                1  2  3  4  5  6  7  8  9 10 11 12 13 14 15 16 17 18 19 20 21 22     (SEQ ID NO:903)
TCATCTTTGGCCCGGCTCCGGGTCTCGGCCCGCACGGTCCGGCCGCCATGCTGGCGGGGCTGGGGCCGGGACAGAGCCCGTGGCGGGGCGGCCTGTGG
.(((...(.((((...(.(((((((((((((((((.(.((((((((...)))))))..)))))))).)))....)))))))))))).))...))).
```

FIG. 2: Con't.

Mmd_100　cand424 probe2　　1 2 3 4 5 6 7 8 9 10 11 12 13 14 15 16 17 18 19 20 21 22　(SEQ ID NO:393)
TGAGTCATGGAGAAGGGAGGGCAAGTCAGGTGACCAGGTGAGACTCAGAACTCCTGAGGTAGCCTGGTTACCTTGACATTCCTGTGATTATGCCA
...(.(((((....(((((....((((((((((((((..((((......)))..)))))))))))).))))..))))))....))))).).

Mmd_101　cand659 probe2　　1 2 3 4 5 6 7 8 9 10 11 12 13 14 15 16 17 18 19 20 21 22　(SEQ ID NO:394)
TGGTGCAGCACTGAGAAATTTTGTCTCCAAGCAAAGGTCATTGGATCGGAGTCTTGGATTTAGTGACGGTGGAGGCTATAATTTTTCTTGCTGGCAGCA
.(.(((((((....((((((((...(((((((((((..((.....))..)))))))))))..))))))))..))))))).).

Mmd_102　mmHP969107 probe3　　1 2 3 4 5 6 7 8 9 10 11 12 13 14 15 16 17 18 19 20 21 22　(SEQ ID NO:395)
GAGATGGAGGAAGCCGAGTCCAGGCCTCCATGCAGCGGGGAGATGGAGAAGTCGGCCTGGGGCTGTGGAGGCACGGCACTCGGGTTGCTAAGGATGCTC
(((.(..((.((.(((((((((..(((((((((((..((((...(((......)))..)))).)))).))..)).)))))))).)).)).)...)...)))

Mmd_104　mmHP2682003 probe7　　1 2 3 4 5 6 7 8 9 10 11 12 13 14 15 16 17 18 19 20 21 22　(SEQ ID NO:397)
GGCAGAGGAATGTGGCTGCTTTTAAAAGGGGTCTCAGGTAAGGCTGTGTGTGCCAGCCTTCCTGACCATCAGTGATAGCAGCTTGGGTGTCTGCT
(((((((.......(((((((((.(((......((((..((.(((((((((.......)))))))))..)).))))...)))..)))))))))....).))))))

Mmd_105　cand310 probe9　　1 2 3 4 5 6 7 8 9 10 11 12 13 14 15 16 17 18 19 20 21 22　(SEQ ID NO:398)
AGGTTGATGCAAAAGAAAGGAAAACATCTTTGAAGTTCTCAGAAAAACAAGACTTCAAAAGATGTTTTCCTTTCTTCTTTCTCGAATCT
(((((((....((((((((((((((((((..((.....))..)))))))))))))))))))..)).)))))

Mmd_107　cand906 probe13　　1 2 3 4 5 6 7 8 9 10 11 12 13 14 15 16 17 18 19 20 21 22　(SEQ ID NO:400)
ATGCCCGTAATGTACAGTAAATGAGGCCCATAACTCATTGGAGCCTCCAATGAGTTATGTGCTAAATTCATATTTCACAACATGGCCAT
(((.(((((..(((..((((((((..(((.((((((((((((.....))))))))))))..)))..)))..)))))).)))..)))

Mmd_109　mmHP121950 probe14　　1 2 3 4 5 6 7 8 9 10 11 12 13 14 15 16 17 18 19 20 21 22　(SEQ ID NO:402)
GGGGGTGTGAGCCCCTTTTTCTGCTTTCCAGCATCTTTGGCATTTGCGCAAAGTTGCTCAGATTGCAATGCTGGGGTGCAGTGGGCGCGCGACTCTT
.(((((((((.((((.....((((..((((((((((..(((((((((.(((....))).)))).)))))..)))))))))).))))....)))).))))))))).

Mmd_112　cand513 probe6　　1 2 3 4 5 6 7 8 9 10 11 12 13 14 15 16 17 18 19 20 21 22　(SEQ ID NO:406)
TGTACCTGTTTCCTCCTGTGGCCCGGAGTTTGATGTGCAGGGCAGTGATGCCCAACTCCTTGCACCTCTGGGCCACATCCTGGGCAGCCAACA
.(((...((((...(((((((((.......(((((((((.((.......)))))))))))....)))))))))....))).

Mmd_114　mmHP1647321 probe8　　1 2 3 4 5 6 7 8 9 10 11 12 13 14 15 16 17 18 19 20 21 22　(SEQ ID NO:408)
GGCCAGGGCACTTTAGGCTACCCCAGTGTGTCAGTGTAGAGCAATGTTGACAAGCTCTGCCTAACTGAGCTGTGGGTGTTCTAGAGGGTATGACC
(((.(((..(((.(((((((......((.((((((((.....)).))))))..)))))))))..)).))))))

Mmd_115　cand456 probe40　　23 24 25 26 27 28 29 30 31 32 33 34 35 36 37 38 39 40 41 42 43 44　(SEQ ID NO:409)
GGACATTTCTGTCCCAGGCCAGCAGCTGTCACCTTAGAAAGATTAAGATTCTCCCACCAGGCGACAAGGCTTGTTGTGCCCGAGACAGATACGGCT
.......((((((.(.(((((((((((((((.(((..(..(((........))..)...)))).))).))).))))).))).).))))))..........

Mmd_116　mmHP1779096 probe17　　1 2 3 4 5 6 7 8 9 10 11 12 13 14 15 16 17 18 19 20 21 22　(SEQ ID NO:410)
AGACTTTATTATGTTCGCCAAACATCTGGCCTTCCCAAGTATGTCATTAGACATTGGGCCAGGTGTGAGGCATCAGAGTGGATTGCT
....(((((((.((...((((..(((((((((((((........(((((...)))))..)))))))))))))..))).))).)))))).....

Mmd_117　cand100 probe35　　23 24 25 26 27 28 29 30 31 32 33 34 35 36 37 38 39 40 41 42 43 44　(SEQ ID NO:411)
AGGTCCTAGGTGAGGCCATGACTGGCATCTCCCAAAATGCCAAGAATGGAAATCTGCCGGAGTTTGGAGATGCCATTGCCACAGCCTCCAAGGCTCT
(((..(((((..(..(((((.((...((((((((.(((((((((........))).))..(((......)))...).)))))).))..)))))..)..))))))..)))

FIG. 2: Con't.

```
Mmd_120                          1  2  3  4  5  6  7  8  9 10 11 12 13 14 15 16 17 18 19 20 21 22   (SEQ ID NO:415)
cand578 probe13
GTGGCCACAGGGGGGTGGGACTGGTCATGTAGCCGTGTGTCAGGAGTAATGATTGTAGAGGGGCGGGGCATGAAGAGTGCCATTCTGGAAAC
(((..(((.....(((((((..(((..(((((((((..((((.(.((.(.(((.....))).).)).).)..))))..)))))))..))).)))))))))..))

Mmd_121                          1  2  3  4  5  6  7  8  9 10 11 12 13 14 15 16 17 18 19 20 21 22   (SEQ ID NO:416)
cand913 probe22
GCTTAGGCCAGCCGCGTCGCCGCTTCATGAATGGAACCCACGTGACCAAACATCATGTGACGTCTGAGGAGCGGCGGCGGCGGCGGATTCTGAGC
((((((..((.((((((((((((((((((.(..(((.....((((((........))))))..)))...)..))))))))))).)))).....))))))

Mmd_122                          1  2  3  4  5  6  7  8  9 10 11 12 13 14 15 16 17 18 19 20 21 22   (SEQ ID NO:417)
mmHP2044575 probe10
CAGTGAGAAATTAGGAGGGATGTAAAGTAAGCTGGCTTTTTGCCTGAGGGCTTAATTTAAAAGAATCCTTTAGGTGCCTCTGTGATTTCTTACTG
(((((((((((((((..((.((((((((....))).....)))))))...............)))))..)).))))))))))))))

Mmd_123                          1  2  3  4  5  6  7  8  9 10 11 12 13 14 15 16 17 18 19 20 21 22   (SEQ ID NO:418)
cand447 probe19
TTCCTGGGGATTAATGAATGGCTGGGTGGAGTTAATTGCCTAAAGTATAGTCTCAGGCCATTAACCTCAGTTGGTCACTAATCTCAAGGAA
.((((.((((((..(((..(((((((....(((((((..(((((.((.....)).).))))).))))))))...))..))))))))))))))..

Mmd_124                          1  2  3  4  5  6  7  8  9 10 11 12 13 14 15 16 17 18 19 20 21 22   (SEQ ID NO:419)
cand168 probe22
AGGCAGGATACAGAGCTCTTTAAATAATGCCCCAGCATTTCCTGGACCAGCATGATATTTAAAGATTTTTGTTCCACCTGCCT
(((((((..(((((((.(((((((((((......))))))....))))))..))))))))).))))))

Mmd_126                         23 24 25 26 27 28 29 30 31 32 33 34 35 36 37 38 39 40 41 42 43 44   (SEQ ID NO:421)
cand496 probe36
GAAGCAAGGAATTAGCTCTCTAAATGCCCCACGATGACTGGCTGACTTGCTGGTCCTCTGAGGGCGATTTGAATATCTAACTCCTCTCTTC
((((..(((((.....((((((((((((..(.(((...((.......))..))..)))))..)))))....))))).))))

Mmd_127                          1  2  3  4  5  6  7  8  9 10 11 12 13 14 15 16 17 18 19 20 21 22   (SEQ ID NO:422)
mmHP157519 probe4
GGGAATGGAGGAGGCATTAGGGGAAGAGGGGACTCTGTCTGATGGATTTTCATTCTTTTTAGGAATTACCCTTGTGTCCCTGGTGGTTCCTGTGGCTTCT
((((.((.(((((..((((((((((...((((........((((((......)))..))))))...))))))))))..)))))).)).))))

Mmd_128                          1  2  3  4  5  6  7  8  9 10 11 12 13 14 15 16 17 18 19 20 21 22   (SEQ ID NO:423)
cand556 probe6
AGCTTTTTTTAAAAATTACTGGTGCCCAGGCTCCACCCTGGACCAATTAAATGAGCTCTCTTGGGGAGGGGCCTGGACATCAGTAATTTTTAAAAGCT
((((((...(((((((..(((((...((((((..((((((((........)).)))...))))..)))))).)))))..)))))))..)))))

Mmd_129                         23 24 25 26 27 28 29 30 31 32 33 34 35 36 37 38 39 40 41 42 43 44   (SEQ ID NO:424)
cand617 probe41
CCCTGACCTCTACCTCCACTGACTCCCTCTTCTCCCCCTCCATCAGCCAATGCTGAGGCCTTGAAGGAGATGCTAGGGGACAGTGAAGGAGAAGGG
(((....(((.((((.(((((....((....))...........))))).)))).))))...))))..)))))))))

Mmd_130                          1  2  3  4  5  6  7  8  9 10 11 12 13 14 15 16 17 18 19 20 21 22   (SEQ ID NO:426)
mmHP115458 probe21
CTCCCCAGAGAGATCTTTCAGTAACTGATCTTCTAGCTGGCATTTTTATAGATTAGGAAGCAGGCCAGCTGGAGGTCATACTAAATTAAACTCTGCTGAG
(((..(((((..(((..((((..(((((((((..((((((.....)))))).))))))))).)))))))))))))))

Mmd_132                          1  2  3  4  5  6  7  8  9 10 11 12 13 14 15 16 17 18 19 20 21 22   (SEQ ID NO:428)
mmHP1181586 probe7
GAAGGAGAAAAGCAAGCAGGGTGTGAGGGGACTCGTCCCACACCTGTGTAAACAATGTCACCTTACACCCCGTCAAGCACCCTCGCCTTC
(((((.(((....((..(.(((((((((((.(((..((..(((.....))).)).)))...))).)))))))))..))...))))))

Mmd_133                         23 24 25 26 27 28 29 30 31 32 33 34 35 36 37 38 39 40 41 42 43 44   (SEQ ID NO:429)
cand50 probe34
GTGAAGGCTATTAATTACACTGAGTGACAAAGACTCTCCGTGTTGTATGATTGACACAAGGATGAATCTTTGTTACTGATTGCAAATAATAGGACCGC
.....((((.(((((..((.(((((((((((((((.....))))).)).))))))))))).)..)).))))....
```

FIG. 2: Con't.

```
Mmd_135                    1  2  3  4  5  6  7  8  9  10 11 12 13 14 15 16 17 18 19 20 21 22        (SEQ ID NO:431)
mmHP291564 probe22
GACAGTGATTGTTGCTATGGGAGACAGTGTGGGTTTGTGACACAAGAAAAATTCTCTTGCTGTTGCAAAAGTGGATCCAGACTGTCCCAATGGATGTC
((((.........((((.((.(((((((.(((((((((...((((((((......)))))..))))..))......)))))).)))))))).))))..))))

Mmd_136                    1  2  3  4  5  6  7  8  9  10 11 12 13 14 15 16 17 18 19 20 21 22        (SEQ ID NO:432)
cand605 probe7
GCAGTTAATGATTGGTTTGTTAGTTAATGGCCCAAGGCAAAGCTGAGGGCGGTTAAGACTCTAACAAACGATTTGTGAATTGT
(((((((.(..(.(((((((((((((((.(((....)))..)))).-))))))))....))))))))).-.)..-.)))))))

Mmd_137                    1  2  3  4  5  6  7  8  9  10 11 12 13 14 15 16 17 18 19 20 21 22        (SEQ ID NO:433)
mmHP3254020 probe13
TGTCTTTTGGATCATCATATTCTTACCAAAACATTTGCTCTGATTGGTGGCCCGGTCAACAAAGACTTTGGCTGAGATGACATGACCAAAAGGGACA
..((((((((((.(((.....((((((((((..(((...(((((((....))))))).-))))...)))))-.))))....))))))))))....

Mmd_138                    1  2  3  4  5  6  7  8  9  10 11 12 13 14 15 16 17 18 19 20 21 22        (SEQ ID NO:434)
cand139 probe2
TCTTATTGTGTTTGGCTGAGGCCTAGTAATTTTCAATAAAGCCCTTAATCCAAGTACTTCACTGAAAATTACCAGGCTTCTCTGTGGAGGATGAGA
(((((((.(.(.(((.((((((((.(((((((((((.(.(((...(((......))).-))).-).-))))))))))).-)))))))).-))).).-.))))))

Mmd_139                    1  2  3  4  5  6  7  8  9  10 11 12 13 14 15 16 17 18 19 20 21 22        (SEQ ID NO:435)
cand238 probe13
GTATTTCCTGAGGATTAATGATCAACTGGAAGAGCCTGTGGTCTTAGGGCCATTAACTCCGGGTGGTCATTAATTCTGTTGGAAATAT
(((((((....(((((((((((((..((((.......((((((....)))))....)))).))))))))))))...)))))))))

Mmd_140                    1  2  3  4  5  6  7  8  9  10 11 12 13 14 15 16 17 18 19 20 21 22        (SEQ ID NO:437)
mmHP2148319 probe5
GTCTTGCCAGCAGAATTCTCAGAGGCAAAAGGAGTGAAATATTTGCTGGAGGGGATACTTTCCTTTCAAGAAGCATTCCTTTGCCTCCTGAACAAGAT
((((.....(((....((((((((.(((.((((((....((((...)))).-))))..)))))))))))))))))).-.))))))

Mmd_141                    1  2  3  4  5  6  7  8  9  10 11 12 13 14 15 16 17 18 19 20 21 22        (SEQ ID NO:438)
cand620 probe22
GGGCTGCCCAAGCAAGGGCTTATTTTGACTTAGGATGCTGCTGAAGCTGTGGCAGCCTTGTCAAAATACATCTGCCTCTTCTTACGCTGCCC
((((.(((.(((((....(((((.(((((((((...(((.(((...(.......)..))).-))).))))))))))....))))..)))))..))..))))

Mmd_145                    23 24 25 26 27 28 29 30 31 32 33 34 35 36 37 38 39 40 41 42 43 44        (SEQ ID NO:442)
cand534 probe28
GTCCACTCCATCAAAGGGTCTAATGGTCAGCAGAGGAGGCTAAATGTCTCCCCTGTGACCTGACATTAACCGAGTGGAC
(((((((((..........(((....((((.(((.((((((.....))))))..))))))))))).)........)))))))

Mmd_146                    1  2  3  4  5  6  7  8  9  10 11 12 13 14 15 16 17 18 19 20 21 22        (SEQ ID NO:443)
cand517 probe6
GGAGAGGTGGGGAAAGAATTAATGTGTGCTCTCTGATTCCTTTCACTGAGGACTTACAGATTAACTCCCCACTTCTCC
(((((((((((((....(((.....((.(((.-(((((((......)..-))).-)).......)))).-))))))))))))))

Mmd_147                    1  2  3  4  5  6  7  8  9  10 11 12 13 14 15 16 17 18 19 20 21 22        (SEQ ID NO:444)
cand356 probe16
GGAAAGACACAGACAAGAGAAAATAAGCCTGCCTAGCAATTACGTCTGGGCTGCTTGGAGGGCTCTCTCTGTTCTCTTTCC
((((((((.(((((..((((....(((((.-(((((((.......)..)))))))-.)))))....))))-.))))))..)))))))

Mmd_148                    23 24 25 26 27 28 29 30 31 32 33 34 35 36 37 38 39 40 41 42 43 44        (SEQ ID NO:445)
cand582 probe38
AGAGCCCTTCTGGCAGCTAATGACCTGCTGGAGTCGTGTGTGCCCAAGGCAAAGCTTAAGGCCATTAGTCCAACAGGTCATTAACTGACAAATGCCT
((.((......((.(((.((((((((((.((((.(....(((.(((...(((((...)))..))))))))).)-)))))-.)))))))))))).)).)..)))

Mmd_149                    1  2  3  4  5  6  7  8  9  10 11 12 13 14 15 16 17 18 19 20 21 22        (SEQ ID NO:446)
cand236 probe19
TTGATTTCCGTGCATAAACAGTGGCCTAGATTCTTGCCCTGTGGAAATCCACGGAATTAAGAACTCTAGGTTCCTGGAGTGATAAGAGGTAAGCAA
...(((((.....(((....(((.-((((((((((((((..(((((((....)))))...))))))).-))))))))...)))-.)))....)))))).......
```

FIG. 2: Con't.

```
Mmd_152
cand789 probe9                1  2  3  4  5  6  7  8  9 10 11 12 13 14 15 16 17 18 19 20 21 22      (SEQ ID NO:450)
GGAAAAGGCTGTAATTCCATCTTGGGGTATCTGGTGAACCAAGCTGTGGGTCTGTGGTTTATGATGTCACCAGAACCCCCAGCTGGAATTACAGCCTTCC
(((..((((((((((((((((..((.(((((.(((((((((...(((...(.....)..)))).....)))))))))))).)).)))))))))))))))

Mmd_153
cand678 probe8                1  2  3  4  5  6  7  8  9 10 11 12 13 14 15 16 17 18 19 20 21 22      (SEQ ID NO:451)
GCTTTGCTTGGCCTTCTGGGAGTTGTAGTTCTAGAGGCACCCGGGTTGCCTGGCTGGCCCCGGAACTGTGGACTACAGCTCCCAGGCCTTCTCTAAGC
((((.....(((((.((((((((((((...(((.((.....((((((..(((.....))))))))).))).)))))))))))))))))))......)))

Mmd_154
cand914 probe16               1  2  3  4  5  6  7  8  9 10 11 12 13 14 15 16 17 18 19 20 21 22      (SEQ ID NO:452)
GGTCATCGTTGTTCAAAGTGTTGTGTTCGGGGCCCTTCCAGGTGATTGAGGCCTTGGGGCGGCCACAGACACGACATCTAAAAACAACGGTCTCC
(((.((((((((....((((((((((..(..(((((((((..(((.......))).).)))))))).).)...)))))))).)).....))))))))

Mmd_155
cand674 probe14               1  2  3  4  5  6  7  8  9 10 11 12 13 14 15 16 17 18 19 20 21 22      (SEQ ID NO:453)
TGTGGTGTGCCTGCCCCCTTCCGTCATTGCTGTGAATGGGCTGGACGGAGGAGGGGCTGGCGAAAATGACG
.(((.(((.((.(((((((((((...(((.......))).)))))))).)))))..))))...)).)).

Mmd_156
cand907 probe14               1  2  3  4  5  6  7  8  9 10 11 12 13 14 15 16 17 18 19 20 21 22      (SEQ ID NO:454)
GCTTATTTTCCTCCTAGGTAATTTAATTCCAAGACACCAGGAGCTATTTTATAAAAATCCTGTGTTTGCTGGAGTAAGGTTGCCTGAGGTCAAAGATGC
(((...(((.(((((...((((((((((((((((.(((.........))))))))).)))))))).))))))))))..)))...))

Mmd_157
cand670 probe9                1  2  3  4  5  6  7  8  9 10 11 12 13 14 15 16 17 18 19 20 21 22      (SEQ ID NO:455)
GGCCACAGCTGCTGCGAGCAGCAGGATGAGGGTTGACCTATATCTGTCCTCTGTAGGTCAACCCCCGAATTTGTTTGTAGAAGCTTCAGTC
(((...(((.((((((((((..((.(((((((((((((((...))))))))))))))....)))))))))).)))...)))

Mmd_158
mmHP207304B probe4            1  2  3  4  5  6  7  8  9 10 11 12 13 14 15 16 17 18 19 20 21 22      (SEQ ID NO:456)
GTCATTTAGAATGATGTGCACAGGGTAAATTCATTGGGCAGCATGTGTTCAAGGACTCCCTGTAGCATTGAGATGAC
((((((.....(((((..((((....(((..(((((((.....))))))..))...)))).))))))).)))))

Mmd_159
cand625 probe3                1  2  3  4  5  6  7  8  9 10 11 12 13 14 15 16 17 18 19 20 21 22      (SEQ ID NO:457)
CTGTTGGAAGGTGGTCAGAGAGCAGGAAATGGCTTCTAATTAGTAGTGTCCTCACAGGATGCAACTGCAGAAGACAATTTCCTGTCCCCTTATTGGATGG
(((((.((((.((......((((((......(((((..((((.(((.....)))))..)))).))))))...))))))))))))..)).))))

Mmd_162
cand339 probe12               1  2  3  4  5  6  7  8  9 10 11 12 13 14 15 16 17 18 19 20 21 22      (SEQ ID NO:461)
GTAAGAAATGAGAAATTTTTAGGGCCATTGAACACCACGTATTTGCAGTGTTCAGTAGCCCTGAAAATTTCTCATTTAAGC
.....(((((((((((((((...((((...((.....))..)))...)))))))))).)))))))....

Mmd_163
cand378 probe7                1  2  3  4  5  6  7  8  9 10 11 12 13 14 15 16 17 18 19 20 21 22      (SEQ ID NO:462)
GCTAAATCATTGCCAGTAGTTTCCAAGACATTCCGCTAGGCTAAGCAAATTGCCCTAAGTGGTAGTCAGAAACGACTGGCATGGTACTGT
.....((((..((((((((((...(((.....((((...(((.....))).)))).))).)))))))))))....

Mmd_164
cand658 probe20               1  2  3  4  5  6  7  8  9 10 11 12 13 14 15 16 17 18 19 20 21 22      (SEQ ID NO:463)
GGGATTTAATGGATCCCCATCCTGTCTTTTGCTACACATTCACAAATTATTATTTACTGAGTGCAGAGCAAAAGGCATGGTGGGTATCTATTTGGTTAC
..((((.(((((((.((((((.(((((((((...((((((.((((.....))))..))))))...)))))))))).))))))..))))))))...

Mmd_165
mmHP3434196 probe13           1  2  3  4  5  6  7  8  9 10 11 12 13 14 15 16 17 18 19 20 21 22      (SEQ ID NO:464)
ACCTAGGAGATTGGCTGTAGGGGCTTCTGAGTCTGATGCCCTTATATCTTAAGGGACATGAGGATAGTCAGTAGTCCAATGTCCCTCTTGATGGT
((((((((((...(((....(((((.((((.(((((((((.....)))))).)))..)))....)))).)))))...))).)))))...))
```

FIG. 2: Con't.

Mmd_167
cand711 probe18    1  2  3  4  5  6  7  8  9  10 11 12 13 14 15 16 17 18 19 20 21 22    (SEQ ID NO:466)
GGCGGTAGCCCAAGGTTTGCAGGCCTGGCCGAATGACCAGGGCAATGGAAGGAAGTCGTGGTCGTCGCGGGCGTGGGGAATGGGCTTACCGGC Mmd_169
cand636 probe14    1  2  3  4  5  6  7  8  9  10 11 12 13 14 15 16 17 18 19 20 21 22    (SEQ ID NO:467)
GTTGATGTCCGTGCCTCACTGTTTGTTAAATATTCTGACCCGGTCACCCTGGGTCAGGGTGACTGACCTGAAGGGTGAGCAGGAGGAAATGATAAGAGC Mmd_170
cand51 probe4      1  2  3  4  5  6  7  8  9  10 11 12 13 14 15 16 17 18 19 20 21 22    (SEQ ID NO:469)
TTTGCTGTGAAAATTGCAAATGTTTGCCTCAAGCAAATATGTGAAAATTTGCAATTTGTTGTAGGTGTGGAATTTTGCTATTTTTCACAGTGGA Mmd_172
cand650 probe9     1  2  3  4  5  6  7  8  9  10 11 12 13 14 15 16 17 18 19 20 21 22    (SEQ ID NO:471)
TTTCAAGTAGTCAAATTCTGGCTCATGGCTCTGGAAGGTGCTGTAAACATTGTATTCTCCTCTGCTATGAGACTGGATTTTGTTCTCACTGGGG Mmd_173
cand687 probe19    1  2  3  4  5  6  7  8  9  10 11 12 13 14 15 16 17 18 19 20 21 22    (SEQ ID NO:472)
TATGGATTTTCTTTCTCAATTGCTACGGAGTCACCCTGAGGCTATTAATTTGGGCTATTAGCTGAGGGTGATTTCAAAATCCATA Mmd_174
mmHP2021933 probe2  1  2  3  4  5  6  7  8  9  10 11 12 13 14 15 16 17 18 19 20 21 22    (SEQ ID NO:473)
GGAGAACAGCTTTAAAGTTTAGTCACTCTGATGAATGTAAAAGCTTCTATCAGTGACAGGTTGACAGAGAAAGCTGTTTTCC Mmd_176
cand651 probe26    23 24 25 26 27 28 29 30 31 32 33 34 35 36 37 38 39 40 41 42 43 44    (SEQ ID NO:475)
AGTCTCCAAAGACAATTGTGAAGGGATTGTGTTTGACTGATCAATCAAAGGCAGCCCCCCCTTGCTTGTCTTCCGAGACT Mmd_177
mmHP1442327 probe17  1  2  3  4  5  6  7  8  9  10 11 12 13 14 15 16 17 18 19 20 21 22    (SEQ ID NO:476)
TAGAAAAGGCAATTAAAATCCACAACTGACTTCCTTCCCGTGTCCAAGGCGAGGGACAGTGCGTGGGTGTGTGCCCTTTTA Mmd_178
cand102 probe21    1  2  3  4  5  6  7  8  9  10 11 12 13 14 15 16 17 18 19 20 21 22    (SEQ ID NO:477)
GTCTGCCCTGGAATTAGGTTTTATCTTAAGTCCACACTGGATCCTCTGGATGGGTCCACTGAGGATTTTGAAGGAAGCATAATTCCTTGAC Mmd_180
cand859 probe42    23 24 25 26 27 28 29 30 31 32 33 34 35 36 37 38 39 40 41 42 43 44    (SEQ ID NO:480)
GAGGAAGGGAGCGGCAGCAGTGAAGGATTTGAGCCCCCTGCCGCAGATGGGCAGTTCTCTGGGGCCAGGAATCAGCTGCGCCGCCCCCAGTATC Mmd_181
cand723a probe8    1  2  3  4  5  6  7  8  9  10 11 12 13 14 15 16 17 18 19 20 21 22    (SEQ ID NO:481)
CCGAGACTTTGAAAACGAACAGAGACCGAGATCTGGATGCAGATCTTGAGCGAGAAGAGCGAGACCCAGACTTGGATTTGTTTGTTTTGACATCTTGG Mmd_182
cand520 probe21    1  2  3  4  5  6  7  8  9  10 11 12 13 14 15 16 17 18 19 20 21 22    (SEQ ID NO:482)
GGTTTGGAGGTGGGCCTGACATCCCTGAGTGTATGTGGTGAACCTGAACTTGCCCTGGGTTTCCTCATATCCATTCAGGAGTGTCAGCTGCCTCTTCGCT

FIG. 2: Con't.

```
Mmd_184                    1  2  3  4  5  6  7  8  9  10 11 12 13 14 15 16 17 18 19 20 21 22        (SEQ ID NO:484)
cand405 probe12
GAATGACTAAACAGCCCTGCATATATTTCTGGAATACTTGGAAATGCCTGTTATTTCTGGAAATGTGTGCTTGTTCAGGTTATTC
(((((((((.(((((....(((((((((((..(((.(((..(((......))).)).....))).)).))))))))))))))..))))))))

Mmd_185                    1  2  3  4  5  6  7  8  9  10 11 12 13 14 15 16 17 18 19 20 21 22        (SEQ ID NO:485)
cand439 probe12
CCACCAGACAGAACGGACGCTGCAGCCTCTGCAGGGACTAATCTGTCTGTGGGGATGG
(((((..(((((((((..((.(.((((((...)))))).).))..)))))))))..))))))

Mmd_186                    1  2  3  4  5  6  7  8  9  10 11 12 13 14 15 16 17 18 19 20 21 22        (SEQ ID NO:486)
cand944 probe6
CTGCCTACTCCTCAAAACTTCCGAGGCTACTTTTTGATTGGGATAAAAGTGCACATACTGATTTTTTAAAATGTGGCTTTAATTAATGGTGGGTGGGCAG
((((((((((.(((.......(((((((((((((..(((.(((....))))).))))))))))).))))))))).))).....)))))))))

Mmd_189                    1  2  3  4  5  6  7  8  9  10 11 12 13 14 15 16 17 18 19 20 21 22        (SEQ ID NO:489)
cand579 probe3
AGGTACTTTCAAAGCAATGTTTGACAGGCACAGGGACAAATCTTGTTAACAAGTAAGAGGATTTGTGCTTGGCTCTGTCACATGCCACTTTGAAAACCT
((((..(((((((((...((((..((((((((((.((((((((((((.(((....))).))))))))))).)))))).))..))).))))...)))))))))))

Mmd_190                    1  2  3  4  5  6  7  8  9  10 11 12 13 14 15 16 17 18 19 20 21 22        (SEQ ID NO:491)
cand147 probe17
TGGCCTGGCTGGCGGCGCTGGCTCTGGGCCTCAGACACTCTGAATCGCCAAGGTCTGAGCTCAGGGCCTGGCCCCCTTCCCAGGCTA
((((((((((..((.(.((((((((((((..((((((.((.(((.....))).))))))))))))))))))).))))))))....))))))))

Mmd_192                    1  2  3  4  5  6  7  8  9  10 11 12 13 14 15 16 17 18 19 20 21 22        (SEQ ID NO:493)
mmHP1050998 probe13
GCCAGGAAGAGGCACATGAAACTGAACACAGTGTCTGGGCTAGCGCCTTGAATTCAGAATCAGGAAGTCATGGTTCTATTCCTGGC
((((((((((..(((((...(((((..((....(((((....))))...)))).....))))).))))))))))))

Mmd_193                    1  2  3  4  5  6  7  8  9  10 11 12 13 14 15 16 17 18 19 20 21 22        (SEQ ID NO:494)
cand372 probe7
TGGCAAGTGGAGGAGCAGCAGGGTGAAACTGACACAGTGCTGGTGAGTTTCACTTTGCTGCTCCTCCTGACTCCCA
.(((..(((((((((((((((((((((.((.(((....))))-)))))))))))))))))))).))).)).

Mmd_195                    1  2  3  4  5  6  7  8  9  10 11 12 13 14 15 16 17 18 19 20 21 22        (SEQ ID NO:496)
cand450 probe11
CTGTAAAGCCTTTACTGCCACTTGTTAAGGAAGACCTGTATAGCTCACTCGTGAGTAATAAGGCGGTCAACCCAAACTCAGGCACTAAAAATTTTATAG
(((((((..(((((.(((....(((..((((.((((.....)))).))).....))))..)).))).))))))))))

Mmd_196                   23 24 25 26 27 28 29 30 31 32 33 34 35 36 37 38 39 40 41 42 43 44         (SEQ ID NO:497)
cand743 probe27
AGAAACATCTCAAAACCTGCTGACAGCATTTTCACTATTAGCGGCAAACAAATCAACTATAATTAAAATGCTGTCAAAGTGATTGGAGATTTTTCT
(((((.(((((....(((..(((((((((........(((.(...........)..)))))....))))))))))).))....)))))).))))))

Mmd_197                    1  2  3  4  5  6  7  8  9  10 11 12 13 14 15 16 17 18 19 20 21 22        (SEQ ID NO:498)
cand127 probe3
AATCTGAATCTTGGAGGCAGGTGCTCACATGTCCTCCTCCATGCTTATAAATACATGGAGGAGGCCATAGTGGCAACTGTCACCATGATTGATT
.....((((.((((.(((.(((((((((((((.((((((((...))))))))).))).)).)))))))))))).))))....

Mmd_198                    1  2  3  4  5  6  7  8  9  10 11 12 13 14 15 16 17 18 19 20 21 22        (SEQ ID NO:499)
cand595 probe11
GGTGGGCGGGGGTTCCTGGCTGACCTCACTCCTGTACTGTTTGTTTGCGGGCTTGTAGGGGGAGAGGAGGACATTTTGGAATCCTTTGTGTCAAATC
....(((((((((((..((.((((..(((((.(((..(((((((....)))))..)).))).)))))..)))).)).)...)))))))))))....

Mmd_199                    1  2  3  4  5  6  7  8  9  10 11 12 13 14 15 16 17 18 19 20 21 22        (SEQ ID NO:500)
mmHP909030 probe18
AAGCACTTAATTGTGGGTGCAGTTAGTCGAGGCGGGCACTCTCTGCAGATTTCAGGGGTGAAGAAACCTAATTATACCTGCAATTGAGTGCTT
((((((((((..(((((.((((((......(...((((.(((........)))...)...)))).))))))..)))))))))))))))
```

FIG. 2: Con't.

Mmd_202
cand831 probe34 (SEQ ID NO:505)
```
                        23 24 25 26 27 28 29 30 31 32 33 34 35 36 37 38 39 40 41 42 43 44
GTGGGAATTCGACTTTGCATCTCTACATCTGTAAACTGAGGAACACTTTCAGTGCTCTCAGTGATGGGTGAGATGACATGTTTGAGCCGAAGAAGC
...(((...((((...(((((((..((((...(((((((..((.....)))..))))))))))...)))))).)).(...))))..))......
```

Mmd_203
cand394 probe43 (SEQ ID NO:506)
```
                        23 24 25 26 27 28 29 30 31 32 33 34 35 36 37 38 39 40 41 42 43 44
GCAGAAATAATCATGTAATCATCTTGTAATTATATGGTACTTACTATGCAATTACATAGTAAACACATTGTAAATTCAAAATAATTACATGGTTATTTGC
(((..(((((((((((((..((.(((...(((((..((..(((((((.....))))))).-)).-.))))..)))...))).)).-))))))))))))))
```

Mmd_204
cand480 probe13 (SEQ ID NO:507)
```
                         1  2  3  4  5  6  7  8  9 10 11 12 13 14 15 16 17 18 19 20 21 22
CCCTGGCAGCAAGCTGCGCTTCGGAAACTGTTGACTCAGAGGGTGGCCTGGCGGCCAGCGTCTGATGTCAGCCTGGAGCCCGGCCGCGCCGGGG
(((((((.((..((((.((((((.....(((((((((.(.((((....)))).)).))))).)))))))))).)))).)))))))
```

Mmd_205
mmHP1788264 probe19 (SEQ ID NO:508)
```
                         1  2  3  4  5  6  7  8  9 10 11 12 13 14 15 16 17 18 19 20 21 22
AGTGGAAGGAGAGGAGATAGCGCGGATCGCTGGTGGGGAATGTTAATGGGCGGGAGCCCAGGCCGCTGGCCACCGAGACGTGGGTATCTCCTCCATT
.........(.((((((((..((((.((..((((((((....)))))).)).))..)).)))).))).))).........
```

Mmd_206
cand274 probe30 (SEQ ID NO:509)
```
                        23 24 25 26 27 28 29 30 31 32 33 34 35 36 37 38 39 40 41 42 43 44
CTGGCAACCATGAGGCCCAGATGCTAAGCACTGGAAGATATTTCTTCCAATAGCAGCATCTGGCATGCTGGCAG
(((.((..(((....(((((((((..((.((((((.....))))))...)))))))))).))..)))
```

Mmd_207
cand689 probe25 (SEQ ID NO:510)
```
                        23 24 25 26 27 28 29 30 31 32 33 34 35 36 37 38 39 40 41 42 43 44
TCCGCTACCAGAAGCAGCTGCAGCACAACTATATCCAGATGTACCGGCGTAACCGGCAGCTGGAGCAGGAACTGCAGCAACTGAGCCTGGAGCTGGA
((((((.((((.((..(((((((.....((....(((((...((..(((((.....)))))..)))))))...)))))))..)).)...))))))))).)))
```

Mmd_208
cand640 probe13 (SEQ ID NO:511)
```
                         1  2  3  4  5  6  7  8  9 10 11 12 13 14 15 16 17 18 19 20 21 22
AGATGATCCTTCCCCTTACCTGTCTTTCTATCAGTGTAGCTGAAGCTAATTCAGTGCACTGATATAAGATTATTATCAGGTTGAGCACTTATCT
(((((((...(((..(((...(((((((..((((((((.......))))))))..)))))))...))).....))))))
```

Mmd_209
mmHP1378833 probe21 (SEQ ID NO:512)
```
                         1  2  3  4  5  6  7  8  9 10 11 12 13 14 15 16 17 18 19 20 21 22
ATTTGGGCAGAAATTCTTGACTCAGCTCCCAAGGAATGTAAACCAGACCCTGGGAGTGGAGGAGAGTTAAGAAAAATCTCAGAT
((((((....(((((((..(((((((..((..(.....))..))...))))))......)))))))).....))))))
```

Mmd_210
mmHP2825016 probe18 (SEQ ID NO:514)
```
                         1  2  3  4  5  6  7  8  9 10 11 12 13 14 15 16 17 18 19 20 21 22
GGTGAGACAGTCAACAGCCCAGTGTCCCTCTTGATGGCACTTTGGAGATGGCTGGAGTGCTCTGTAAGGCCTGGGCTCAATGACCCTCCTCATC
(((((...(((..((((((..((..(((((((..(......)..))))))).....)))))))))))).....))))))
```

Mmd_211
cand881 probe38 (SEQ ID NO:515)
```
                        23 24 25 26 27 28 29 30 31 32 33 34 35 36 37 38 39 40 41 42 43 44
GCGTCAAAAGGCTTATTTTGGGCCTCAATCCTCTCCTTCTCCGATTTTCGGAGGTAAGGAGCAGCTTCGCCAAAAATAGCCATCTCCGC
(((......((((.(((((.(((....((((((((((((((.....))))))))..)))))...)))).)))))))).....)))
```

Mmd_213
cand751 probe17 (SEQ ID NO:517)
```
                         1  2  3  4  5  6  7  8  9 10 11 12 13 14 15 16 17 18 19 20 21 22
GTCTTCCTGTAGCAACAGTGGCAGCAGCTCTCTGGTTTCCTGTGGTGTAAACAGGAAGCCAGACTGTGTCAAAACGGTAGTCTACAGCTGTGAGAAGGC
((((((((((((.((.(((..((((((((((......)))))).......))....))))...)).))))))).))))))
```

Mmd_214
mmHP432573 probe3 (SEQ ID NO:518)
```
                         1  2  3  4  5  6  7  8  9 10 11 12 13 14 15 16 17 18 19 20 21 22
CTAGGAGATAAGTTGGAGGGTTATCTAGGAGTGATGTCCCCCTGTTTTGTGTAACATGGGGGCAATCAACAGCCTAATGTCCCTCTTGATGGCACCTAG
((((.(.......((((..(((.((((.(((.((((((((..(((.......)))..)).)))))).))).)))).))).......).)))))
```

FIG. 2: Con't.

```
Mmd_216                       1  2  3  4  5  6  7  8  9 10 11 12 13 14 15 16 17 18 19 20 21 22    (SEQ ID NO:520)
mmHP855413 probe3
TCAGCATGGAATGAACTGTTAGACTATAGCCAGGGCCTCTGGATTCTATTAGAGGCTCCTGGAATTTCTGAACCACTCCTAAGTTGA
((((....(((.(((......((((......(((((((((((((......)))))))).)))))....))))).)).)))...)))))

Mmd_217                       1  2  3  4  5  6  7  8  9 10 11 12 13 14 15 16 17 18 19 20 21 22    (SEQ ID NO:521)
cand448 probe8
TTGAGCTGTAATTCCACTGAGGGTTTCTAGTGACTCCAGCTTCACACTTGTGGTTATAGTATTCCCAGAACCCCTCGGTGGAGTGATTTCCTGAA
..........(((((((((((((.((((.(...(((..(((((.((....)).)))))..))).....).)))).)))))))))))))......

Mmd_218                       1  2  3  4  5  6  7  8  9 10 11 12 13 14 15 16 17 18 19 20 21 22    (SEQ ID NO:522)
cand418 probe16
CGGATTCTTCTCTGTTTTAGGGTTCTTGTGGTGCCTGCTGGGCTTTCAGTGCTGTGGGGGCCCTTGAAGGGCAGCTGAAGCTGAAAACGGGGAAGCTG
.....(((((((((((.((.(((......(((((((...(((((((.((....)).)).))))).....)))))))))).)).)))))))))))...

Mmd_219                       1  2  3  4  5  6  7  8  9 10 11 12 13 14 15 16 17 18 19 20 21 22    (SEQ ID NO:523)
cand478 probe21
GAGCGGAGTCTCCTGGACATAGTGTTCTGGGGGACTTTTGGGTGTCTGAGCACCACTTTTGGAGGGAGACTTGGCTC
((((.((((((((...((.((((...((.(((.(((....))).))).)).)))).))..))))))))).)))

Mmd_220                       1  2  3  4  5  6  7  8  9 10 11 12 13 14 15 16 17 18 19 20 21 22    (SEQ ID NO:525)
cand921 probe13
GGTAAAACCTACTTGAAAGGAGTGTTTGTAGGTTCTAGTAAAGCTTTGTGACGGAGTATTGCAGGGCCTGCAGACACATTCTCCTCAGAAGTGTGACT
(((...((((.((.((.(((((((((((((.((((((.((((....)))))).))))))))))))))))).))..)))).))..))..)).)))

Mmd_221                       1  2  3  4  5  6  7  8  9 10 11 12 13 14 15 16 17 18 19 20 21 22    (SEQ ID NO:526)
mmHP1210358 probe10
CTCTGCCCCTGCTTTGTCTTTCAGAATAACTGCCATGGAAGGATGCTCCTCCTGCCAATTGGCACTTATCAATGACATCGAGGGAGAGGGACAGAG
(((((((((((.((((.....(((..(((((((((((.((((......))))).)))....)))))..)).)))...))))).)))).)))))

Mmd_222                       1  2  3  4  5  6  7  8  9 10 11 12 13 14 15 16 17 18 19 20 21 22    (SEQ ID NO:527)
cand166 probe4
GCTGAAGAGGAACCAGCCCTGATGGTGTGTCCGCCAAGACATGGAAGTGAGAGGTGGGTGGAGGCCCCATTGGGGTTGGTCGGCTCTCAGC
((((((.(((((((((...((((.((((((((.....)))........)))))))))).))))))))).))))))

Mmd_223                       1  2  3  4  5  6  7  8  9 10 11 12 13 14 15 16 17 18 19 20 21 22    (SEQ ID NO:528)
cand642 probe13
GCTGTAATTCCATCTTGGTGTTATGGTGACATGAAAATCCACTCAAGCTGGGTTGTCAGGGTTTATGAAGTTATCAAAGCCCCTTGATGGAATTATAGC
((((((((((((((..((.((((.(((((((.(.((((((((((.....)))).....)))))).).).)))))))).))).)).))))))))))))

Mmd_224                       23 24 25 26 27 28 29 30 31 32 33 34 35 36 37 38 39 40 41 42 43 44    (SEQ ID NO:529)
cand446 probe26
TCATTGTCATCGTCTTGGAGGGACATCATTGTGTCACTAGTCTGCCAGGTTGTTCAGACAGTCCGACCTGATGTCAAGCACCAGGATGATGACATGG
.(((.(((((((((...(.(((((((.(..(.(((((((((.((((.........))))..)))))))))....).))))))).)))))))))))).

Mmd_225                       1  2  3  4  5  6  7  8  9 10 11 12 13 14 15 16 17 18 19 20 21 22    (SEQ ID NO:177)
cand458 probe12
TGCATTTCAGAGAATATGCATTTTACCTTTGGGAATATGTTAATTTCAGGCAGCATTCCCTATGGGAAAGGTGATACCAGCTCTGATATGCA
.(((((.(((((......((((((.(((.(((((((.((((......))))..))))))).)))..)).)))))........)))))).))))

Mmd_226                       1  2  3  4  5  6  7  8  9 10 11 12 13 14 15 16 17 18 19 20 21 22    (SEQ ID NO:530)
cand320 probe1
TTAATGTATCCATTTTTCTCAGTTAGTGTCAGGTTTCATTAGGAAACACGGGAGGCCTGACATTAATCGCATGAAAAATGTGTCTCAGGGA
....((..((((((((.(.(((((((((.(((...)))))))))))).)...)))))))).).....

Mmd_227                       1  2  3  4  5  6  7  8  9 10 11 12 13 14 15 16 17 18 19 20 21 22    (SEQ ID NO:531)
cand869 probe3
CAGCAAGAGGCACTTTGTACTTCTGCCAGGAGACCATATGATATCTCTCAGCGACTCTCCTGCATGCCAGGAATACGGAACCATGCCTCTCAGCTG
((((.((((((((((.(((((((((((((......(((.....)))))))).)))))).))).)))))).))))..))))
```

FIG. 2: Con't.

```
Mmd_229
cand281 probe12                1  2  3  4  5  6  7  8  9 10 11 12 13 14 15 16 17 18 19 20 21 22   (SEQ ID NO:532)
GCAGCCCAGTGAAGTGGAGTTCTGTCGTTCCAGTCTGCATCTTTGTAGTTTGGGTCACAGAGACCTTTCTTTAAAATCTTCTTCACTGAATTGC
((((..(((((((((..(((.(((((((...((((.((((((....)))).)))))..)))))))............))).))))))))..))))

Mmd_230
cand330 probe21                1  2  3  4  5  6  7  8  9 10 11 12 13 14 15 16 17 18 19 20 21 22   (SEQ ID NO:534)
TATTCTCATCTTGATGTGTGGGGCTGTACAGACAGAAATGCCATTAGCATTAATGGTAATTATGCGCGTGAGTCCCCGTGCTCCATGAGAATA
((((((((((...((.(...(((((((((..((((.(((.(.((.((.(((((((((....))))))))).)).)).)))))))))))..)))).))))))))))

Mmd_231
cand589 probe13                1  2  3  4  5  6  7  8  9 10 11 12 13 14 15 16 17 18 19 20 21 22   (SEQ ID NO:535)
GTAGGTACTGATTTATGAAAAGCTGTAAAAGATCAGGTGGAACTCCGTAGGACATCGTTTACAGCTGCATGGATTGAAACCTAT
((((((..(((((((((((...((((((((.(((((..((((....))))..)).))..)).)))))))).)))))))))..))))))

Mmd_232
cand549 probe9                 1  2  3  4  5  6  7  8  9 10 11 12 13 14 15 16 17 18 19 20 21 22   (SEQ ID NO:536)
GCTTTCCTCACTTCTGTTTATTTTCAGTCACTCAAACTGACGTGTGCTGTCAGTATCTCCTCACTGTAAGTGTAAGCAGGAGTATTTAAAGAAAGC
((((((..(((((((((((((........((((((......))))))..........))))..)))))))))))))........))))))

Mmd_234
mmHP1505538 probe23            23 24 25 26 27 28 29 30 31 32 33 34 35 36 37 38 39 40 41 42 43 44   (SEQ ID NO:538)
TCCTGGAAATGCCCTTTAGGTCAGAGTCTGGGATGCAGCTTCTGACTAACAATGAAGTCCACTCCCACTTCCTCCAGACCTGGCAACCAGGG
.((((..((((....(((((((.(((.((((((((..((((....))))....))))))))..)).)))..)))..))))))))).))))).

Mmd_235
cand466 probe13                1  2  3  4  5  6  7  8  9 10 11 12 13 14 15 16 17 18 19 20 21 22   (SEQ ID NO:539)
GTGTGCTTGTTGTCGAAGATGAGGGCCTCCTGGATGAGCTGGTGCTGCTGCTCCAGCAGGTCCAGGCTGGGCTTGTAGTCCACGATGCTGCGCTC
..((((..((.((((..(((.(((((((((((((..((((.((...))..)).))))))..)))))))..)))))...)))..))))))).))))..

Mmd_236
cand113 probe9                 1  2  3  4  5  6  7  8  9 10 11 12 13 14 15 16 17 18 19 20 21 22   (SEQ ID NO:540)
GCATTTCAGGAGATTAATGGTAGACCGAAGCTAATAGCCTTTGGCTGACTCTCCAGCCATCAGCTTTTCCCAGCTGCTCATTAATTCCCAGAAAATGT
(((((((..((..((((((((((((((((...(((.(((((......)))))...))))))))))....))).))))))..)).).))))))

Mmd_237
cand733 probe35                23 24 25 26 27 28 29 30 31 32 33 34 35 36 37 38 39 40 41 42 43 44   (SEQ ID NO:541)
GCAAGATGGCGGCGCTGGCGGAGGAGCAGACGGAGGTGGCGGTCAAGCTAGAGCCTGAGGGACCGCCGACGCTGCTACCTCCGCAGGCTGGCGACGGC
((.....((.((((.(((.((((((((((((..((..(((((((...(((.(((......)).))))..))))))))..)))))).))))))))))))).)).))

Mmd_238
mmHP1679825 probe38            23 24 25 26 27 28 29 30 31 32 33 34 35 36 37 38 39 40 41 42 43 44   (SEQ ID NO:542)
CCCGCCTTGCCCGCTGGTAGGGCCTACTAGGCCGCCGGGACATCCCGGGTCTCAAGTAGGCCTAGTCTGCCAGCAAGGGCGTCCCAAAGGCGGG
((((((((((((((((((((((.((....(((..((((.((((((....)))))).))))..)))....))))))))))))..)))).......))))))))

Mmd_242
mmHP1170304 probe1             1  2  3  4  5  6  7  8  9 10 11 12 13 14 15 16 17 18 19 20 21 22   (SEQ ID NO:546)
TTCTGCAATGTTTTGCAGCCAGGCACACACACTACAGGTGCTCTCAGAGATTGAGCTGATGGCCCTGCTGTGTGCACTGTAAACAATTATTATAGAA
..(((((((....))))))).(((((((((.....((((.(((.(((.....))))))))....))))).))))))..

Mmd_243
cand129 probe40                23 24 25 26 27 28 29 30 31 32 33 34 35 36 37 38 39 40 41 42 43 44   (SEQ ID NO:547)
GAGAAGCGAAAAGTTCAATCAGTTGCCCAGATGTATGTATTGCCAAATAACAGGGTACTTGGGTACATCTGGACAGCCGAATGAACTCTTAACCCCTC
(((..(..((.(((((((.((.(((((((..((((..((((((((((....))))).)).)))))))..)))..)).)))))).)))...)))

Mmd_244
cand311 probe25                23 24 25 26 27 28 29 30 31 32 33 34 35 36 37 38 39 40 41 42 43 44   (SEQ ID NO:548)
GTGAAACATAGCCTCAGTATTTTCAGGTGATTTTAATGAACACCTGATAAAACTGAGGTATAGTACCAC
(((..((...(((((((((.((.(((((((.(((....)))))))))))))..))))))))...))..)))
```

FIG. 2: Con't.

Mmd_246  
cand410 probe35  
23 24 25 26 27 28 29 30 31 32 33 34 35 36 37 38 39 40 41 42 43 44  (SEQ ID NO:550)  
TGACCCCAAGAAACCAAAGGGCAAGATGTCTGCTTATGCCTTCTTTGTGCAGACATGCAGGGAAGAACATAAGAAGAAAAACCCAGAGGTTCCCGTCA  
.(((......(.((((....(((.......(((..((((((..((((((((((........))))))))))..))))))..))....))))...)))))..).))).

Mmd_247  
cand309 probe17  
1 2 3 4 5 6 7 8 9 10 11 12 13 14 15 16 17 18 19 20 21 22  (SEQ ID NO:551)  
GCCACTTTGAGAGCATCGGTTTTTATTTAAAAGGCTTAATTGGAAGTTTTTATTACTCCCAATTAGGCTTTTTAATTAAAAGGAAAAGTTGAGAGAGGC  
(((.(((((.(((....(((..((((((.((((((((((((((.((((.(.......)))))))))))))))).)))))))).)))))).)).)))).))))

Mmd_248  
cand811 probe37  
23 24 25 26 27 28 29 30 31 32 33 34 35 36 37 38 39 40 41 42 43 44  (SEQ ID NO:552)  
CCATTTTCAAGTGCGGTGGATTTACACTTCAAAAAGTCAGGCGCGACTTCATAATTGAATTGCACCTGATCTTTTCAAGTGCCAGGCACCGGAGCCGGG  
((...(((..((((..((((.(((((((..(((((.((((.((((((....))))))))))..)))).)))))))).)))))))..)))...))

Mmd_249  
cand816 probe3  
1 2 3 4 5 6 7 8 9 10 11 12 13 14 15 16 17 18 19 20 21 22  (SEQ ID NO:553)  
TAACTCTTTGACTGCCATGGCACAAACCATGCTGATGATTCTAGATTGTGACCGTTGTATGGTTAAGGTTGCCACAGCAGTCAAAGGGTTA  
(((((((((((((((((..(((((..(((((((((.(((....((.........)).))))))))))))...).))))..))))))))))))))))))

Mmd_250  
cand82 probe8  
1 2 3 4 5 6 7 8 9 10 11 12 13 14 15 16 17 18 19 20 21 22  (SEQ ID NO:555)  
ACCAAAGGAGCTTTTCTGGTCTATTGGGTAAATATGTATTAAAGTAATTTTTAAAATACTTATGTACTCAATAGGCTGGAAGTGGTCAATGGT  
((((...((.(.((((((((((((((((.(((.(.((((((((((....))))..)))).).))).)))))))))))))))))..).)).))))

Mmd_253  
cand48 probe12  
1 2 3 4 5 6 7 8 9 10 11 12 13 14 15 16 17 18 19 20 21 22  (SEQ ID NO:194)  
CCTTGATTTCAATGTTTCCCACTTTGGTGGTTGATCTGATAATAGGTCTTCCAACCAAAGCTGGGAAGATGTGTTCTGG  
((..(((..((((((((((((((..(((((....)))))..)))..)))))))).)))..)).))

Mmd_254  
mmHP2341379 probe21  
1 2 3 4 5 6 7 8 9 10 11 12 13 14 15 16 17 18 19 20 21 22  (SEQ ID NO:558)  
GCAATGAGCCATGGGCCAACAATGTGAGTAATGGCTAGTTTTGTTATTTTGAACTTGGGTAGTTGGCTGATGGGTGTTTATTGC  
(((((((((((((.(((((((((.((.(((((((((.......))))))....)))))).)).)))))))).)))...)))))))

Mmd_255  
cand538 probe14  
1 2 3 4 5 6 7 8 9 10 11 12 13 14 15 16 17 18 19 20 21 22  (SEQ ID NO:559)  
GTGCTGAAGTTGGTATGGCAGCCTGCACCATCCCAGTTCCCTGGAATGGGCTTGGGGTCAAAGGTTGCTATCACCCCAAAGTCTTCGCAT  
((((..((((.(((((((((.....(((((((..(((.......))).)))))))))...))))))))))....)))..))..)))...

Mmd_256  
cand960 probe22  
1 2 3 4 5 6 7 8 9 10 11 12 13 14 15 16 17 18 19 20 21 22  (SEQ ID NO:560)  
GCGGCCCGAGCCGGTAGGCCCCGAGGAGGGTTGTGGGCCCTTCTTTTTGTGAATGAAGCTCCACGGAACATCCCTCCTGGGGGTCCCCGGGAGCCGC  
((((((.(...(((((..(((((((((((.((((((((....))).)))))..)).))))))....)))))..))))))).).)))))..))))))

Mmd_257  
cand511 probe9  
1 2 3 4 5 6 7 8 9 10 11 12 13 14 15 16 17 18 19 20 21 22  (SEQ ID NO:561)  
GTGTGCTCAGCTGGAGTAATTAGAGGAAAAACCTGAGGGAAGTCTACCCCAGAAGACTCACTCAGCCTTCTCCAGCTGAGTCTCAC  
(((.((((((((((((.....((((......((((((.(((.((((........)))))).))))))..))))))))).)))...)))

Mmd_258  
cand713 probe11  
1 2 3 4 5 6 7 8 9 10 11 12 13 14 15 16 17 18 19 20 21 22  (SEQ ID NO:562)  
GGGGTGCTGCCTTCTTTCTCGGTCTGCTGGTTGGAGGACGAAGATGACGAGGAGCTGGTGCTGGCCCTCGAATCGTCATCCGACATAGCGAACCCCCC  
(((((...(((...........)))..((((((((((.((((......(((((.(((......))))))))))).))))).))))))..))))...

Mmd_259  
cand376 probe15  
1 2 3 4 5 6 7 8 9 10 11 12 13 14 15 16 17 18 19 20 21 22  (SEQ ID NO:563)  
TCCCCTGCTGCACTAAATTGACACTTGTGCAAGCAATGGCTCTCGTCAGTCACTCTGAAGCTGCTGCCTCCAGAAGTGTCGATTTAGTGCAGCGGGAGA  
((..(((((((((((((((((((((((.((....(((..(((.....(((......))))))..))).)).))))))))))))))))))))))).))

FIG. 2: Con't.

Mmd_261  
cand873 probe8      1 2 3 4 5 6 7 8 9 10 11 12 13 14 15 16 17 18 19 20 21 22   (SEQ ID NO:565)  
```
AGAATCTTCTGACAATGAAGGTAGGCGTACAACTAGGAGATTGCTGTCACGGATAGCTTCTAGCATGTCATCTACTTTTTTCTCACGAAGATCT
((((.(((((((((.....(((((.((((.((((((....(((((.((...)))..))))...))))))))..))))..)))))))))...)))))))))
```

Mmd_262  
cand360 probe7      1 2 3 4 5 6 7 8 9 10 11 12 13 14 15 16 17 18 19 20 21 22   (SEQ ID NO:566)  
```
TTACACCTGAAACTTCTCACTTGGGGGTACAATTAGCCTCTGGCGCCTTTAGAATGAGTTGCCAGTGACTAATGGTGCCCTCAAGGAAGCATTTGTAA
.(((((..((....(((((...(((((((((((.(((((.(.(((((.(((......))).)))))).).)))))..)))))))))))))))))))..)))).
```

Mmd_263  
cand568 probe21      1 2 3 4 5 6 7 8 9 10 11 12 13 14 15 16 17 18 19 20 21 22   (SEQ ID NO:567)  
```
GAGGACAGCTGGCAGAAAGTGTTACAGGTATAACCCTAATTCTCCTTGTTTCTGTTGGTGTTGTAGGAGAGATCTGTAGGCCTTTCTGTCCAGCGCTC
(((....(((((((((((...(((((((....((((.(.((.............))).)...))))....))))))))..))))))))-)))))-)))
```

Mmd_264  
cand393 probe14      1 2 3 4 5 6 7 8 9 10 11 12 13 14 15 16 17 18 19 20 21 22   (SEQ ID NO:568)  
```
AAACGCTGTGACTCAAACTCGGGGAAATTGTTCCTGTAATGGAGTTCTCAATTTATTGGTCAATTTCACCTTGATTTTGTGTCACTGTTGGTTT
((((((..(((((((.((((.((((((((((((((..((.(((((..((....)))...)))))))).).)))))))))..)).)))).)))))).))...))))
```

Mmd_269  
cand570 probe12      1 2 3 4 5 6 7 8 9 10 11 12 13 14 15 16 17 18 19 20 21 22   (SEQ ID NO:572)  
```
TCTCGGGCTCTGGGGGACTATGACTACAAGTGTGTGGATGCAAGGGCCCTACAGAGCAGCTTGTTTCTCCAGAGCCTGAGG
.((((.((((((((((((.....((((((.((((..(((.((.....))))))..)))).))))))..))))))))))))).
```

Mmd_270  
cand126 probe18      1 2 3 4 5 6 7 8 9 10 11 12 13 14 15 16 17 18 19 20 21 22   (SEQ ID NO:574)  
```
TTGGGTGTGGGGATAGGGGCACTTCTGTTCCTGATAACCTTATTATGTGTTTATCAGGAGCAGACACTGCCCAGGTTGTCACGACAACCAG
.(((.((((((.(((..(((((((((((((((((((.(.........)..))))))))))))))...)))))))..)).))))))....))).
```

Mmd_271  
cand377 probe20      1 2 3 4 5 6 7 8 9 10 11 12 13 14 15 16 17 18 19 20 21 22   (SEQ ID NO:575)  
```
CTTGGAGGCTTTGCCTCATCCACAGGCATTTGGCATCGGAGATGGAAAATTTCACTTGTCAGGTCACCATGGAAACAAGCAGAGCCACTGAG
((..(.(((((((....(((((.((((..((.((.((((((....(((((.....))))))..))))))..)).)).)).))))))))))....)))))
```

Mmd_272  
cand19 probe18      1 2 3 4 5 6 7 8 9 10 11 12 13 14 15 16 17 18 19 20 21 22   (SEQ ID NO:576)  
```
TTAGCATGTTAATAGGTCTTTGTGCCCAAAGGCTTTGGATTATAAATTATCAAGACTGCATTAGCCAGATGGGCAGGATTAATTAGCATGCTAG
.((((((((((...(((((....(((((....(((...)))....))))....)))))))))))..))))))))).
```

Mmd_274  
cand275 probe10      1 2 3 4 5 6 7 8 9 10 11 12 13 14 15 16 17 18 19 20 21 22   (SEQ ID NO:578)  
```
GGGTGGCTGGGGTCATACATCTGTGGGTAAGGATAAGCATGCAAGTATTGTATGTAGGACTGGTGCTGACTCATGGGTGAGGACACGGCCACTC
(((((((((..(((..(((((((.(((((.((.((.......)))).)).)).)))))))..)))..)))))))))
```

Mmd_275  
cand616 probe16      1 2 3 4 5 6 7 8 9 10 11 12 13 14 15 16 17 18 19 20 21 22   (SEQ ID NO:579)  
```
GGCACCAGCTCCGTCAGCTCCAGCCCCAGGTCCTGCGCGATGCGGCCCACAAAGGTGCCGTGTTTGGCCTCCTCTGGGACGGAGTAGCGGAGCTGGCC
....(((((((((((..((((((.(.((((((((.....((..(((((((((.....))))))))).)).)))))))))))))))))))...))))))))).
```

Mmd_276  
cand723a probe15      1 2 3 4 5 6 7 8 9 10 11 12 13 14 15 16 17 18 19 20 21 22   (SEQ ID NO:580)  
```
CCGAGACTTTGAAAGCAAACGAGACCGAGATCTGGATGCAGATCTTGAGCGAGAAGAGCGAGACCCAGACTTGGTTTGTTTGTTTTTGACATCTTGG
((((((...(..(((((((((((.((((((((.(((.(((...(((....)))...)))....))))))))))))))))))))))).)....)))))))
```

Mmd_277  
cand318 probe13      1 2 3 4 5 6 7 8 9 10 11 12 13 14 15 16 17 18 19 20 21 22   (SEQ ID NO:581)  
```
TAGTTAGCTAATTGCAGGTGCAATTGGCCACTTGCTCCATCAGATGAAGGGTAAGTGGTTAATTGAACTCATGAGTGACCTA
..((((.(((...((.((((((((.((.(((((((.((.((....))..))))))))))..)))))))))..)))))).))...
```

FIG. 2: Con't.

```
Mmd_279                     1  2  3  4  5  6  7  8  9 10 11 12 13 14 15 16 17 18 19 20 21 22    (SEQ ID NO:583)
cand666 probe18
GGCTTGTTTTGAGTTCATTGTTCAGCAGATGAGCTAGTTCAGGTTTTAGCTTTCAGCAGTTCATTTGATTGAACTTGGGACCAATAAAAGTGAGAGGCC
(((((((.((((((...(((((((((((((((((.((.((((....)))).)).))))))))))))))).)))))...))))))))....)).)))))

Mmd_280                     1  2  3  4  5  6  7  8  9 10 11 12 13 14 15 16 17 18 19 20 21 22    (SEQ ID NO:585)
cand860 probe10
CCTGGCTGCAAGAGGCTTGCTGCCTAGTCCGAGGCCAGCAGTGTTGTGTCTGGCCTGTAAGAGGCAGGTAGCAAGCCGAGACTATGTCCAAAGG
(((....(((((.(((((((((((((.((((.((((((((......)).))))))))....).))))))))))))).....))..))))....)))

Mmd_283                    23 24 25 26 27 28 29 30 31 32 33 34 35 36 37 38 39 40 41 42 43 44    (SEQ ID NO:588)
cand680 probe23
GTTAGCGCAGAGCTTCAAGCTAAGCAAGGCATCTCAGCACGAGGTGTCAAACATAAGACAGCTAATGCTGGAAGCCAGAGCAAGAAGGCTCTTCTTGAC
(((((.(.(((((((((...(((((.((.(((((((.((..........))).))..))))))).))).))).)).)))))..))))).))))))

Mmd_284                    23 24 25 26 27 28 29 30 31 32 33 34 35 36 37 38 39 40 41 42 43 44    (SEQ ID NO:589)
cand149 probe35
ACGTTAGTCCATTTGCTCAGCAGCCGGCCCTTCCACGATGGACGCCATCTTGGGAGCCGCCAATGACAACAAACGGCCTGACGT
(((((((.((.(((((.(((((((((.(((((((((...)))).))...)))).)))))).))))).))

Mmd_285                     1  2  3  4  5  6  7  8  9 10 11 12 13 14 15 16 17 18 19 20 21 22    (SEQ ID NO:590)
cand488 probe10
ATTAATTGAGCCAAGCCAAGCTCAACCTTGAAGATGCTACTTTGGTGTGTTCCCGAAATAGGGCTGAGCTTATGGCTGGTTCTTACTTGTTAGT
........(((((.((((((((((.((((.(((((((.....))))..))).........))))))).).)))..))))))))...........

Mmd_288                    23 24 25 26 27 28 29 30 31 32 33 34 35 36 37 38 39 40 41 42 43 44    (SEQ ID NO:593)
mmHP1540701 probe28
TTGGCTGTTTTCCTATTAGCATATGAGGAACCTAGGACTGTCCCTTGTTGTCAAGGTAACAGCTATTCCTTGGGTAGCTGCAATAGAAAAGAAGCCAA
.(((((.((((.(((((((((.(((((((((....((.(((((((....))))).....))))))).).)).)))))).)).)))).))))-))))).

Mmd_290                     1  2  3  4  5  6  7  8  9 10 11 12 13 14 15 16 17 18 19 20 21 22    (SEQ ID NO:596)
mmHP1876696 probe21
GCTGGCCTCACTGACCCAGGAATTCATAGCAGGAAATTAGGCAGGATTAAGGAAGGCTAGTTTTCTTGTGTGAGAAGGGTAAAGGTGGAGGAAAGC
(((..(((((((((.((((((....)))))))).))))))).))).))))).....))).))).

Mmd_291                     1  2  3  4  5  6  7  8  9 10 11 12 13 14 15 16 17 18 19 20 21 22    (SEQ ID NO:597)
cand498 probe20
GTCGCAGCGCGTGGCCGATCGCCTGGGCCTGGAGCTGGGCAAGGTGGTCACCAAGAAGTTTAGCAACCAGGAGACCAGGTGGGAGCCTCGCTGGGGC
(((.((((.(..(((((((....(((((((.(.(((((.(((((....(((.))))...)))))).)))))).))))))...)))))))..)))).)))

Mmd_292                     1  2  3  4  5  6  7  8  9 10 11 12 13 14 15 16 17 18 19 20 21 22    (SEQ ID NO:598)
cand710 probe3
AGCTTCTTTTCCCGGGCGAGCTGCCTACGGGTCCGCTGCTGGCACACAGCCAGCTGGGTCTTGGCGGCTTTGTTGCTGGGATAGAGCT
((((.((((..(((((((((((((((((...((.(((.(((((......))))))).)).))))))))..))))))))).))))).

Mmd_293                     1  2  3  4  5  6  7  8  9 10 11 12 13 14 15 16 17 18 19 20 21 22    (SEQ ID NO:599)
cand138 probe15
GCTTGAGCTGAGGGGCCTACCTCAAGCTATGGAAAAAATTAGGGTTAGACAAGAAGCATTTTTTTATAGCCTGAGGAAGGCCCATGGCAAGAGC
((((..((((...((((((((.(((((((((((((((((((((.((.(.......)...))....))))))))))).))))).)))))...)))).

Mmd_294                     1  2  3  4  5  6  7  8  9 10 11 12 13 14 15 16 17 18 19 20 21 22    (SEQ ID NO:600)
cand214 probe3
CGTCACCTAGGGATCTTGTTAAAAAGCAGAGTCTGATTGAGGGGCCAAGATTCTGCATTTTTAGCAAGCTCTCAAGTGATG
((((((...(((.(((((((((((((((((((..........)))))))).))))))))))))...))))))

Mmd_295                     1  2  3  4  5  6  7  8  9 10 11 12 13 14 15 16 17 18 19 20 21 22    (SEQ ID NO:601)
mmHP2669067 probe14
GGTCAGGATGCTTTGTTGTCTGGATTCTCAGTTGCTTGTATTGGCTTTTGAAAAGGTCATTATGAGAAAAGGGATCTGAATAGCAAAAGGATTCCAGCT
(((...((((.(((((((((...(((((..((.((.(((((....)))))..)).)).)))))..))))))))).)))))...))).)))).)))))
```

FIG. 2: Con't.

```
Mmd_297
cand461 probe9                1  2  3  4  5  6  7  8  9 10 11 12 13 14 15 16 17 18 19 20 21 22   (SEQ ID NO:603)
TAGACTAATTAATGTTTGAGTGTTTAAACACAATGCCTTTACAGAAGCAATGGCATTATAATGTGTTGGGACACTCTAGCATTGTAATTAGCACTA
..(.(((((((((((.(((((((...(((((((((((..............)))))).....))))))..))))))).))))))..)))))))....

Mmd_298
cand248 probe6                1  2  3  4  5  6  7  8  9 10 11 12 13 14 15 16 17 18 19 20 21 22   (SEQ ID NO:604)
CTTCAGCAACCTTGCAGCCCCATCGCTCATTTGCATAATGGATGCCTTTTTATCCATTATGCAAATGGTATGAGAGGAAAATTAGGCAATAAGGGAAG
.........((((..((((.(((.(((((((((((((((((....)))))))))))))))))...)))..))........))))..))))....

Mmd_299
cand686 probe10               1  2  3  4  5  6  7  8  9 10 11 12 13 14 15 16 17 18 19 20 21 22   (SEQ ID NO:605)
GGTGATGAATGTATATTGGTAAGGAGGGTGAAGTTGAAGGGGCAGAGACCTCTCAAATGAATTGACTTTTCTTTACCAACATATTCAGAACACC
((((.((((((((...(((((((((((((.((..(((((.((((.....))))..)).)).)))))))))))))..)))))))...))))

Mmd_300
cand420 probe12               1  2  3  4  5  6  7  8  9 10 11 12 13 14 15 16 17 18 19 20 21 22   (SEQ ID NO:608)
CAGCTAGAACTCCCCTGGCGAGTGGAAACAGCTTTTTACCGCGGCTGTAGCTGTGGTTTTGGAATTTTCCAACGCCCCCTGTGATTGGCTG
(((((((.((......(((...(((((((.((...(((((((....)))))))..)))..)))))))..))))....)).)))))))

Mmd_301
cand445 probe4                1  2  3  4  5  6  7  8  9 10 11 12 13 14 15 16 17 18 19 20 21 22   (SEQ ID NO:609)
GGCTATGATTCCACTGAGGGGTGCTGGCGGTGACATGTGCCATGAAGTCAATCTGAGTGGTTTATCACCAGAACTCCCAGGGTGGAATTATAACC
((.((((((((((..(((((.((((.(.((((((..((......)).))))))..)))))))).)).)))..))))))))))..))

Mmd_302
cand615 probe36              23 24 25 26 27 28 29 30 31 32 33 34 35 36 37 38 39 40 41 42 43 44   (SEQ ID NO:610)
GCAGTGCCTAAGGAATTAATGACCAGCTGAGGTTAATGAGTCCCCACTCAGCTCCGGGCCATCAACTCTCCCAGCTGGCCATTAATCCCCTGGAAATGC
(((...((....((.((((((((.((((((((.(((...(((......)))...)))...)))))))..)))))))).)).)))...)))

Mmd_304
cand467 probe44              23 24 25 26 27 28 29 30 31 32 33 34 35 36 37 38 39 40 41 42 43 44   (SEQ ID NO:612)
TTCCAGCCAGGCCACCTCTCCTTTATCTGCACAGTCTATTTTAAGAGTACTCTACTGCAAGGAGAATGGGGCCTAGGCAGGAA
.(((.((((((((.((((((((.....(((((.((...(((((...)))))..))..))))))..))))))).))).))).

Mmd_305
cand657 probe8                1  2  3  4  5  6  7  8  9 10 11 12 13 14 15 16 17 18 19 20 21 22   (SEQ ID NO:613)
GCGAAGCATTGCATTTGGGTGACAGGCAGTTGTTCGTGCTTGAATAACTCAGGATTTGAATTCTACAGTTTGTGGCACCCGTGTAATGCTTAGC
((.((((((((((...(((((((((((((.((.((((..((((.....)))))..)))))..)).)))))))))))))))))))).))

Mmd_306
mmHP1541151 probe27          23 24 25 26 27 28 29 30 31 32 33 34 35 36 37 38 39 40 41 42 43 44   (SEQ ID NO:614)
CCACATTTTCTTCGCCACAGAATGACTCCTCTGAGAACAAAGTCATTGTTGACTTCAAAGAACTCTGAGGAAGTTCAGTGGATGGAAAGAATTTGG
(((.(((((.(((((((..(((((....(((((.(((....))))..))))))))..))))))).)))).)))).)))

Mmd_309
mmHP874966 probe9             1  2  3  4  5  6  7  8  9 10 11 12 13 14 15 16 17 18 19 20 21 22   (SEQ ID NO:616)
GGCCTTTTCCATGTTGGGTAACTGCTGTGCATGCTACCCAGTTACCCAAGCCAGGAAGCAGGCC
(((((((((((.(((((((((((.(((.....))).))))))))))))..))))))))..))))

Mmd_311
cand124 probe1                1  2  3  4  5  6  7  8  9 10 11 12 13 14 15 16 17 18 19 20 21 22   (SEQ ID NO:619)
ATTGGTCAGGAAAGACACTTTTTATATTGTCAAGTGGCACTTAAGCCACTAATTCTTGACTGTGAAACTGCTTTTCCTGGGCAAT
((((.(((((((((..((.(((((((((..((((((((......)))))....))))))))))).))..))))))))).))))

Mmd_312
cand421 probe39              23 24 25 26 27 28 29 30 31 32 33 34 35 36 37 38 39 40 41 42 43 44   (SEQ ID NO:620)
GGGAGGAGGCGGAAAGCCGACATTGTTTACTTAATTAAAAGTAAACAACAATTTGCCGCTGCCAGCCTCCC
((((((.((((....((.(.(((((((((......)))))))))...)).)..)))))..)))))))
```

FIG. 2: Con't.

```
Mmd_314                     1  2  3  4  5  6  7  8  9 10 11 12 13 14 15 16 17 18 19 20 21 22     (SEQ ID NO:622)
cand148 probe7
AAATTAATGACCAAAAATGTCAGATGTGTCCACAGCTAATTATTCATTAGATGCTTAATTAGTGTGGGATGATCATGACATTTTAATGTTATTAATTT
(((((((((((...(((((((((((((...(((((((.((((((((..(((...)))..)))))))))))))...))).)))))))))...)))))))))))

Mmd_316                     1  2  3  4  5  6  7  8  9 10 11 12 13 14 15 16 17 18 19 20 21 22     (SEQ ID NO:233)
cand367 probe7
TCCTCTTTGCAAAATCATATTTTTGTGGGAATGGGCCCTGCTTTTTGTGGCAAGGCCTGTTCTGATTAATAAAGGATCGTGAAAAAGTAGGG
.((((((((((..(((.(((((....((.(((((((((((((......))))-))))))))))-)).-))))....))..)))))).))).

Mmd_317                     1  2  3  4  5  6  7  8  9 10 11 12 13 14 15 16 17 18 19 20 21 22     (SEQ ID NO:624)
cand608 probe16
AGGAAGGATCTGGGCCAATTTTCTGGTTGCTTCTTGGCACTGAGTTCTTGTGTTTTTACAGCAGTCACACAGGCCCTACATCCTTCCT
(((((((((((..(((((((..((..((((.((((((((((.......)))))...))))-..)).....)))))))...))))))))))

Mmd_318                     1  2  3  4  5  6  7  8  9 10 11 12 13 14 15 16 17 18 19 20 21 22     (SEQ ID NO:625)
cand543 probe12
GACGGCTAATGCCCATTAGTGTTGGGGACTGTTACCTCGATCAGGAGTGACAGAGCCCTAATTATTAAGGTAATTAGAAGTT
(((..((((((..((.((((((((((((.(((((((..(.....)..)))))))))..))))))))).))))))))..)))

Mmd_320                     1  2  3  4  5  6  7  8  9 10 11 12 13 14 15 16 17 18 19 20 21 22     (SEQ ID NO:628)
mmHP325598 probe5
AGGTGCCTGTGACTCATCTGGTACCTATTGTGCTCTCTGCAAAGGCGCGGAGGCTTGCTTGTGTGATGGGTGCCATTTGAGAGCCACTT
(((((..((((.((((((((((((((((.(((((((((((......))))))).......)))..)))))))))))..))))).)))))

Mmd_321                     1  2  3  4  5  6  7  8  9 10 11 12 13 14 15 16 17 18 19 20 21 22     (SEQ ID NO:629)
cand597 probe9
AGTATATGACGCTATAACTTGTTTTTACAGATGATTAAATGCTCGGTTGAAGCTGAGGCTTTGATGACTGTTGGAGCCATTTATGACCTCATATACT
(((((((((((.(.(((((((...(((((((..((..(((((((((.....)))))))))...))...)))))))...)))))))...)))))))))))

Mmd_324                     1  2  3  4  5  6  7  8  9 10 11 12 13 14 15 16 17 18 19 20 21 22     (SEQ ID NO:632)
cand224 probe10
GGCCGCATGGACCACGTGGACCGCTGCTTCGATGTGCTGGCTGTGGAGTACTACGTGCCGGATGCCGACCAGTGGACCAGTGTGACACCCATGCGAGCT
((((((((((...((((((....((((...((((......)))).)))).))))))...)))))))))).)))

Mmd_325                     1  2  3  4  5  6  7  8  9 10 11 12 13 14 15 16 17 18 19 20 21 22     (SEQ ID NO:633)
cand101 probe16
CCCTGGTGTGAGCGTATGTGCCTTTGGACTACATCGTGAACGCAGCACCATGCAGTCCACGGGCATATACACTTGCCTCAAGG
((.(((.(..((.((((((((((((((.(((((((..(((........))).)))).)))))))))))).))..))).)).))

Mmd_326                     23 24 25 26 27 28 29 30 31 32 33 34 35 36 37 38 39 40 41 42 43 44     (SEQ ID NO:634)
cand522 probe43
CCTAGCTTTCCTAAGTGATGTCAGCCCCTGCGAGCTTCCAATAGGAACCAGGCATAAATCAGGGAGCTGACCTTATCCAATAGGAAACTTTATTATAGG
(((((...(((((((((..(((((.(((((((.....(((((....))).......))))))).))))).))))))...)))))))))..........)))

Mmd_327                     1  2  3  4  5  6  7  8  9 10 11 12 13 14 15 16 17 18 19 20 21 22     (SEQ ID NO:635)
mmHP527107 probe22
AGGAATTAGGGTCAGGACCCAGAAACTTTGCTCTATCAGCTGGTGTTTGTTTCAGCTCAGGTGGGGTGGGTTTCCCCTTTGATGGGTCATTTCCTCCT
((((....((((....(((((((((..((((((((((((........))))))..))))))..)))))))))....))))))))))

Mmd_328                     23 24 25 26 27 28 29 30 31 32 33 34 35 36 37 38 39 40 41 42 43 44     (SEQ ID NO:636)
cand697 probe25
CCAAGCAGGGACTTCTTGCCAGCCCTTGGCAGCTTGAGGCCTCCCATCATCATCCACCGAGCTGGCAAGAAGTATGGCTTCACCCTGCGGG
....((((.((((((....((((((((((((...(((((.....))))))..).)))))))))))))))...

Mmd_330                     1  2  3  4  5  6  7  8  9 10 11 12 13 14 15 16 17 18 19 20 21 22     (SEQ ID NO:639)
cand545 probe17
GTGCCCCGAGGGGTGGCTGTGATGAGCGGGATGCGGAAAGTGTCTACAGAGCCGATCTGCTTCCCGCTCACCCACAGCAGCTGCTCCATGGTCAC
(((((..(((..(((.(((((((((((((((..(..((.....))..)))..).)))))))))))))).))))))).))...)))
```

FIG. 2: Con't.

Mmd_332
mmHP2109324 probe14      1 2 3 4 5 6 7 8 9 10 11 12 13 14 15 16 17 18 19 20 21 22    (SEQ ID NO:641)
TACTCCACGGGTAGCATGTTGGAGATGGTCAGGTGGAATAATAAGGAGAGTCCACAGACCAGGAGCTTCTCCGTAACTGCTGCCTGGAACGGGTG
(((((..(((((((((((..(((((((((((((((..((((.........))))).))))).......))))).))))))))))))))....)))))

Mmd_333
mmHP1301606 probe19      1 2 3 4 5 6 7 8 9 10 11 12 13 14 15 16 17 18 19 20 21 22    (SEQ ID NO:642)
GGGCTGATGAGCAGTTCAAGCTCCCTGCATAGAAATAGCCTCAGAATAGTTGTGGTGTTGTTTCTAATTGCAATGGGTGAGCAGACTGGCTCATTAATCC
((..(((((((((((...(((((((((((((((((((-(((-(......)-))).))))))))))..))))...)))-)))))))))).))))))))...))

Mmd_334
cand787 probe21          1 2 3 4 5 6 7 8 9 10 11 12 13 14 15 16 17 18 19 20 21 22    (SEQ ID NO:643)
TCCTTCACAAAGTACAAAGGGTTTCAGAATCAAGTGTATTCCAGCAGCAGCCCAGGCTTGCTGACAAGATATTTTGAAACAACTTGCTATTAGGAAGGA
(((((....(((((((...(((((((((...(((..(((.......)))))))))))....)))))))....))).)))))..))))))

Mmd_335
cand781 probe9           1 2 3 4 5 6 7 8 9 10 11 12 13 14 15 16 17 18 19 20 21 22    (SEQ ID NO:644)
GAGGCGAGTGTGGATCTAATCTTCAGCTGATTAAATGTCCCTCATTAATGAGTTTCTTTAATTAATGAAGTTTTGGGGCCTGCTCCACTTGCTTT
((((((....(((((-((...((((((((....(((((......))))).)))))))).)))))))))....)))))))

Mmd_336
cand430 probe8           1 2 3 4 5 6 7 8 9 10 11 12 13 14 15 16 17 18 19 20 21 22    (SEQ ID NO:645)
GCATGCCAGTGGGAATCATAGGCTGGAGAGACCTTCCTTCTGCAGGAGATGAAATTCTTGAAGTAGAATCTGAGGTATTCAAGCCTAATTCCCTAATGT
((((.......((((((((((...(((((...(((((((((.......)))))...)))))..)))).))).))).)))))))))

Mmd_337
cand246 probe3           1 2 3 4 5 6 7 8 9 10 11 12 13 14 15 16 17 18 19 20 21 22    (SEQ ID NO:646)
AATTTATTTTCGCTAGGAGAGGAATGACCCATAACTCACGAACGGTGATGCTTAAAGTGAGTTATGGAGGTTACTCTCCTGTGAGAGGAAATGGATT
.((((.(((((((((.(((((((.((.....(((.....((.......)).....)))))))))))))))))))....)))).....

Mmd_338
cand307 probe2           1 2 3 4 5 6 7 8 9 10 11 12 13 14 15 16 17 18 19 20 21 22    (SEQ ID NO:647)
TCCAAGTTCATGATGAAGAGTTTGTCAGTGGGAGTCAGTTCCACAGGCTGCCTGGTGAACTCTTTGTCGAAGTTGGA
(((((..(((...(((((((((...((..(((((((.....))))))).)))))))))..)))))..)))))

Mmd_339
cand434 probe18          1 2 3 4 5 6 7 8 9 10 11 12 13 14 15 16 17 18 19 20 21 22    (SEQ ID NO:648)
GGCCCCCATCTGGGAGGATGATGTCATCTATCTCCCCAAAGAAAAGGCCACACTTTCCTTTGTGGAAGTCCATGGTGACATCACCTCCTGATCACATGCC
((((...(((.((((((((((((((((((((((((...((((........))))..))).)).))..))))))))))).)))))))))..)).......)))

Mmd_340
cand863 probe27         23 24 25 26 27 28 29 30 31 32 33 34 35 36 37 38 39 40 41 42 43 44    (SEQ ID NO:650)
GGCCCAGCCACAGTGACATTCATCCCCCGGTGGGTCTGGCTGCCTCCTCACAACCCACCGACAACAATGAATGTTAATTGTGACCTTTGCTGTGGCC
(((((((((((((.......(((((((((.((.........))))))))))))........)))))))).))))).......)))).))))

Mmd_341
cand86 probe20           1 2 3 4 5 6 7 8 9 10 11 12 13 14 15 16 17 18 19 20 21 22    (SEQ ID NO:651)
GCAATGTGGAGAAGCCTAGGGCTTGCCCTGGCTCTCTGTCTCCTCCCCTATGGAGGAGCAGAGAGCCAAGGCCAAAGCTCTGCTTGTTACAAAGC
((..(((((..(((..((((((((((..((((((((...((((((.....)))))))))))))))..))..)))))))))).))))....))

Mmd_342
cand403 probe29         23 24 25 26 27 28 29 30 31 32 33 34 35 36 37 38 39 40 41 42 43 44    (SEQ ID NO:652)
TTATTCACCTGGAAACTGCTGAGGAGCACAAATGTCACAAGATAAATCAAACCTGTGAGATTGGCATCTCTCAGCAGCAGGATGGGTAG
.(((((((((....(((((((((((((....(((.((((............)))).)))...))).))))))))))))).))))).

Mmd_343
cand673 probe6           1 2 3 4 5 6 7 8 9 10 11 12 13 14 15 16 17 18 19 20 21 22    (SEQ ID NO:653)
CAGGGTGATGGTTAGGGATTTGGCAGCATGGCCCCATTAACATTAGTGGGAGTTAGTCAGCTAAATCCCAGACATGGAACAGAATCCTG
((((..(((..(((((((((((((((....))))))))...)))))))))))...........))..)))))

FIG. 2: Con't.

```
Mmd_346                      1  2  3  4  5  6  7  8  9 10 11 12 13 14 15 16 17 18 19 20 21 22        (SEQ ID NO:656)
cand365 probe11
CTCAGGCGGGGTGGGGAGGATGTTTTGGATGCCGCTCTGCTGACGTTGGTGCCCTCTGTTCTTACATCCTCCTTAATTTACTGCCTGAG
((((((((((....((((((((((((..((...(((((((((....)))..)..))))..))..........)))))))))))......)))))))))

Mmd_347                            23 24 25 26 27 28 29 30 31 32 33 34 35 36 37 38 39 40 41 42 43 44  (SEQ ID NO:657)
cand492 probe32
GCGGCGGGCTGAGTTTTGAAAACTTAGGATTCTAAATGTATAAATTGTTTGGAACATTTAACATCTAGTCATTAAGCAGTCACCCTCTTGCCCTCCGC
((((-((((-(((....(((-((((((((....(((-((((-((((((-(((.....))))))))))))).)))...)))...)))..))))-))))

Mmd_348                      1  2  3  4  5  6  7  8  9 10 11 12 13 14 15 16 17 18 19 20 21 22        (SEQ ID NO:658)
cand596 probe12
GGCCTTCTTAGCTGCTCTAATTAGGATCCCCTTAGTCCCTCCCGGTTTCTCCGGAGAGGACAGGGGGCTTTTTAATTGAGGCTATTAGGAGTTC
....(((((((((.-((-(((((((((((-(((((((-(((((((((-((.....))))))-)))))))))-.))))))))))..)).))))))))))..

Mmd_349                      1  2  3  4  5  6  7  8  9 10 11 12 13 14 15 16 17 18 19 20 21 22        (SEQ ID NO:659)
cand690 probe14
AGCCATTAACATGTCACCCCTGCTTGAAACAATGACTCAGCTTGGTTCTGCATAATAGGACAAGTGAGGGAGACAAGCAGAGGTGACAGGAAGGTT
(((((-((.....((((((((-((..(((((((((....(...((((-((((-(((((((.....))))))))))))))))..).)..)))))))))..))).))))))

Mmd_350                      1  2  3  4  5  6  7  8  9 10 11 12 13 14 15 16 17 18 19 20 21 22        (SEQ ID NO:661)
cand264 probe4
TTCCAAATTTTATGGGCCAAATTCTGCCCTCAATTATGCACATGCAACTAATTGCACACATATAACAGAGGGCAGAATTTCGCTTTTGGAACTGGAA
.((((..(((((..(((..((((((((((..((((....(((((....))))....)))))..))))))))..)))..))))).)))).

Mmd_351                      1  2  3  4  5  6  7  8  9 10 11 12 13 14 15 16 17 18 19 20 21 22        (SEQ ID NO:662)
cand631 probe10
CAAAAGCAGATATTTTCCCAAGCAGACACCAGCCACAGCCTTCTTGGCTGAAAAGGCTAAATGGCTGGCTACTCATGTACTGTTGAATGTCTGAGTATG
......((((((((((((((((((((((..((((((((.....).))))))....)))))))))))))))))))........

Mmd_352                      1  2  3  4  5  6  7  8  9 10 11 12 13 14 15 16 17 18 19 20 21 22        (SEQ ID NO:663)
cand21 probe20
GTTTAAGTACCTGTGGGCAGCATCAGGGTCTGCCTTGCGGTGGGACCTTTTGGGTTTCAGCGCAGGGTCTCTGGTGTTTCCTGACAGGCGATCTGAAGC
((((-((..(((((((((((((((((...((((((((.((-(((.....))))-)-)))))))))))))))).))).-)))))....)).))))

Mmd_353                      1  2  3  4  5  6  7  8  9 10 11 12 13 14 15 16 17 18 19 20 21 22        (SEQ ID NO:664)
cand395 probe7
GCATTTTCTGCAGATTAATAATTAGCTAGAAGGAGTTGATGGTCCTTGGCTAAAACGTGGGTCATTAACTCCAGCCAGTCATTAATTGCCTGGAAATGT
(((((((((.((((.(((((.(((.((((((....((.((.....))))..)).-)))))).))).-)).).)))))))))..)))))))

Mmd_354                      1  2  3  4  5  6  7  8  9 10 11 12 13 14 15 16 17 18 19 20 21 22        (SEQ ID NO:665)
cand704 probe5
GACTCTGTATTTAATTTGGCTCAGCCGGGAAGATTTTTTGGCTCTGTGTGTGTATGTGTATTCTGAAAAATCTTTCCGAGCAAGCCCCAGGGTC
((((((((....((((..((((((((((((((((...(...(((...)..))).).-)))))))))))))).)).)))).)))))))

Mmd_355                      1  2  3  4  5  6  7  8  9 10 11 12 13 14 15 16 17 18 19 20 21 22        (SEQ ID NO:666)
cand323 probe1
TTGTAGCATGTGGTTGTATTAATGAACGTTACAGGACAGCTTTATAATCATTTATAAATCTGTAACATTCAATAAAGAAGCACATGTGGCAA
.(((-((((((((-((.-.(((-((((((((((((.....(((((((.....)))))))..))))))))).)))).))..)).))).-.

Mmd_356                      1  2  3  4  5  6  7  8  9 10 11 12 13 14 15 16 17 18 19 20 21 22        (SEQ ID NO:667)
cand182 probe10
TTGGTGTTGTCAATTTGTGAGACCAGTCTGGAATTTTCAGCCTTGGTACACAAGATCTAGAATTAAGAGATTGCACACACAAATGAGACAAACACCAG
.(((((((((((.(((((((.-..(((((((..((((((((-((.(((((.....)))).))-.))))))))...)))))))...).))))))))).

Mmd_358                            23 24 25 26 27 28 29 30 31 32 33 34 35 36 37 38 39 40 41 42 43 44  (SEQ ID NO:669)
cand668 probe30
GCGACGTCCGTCAGCGGAGAAGCAGAGGATAATGGCCGTCTGCAGCGCTGTCGCCTGTAGCGCCCTCCTCCTTTCTCGTTCGCGCACTCTGTGGT
((.(((....(((((.(((((-((.(((((.....((((-((((((-(((.....))))))))))...))))))))..))))))))..))).)))
```

FIG. 2: Con't.

```
Mmd_360
mmHP811508 probe6    1  2  3  4  5  6  7  8  9 10 11 12 13 14 15 16 17 18 19 20 21 22   (SEQ ID NO:672)
GGCACTGGGGGCAGAAGGCCATTTGAAAATTTTCCACATTGAAATTTTGATTAATTAAATTTGTCTCAAGTGGCTGGCTTTCAGTGTC
(((((((..(((.....(((((((((((((((...((..(....)..))..)))))))...)))))))))..)))..)))))))

Mmd_361
cand18 probe11       1  2  3  4  5  6  7  8  9 10 11 12 13 14 15 16 17 18 19 20 21 22   (SEQ ID NO:673)
AGAAGGATGCTGAAACCAATGAAACAATATATTGTACAAAAGAGCCTTTCATCCAGGCTCGGGTTATTGTCATTCGTTGGCTGGTTTCTTTCT
(((((((.(((....(((((((((((((.....((....((((((.......))))))..))))))))))..))))))).))))..))))))

Mmd_363
mmHP2216591 probe41             23 24 25 26 27 28 29 30 31 32 33 34 35 36 37 38 39 40 41 42 43 44  (SEQ ID NO:675)
AGGCAAACCCTACAAATGTAGCAGAAGCATTTCCGCACACTGGCATCAACATCTAGTTTGTGCAGAAATGTTTCCACTAGATTCATAGAGTGTTCTT
(((....((.(((...(((.(((.(((((((((((.(((((((((((.((.(....)))))))).)).))))..)))).)))))))))))...)))

Mmd_364
mmHP1290061 probe10   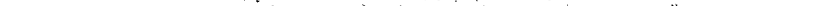  1  2  3  4  5  6  7  8  9 10 11 12 13 14 15 16 17 18 19 20 21 22   (SEQ ID NO:676)
CCATGGCTGCTGCTGTAGCAGAAGGGTTGAGCCAGTCCAGGCTGGAAGGATCTGTCACCCGATCCCAGGTCTGTGCTACAGCCAGTCTTGG
(((.(((((....((((((((....(((..(((..((((....))))..((((........)))).))))))).)))))))))))).)))

Mmd_365
cand682 probe37               23 24 25 26 27 28 29 30 31 32 33 34 35 36 37 38 39 40 41 42 43 44  (SEQ ID NO:677)
GGAAGGATATCTGAGGACTGGATGTGTTCATGTTTTACACCAAATGCTTTCAACATGAGAATCCGCCCAGTCGTATCTAATAAAAATATCCTTCC
(((((((((....(.((((((.(.(.((((((((((............))..)))))))).)..)))))).)............)))))))))

Mmd_366
cand390 probe17       1  2  3  4  5  6  7  8  9 10 11 12 13 14 15 16 17 18 19 20 21 22   (SEQ ID NO:678)
GTCACCTCTTCAAGGTGTTTGGGATTCGCTTTGATATCCTTGTGGATGGCAAGGTAAGTGTCCTATGTGAAGGGATGGC
(((((((((((.........((((((...((((((..(((((....))))...)))))..)))))).))))))).)))

Mmd_367
cand558 probe1        1  2  3  4  5  6  7  8  9 10 11 12 13 14 15 16 17 18 19 20 21 22   (SEQ ID NO:679)
CACAGCTTGGCACTGGAAATTTTATTTGAATCAGGGGAGAATATTATTTGCGATATTTCCTAAATGACAAATGAATGATTTACCGGCAGCAATGTG
((((.....((.(((((((((((((((..(((.((((((((((.....)))))))))))...))))))))))).))))).)))..))..))))

Mmd_368
mmHP2418251 probe5    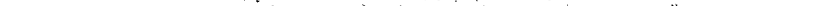  1  2  3  4  5  6  7  8  9 10 11 12 13 14 15 16 17 18 19 20 21 22   (SEQ ID NO:680)
CCGCATTTGCTCCAGTGGACACTGGTGCGCACCCACTTCAAGATACACTGGGCTAGTGTCAGTCTCCAAGGAGCGCGTGCGG
((((((.((((((..(((((((((...(....(((((.....))))))...)..)))))).)))))))..))))))

Mmd_369
cand399 probe3        1  2  3  4  5  6  7  8  9 10 11 12 13 14 15 16 17 18 19 20 21 22   (SEQ ID NO:681)
TGAGACCTTTCTGCTCTCGCTGTGGTTATGTGTCTCACTGTTTCTCTACAAGGGTGAGACAAAGCAATTTCACAGTTATCAGAAGGGTTATCA
.((((((((....(((((((((((((((.((((((((.-.(((((((((.........))))))))...))))))))...))))))))))))).

Mmd_370
cand546 probe16       1  2  3  4  5  6  7  8  9 10 11 12 13 14 15 16 17 18 19 20 21 22   (SEQ ID NO:683)
ATGCCATGCAAATTGGCACGAAGGCAATCAGTCTGACTCTGAAGGCTGCCCACCGGCCGCAGGCTGGCTCATTGTCTTTTCTGTCAATTTGCATCTCAT
((((.((((((.((((((((((......((((.((.(.(..(((.....((((.....)))).)))..)))))..)))).))))))))))...))).

Mmd_371
cand854 probe3        1  2  3  4  5  6  7  8  9 10 11 12 13 14 15 16 17 18 19 20 21 22   (SEQ ID NO:684)
AGAGGCTGCCAGGTGCTGGTGGAAATAGAGGCCGAAGAGGCTGGAGAGCAGCTGGCAGGCAGCTGTCCACCAGATGATGTAAGCCAGCATGCCTCT
((((((((....(((.(((((((.......(((...((((((.....))))))...))).)))))))..)))))))))).)))))

Mmd_372
cand181 probe20       1  2  3  4  5  6  7  8  9 10 11 12 13 14 15 16 17 18 19 20 21 22   (SEQ ID NO:685)
GTCCCCGTTGTCTGCGTCCTTGCCTGTCTCTTCCCTGCCCAGTGGCCTCCTTGTCCGGCTCACTGGGCAGGAGCCCTAATCGGATTGGACAGCTGAGAT
(((.(.(((((((..((((.........(((((((((((((.......)))))))))))))........))))))))))).)))
```

FIG. 2: Con't.

Mmd_374  
cand273 probe11      1 2 3 4 5 6 7 8 9 10 11 12 13 14 15 16 17 18 19 20 21 22    (SEQ ID NO:687)  
GGCAGTCGTCACCTTTCTTCCGGGCACTGGCCAAGCCAAAGTCAGTGATGATGATCTTGGAGTCAGTGCCTGGGTGGTAGTAAAGGAGATTCTCAGGCT  
((((....(((.((((((((((((((((((((((....(((...(((........)))..))))).)))))))))))))....)).)))))..))).......)))

Mmd_375  
cand580 probe18      1 2 3 4 5 6 7 8 9 10 11 12 13 14 15 16 17 18 19 20 21 22    (SEQ ID NO:688)  
AAAAGCTTGGCGTAATTATCTCTGAACAGGTTGAGCGCAAGGTCTCTGCAAAAATCTGCTCAGGGTGATTATTTTGCTGGGGTTTT  
((((....(((.((((((((((((.((((.(((((((((..(.....).))......)))))))))).)))))))))))...)).))..))))

Mmd_376  
cand294 probe16      1 2 3 4 5 6 7 8 9 10 11 12 13 14 15 16 17 18 19 20 21 22    (SEQ ID NO:689)  
GTTATCAGGAAATAATCATAGCCCTCGGGTGCTGGGAGACACTGGGTGTAGCTAAGTGTCTCTAATTCCCCAAGGGTATGATTAGCTCACGTTAAC  
((((....((..(((((((((((.(((.(((((((((((((((((.......)).)))))))))....)))).))))))))))...))....))))

Mmd_377  
mmHP1218232 probe15      1 2 3 4 5 6 7 8 9 10 11 12 13 14 15 16 17 18 19 20 21 22    (SEQ ID NO:690)  
ACTCGGGAAGCAGCATTCAGGTCTCTGGGTCCTGGATGTCCTTGGTGCACACTCCAAGGACTCCTCGTCCTTAAGTTCATAGTCTGTATTCCCTGAGT  
(((((((((((((.(((...(..((..(((.(..(((.(((((((.........))))))))))..).))).)).))..)...)))))))).)))))..))))

Mmd_378  
cand136 probe8      1 2 3 4 5 6 7 8 9 10 11 12 13 14 15 16 17 18 19 20 21 22    (SEQ ID NO:691)  
CGAACACCCAAAATAATGTGAGATCAGGCTCATGCGTTATGCATGAGGTCTGATTTAACATGAACATTATTTCTTGTGTACG  
((.((((...(((((((((.(.((((((((((((((......))))))).)))))))))))......)))))))))...))))..))

Mmd_379  
cand70 probe16      1 2 3 4 5 6 7 8 9 10 11 12 13 14 15 16 17 18 19 20 21 22    (SEQ ID NO:692)  
CATTCCAAGCCACTCTCTGATTTGCTGTGAGTGGCAGAATCATTCACCGTGGTGAATCACAGAGAGCGAGCCATGTGGAGTG  
(((((((((.(((.(((((((((((..(((((((.....))))))...))..))))..)))))))).).))....)))))))

Mmd_382  
mmHP1665736 probe7      1 2 3 4 5 6 7 8 9 10 11 12 13 14 15 16 17 18 19 20 21 22    (SEQ ID NO:696)  
CGGGAGAGCTCAGTGAAGGACTCAATGACGTTGAAGTTGCACAGGGGGCTGACTTCAAAGAAGGTCATGCAGTTCTTCTCTGCATAGGCTCTGGCCTG  
((((((((((((.(((((((((.((((((..(((((......)).)))))....)))))..))))))).))).))).))....))))))..)))

Mmd_383  
cand675 probe1      1 2 3 4 5 6 7 8 9 10 11 12 13 14 15 16 17 18 19 20 21 22    (SEQ ID NO:697)  
TTCACCTGGCGCACTGGGCAGGAAGACTTTATTCAGATCCAAGGAGGAGGCTCTGGAATGGGTTTTCTGTGGCCGTGGTGGTGGGGTGGG  
.((((((.((.((((((((((((((((..((((((.((........)).))))))..))))))...)))))))).)))))).

Mmd_384  
mmHP2197503 probe16      1 2 3 4 5 6 7 8 9 10 11 12 13 14 15 16 17 18 19 20 21 22    (SEQ ID NO:698)  
CATCTGGAATTTCTATTGCTCAATGGGAGGCTGATGGGGGAGCTGATCTGGAAAGAGCCTCCAAAAAGAAATAATGAGTTCCAGATG  
((((((((((((.((((.((....(((((((((((((.((....)).)))........)))))))))....))))..))))))))))))

Mmd_387  
cand265 probe18      1 2 3 4 5 6 7 8 9 10 11 12 13 14 15 16 17 18 19 20 21 22    (SEQ ID NO:700)  
CAACTAGAGAGACCCGGTTGCTTGGGTGGATCCAGACAAAGGTGGATTTCCATCCCTGGATTTTGTGCCCACGCCTCTGGGTCACCCTGTCTCCCTTG  
.....((((((((((((..((.((((((((((.....(((((.....)))).)))))))).)))...))))).))..))))))........))))......

Mmd_388  
cand635 probe43      23 24 25 26 27 28 29 30 31 32 33 34 35 36 37 38 39 40 41 42 43 44    (SEQ ID NO:701)  
AGGGTGCGTATTACAGACGAACAATGATATGCCTTGCCAGTAATGGCACTCAGTCAAAACTACCAGGGCATGTCATTATTAGGTCATAATACCCACCCT  
((((((.((((((((...(((.((.((((((((.....(((((....(((.((((.....))))..)))..))))))))))).))..))).))))))).))))))

Mmd_390  
mmHP3025219 probe1      1 2 3 4 5 6 7 8 9 10 11 12 13 14 15 16 17 18 19 20 21 22    (SEQ ID NO:703)  
TCTACTAGGAATGGGATACATTCACAGGTGTGGTTGTTGGAGACATGCTGCGCAAAGCTGTGAGTTAAAATCTGATTTCTCTCCTAGGGGA  
((((.((((((((((.(((((((((((((((((((.....((.....))..))....)))))))).....))))).)).)....)))))))))).)))

FIG. 2: Con't.

Mmd_393  
cand12 probe10  (SEQ ID NO:706)
```
CTCTCCATATGCTGTGGCATCTGTAACTGGCATGTAAGGGACTCATTTTCCTCACATATCTCATTAAAGATGCAAAGCAAAATGGAGGG
((((((((.(((((...(((((((.(((...(..(((((.(((((((......))))).))))..)...))).)))))))..)))))..))))))))
```

Mmd_394  
mmHP2549249 probe8  (SEQ ID NO:707)
```
ATTTACTATTTTAGTGCTGGATCCAGTTGCAGCTGAAACATTTCAACCAGGCTGCGGAGTTGGGCCAGCTCTGTGATGGTCAGT
....(((((((.(((((.((((((.((((((((.............))))))))...))))))))).)))).)))))....
```

Mmd_396  
cand187 probe38  (SEQ ID NO:709)
```
TACAGGACGTCTGTGCAATTCGATGGAGCTCATCACTTTCCGGTCTATGAGCAATTAAATTGCACCAGGAAGCCCTGTA
(((((((.(.((((((((((...((...(((((.(((((.....)))..))))))).)).)..))))))).))..))).)..))))))
```

Mmd_398  
cand361 probe11  (SEQ ID NO:711)
```
TGCTTGATTAGTCAGATTGATGGAGGAGGCCATATGTGGCCGTGTCAAAACTTGGCTACCAGGCTCCTTTCCTCTCTGAAGGACAGGCA
.((((((.(((..(((((..((.(((((..((.....(((((((.((.....)).)))))))))-))).-)))).)..))))))..))))))).
```

Mmd_399  
cand694 probe2  (SEQ ID NO:712)
```
GCTCACCCTGGAGGCCACAGATGCTGATGGAAGCCGCACCCATGCTACTGTGGACTACAGCATCATCAGTGGCAATCGGGGCCGAGT
((((.((((((...(((((..(((.((((...(((....))))..))))))))..))).)..))))))..)))
```

Mmd_400  
cand516 probe21  (SEQ ID NO:715)
```
TCATGCCGAGCGAAAAAGCCCCTGACGTCACCTGCAGCCAATCAGAGTGAGCCGCTCGGGGGCAGGTGACGTCAGCGGAGCGGGCGCTGGGTGCGG
.(..((((.(((((.....((((((((((((((((((..((......(((((....)))))-))-)-))))))))))))-))-)-.....))))))))..).
```

Mmd_403  
cand978 probe3  (SEQ ID NO:718)
```
AAGGGAGGGTATGGTGAGGATGGTGGTCTTGGAGGCGGACATTTATCCAACAGAATGCTACTATTAGACAGGCCGTTTTTACCTAGATTCCTTT
((((((((..((.(((((((((((.((((....((..((.(((((........))))))..)).....))))..)))))))))))))..)))))))
```

Mmd_404  
mmHP1595839 probe41  (SEQ ID NO:719)
```
CTTGACATGTCCCTTTAACGTTAGAGGCATTTGCTGATGCCACTAACTTATGGGTCAAATGTGGTCAAG
(((((((.((.(((..(((((.((((((.))))))).)))))))).)).....))))))
```

Mmd_406  
cand484 probe5  (SEQ ID NO:721)
```
CCTTATCATAGAGTTTACTGAAGTGGGGCCAGTTCCCCGCCTCTTCCAGCTTTGCTGCCAAAGTTGGAGAGGGGTGGAGTGGCCTGGAAGACTGTTGGG
.....(((.((((((.((....(((((((.(((((.(((((((.....))))))).))))).)))))))....)))))).))).....
```

Mmd_407  
cand703 probe4  (SEQ ID NO:722)
```
GATGATGAGCTGTCCTTTCCCGAGGGAGCAATTATTCGCATCTTGAACAAAGAAAACCAAGATGATGATGGCTTCTGGGAAGGGGAGTTCAGTGGTC
(((.(((((((((.(((((((((.((((((....((((((.........))))))..))))))).)))))))))))))))))).).)))
```

Mmd_408  
cand547 probe13  (SEQ ID NO:723)
```
GAGAAATCAGCTTTAATTAATTTGAGTGCCAGCTCTGTGTATAATTACCCAGCATGAGAGTTTGCATGCAAATGCGGAAATGCTGATTCTT
((((((.(((((........(((((.(((((.((((((((((...........))).))))))).)))).))))).........))))))))
```

Mmd_409  
cand292 probe2  (SEQ ID NO:724)
```
CCATCAGTCAGGAAATTGTATGATAAATAGGAGGTAGCCAGGTTTAGTGGCACTTCCTTCTGCTTCAGCAGTTTTTGCCTGACTTTGG
(((...((((((((((..(((.(((((.....(((((((.(((.......)))))))))))...))))).)))...)))))))).)))
```

FIG. 2: Con't.

```
Mmd_411
cand257 probe3                  1  2  3  4  5  6  7  8  9 10 11 12 13 14 15 16 17 18 19 20 21 22   (SEQ ID NO:727)
CTTCTTGTATAAGCACTGTGCTAAAATTGCAGGAACTAAGATTCTATCTTGGTTTTTGTAATAATGCTAGCAGAGTACACACAAGAAG
(((((((....(.(((.(((((...(((((((((((((((((...)))))))))))))))))....)))))-))).-)..))))))))

Mmd_412
mmHP453167 probe8               1  2  3  4  5  6  7  8  9 10 11 12 13 14 15 16 17 18 19 20 21 22   (SEQ ID NO:728)
CCACCAGTTAGCAGCAGGCTGTGGATTAGGAGTGGCAGAAAGGATGTCTTTAAATAGGTTTCCGTTTCTGTTTGTTTGGTTTGAGGCTTGGTGATGGAGG
((.(((......((.(((((((...(((((((...(((((((((...(((.......))).-.))).-))).))))))))...))))))...).-))))))).)).-))).))

Mmd_413                                        23 24 25 26 27 28 29 30 31 32 33 34 35 36 37 38 39 40 41 42 43 44   (SEQ ID NO:729)
cand718 probe33
GCAGGCGTTTCCTGGGGATTAATGACCAGCTGGGAAGAACCAGTGGCCCTCGGCTCTGCCTCCCAGCCAGCCATTAACTCCAAGGAAATGTCTTTTGC
..(((((((((((((((.-((((((((.(...((((((.-.((((((...)))))).)).))))).-.)))))))).-.)))))))))))))))......

Mmd_416                                         1  2  3  4  5  6  7  8  9 10 11 12 13 14 15 16 17 18 19 20 21 22   (SEQ ID NO:732)
cand8 probe3
TGGGGGAGGCGGGCTGTGCTGGTGCCCGGTGTATAATCGGGTTAATCCAGTAGACAAAGAATAAACCAATAGCCCTCCCA
.(((((.-(((.-(((.-.(((((((.-((((((.....))))))....)))))).)..............)))...))))))).

Mmd_417                                        23 24 25 26 27 28 29 30 31 32 33 34 35 36 37 38 39 40 41 42 43 44   (SEQ ID NO:733)
cand193 probe30
CTATCGAATTTGTGGCTTTTGCTAGCTTTGCAGAAAGGGACTTTTAAAAATACTTCTCTTGATAGTGTAAAACTAGCGAAAGCCACAAATGGAATGG
(((....(((((((((((((((((((....((((.............)))))....))))))-.))))))..))))))))...))))

Mmd_418                                        23 24 25 26 27 28 29 30 31 32 33 34 35 36 37 38 39 40 41 42 43 44   (SEQ ID NO:734)
cand425 probe43
CACTAGTTCTCCTCCCATCCCCCTACCCCAAACTTCTCTACTCTGGTTTACCAGCACCAACAACCACGTGGGGGAGGGGTAAGAGAGTAGAACCGGTG
(((.-.(((((.(((.(....((((((.-.(((((.............(((((..-))))).-..............)))))-))))))...-.))).-.)))).--.))).

Mmd_419                                         1  2  3  4  5  6  7  8  9 10 11 12 13 14 15 16 17 18 19 20 21 22   (SEQ ID NO:735)
mmHP683 probe18
CAGCCTTTTCTTTGGTGTGCGAATGTGAGTGTGTGTAATGATGTTATCTATATGCCGTCGGGGCACCTGCACATTTGCATATTGGGGAAGAACTG
(((((.(.......(((((((...((((..-.(((((.-.(...-)))))..)))))..)))))))..)))))).)))

Mmd_422                                        23 24 25 26 27 28 29 30 31 32 33 34 35 36 37 38 39 40 41 42 43 44   (SEQ ID NO:739)
cand196 probe33
CCCATTTCGAGTCATAATCCCCTTTTGTGACATCACAATTAGCCACTTGTGGTGATGATTATAATGTCACAAACGCAGGATTAGGACAAGGAATGGG
(((((((....(((.(((((((.-.((((((((-.(((((((....)))).)))).-).-))))))-.)))))))...)).))))))

Mmd_423                                         1  2  3  4  5  6  7  8  9 10 11 12 13 14 15 16 17 18 19 20 21 22   (SEQ ID NO:740)
cand408 probe22
CAGTGTAACCCATGCTGGCTGCAGCAATGAGGGCCTGCTGGATGGCGTGGCTCTTCTTAAACACTCCTTGCTGCTGGCCAGCCATTGTCCAGTCACACTG
((((((.-.((.-(((.(((((((((((((.-.(((((((((((....))))).-.))))............)))).-.))))))).-))))))...)).....))-.))))))

Mmd_424                                         1  2  3  4  5  6  7  8  9 10 11 12 13 14 15 16 17 18 19 20 21 22   (SEQ ID NO:741)
cand443 probe6
GTCCCGAGAGTTGCTGATACAAGCTCTACAACCATTGAGCTGGAGTGGGAACCCCCAGCTTTCAATGGTGGTGGGGAAATTATGGGCTACTTTGTTGAT
......(((((.-.(((.-(((-...((((((.(((((((((((((((.-.(.-.(......)).))))))))..)))))))).....)))).-.))))......

Mmd_426                                         1  2  3  4  5  6  7  8  9 10 11 12 13 14 15 16 17 18 19 20 21 22   (SEQ ID NO:743)
cand427 probe13
GCCTGTTGACATGTCCAGACACTACTCCAGCAGAGGCACTGGGCCTGGCAAGAGGCCAGGCCTGAGTCACAGCTGCTGGATATATCAACGTGGC
((((((((((.(((((((.........((((.(.-.(((.-.((((((((((.....)))))))))).-))).-.)))))))))))))).-.)))

Mmd_427                                         1  2  3  4  5  6  7  8  9 10 11 12 13 14 15 16 17 18 19 20 21 22   (SEQ ID NO:744)
mmHP1499491 probe4
CTGGACGTGTTAGTGGAGGCCTTAAGGCCTGTGGGCACCTTTAAGAAAATCGGAAAGGTGTTCCGCAAAGAAGAGGACTCCACGGTGGGGATGCTGCAG
((..(((((.-((.-((((((.-.((((.......(((((((((((((((((.(.......)..).))..)))))))))))))).......)))).)))))))....)).-))).))
```

FIG. 2: Con't.

```
Mmd_429                        1  2  3  4  5  6  7  8  9 10 11 12 13 14 15 16 17 18 19 20 21 22    (SEQ ID NO:746)
cand685 probe7
GTTTTACAGCTCAGAGGGGATTAGGACAAGAGATGTGTTTAAAATACGATGTGTCTCTCTGTCTCTCTGCAGCTGATGGAGC
((((((((((((((((((((((....(((...(((((..((..........))..))))))))).))))))).))))).)))))

Mmd_430                        1  2  3  4  5  6  7  8  9 10 11 12 13 14 15 16 17 18 19 20 21 22    (SEQ ID NO:748)
cand607 probe6
TGGAAGACCATCGTGCAGGACTACATTTGTTCTCCCCATGCAGAGAGCATGAGGAAGAGAAACCAGATTGTGTTCACGATGGTGGAGGCCG
.(((...(((((((((..((..(((((((((((((((((.....))))).)).)))))))...))))))).)).)))))))))....)).

Mmd_431                        1  2  3  4  5  6  7  8  9 10 11 12 13 14 15 16 17 18 19 20 21 22    (SEQ ID NO:749)
mmHP2175366 probe12
GCTGGTTTTGGCACTTCTCTCACTCTAGTGAGTTGCAAAAAAACAAGCAGGTGCTAGCAATCTGAGAGACCACATGCCAGCTCCAGC
((((((..((((((((((...(((((.(.(((...........)))).)))))..)))))))))))..))))

Mmd_432                        23 24 25 26 27 28 29 30 31 32 33 34 35 36 37 38 39 40 41 42 43 44   (SEQ ID NO:750)
cand134 probe34
CTGAGGCAGCTGAGGCCATGCTGTCTGGCTCAATGAGGCCCTCAGGAACAGAGGAGCCAAAGCCACGGGACAGGGCCTCAGATGCGATTTCAG
(((((((((.((((((((..((((((((((.....(((((((........)))).))).)).))))))))))))))).)))...)))))

Mmd_433                        1  2  3  4  5  6  7  8  9 10 11 12 13 14 15 16 17 18 19 20 21 22    (SEQ ID NO:751)
cand192 probe4
GTTGGTGCCCTGATAAAGCCGGAGCCCTGGCAGATAAATGCTGAGGTGGAGCCAAGCCATTTATTTGAGGAGCAGCAGGGCTCCTATCAGGGCGCCGGC
(((((((((.....(((((((((((((..((.....)).)).))))))))))).........))))))))))))))))

Mmd_434                        1  2  3  4  5  6  7  8  9 10 11 12 13 14 15 16 17 18 19 20 21 22    (SEQ ID NO:752)
mmHP2810075 probe14
GACAGGATAGGGTCCTTAAAATAAACTCTCTGGTTTCCTTCCTTTCTTTATCTAAGGGGAGGCTAAAGTGGGTTTGCACAAAGGGCTCTTCGTGTT
((((.((.((((((((((....(((((((..((((((((((.........))))))))....)).)))))))....))))))))))))))

Mmd_435                        1  2  3  4  5  6  7  8  9 10 11 12 13 14 15 16 17 18 19 20 21 22    (SEQ ID NO:753)
cand125 probe11
TTTGTGTGTATAAAATGGGTAATTGCACACACAAATGAACAATTTTGTATGCAATTATCCATTTTGCATACAGA
(((((((((..(((((((((((.((.((((((.))))))))))))))))))))))))))))

Mmd_436                        1  2  3  4  5  6  7  8  9 10 11 12 13 14 15 16 17 18 19 20 21 22    (SEQ ID NO:754)
cand544 probe10
CAGGTATCCACCAAGGACATGCCCCTGGCACTGATGGCCTGTGCCCTCCGAAAAAAGGCCACAGTGTTCCGGCAGCCTCTGGTGGGAGCAGCCTG
(((((..(((((((((...(((((((.((((.(((((.........)))))))))..))))).))).)))))))...)))))

Mmd_438                        1  2  3  4  5  6  7  8  9 10 11 12 13 14 15 16 17 18 19 20 21 22    (SEQ ID NO:756)
cand957 probe5
GTTGTTCTTAAATCACCTTGAAGTGTCTCTTGTCAAAGATAACTCCCTGCATTGTAGAAACGTCTTTGACAAGAGAGGATTAGGGTGAAATTGCAAT
(((((........(((((((((..(.(((((((((((((((......)))....))))....))))))))))))).).)))))))))....))))

Mmd_439                        1  2  3  4  5  6  7  8  9 10 11 12 13 14 15 16 17 18 19 20 21 22    (SEQ ID NO:302)
cand165 probe14
TCTAGGGAGCCACCAGTGGTGTAAGTGCTTTGGCTAAGTGATGGAGACAACTGAGGAGGAGTGTGATTACCACTGGGTTCCTGAATGGA
((((((((((..(((((((((..(..(((((..((.(((..((....))))).)))...))))..)...)))))))))))))...)))

Mmd_442                        1  2  3  4  5  6  7  8  9 10 11 12 13 14 15 16 17 18 19 20 21 22    (SEQ ID NO:760)
mmHP1626774 probe9
CAGCAGAGGTAAGCCTGTGAGACTAACAGCTTTAGCGCAGGATTCATCTTTCCTTCTTGACTGTGGTTTACAGAGTGCTTTACCTCCAGCTG
((((.((((((((((((..(((((((.((...(((((.(.((((........))))).))))).)).)))))))))).))))))..))))

Mmd_443                        1  2  3  4  5  6  7  8  9 10 11 12 13 14 15 16 17 18 19 20 21 22    (SEQ ID NO:761)
cand73 probe10
CAGAGATGGGATTCACATGAACCACAGCTGAGTTCACAGAGATGATTTGTGAGCCTCAGTATTTGCACATATGTGGTCATGCGGGACCTCTCTG
(((((((.((((((((.(((((((((((((((((((.....))))))).))))))...........)))))))))).))).))))))))
```

FIG. 2: Con't.

Mmd_445  
cand761 probe23  (SEQ ID NO:763)
GAACCCAGGGCTTCTTAAGGGAACTACAACTCCCAGTGTACATGCAAAGCAGCTGTGATGCACACTGGGAGTTGTAGTCCTTGAGCTCTCAGTTT Mmd_446  
cand843a probe19  (SEQ ID NO:764)
TCCCACCTGAAGCCTAATCCCTGCTTTGCTACAACACAATTGGTTGCGGTGGAAATGATTATGTTGTCACAAACAGAGGATTAGAACTTCGGGTGGAGA Mmd_447  
cand327 probe37  (SEQ ID NO:765)
TCAAAATAATGCTGCTAATTACCTCTGATCTCCTTTAATGGGAAGCTGCTCCCAACTCCACAAAGGAGTAAATGAGAGGTCCACAGCACAGACCCAGGA Mmd_449  
mmHP693133 probe7  (SEQ ID NO:767)
GGCTTCTGAGTCTGATGCCCTCATACCTTGAGGGACATGATCATCAGTAGCCCAATGTCCCTCTTGATGGCAACTTAGACATAGTCAGAATAGCT Mmd_450  
cand536 probe8  (SEQ ID NO:769)
GCAGCTGGAAAGGGCTTAGCCCTTTAATGCCAGCAGCTGTATCTCCAATGTGGCTGCTCTGCTGAGGGGCTGGATGCTATCCAGAAGC Mmd_452  
cand167 probe11  (SEQ ID NO:771)
GGATTATAATAAATTAAATGCCTAAACTGGCAGAGTGCAAACAATTTTGACTCAGATCTAAATGTTTGCACTGGCTGTTTAAACATTTAATTTCTTCC Mmd_453  
mmHP1778980 probe5  (SEQ ID NO:772)
GGTGGAGGTGGGTGGGCTGCCTCCCAATCCTGGCTCAGGCAGGGTGGCCTCTGATCTGGGCTCCGGAGTTGGGAAAGGGAGCTGACCCATGGAAGACACC Mmd_454  
mmHP3397717 probe17  (SEQ ID NO:773)
GATATATACATTCTATTGTCCCTAGAAGGTGTATTCCTTCTAGGGACAATGTGTTGGCTGTGTGAGTC Mmd_455  
cand190 probe12  (SEQ ID NO:774)
GTCTTTGTCGTGGTGTCAGAAGATTAATTACACTCATGTGAGAACAACTTTCTCATTGGGTGAAAAGAGACATTATCCTTCTGACTTGTGATAGACGAC Mmd_456  
cand239 probe7  (SEQ ID NO:775)
GCATGCAGCTTTGGAGACGCCAAGGGGAAAATGGATTTAATTGATTCGTTACCTTTGGTATTGTAATGCCTGCTGCGATGT Mmd_457  
mmHP2347 probe4  (SEQ ID NO:776)
TGCCTTAGCTAGTTAAACCGGAAGCCTATGGTAATCAGAGAGAGGCACTTCTTGCCTTCTCCTATGGTTTCTTCATTAGCAGAGGTA Mmd_459  
cand681 probe30  (SEQ ID NO:778)
GACCAGCTCACGGGAAGTGGCCTTCAATAGTCCGATAGCTTCCTGTATCCTGACATTGTGAAGGCCCACTTCCTGCTCTGTC

FIG. 2: Con't.

Mmd_462
mmHP1121223 probe5       1 2 3 4 5 6 7 8 9 10 11 12 13 14 15 16 17 18 19 20 21 22    (SEQ ID NO:782)
AGAGGCTTGGAGCTCGAGGCTAATTGTGAATTAGGAGCCCAATTATGCCCTGCACAATTGGCTCCACGCTACCTTCTCT
(((((...(((((...(.(((((((((((...((((.((.........)))))))))))))..)..))).)).)))))

Mmd_464
cand688 probe8           1 2 3 4 5 6 7 8 9 10 11 12 13 14 15 16 17 18 19 20 21 22    (SEQ ID NO:783)
TTAGGCAGCTGGAGAAAACAATGGGCCAGATTCTCACTCTGTGTAATCACAGAGGACGACTCCATTGTATAGCCCATTGTTTCTCCCATGTACTGCCTGA
(((((((((...(((((((..((((((((((((.((((..(((((((((....))))))))))).)).).))...))....)))))))))))))......)))))))).

Mmd_465
cand449 probe19          1 2 3 4 5 6 7 8 9 10 11 12 13 14 15 16 17 18 19 20 21 22    (SEQ ID NO:784)
CCGTGTGAGTTTGCGCTGCAAAGCTCCTTGGCATCCTTGCATGGGTTGGGTGTTGGGGAGCTCAAATTGCAGCTACAACTGGCTGG
(((-((-(((((...((((((((((((((((...(((((((..((.....))))))))..))))))))....))))-))))))

Mmd_466
cand438 probe6           1 2 3 4 5 6 7 8 9 10 11 12 13 14 15 16 17 18 19 20 21 22    (SEQ ID NO:785)
GTGTTTATTTGAATGTGTGATGAGGAGGTCATCAAAATGAACACGCTCGTTGTGTTTATTTGAATCTCACATCGCTCATGAGAGAATACACGC
((((-(((((((...(((((((((((.((((...((((-(((((.((((.....)))))))))))))))))..))))))..)))))).))))

Mmd_468
cand58 probe19           1 2 3 4 5 6 7 8 9 10 11 12 13 14 15 16 17 18 19 20 21 22    (SEQ ID NO:786)
CCGCGGAGTCTCTAACTGGCGACAGATGGGCCACTTTCTTCTGGCCACAAAGGGGCCGGAATGGAGCGCTCCGCGG
(((((((((((((.(((((...(...(((((((.........))))))).)...)))..)...))))))))))))

Mmd_471
cand428 probe21          1 2 3 4 5 6 7 8 9 10 11 12 13 14 15 16 17 18 19 20 21 22    (SEQ ID NO:790)
AAAATTTTTGTAGGTGGACTGGGAAAGCAGCGGATTGCAGATGCGTTTAACAGCAGGGTATTTTCCGCTGCCATGACCAGTTAAGGGACGATTTT
((((((((((.(.....(((((((....(((((((....(((..(((((((((.......)))..)))...))))))))).....)))))))).)-)))))))))

Mmd_472
cand141 probe5           1 2 3 4 5 6 7 8 9 10 11 12 13 14 15 16 17 18 19 20 21 22    (SEQ ID NO:791)
GGCCCCTCTGTGTGGCTGCTGCTGGCTCAGACCCCAGCCCACCTTGGGCGGTGGGTTTGGGTTTTGGCTGGCACATTCACCAAGGGGCC
((((((((-(((-((-(((((-((....(((((((((((((.......))))).)..)))))))).)..-))))))..)))))))))))

Mmd_474
cand55 probe43           23 24 25 26 27 28 29 30 31 32 33 34 35 36 37 38 39 40 41 42 43 44    (SEQ ID NO:792)
GAAGTCAGACTTGCCTCCGCAACTGCATCACAGCTACATCTTTGGAGCTGTTGAAATCCAGCTGACGGAGGAATCGGTCCTTT
........((((...(((((((((..(((..(((((((((.(((.....)).))))))))).))))....)))-))-)))))))....

Mmd_475
cand411 probe13          1 2 3 4 5 6 7 8 9 10 11 12 13 14 15 16 17 18 19 20 21 22    (SEQ ID NO:793)
GAGTTTGCTGGCTCTGAATGGGGTATGAGACTTGTTCTTACCCAAAGCCCTGATGCACTCTTTCAGGGCTAGCAGACTT
(((((((((((((((((.((((((((.((.(((.........))).))-)))))))).)))))))))))))))))

Mmd_476
cand416 probe11          1 2 3 4 5 6 7 8 9 10 11 12 13 14 15 16 17 18 19 20 21 22    (SEQ ID NO:794)
CGGGTCTCAGAAATCAGGCTTCCGGAGAGTGTAGTTTGTTTGTAATAATAATACGAATTATTCTCTCAGCCTGAGGTCACTAGGGCGTG
((-(((((..((-(.(((((((....((((((-(((((((((((((((...))))..)))))))))))).)))))))))..)-))....))))-))

Mmd_477
cand415 probe21          1 2 3 4 5 6 7 8 9 10 11 12 13 14 15 16 17 18 19 20 21 22    (SEQ ID NO:795)
GTCCAGCAATATTTTAAGCTCCCAGCCAGACAGCTTTTATGAAGGGAGGGATGTTTGGAAAACAATGGGAGAGAGAGAATGGGAGCTGTGCTGGGC
((((((((((.((((((((...(((((((.(((((((....))))))))...........))))))))....)))))))..........)))))))

Mmd_478
cand622 probe21          1 2 3 4 5 6 7 8 9 10 11 12 13 14 15 16 17 18 19 20 21 22    (SEQ ID NO:796)
CTGTCCGGAATATGGTTGGTTGGTCCTGAGCCATGTTAGAGGAATTCCTGTTCAGCATGACATGCTCAGAGGCCACTTGGCCAGAGAGATGAGCTGGGAGG
((.(((((.((.((((((((((((((((.(((((((((....))))..-).)))))))..))))).)..)))))...))......)))))))).

FIG. 2: Con't.

Mmd_480  
cand963 probe9　　　　1 2 3 4 5 6 7 8 9 10 11 12 13 14 15 16 17 18 19 20 21 22　(SEQ ID NO:799)  
GATCACGTCACCATGGCCAACCGGGAGTTGGCATTTAAGGCTGGCGACGTCATCAAAGTCTTGGATGCTTCCAACAAGGATTGGTGGTGGGGCCAGATC Mmd_481  
cand269 probe2　　　　1 2 3 4 5 6 7 8 9 10 11 12 13 14 15 16 17 18 19 20 21 22　(SEQ ID NO:800)  
GCGGTTTGGAGGGCTGCATTCATTTTGAGTGCTGTTGTAATCAATTTTAGATACAGTATTCCACAATGGATCAGTTTGCATCCAAACCTGC Mmd_482  
cand486 probe16　　　　1 2 3 4 5 6 7 8 9 10 11 12 13 14 15 16 17 18 19 20 21 22　(SEQ ID NO:801)  
TCCCTGGAGCCGCTCCACTGACGGCACCATCTTGGCACAAAAACTAGCCGAGGAGGTGCCCGTGGACGTGGCCTCTTACCTCTACACTGGGGA Mmd_483  
cand271 probe10　　　　1 2 3 4 5 6 7 8 9 10 11 12 13 14 15 16 17 18 19 20 21 22　(SEQ ID NO:802)  
CCAGCTGCCCGGGAAGCTTGGCGGCCAGGCTGAGGGAAGGAAGCGTCGGCTCTCTTTGAAGGTCGGCTGCCAGTGAATCTCAGGCAGCTGG Mmd_485  
cand57 probe38　　　　23 24 25 26 27 28 29 30 31 32 33 34 35 36 37 38 39 40 41 42 43 44　(SEQ ID NO:804)  
ACTCTTATTTCCTCCACTGCCTGACTTTATTGAATGCCGTGGGGCATATTAATCAGTAAAGCCAAGTAGTGCATGAAATAAAAGT Mmd_486  
cand38 probe12　　　　1 2 3 4 5 6 7 8 9 10 11 12 13 14 15 16 17 18 19 20 21 22　(SEQ ID NO:805)  
GAGCGGTTACATTTGGCAGCATTCCTTGTTAGCATTTGATAAACAATTATTGCCAAATGTTAGCAAGGAAACCTGCCAAATGTTACAGCTC Mmd_487  
cand780 probe8　　　　1 2 3 4 5 6 7 8 9 10 11 12 13 14 15 16 17 18 19 20 21 22　(SEQ ID NO:806)  
TGCTGTTGTCCTTGGAGAAATCTGGGCCTGAGACAGAGGAGGGATGTAATTTGAGTGCTCCTTTGTCACAGGTTACCAGGGTGTGCTTGAGGGGACGGTA Mmd_488  
cand255 probe13　　　　1 2 3 4 5 6 7 8 9 10 11 12 13 14 15 16 17 18 19 20 21 22　(SEQ ID NO:807)  
GGAGCAGCCGGCTTCATTTGTGATCCGGGAGCCTGGTGCCAGCAAGACCTGGAATTTCCGGTCTGGTTGGTCTTGGGCCCCGTGGAGCCAGGTTGATACC Mmd_489  
cand604 probe27　　　　23 24 25 26 27 28 29 30 31 32 33 34 35 36 37 38 39 40 41 42 43 44　(SEQ ID NO:808)  
GGTGGAGGAGGACTGTTATTTAAAAGGCTTTTAAATGATGTCACTATATATTCTTTTAACATCCTCTAAAAGCCTTTGAAAAAACAGTCTCTACCTCCCT Mmd_491  
cand247 probe17　　　　1 2 3 4 5 6 7 8 9 10 11 12 13 14 15 16 17 18 19 20 21 22　(SEQ ID NO:811)  
TGAGCTGCTTCTTCCTCTCTCCTCTTTTGCACAAAGAGTCTCATGTCTGATATTTAGACATGATGAGCTTTGTGCAAAGTGGAACCTGGTTTCTTCTCA Mmd_492  
cand243 probe7　　　　1 2 3 4 5 6 7 8 9 10 11 12 13 14 15 16 17 18 19 20 21 22　(SEQ ID NO:812)  
AAGGATTTGGCATTTCAATCGATGGGAAATGATGTGTGATCATTCTAATTTATTATACATCATTCCCATCAATCGCGGGTTGAAGCCTT Mmd_493  
mmHP3423784 probe36　　　　23 24 25 26 27 28 29 30 31 32 33 34 35 36 37 38 39 40 41 42 43 44　(SEQ ID NO:813)  
CCTAGGTGCCATCAGGAGGGACATCAGGCTGTCGATTGCCCTCGAGTAGCACAGAACAGAGGGACATCACCCCCAAGTGACCTCCAGCTGACCTCCTAGG

FIG. 2: Con't.

Mmd_495  
mmHP200292 probe14     1 2 3 4 5 6 7 8 9 10 11 12 13 14 15 16 17 18 19 20 21 22    (SEQ ID NO:815)  
TCATTCATTGTCTTTCTTATGTTTCCCAACAGACACTGAGCACATTGAAGAGCTGCAGTGGGTGTGGAGAACATACTTGAACAATCAGAAATGAATGA  
((((((((((..(((((.((((((...(((.((.(((((((((.(......).))).)))))...))))).))))))...))).....)))))))))))

Mmd_496  
mmHP2299700 probe14    1 2 3 4 5 6 7 8 9 10 11 12 13 14 15 16 17 18 19 20 21 22    (SEQ ID NO:816)  
GCTCATTTTTGCCATGTGGAGTCAGTCATTCTGGAGTGGCTGGGGACAGCAGGAAAGCCAGCAGAGTGGCTGACCCGGGATGGTTTCAAGGGC  
((((.....(((((..(.(.((((((((((((((.....(((.(....))).((....)).)).))))))))))))).).).)))))....))))

Mmd_497  
cand451 probe7     1 2 3 4 5 6 7 8 9 10 11 12 13 14 15 16 17 18 19 20 21 22    (SEQ ID NO:817)  
CTAGACTAGCCTAGACTGGGAAGCCTGGGCTAAGATGCAGTAAACTATTTTCAGTTTATAAACAAGTCCTGACATCCCAGTTTGGGTGTTGG  
((((.....(((((((((((((.(..(((....(((((((.....))))))...)))))).).).))))))))))))..))))

Mmd_498  
cand145 probe42     23 24 25 26 27 28 29 30 31 32 33 34 35 36 37 38 39 40 41 42 43 44    (SEQ ID NO:818)  
AGAGTGTTCCAGCCCTGAGCCACCCTCCCAGGAGCCCCACAGATCCAGTCTTGACTGTCCCAATGGGGCAGGGAGGAAAGGTGGCCGCTGGGATTTTTT  
((((.((((((((....(((((..((((((((((((......)))))....))))))))).))))).(((.....)))))))))))).))))

Mmd_499  
cand835 probe2     1 2 3 4 5 6 7 8 9 10 11 12 13 14 15 16 17 18 19 20 21 22    (SEQ ID NO:819)  
CTCGAAAGGTCACACATGTAATGAATTGTGGGTGCTTGCCTGGCTTCCCAGGCGAGAACCGTAAGCAATTATTAAATGCCATTGTGTGTCAGGAAGGG  
(((.....(..(((((.(((.(.(((((.(((.((((((((((....))))))))).).))).....))))).....)...))).)))))).)....)))

Mmd_500  
cand322 probe32     23 24 25 26 27 28 29 30 31 32 33 34 35 36 37 38 39 40 41 42 43 44    (SEQ ID NO:822)  
GACATTCCAACATTTTATGGCAATTTGTTTCATTTGCCGCAGGCCCATAACGATGCAAATTGCCATAAAGTGGGATAATC  
.....((((...((((((((((((((.((.((.(((...)))....)).)).)))))))))))))))))......

Mmd_501  
cand7 probe8     1 2 3 4 5 6 7 8 9 10 11 12 13 14 15 16 17 18 19 20 21 22    (SEQ ID NO:823)  
TAATGGTCAGATAATGGATGACAATAAAAGTTATGGGTCCCTAGCTGGGGTGTAGCTCATAATGGTTGGCAAGATCCATTATTAGACCATTA  
(((((((.(..(((((..(((((((((((((....))))))))))))).))))).))...)))))))

Mmd_503  
cand887 probe4     1 2 3 4 5 6 7 8 9 10 11 12 13 14 15 16 17 18 19 20 21 22    (SEQ ID NO:825)  
GGCCAAAAGCTGCCCTCAGCTATGCATGCACAGCTTCCATTGACGTCAGTAAGAACTGTGCTCATGTAACAGGAGGCAGAAATTTGGCT  
(((((((..(((((.((((.....(((((((..(((.(((((...))))..))))).)))))))...))))....))))))...)))))))

Mmd_505  
cand949 probe25     23 24 25 26 27 28 29 30 31 32 33 34 35 36 37 38 39 40 41 42 43 44    (SEQ ID NO:826)  
TCCCATGTGCCTTTAAGGAATCACTCTTGATCTCAGTCATAAAATTGGAAAGCCACACAACTGACAAGATGATCCCCCAAGGCAGCTGAAATATGGGG  
.((((((((((......((..(((..((((((....((((.....(((...)))..)))).))))))..))).))......))))))).

Mmd_506  
cand93 probe8     1 2 3 4 5 6 7 8 9 10 11 12 13 14 15 16 17 18 19 20 21 22    (SEQ ID NO:827)  
GTCTTTTAACTCTCTATTGCTGGTGGCTCTGATTTCATGATGCATTTTGCTTATGAAACTCTAGCTTTCAGCACTAAATTGAGTTAAAGAT  
((((((..(((((..((.((((((..(((((((((((..((......((.(((((..).))))..)))))..)))))))))))

Mmd_507  
cand244 probe12     1 2 3 4 5 6 7 8 9 10 11 12 13 14 15 16 17 18 19 20 21 22    (SEQ ID NO:828)  
GGTGCGGGGCGCGTCGCCCCCCTCAGGCCACCAGAGCCCGGATACCTCAGAAATTCGGCTCTGGGTCTGTGGGGAGCGAAATGCAACCCAAACC  
(((..(((..((.(((((.(((((.....((((((..(((..((......))))))))))))))..)))))..))))....))))..))))

Mmd_508  
cand801 probe10     1 2 3 4 5 6 7 8 9 10 11 12 13 14 15 16 17 18 19 20 21 22    (SEQ ID NO:829)  
AGCTTGAAGTAGAAAAACAAAAATGGGAAACAGATGGGTAATACCCAGAAAGAAAATTTTCTCGGTATTGCCCATCTGCTTCTCTGCCTGAAAGCT  
(((((....(((((......(((..(((.((((((((((((((.(((((....)))))...))))))))))).)))))))..))))....)))))

FIG. 2: Con't.

```
Mmd_510                          1  2  3  4  5  6  7  8  9 10 11 12 13 14 15 16 17 18 19 20 21 22    (SEQ ID NO:832)
cand692 probe9
CAAGGTCTTGGTATGGTAGCGCCCCAGGATGGAGTAGGCAGGGCCAAGGTCCTTGCCAGTCTTCAGGATCTTGGGGTTCACACTGTAGCGGGGCCCTG
...(((((((..(((((((..(.(((((((((((((...(((((((((....).))))))))...))))...))))))))).)...))))))..)))))))...

Mmd_511                          1  2  3  4  5  6  7  8  9 10 11 12 13 14 15 16 17 18 19 20 21 22    (SEQ ID NO:833)
cand683 probe8
GGAAGGTACTCTGTGGGAGGGAGGAGATCAGAGCCAAGGATGACATTCCTCCTTCACACTTGCAGTACCTCC
(((..((((((((..(((..((((((((((((..(((...(.....).))).)).))))))))))).))..)..)))))))))

Mmd_512                          1  2  3  4  5  6  7  8  9 10 11 12 13 14 15 16 17 18 19 20 21 22    (SEQ ID NO:834)
mmHP668435 probe3
GGCTGCTCCTTGCCTTTGATGTGAGGCAAGCTGGGGCAGTGCAGCCCCTGTTCTGGTTGCCTTTTGTCAGATAGGAGTTGACAGCC
(((((((((....((((((...(((((.(..((((((.......))))))..).))))).)))))))....)))))

Mmd_515                          1  2  3  4  5  6  7  8  9 10 11 12 13 14 15 16 17 18 19 20 21 22    (SEQ ID NO:350)
cand389 probe14
GGGCATAGTTGGACGAGAGGGCGTCTTGGCAGGTCTCTGTGTTTAAAGAGCACAGGTGTGAGACACTGGGACGCACGCTTTCGGCTCAACATTGCCT
((((...((((((..(((((.(..(...((((((((((...)))))))......)))))..).)..)))))).)..)))))

Mmd_516                          1  2  3  4  5  6  7  8  9 10 11 12 13 14 15 16 17 18 19 20 21 22    (SEQ ID NO:836)
cand722 probe18
TTACAGCTGATTGGACGGGGTCGATACGGGAGCAGTATATAAAGGTTCCTTGGATGAGCGTCCAGTTGCTGTAA
.((((((..((((((((..(((.(....((((...(......)...))))).).)).))...))))))))))).

Mmd_517                          1  2  3  4  5  6  7  8  9 10 11 12 13 14 15 16 17 18 19 20 21 22    (SEQ ID NO:837)
cand842 probe10
GCACACCGCACAGAAGTCCTCATTCTCTATGGGGGCCGGGTGTTCTTCTTGGCTCCTGGAGCTCGGGGGATGAGTCTGTGTTCCTCAGATGTGC
(((((..(((((((((..((((((....((((..((((((((((......)))))))))))))....)))))...)))))))))......)..)))))

Mmd_518                          1  2  3  4  5  6  7  8  9 10 11 12 13 14 15 16 17 18 19 20 21 22    (SEQ ID NO:838)
cand790 probe5
CGCATGTCACACAGCCGGATTGTCCCCTTGCTGCTGCTGTATACGAAGGTGTTGCAGTGGTGGGGGTGGAACTCAGCTGCAGTGATCACCTCTGTG
((((((((((..((((..(((.(.((((.(...((((...((((....)))).)))).)....))...))))..).))..)))).)....))))

Mmd_519                          1  2  3  4  5  6  7  8  9 10 11 12 13 14 15 16 17 18 19 20 21 22    (SEQ ID NO:839)
cand676 probe12
GGAGGTGCCCAGGTCAGTGCGCTGGTTCATGGAGGCGGACGTATCTATGAGGAACAGCAGGATGGGCATCTTC
(((((((((..((..(((((..(((((((((((.((....))..)))))))))))..)))))))))))))))

Mmd_520                          1  2  3  4  5  6  7  8  9 10 11 12 13 14 15 16 17 18 19 20 21 22    (SEQ ID NO:840)
cand627 probe2
TGCACCAGGGAGAACAGCTGATGGATCACAAATCTCTGCATTTCACCAACAGAAATGAATTTGAATCCATCAATTTTATTCCCTTATGCA
.(((..(((((((((((..((((.(((((((((.........))))))))).)))))).))))))))))))..

Mmd_521                          1  2  3  4  5  6  7  8  9 10 11 12 13 14 15 16 17 18 19 20 21 22    (SEQ ID NO:841)
mmHP1528040 probe19
GGGTCTGCTTACACATTAGCAACTGACTGTCTCCTTCAACCAAACATGATCCCACAGACAGTCAGGAGCTGTGGAAGCAAAGAAAACC
((.(((((((((.((((((...(((((((((((...(((.......))).....)))))))))..))))))).))))..)))...))

Mmd_523                          1  2  3  4  5  6  7  8  9 10 11 12 13 14 15 16 17 18 19 20 21 22    (SEQ ID NO:843)
cand433 probe8
CCGTTCAAATAAAAGATTGAAGGATGCTGTGGCCCACTGCCATGAGGCAGACAGGAACACAGCTTTACGTTCAAGTTTAGAATGG
((((((...(((((..(((((..(((.((..(.(((((....))))...))..).)..).))))....).))))).)))))))))

Mmd_524                          1  2  3  4  5  6  7  8  9 10 11 12 13 14 15 16 17 18 19 20 21 22    (SEQ ID NO:357)
cand89 probe16
GGGTGTGATAGGTATACAGCTGGTTGTTACCATGGTGATGGCCAGTGTCATGCAGAAGATTATACCT
(((((((((..((((((..(.(((((...(((....)))..)))))))))).))))))..)))))))
```

FIG. 2: Con't.

```
Mmd_527                       1  2  3  4  5  6  7  8  9  10 11 12 13 14 15 16 17 18 19 20 21 22   (SEQ ID NO:845)
cand332 probe20
GTCTGTGCTGTGGACCTCTCATTTACTCCTTTGTGGAGTTGGGAGCAGCTTCCCATTAAAGGAGATCAGAGGTAATTAGCAGCATTATTTTGAC
(((.(((((((..((((((.((..(((((((((((((((....))))..))).)))))))))..))))))....))))))......)))

Mmd_528                       1  2  3  4  5  6  7  8  9  10 11 12 13 14 15 16 17 18 19 20 21 22   (SEQ ID NO:846)
mmHP166179 probe15
TGAGCAGCTGTTCCATAGAGGCTACTATAGAAACAGCTACAACAGCATAACCAGCGCGAGTAGCGATGAGGAGCTCCTAGATGGAGCAGGTGCCA
.(.(((.(((((((((..(((..........((((....((........))....)))))....)).))).).)))..)))))))).))).

Mmd_529                                          23 24 25 26 27 28 29 30 31 32 33 34 35 36 37 38 39 40 41 42 43 44   (SEQ ID NO:847)
cand741 probe25
GTATAAAATTTCTAAGCAGTGTGTGAGAGGTGTACGCAGAAATCATGTTGGCAAAATATTTTGTGTAAGTGCCTCCCACACACAGCTTTAAAATGTTAC
(((.....(((((..((((((((.((((((((((..(((((.....)))))))))))))))...)))))).))))))..))..)))

Mmd_530                       1  2  3  4  5  6  7  8  9  10 11 12 13 14 15 16 17 18 19 20 21 22   (SEQ ID NO:849)
cand523 probe3
TGGGCTCCATGGGTGTCCAGATGCCTGATACATTCTCCAGGCCAAGGTATATAAGAACCTGTGGCCTGGGGAGGCGAGGACAGCTGGACAAACAGCTTA
((((((....(..(((((((..(((((.....((((((((((((((........)))).)))))))))).).)))))..))))))..))))))

Mmd_531                       1  2  3  4  5  6  7  8  9  10 11 12 13 14 15 16 17 18 19 20 21 22   (SEQ ID NO:850)
mmHP141642 probe4
GCCGCGTAGTGAAAGAGCTAGCGTGGGCAGTTCTTTTGTACTCCAGCTGGAGTAAAATGAACGCAGGCTCGCGTGTTTTCATCGCTGGT
((((.(...(((((((.....((((((((.((((((.....((((((....))))).))))....))))))).)))))))...)))))

Mmd_532                       1  2  3  4  5  6  7  8  9  10 11 12 13 14 15 16 17 18 19 20 21 22   (SEQ ID NO:851)
cand111 probe13
GCTCGCAGGCAGGGGATTTGAGGAGCGGTTGTGTGATTTGTACAGCTGTCATTAGGGTAATTGCACGATATTTTCCCAAATTTCTCCTGCAGC
(((.((((((((..((..(((((.((((((..(((((((..((...(((.(((....))).)))))..)))))))..)))))).))))))))))))

Mmd_533                       1  2  3  4  5  6  7  8  9  10 11 12 13 14 15 16 17 18 19 20 21 22   (SEQ ID NO:852)
cand95 probe8
TTAAGCTGAGTGCATTGTGATTTCCAATAATTGAGGCAGTGGTTCTAAAAGCTGTCTACATTAATGAAAGAGCAATGTGGCCAGCTTGA
(((((((((.(((((((..(((.((.(((((.......))))))).))).)))))))..))).))))))).

Mmd_534                       1  2  3  4  5  6  7  8  9  10 11 12 13 14 15 16 17 18 19 20 21 22   (SEQ ID NO:853)
cand477 probe12
TACCCTCAGAGCTGATCTGAGTGTGGAGATTCCATTGACTTCAAAGGAAGCTTCATGCTTGGATCTTCTCCACAGGGGTG
((((((..(((..(((((.(((((((((.((((.(((.....))).)))).)))))))))..))).....))))))

Mmd_536                                          23 24 25 26 27 28 29 30 31 32 33 34 35 36 37 38 39 40 41 42 43 44   (SEQ ID NO:365)
cand109 probe41
GGCTGGGGCTGAACCGAATGCTGGCACCCCTCCAAACCCAGGGGATCCCCCAAAAGTAGGAGGGCTGCCAAACACTGGAGCAGCACCCGAAGCC
((((.(((((.(((.....(((((.((((((........((((...)))).........)))))))))))......)))..)))).)).))))
```

FIG. 4: A collection of nucleic acid molecules.

SEQ. ID. NO: 913, SEQ. ID. NO: 916, SEQ. ID. NO: 919, SEQ. ID. NO: 920, SEQ. ID. NO: 921, SEQ. ID. NO: 922, SEQ. ID. NO: 923, SEQ. ID. NO: 929, SEQ. ID. NO: 930, SEQ. ID. NO: 931, SEQ. ID. NO: 932, SEQ. ID. NO: 933, SEQ. ID. NO: 934, SEQ. ID. NO: 936, SEQ. ID. NO: 938, SEQ. ID. NO: 942, SEQ. ID. NO: 943, SEQ. ID. NO: 945, SEQ. ID. NO: 948, SEQ. ID. NO: 949, SEQ. ID. NO: 952, SEQ. ID. NO: 956, SEQ. ID. NO: 967, SEQ. ID. NO: 970, SEQ. ID. NO: 972, SEQ. ID. NO: 976, SEQ. ID. NO: 977, SEQ. ID. NO: 982, SEQ. ID. NO: 984, SEQ. ID. NO: 986, SEQ. ID. NO: 987, SEQ. ID. NO: 988, SEQ. ID. NO: 989, SEQ. ID. NO: 990, SEQ. ID. NO: 991, SEQ. ID. NO: 992, SEQ. ID. NO: 993, SEQ. ID. NO: 995, SEQ. ID. NO: 996, SEQ. ID. NO: 999, SEQ. ID. NO: 1000, SEQ. ID. NO: 1001, SEQ. ID. NO: 1002, SEQ. ID. NO: 1005, SEQ. ID. NO: 1006, SEQ. ID. NO: 1007, SEQ. ID. NO: 1008, SEQ. ID. NO: 1010, SEQ. ID. NO: 1011, SEQ. ID. NO: 1014, SEQ. ID. NO: 1015, SEQ. ID. NO: 1016, SEQ. ID. NO: 1017, SEQ. ID. NO: 1019, SEQ. ID. NO: 1020, SEQ. ID. NO: 1021, SEQ. ID. NO: 1022, SEQ. ID. NO: 1023, SEQ. ID. NO: 1024, SEQ. ID. NO: 1032, SEQ. ID. NO: 1033, SEQ. ID. NO: 1034, SEQ. ID. NO: 1035, SEQ. ID. NO: 1036, SEQ. ID. NO: 1037, SEQ. ID. NO: 1038, SEQ. ID. NO: 1039, SEQ. ID. NO: 1040, SEQ. ID. NO: 1047, SEQ. ID. NO: 1050, SEQ. ID. NO: 1051, SEQ. ID. NO: 1052, SEQ. ID. NO: 1053, SEQ. ID. NO: 1054, SEQ. ID. NO: 1057, SEQ. ID. NO: 1058, SEQ. ID. NO: 1059, SEQ. ID. NO: 1062, SEQ. ID. NO: 1063, SEQ. ID. NO: 1064, SEQ. ID. NO: 1065, SEQ. ID. NO: 1066, SEQ. ID. NO: 1067, SEQ. ID. NO: 1068, SEQ. ID. NO: 1069, SEQ. ID. NO: 1070, SEQ. ID. NO: 1071, SEQ. ID. NO: 1072, SEQ. ID. NO: 1074, SEQ. ID. NO: 1076, SEQ. ID. NO: 1078, SEQ. ID. NO: 1079, SEQ. ID. NO: 1080, SEQ. ID. NO: 1082, SEQ. ID. NO: 1084, SEQ. ID. NO: 1085, SEQ. ID. NO: 1086, SEQ. ID. NO: 1094, SEQ. ID. NO: 1095, SEQ. ID. NO: 1096, SEQ. ID. NO: 1097, SEQ. ID. NO: 1098, SEQ. ID. NO: 1099, SEQ. ID. NO: 1100, SEQ. ID. NO: 1101, SEQ. ID. NO: 1105, SEQ. ID. NO: 1109, SEQ. ID. NO: 1244, SEQ. ID. NO: 1391, SEQ. ID. NO: 8833, SEQ. ID. NO: 8834, SEQ. ID. NO: 8835, SEQ. ID. NO: 8836, SEQ. ID. NO: 8837, SEQ. ID. NO: 8838, SEQ. ID. NO: 8839, SEQ. ID. NO: 8840, SEQ. ID. NO: 8841, SEQ. ID. NO: 8842, SEQ. ID. NO: 8845, SEQ. ID. NO: 8846, SEQ. ID. NO: 8847, SEQ. ID. NO: 8848, SEQ. ID. NO: 8849, SEQ. ID. NO: 8850, SEQ. ID. NO: 8851, SEQ. ID. NO: 8852, SEQ. ID. NO: 8853, SEQ. ID. NO: 8854, SEQ. ID. NO: 8855, SEQ. ID. NO: 8856, SEQ. ID. NO: 8857, SEQ. ID. NO: 8858, SEQ. ID. NO: 8859, SEQ. ID. NO: 8860, SEQ. ID. NO: 8861, SEQ. ID. NO: 8862, SEQ. ID. NO: 8863, SEQ. ID. NO: 8864, SEQ. ID. NO: 8865, SEQ. ID. NO: 8866, SEQ. ID. NO: 8867, SEQ. ID. NO: 8868, SEQ. ID. NO: 8869, SEQ. ID. NO: 8870, SEQ. ID. NO: 8871, SEQ. ID. NO: 8872, SEQ. ID. NO: 8873, SEQ. ID. NO: 8874, SEQ. ID. NO: 8875, SEQ. ID. NO: 8876, SEQ. ID. NO: 8877, SEQ. ID. NO: 8878, SEQ. ID. NO: 8879, SEQ. ID. NO: 8880, SEQ. ID. NO: 8881, SEQ. ID. NO: 8882, SEQ. ID. NO: 8883, SEQ. ID. NO: 8884, SEQ. ID. NO: 8885, SEQ. ID. NO: 8886, SEQ. ID. NO: 8887, SEQ. ID. NO: 8889, SEQ. ID. NO: 8890, SEQ. ID. NO: 8891, SEQ. ID. NO: 8892, SEQ. ID. NO: 8893, SEQ. ID. NO: 8894, SEQ. ID. NO: 8895, SEQ. ID. NO: 8896, SEQ. ID. NO: 8898, SEQ. ID. NO: 8899, SEQ. ID. NO: 8900, SEQ. ID. NO: 8903, SEQ. ID. NO: 8905, SEQ. ID. NO: 8906, SEQ. ID. NO: 8908, SEQ. ID. NO: 8909, SEQ. ID. NO: 8910, SEQ. ID. NO: 8911, SEQ. ID. NO: 8912, SEQ. ID. NO: 8914, SEQ. ID. NO: 8915, SEQ. ID. NO: 8916, SEQ. ID. NO: 8917, SEQ. ID. NO: 8918, SEQ. ID. NO: 8921, SEQ. ID. NO: 8922, SEQ. ID. NO: 8923, SEQ. ID. NO: 8924, SEQ. ID. NO: 8925, SEQ. ID. NO: 8926, SEQ. ID. NO: 8927, SEQ. ID. NO: 8929, SEQ. ID. NO: 8930, SEQ. ID. NO: 8931, SEQ. ID. NO: 8932, SEQ. ID. NO: 8933, SEQ. ID. NO: 8934, SEQ. ID. NO: 8935, SEQ. ID. NO: 8936, SEQ. ID. NO: 8937, SEQ. ID. NO: 8938, SEQ. ID. NO: 8939, SEQ. ID. NO: 8940, SEQ. ID. NO: 8941, SEQ. ID. NO: 8942, SEQ. ID. NO: 8943, SEQ. ID. NO: 8944, SEQ. ID. NO: 8945, SEQ. ID. NO: 8950, SEQ. ID. NO: 8951, SEQ. ID. NO: 8952, SEQ. ID. NO: 8953, SEQ. ID. NO: 8954, SEQ. ID. NO: 8955, SEQ. ID. NO: 8956, SEQ. ID. NO: 8957, SEQ. ID. NO: 8958, SEQ. ID. NO: 8959, SEQ. ID. NO: 8960, SEQ. ID. NO: 8961, SEQ. ID. NO: 8962, SEQ. ID. NO: 8963, SEQ. ID. NO: 8964, SEQ. ID. NO: 8965, SEQ. ID. NO: 8966, SEQ. ID. NO: 8968, SEQ. ID. NO: 8969, SEQ. ID. NO: 8971, SEQ. ID. NO: 8972, SEQ. ID. NO: 8975, SEQ. ID. NO: 8976, SEQ. ID. NO: 8977, SEQ. ID. NO: 8978, SEQ. ID. NO: 8979, SEQ. ID. NO: 8980, SEQ. ID. NO: 8981, SEQ. ID. NO: 8982, SEQ. ID. NO: 8983, SEQ. ID. NO: 8984, SEQ. ID. NO: 8985, SEQ. ID. NO: 8986, SEQ. ID. NO: 8987, SEQ. ID. NO: 8988, SEQ. ID. NO: 8989, SEQ. ID. NO: 8990, SEQ. ID. NO: 8991, SEQ. ID. NO: 8992, SEQ. ID. NO: 8993, SEQ. ID. NO: 8994, SEQ. ID. NO: 8995, SEQ. ID. NO: 8996, SEQ. ID. NO: 8997, SEQ. ID. NO: 8998, SEQ. ID. NO: 8999, SEQ. ID. NO: 9000, SEQ. ID. NO: 9001, SEQ. ID. NO: 9003, SEQ. ID. NO: 9004, SEQ. ID. NO: 9005, SEQ. ID. NO: 9006, SEQ. ID. NO: 9007, SEQ. ID. NO: 9008, SEQ. ID. NO: 9009, SEQ. ID. NO: 9010, SEQ. ID. NO: 9011, SEQ. ID. NO: 9012, SEQ. ID. NO: 9013, SEQ. ID. NO: 9014, SEQ. ID. NO: 9015, SEQ. ID. NO: 9016, SEQ. ID. NO: 9017, SEQ. ID. NO: 9019, SEQ. ID. NO: 9022, SEQ. ID. NO: 9024, SEQ. ID. NO: 9025, SEQ. ID. NO: 9027, SEQ. ID. NO: 9031, SEQ. ID. NO: 9032, SEQ. ID. NO: 9034, SEQ. ID. NO: 9035, SEQ. ID. NO: 9039, SEQ. ID. NO: 9041, SEQ. ID. NO: 9043, SEQ. ID. NO: 9044, SEQ. ID. NO: 9046, SEQ. ID. NO: 9048, SEQ. ID. NO: 9049, SEQ. ID. NO: 9050, SEQ. ID. NO: 9058, SEQ. ID. NO: 9061, SEQ. ID. NO: 9062, SEQ. ID. NO: 9064, SEQ. ID. NO: 9065, SEQ. ID. NO: 9066, SEQ. ID. NO: 9070, SEQ. ID. NO: 9072, SEQ. ID. NO: 9074, SEQ. ID. NO: 9080, SEQ. ID. NO: 9082, SEQ. ID. NO: 9084, SEQ. ID. NO: 9086, SEQ. ID. NO: 9087, SEQ. ID. NO: 9088, SEQ. ID. NO: 9089, SEQ. ID. NO: 9090, SEQ. ID. NO: 9091, SEQ. ID. NO: 9092, SEQ. ID. NO: 9093, SEQ. ID. NO: 9094, SEQ. ID. NO: 9095, SEQ. ID. NO: 9096, SEQ. ID. NO: 9097, SEQ. ID. NO: 9100, SEQ. ID. NO: 9101, SEQ. ID. NO: 9102, SEQ. ID. NO: 9103, SEQ. ID. NO: 9104, SEQ. ID. NO: 9105, SEQ. ID. NO: 9106, SEQ. ID. NO: 9107, SEQ. ID. NO: 9108, SEQ. ID. NO: 9109, SEQ. ID. NO: 9110, SEQ. ID. NO: 9111, SEQ.

FIG. 4: Con't.

ID. NO: 9112, SEQ. ID. NO: 9113, SEQ. ID. NO: 9114, SEQ. ID. NO: 9115, SEQ. ID. NO: 9116, SEQ. ID. NO: 9117, SEQ. ID. NO: 9118, SEQ. ID. NO: 9119, SEQ. ID. NO: 9120, SEQ. ID. NO: 9121, SEQ. ID. NO: 9122, SEQ. ID. NO: 9123, SEQ. ID. NO: 9124, SEQ. ID. NO: 9125, SEQ. ID. NO: 9126, SEQ. ID. NO: 9127, SEQ. ID. NO: 9128, SEQ. ID. NO: 9129, SEQ. ID. NO: 9130, SEQ. ID. NO: 9131, SEQ. ID. NO: 9132, SEQ. ID. NO: 9133, SEQ. ID. NO: 9134, SEQ. ID. NO: 9135, SEQ. ID. NO: 9136, SEQ. ID. NO: 9137, SEQ. ID. NO: 9138, SEQ. ID. NO: 9139, SEQ. ID. NO: 9140, SEQ. ID. NO: 9141, SEQ. ID. NO: 9142, SEQ. ID. NO: 9143, SEQ. ID. NO: 9144, SEQ. ID. NO: 9145, SEQ. ID. NO: 9146, SEQ. ID. NO: 9148, SEQ. ID. NO: 9149, SEQ. ID. NO: 9150, SEQ. ID. NO: 9151, SEQ. ID. NO: 9154, SEQ. ID. NO: 9155, SEQ. ID. NO: 9156, SEQ. ID. NO: 9157, SEQ. ID. NO: 9158, SEQ. ID. NO: 9159, SEQ. ID. NO: 9160, SEQ. ID. NO: 9161, SEQ. ID. NO: 9162, SEQ. ID. NO: 9163, SEQ. ID. NO: 9164, SEQ. ID. NO: 9165, SEQ. ID. NO: 9166, SEQ. ID. NO: 9167, SEQ. ID. NO: 9168, SEQ. ID. NO: 9170, SEQ. ID. NO: 9175, SEQ. ID. NO: 9176, SEQ. ID. NO: 9182, SEQ. ID. NO: 9183, SEQ. ID. NO: 9184, SEQ. ID. NO: 9185, SEQ. ID. NO: 9186, SEQ. ID. NO: 9187, SEQ. ID. NO: 9188, SEQ. ID. NO: 9189, SEQ. ID. NO: 9190, SEQ. ID. NO: 9191, SEQ. ID. NO: 9192, SEQ. ID. NO: 9194, SEQ. ID. NO: 9196, SEQ. ID. NO: 9197, SEQ. ID. NO: 9198, SEQ. ID. NO: 9199, SEQ. ID. NO: 9200, SEQ. ID. NO: 9206, SEQ. ID. NO: 9207, SEQ. ID. NO: 9208, SEQ. ID. NO: 9209, SEQ. ID. NO: 9210, SEQ. ID. NO: 9211, SEQ. ID. NO: 9212, SEQ. ID. NO: 9213, SEQ. ID. NO: 9214, SEQ. ID. NO: 9217, SEQ. ID. NO: 9218, SEQ. ID. NO: 9219, SEQ. ID. NO: 9221, SEQ. ID. NO: 9222, SEQ. ID. NO: 9223, SEQ. ID. NO: 9224, SEQ. ID. NO: 9225, SEQ. ID. NO: 9226, SEQ. ID. NO: 9228, SEQ. ID. NO: 9231, SEQ. ID. NO: 9233, SEQ. ID. NO: 9235, SEQ. ID. NO: 9236, SEQ. ID. NO: 9237, SEQ. ID. NO: 9238, SEQ. ID. NO: 9239, SEQ. ID. NO: 9241, SEQ. ID. NO: 9242, SEQ. ID. NO: 9243, SEQ. ID. NO: 9244, SEQ. ID. NO: 9245, SEQ. ID. NO: 9246, SEQ. ID. NO: 9249, SEQ. ID. NO: 9251, SEQ. ID. NO: 9257, SEQ. ID. NO: 9258, SEQ. ID. NO: 9260, SEQ. ID. NO: 9262, SEQ. ID. NO: 9263, SEQ. ID. NO: 9264, SEQ. ID. NO: 9265, SEQ. ID. NO: 9268, SEQ. ID. NO: 9274, SEQ. ID. NO: 9276, SEQ. ID. NO: 9278, SEQ. ID. NO: 9279, SEQ. ID. NO: 9280, SEQ. ID. NO: 9299, SEQ. ID. NO: 9303, SEQ. ID. NO: 9304, SEQ. ID. NO: 9305, SEQ. ID. NO: 9308, SEQ. ID. NO: 9319, SEQ. ID. NO: 9320, SEQ. ID. NO: 9321, SEQ. ID. NO: 9322, SEQ. ID. NO: 9323, SEQ. ID. NO: 9324, SEQ. ID. NO: 9325, SEQ. ID. NO: 9326, SEQ. ID. NO: 9327, SEQ. ID. NO: 9328, SEQ. ID. NO: 9329, SEQ. ID. NO: 9330, SEQ. ID. NO: 9331, SEQ. ID. NO: 9332, SEQ. ID. NO: 9333, SEQ. ID. NO: 9334, SEQ. ID. NO: 9335, SEQ. ID. NO: 9336, SEQ. ID. NO: 9337, SEQ. ID. NO: 9338, SEQ. ID. NO: 9339, SEQ. ID. NO: 9340, SEQ. ID. NO: 9341, SEQ. ID. NO: 9342, SEQ. ID. NO: 9343, SEQ. ID. NO: 9344, SEQ. ID. NO: 9345, SEQ. ID. NO: 9346, SEQ. ID. NO: 9347, SEQ. ID. NO: 9348, SEQ. ID. NO: 9349, SEQ. ID. NO: 9350, SEQ. ID. NO: 9351, SEQ. ID. NO: 9352, SEQ. ID. NO: 9353, SEQ. ID. NO: 9354, SEQ. ID. NO: 9355, SEQ. ID. NO: 9356, SEQ. ID. NO: 9357, SEQ. ID. NO: 9358, SEQ. ID. NO: 9359, SEQ. ID. NO: 9361, SEQ. ID. NO: 9362, SEQ. ID. NO: 9363, SEQ. ID. NO: 9364, SEQ. ID. NO: 9365, SEQ. ID. NO: 9366, SEQ. ID. NO: 9367, SEQ. ID. NO: 9368, SEQ. ID. NO: 9369, SEQ. ID. NO: 9370, SEQ. ID. NO: 9371, SEQ. ID. NO: 9372, SEQ. ID. NO: 9373, SEQ. ID. NO: 9374, SEQ. ID. NO: 9375, SEQ. ID. NO: 9376, SEQ. ID. NO: 9377, SEQ. ID. NO: 9378, SEQ. ID. NO: 9379, SEQ. ID. NO: 9380, SEQ. ID. NO: 9381, SEQ. ID. NO: 9382, SEQ. ID. NO: 9383, SEQ. ID. NO: 9384, SEQ. ID. NO: 9385, SEQ. ID. NO: 9386, SEQ. ID. NO: 9387, SEQ. ID. NO: 9388, SEQ. ID. NO: 9389, SEQ. ID. NO: 9390, SEQ. ID. NO: 9391, SEQ. ID. NO: 9392, SEQ. ID. NO: 9393, SEQ. ID. NO: 9394, SEQ. ID. NO: 9395, SEQ. ID. NO: 9396, SEQ. ID. NO: 9397, SEQ. ID. NO: 9398, SEQ. ID. NO: 9399, SEQ. ID. NO: 9400, SEQ. ID. NO: 9401, SEQ. ID. NO: 9402, SEQ. ID. NO: 9403, SEQ. ID. NO: 9404, SEQ. ID. NO: 9405, SEQ. ID. NO: 9406, SEQ. ID. NO: 9407, SEQ. ID. NO: 9408, SEQ. ID. NO: 9409, SEQ. ID. NO: 9410, SEQ. ID. NO: 9411, SEQ. ID. NO: 9412, SEQ. ID. NO: 9413, SEQ. ID. NO: 9414, SEQ. ID. NO: 9415, SEQ. ID. NO: 9417, SEQ. ID. NO: 9418, SEQ. ID. NO: 9419, SEQ. ID. NO: 9421, SEQ. ID. NO: 9422, SEQ. ID. NO: 9423, SEQ. ID. NO: 9424, SEQ. ID. NO: 9425, SEQ. ID. NO: 9426, SEQ. ID. NO: 9427, SEQ. ID. NO: 9429, SEQ. ID. NO: 9430, SEQ. ID. NO: 9431, SEQ. ID. NO: 9432, SEQ. ID. NO: 9433, SEQ. ID. NO: 9434, SEQ. ID. NO: 9435, SEQ. ID. NO: 9436, SEQ. ID. NO: 9437, SEQ. ID. NO: 9438, SEQ. ID. NO: 9439, SEQ. ID. NO: 9440, SEQ. ID. NO: 9441, SEQ. ID. NO: 9442, SEQ. ID. NO: 9443, SEQ. ID. NO: 9444, SEQ. ID. NO: 9445, SEQ. ID. NO: 9446, SEQ. ID. NO: 9447, SEQ. ID. NO: 9448, SEQ. ID. NO: 9449, SEQ. ID. NO: 9450, SEQ. ID. NO: 9451, SEQ. ID. NO: 9452, SEQ. ID. NO: 9453, SEQ. ID. NO: 9454, SEQ. ID. NO: 9455, SEQ. ID. NO: 9456, SEQ. ID. NO: 9457, SEQ. ID. NO: 9458, SEQ. ID. NO: 9459, SEQ. ID. NO: 9460, SEQ. ID. NO: 9461, SEQ. ID. NO: 9462, SEQ. ID. NO: 9463, SEQ. ID. NO: 9465, SEQ. ID. NO: 9466, SEQ. ID. NO: 9467, SEQ. ID. NO: 9468, SEQ. ID. NO: 9471, SEQ. ID. NO: 9472, SEQ. ID. NO: 9473, SEQ. ID. NO: 9474, SEQ. ID. NO: 9475, SEQ. ID. NO: 9476, SEQ. ID. NO: 9477, SEQ. ID. NO: 9478, SEQ. ID. NO: 9479, SEQ. ID. NO: 9480, SEQ. ID. NO: 9481, SEQ. ID. NO: 9482, SEQ. ID. NO: 9483, SEQ. ID. NO: 9484, SEQ. ID. NO: 9485, SEQ. ID. NO: 9486, SEQ. ID. NO: 9487, SEQ. ID. NO: 9488, SEQ. ID. NO: 9489, SEQ. ID. NO: 9490, SEQ. ID. NO: 9491, SEQ. ID. NO: 9492, SEQ. ID. NO: 9493, SEQ. ID. NO: 9494, SEQ. ID. NO: 9495, SEQ. ID. NO: 9496, SEQ. ID. NO: 9497, SEQ. ID. NO: 9498, SEQ. ID. NO: 9499, SEQ. ID. NO: 9500, SEQ. ID. NO: 9501, SEQ. ID. NO: 9502, SEQ. ID. NO: 9503, SEQ. ID. NO: 9504, SEQ. ID. NO: 9505, SEQ. ID. NO: 9506, SEQ. ID. NO: 9507, SEQ. ID. NO: 9508, SEQ. ID. NO: 9509, SEQ. ID. NO: 9510, SEQ. ID. NO: 9511, SEQ. ID. NO: 9512, SEQ. ID. NO: 9513, SEQ. ID. NO: 9514, SEQ. ID. NO: 9515, SEQ. ID. NO: 9516, SEQ. ID. NO: 9517, SEQ. ID. NO: 9518, SEQ. ID. NO: 9519, SEQ. ID. NO: 9520, SEQ. ID. NO: 9521, SEQ. ID. NO: 9522, SEQ. ID. NO: 9523, SEQ. ID. NO: 9524, SEQ. ID. NO: 9525, SEQ. ID. NO: 9526, SEQ. ID. NO: 9527, SEQ. ID. NO: 9528, SEQ. ID. NO: 9529, SEQ. ID. NO: 9530, SEQ. ID. NO: 9531, SEQ. ID. NO: 9532, SEQ. ID. NO: 9533, SEQ. ID. NO: 9534, SEQ. ID. NO: 9535, SEQ. ID. NO: 9536, SEQ. ID. NO: 9537, SEQ. ID. NO: 9538, SEQ. ID. NO: 9539, SEQ. ID. NO: 9540, SEQ.

FIG. 4: Con't.

ID. NO: 9541, SEQ. ID. NO: 9542, SEQ. ID. NO: 9543, SEQ. ID. NO: 9546, SEQ. ID. NO: 9547, SEQ. ID. NO: 9548, SEQ. ID. NO: 9549, SEQ. ID. NO: 9550, SEQ. ID. NO: 9551, SEQ. ID. NO: 9552, SEQ. ID. NO: 9553, SEQ. ID. NO: 9554, SEQ. ID. NO: 9556, SEQ. ID. NO: 9557, SEQ. ID. NO: 9558, SEQ. ID. NO: 9559, SEQ. ID. NO: 9560, SEQ. ID. NO: 9561, SEQ. ID. NO: 9562, SEQ. ID. NO: 9563, SEQ. ID. NO: 9564, SEQ. ID. NO: 9565, SEQ. ID. NO: 9566, SEQ. ID. NO: 9568, SEQ. ID. NO: 9569, SEQ. ID. NO: 9570, SEQ. ID. NO: 9571, SEQ. ID. NO: 9572, SEQ. ID. NO: 9573, SEQ. ID. NO: 9574, SEQ. ID. NO: 9575, SEQ. ID. NO: 9576, SEQ. ID. NO: 9577, SEQ. ID. NO: 9578, SEQ. ID. NO: 9579, SEQ. ID. NO: 9580, SEQ. ID. NO: 9581, SEQ. ID. NO: 9583, SEQ. ID. NO: 9584, SEQ. ID. NO: 9585, SEQ. ID. NO: 9586, SEQ. ID. NO: 9588, SEQ. ID. NO: 9589, SEQ. ID. NO: 9590, SEQ. ID. NO: 9591, SEQ. ID. NO: 9592, SEQ. ID. NO: 9593, SEQ. ID. NO: 9595, SEQ. ID. NO: 9596, SEQ. ID. NO: 9597, SEQ. ID. NO: 9598, SEQ. ID. NO: 9599, SEQ. ID. NO: 9600, SEQ. ID. NO: 9601, SEQ. ID. NO: 9602, SEQ. ID. NO: 9603, SEQ. ID. NO: 9604, SEQ. ID. NO: 9605, SEQ. ID. NO: 9606, SEQ. ID. NO: 9607, SEQ. ID. NO: 9608, SEQ. ID. NO: 9609, SEQ. ID. NO: 9610, SEQ. ID. NO: 9611, SEQ. ID. NO: 9612, SEQ. ID. NO: 9613, SEQ. ID. NO: 9614, SEQ. ID. NO: 9615, SEQ. ID. NO: 9616, SEQ. ID. NO: 9617, SEQ. ID. NO: 9619, SEQ. ID. NO: 9620, SEQ. ID. NO: 9621, SEQ. ID. NO: 9622, SEQ. ID. NO: 9623, SEQ. ID. NO: 9624, SEQ. ID. NO: 9625, SEQ. ID. NO: 9626, SEQ. ID. NO: 9627, SEQ. ID. NO: 9628, SEQ. ID. NO: 9629, SEQ. ID. NO: 9630, SEQ. ID. NO: 9631, SEQ. ID. NO: 9633, SEQ. ID. NO: 9634, SEQ. ID. NO: 9636, SEQ. ID. NO: 9637, SEQ. ID. NO: 9638, SEQ. ID. NO: 9639, SEQ. ID. NO: 9640, SEQ. ID. NO: 9641, SEQ. ID. NO: 9642, SEQ. ID. NO: 9643, SEQ. ID. NO: 9644, SEQ. ID. NO: 9645, SEQ. ID. NO: 9646, SEQ. ID. NO: 9647, SEQ. ID. NO: 9648, SEQ. ID. NO: 9649, SEQ. ID. NO: 9650, SEQ. ID. NO: 9651, SEQ. ID. NO: 9652, SEQ. ID. NO: 9653, SEQ. ID. NO: 9654, SEQ. ID. NO: 9655, SEQ. ID. NO: 9656, SEQ. ID. NO: 9657, SEQ. ID. NO: 9658, SEQ. ID. NO: 9659, SEQ. ID. NO: 9661, SEQ. ID. NO: 9662, SEQ. ID. NO: 9663, SEQ. ID. NO: 9664, SEQ. ID. NO: 9665, SEQ. ID. NO: 9666, SEQ. ID. NO: 9667, SEQ. ID. NO: 9668, SEQ. ID. NO: 9669, SEQ. ID. NO: 9670, SEQ. ID. NO: 9671, SEQ. ID. NO: 9672, SEQ. ID. NO: 9673, SEQ. ID. NO: 9674, SEQ. ID. NO: 9675, SEQ. ID. NO: 9676, SEQ. ID. NO: 9677, SEQ. ID. NO: 9678, SEQ. ID. NO: 9679, SEQ. ID. NO: 9680, SEQ. ID. NO: 9681, SEQ. ID. NO: 9683, SEQ. ID. NO: 9686, SEQ. ID. NO: 9688, SEQ. ID. NO: 9689, SEQ. ID. NO: 9690, SEQ. ID. NO: 9691, SEQ. ID. NO: 9692, SEQ. ID. NO: 9693, SEQ. ID. NO: 9694, SEQ. ID. NO: 9695, SEQ. ID. NO: 9697, SEQ. ID. NO: 9698, SEQ. ID. NO: 9699, SEQ. ID. NO: 9700, SEQ. ID. NO: 9701, SEQ. ID. NO: 9702, SEQ. ID. NO: 9703, SEQ. ID. NO: 9704, SEQ. ID. NO: 9705, SEQ. ID. NO: 9706, SEQ. ID. NO: 9707, SEQ. ID. NO: 9708, SEQ. ID. NO: 9709, SEQ. ID. NO: 9710, SEQ. ID. NO: 9711, SEQ. ID. NO: 9712, SEQ. ID. NO: 9713, SEQ. ID. NO: 9714, SEQ. ID. NO: 9715, SEQ. ID. NO: 9716, SEQ. ID. NO: 9717, SEQ. ID. NO: 9718, SEQ. ID. NO: 9719, SEQ. ID. NO: 9720, SEQ. ID. NO: 9721, SEQ. ID. NO: 9722, SEQ. ID. NO: 9723, SEQ. ID. NO: 9724, SEQ. ID. NO: 9725, SEQ. ID. NO: 9726, SEQ. ID. NO: 9727, SEQ. ID. NO: 9728, SEQ. ID. NO: 9729, SEQ. ID. NO: 9730, SEQ. ID. NO: 9731, SEQ. ID. NO: 9732, SEQ. ID. NO: 9733, SEQ. ID. NO: 9734, SEQ. ID. NO: 9735, SEQ. ID. NO: 9736, SEQ. ID. NO: 9737, SEQ. ID. NO: 9738, SEQ. ID. NO: 9739, SEQ. ID. NO: 9740, SEQ. ID. NO: 9741, SEQ. ID. NO: 9742, SEQ. ID. NO: 9743, SEQ. ID. NO: 9744, SEQ. ID. NO: 9745, SEQ. ID. NO: 9747, SEQ. ID. NO: 9748, SEQ. ID. NO: 9749, SEQ. ID. NO: 9750, SEQ. ID. NO: 9751, SEQ. ID. NO: 9752, SEQ. ID. NO: 9753, SEQ. ID. NO: 9754, SEQ. ID. NO: 9755, SEQ. ID. NO: 9756, SEQ. ID. NO: 9757, SEQ. ID. NO: 9758, SEQ. ID. NO: 9759, SEQ. ID. NO: 9760, SEQ. ID. NO: 9764, SEQ. ID. NO: 9765, SEQ. ID. NO: 9766, SEQ. ID. NO: 9767, SEQ. ID. NO: 9768, SEQ. ID. NO: 9770, SEQ. ID. NO: 9771, SEQ. ID. NO: 9772, SEQ. ID. NO: 9773, SEQ. ID. NO: 9774, SEQ. ID. NO: 9775, SEQ. ID. NO: 9777, SEQ. ID. NO: 9778, SEQ. ID. NO: 9779, SEQ. ID. NO: 9780, SEQ. ID. NO: 9781, SEQ. ID. NO: 9782, SEQ. ID. NO: 9783, SEQ. ID. NO: 9784, SEQ. ID. NO: 9785, SEQ. ID. NO: 9786, SEQ. ID. NO: 9787, SEQ. ID. NO: 9788, SEQ. ID. NO: 9789, SEQ. ID. NO: 9790, SEQ. ID. NO: 9791, SEQ. ID. NO: 9792, SEQ. ID. NO: 9793, SEQ. ID. NO: 9794, SEQ. ID. NO: 9795, SEQ. ID. NO: 9796, SEQ. ID. NO: 9797, SEQ. ID. NO: 9798, SEQ. ID. NO: 9799, SEQ. ID. NO: 9800, SEQ. ID. NO: 9801, SEQ. ID. NO: 9802, SEQ. ID. NO: 9803, SEQ. ID. NO: 9804, SEQ. ID. NO: 9805, SEQ. ID. NO: 9806, SEQ. ID. NO: 9807, SEQ. ID. NO: 9808, SEQ. ID. NO: 9809, SEQ. ID. NO: 9810, SEQ. ID. NO: 9811, SEQ. ID. NO: 9812, SEQ. ID. NO: 9813, SEQ. ID. NO: 9814, SEQ. ID. NO: 9815, SEQ. ID. NO: 9816, SEQ. ID. NO: 9817, SEQ. ID. NO: 9818, SEQ. ID. NO: 9819, SEQ. ID. NO: 9821, SEQ. ID. NO: 9822, SEQ. ID. NO: 9823, SEQ. ID. NO: 9824, SEQ. ID. NO: 9825, SEQ. ID. NO: 9826, SEQ. ID. NO: 9827, SEQ. ID. NO: 9829, SEQ. ID. NO: 9830, SEQ. ID. NO: 9831, SEQ. ID. NO: 9832, SEQ. ID. NO: 9833, SEQ. ID. NO: 9834, SEQ. ID. NO: 9835, SEQ. ID. NO: 9836, SEQ. ID. NO: 9837, SEQ. ID. NO: 9839, SEQ. ID. NO: 9840, SEQ. ID. NO: 9841, SEQ. ID. NO: 9842, SEQ. ID. NO: 9843, SEQ. ID. NO: 9844, SEQ. ID. NO: 9845, SEQ. ID. NO: 9846, SEQ. ID. NO: 9847, SEQ. ID. NO: 9849, SEQ. ID. NO: 9850, SEQ. ID. NO: 9851, SEQ. ID. NO: 9852, SEQ. ID. NO: 9853, SEQ. ID. NO: 9854, SEQ. ID. NO: 9856, SEQ. ID. NO: 9857, SEQ. ID. NO: 9858, SEQ. ID. NO: 9859, SEQ. ID. NO: 9860, SEQ. ID. NO: 9861, SEQ. ID. NO: 9863, SEQ. ID. NO: 9865, SEQ. ID. NO: 9866, SEQ. ID. NO: 9867, SEQ. ID. NO: 9868, SEQ. ID. NO: 9869, SEQ. ID. NO: 9870, SEQ. ID. NO: 9871, SEQ. ID. NO: 9873, SEQ. ID. NO: 9874, SEQ. ID. NO: 9875, SEQ. ID. NO: 9876, SEQ. ID. NO: 9877, SEQ. ID. NO: 9878, SEQ. ID. NO: 9879, SEQ. ID. NO: 9880, SEQ. ID. NO: 9881, SEQ. ID. NO: 9882, SEQ. ID. NO: 9883, SEQ. ID. NO: 9884, SEQ. ID. NO: 9885, SEQ. ID. NO: 9886, SEQ. ID. NO: 9887, SEQ. ID. NO: 9888, SEQ. ID. NO: 9890, SEQ. ID. NO: 9891, SEQ. ID. NO: 9892, SEQ. ID. NO: 9893, SEQ. ID. NO: 9894, SEQ. ID. NO: 9895, SEQ. ID. NO: 9896, SEQ. ID. NO: 9897, SEQ. ID. NO: 9898, SEQ. ID. NO: 9899, SEQ. ID. NO: 9900, SEQ. ID. NO: 9901, SEQ. ID. NO: 9905, SEQ. ID. NO: 9907, SEQ. ID. NO: 9909, SEQ. ID. NO: 9910, SEQ. ID. NO: 9911, SEQ. ID. NO: 9912, SEQ. ID. NO: 9913, SEQ. ID. NO: 9914, SEQ. ID. NO: 9915, SEQ. ID. NO: 9916, SEQ. ID. NO: 9917, SEQ.

FIG. 4: Con't.

ID. NO: 9918, SEQ. ID. NO: 9919, SEQ. ID. NO: 9920, SEQ. ID. NO: 9921, SEQ. ID. NO: 9922, SEQ. ID. NO: 9923, SEQ. ID. NO: 9924, SEQ. ID. NO: 9925, SEQ. ID. NO: 9926, SEQ. ID. NO: 9927, SEQ. ID. NO: 9928, SEQ. ID. NO: 9929, SEQ. ID. NO: 9930, SEQ. ID. NO: 9931, SEQ. ID. NO: 9932, SEQ. ID. NO: 9933, SEQ. ID. NO: 9934, SEQ. ID. NO: 9936, SEQ. ID. NO: 9937, SEQ. ID. NO: 9938, SEQ. ID. NO: 9939, SEQ. ID. NO: 9940, SEQ. ID. NO: 9941, SEQ. ID. NO: 9942, SEQ. ID. NO: 9943, SEQ. ID. NO: 9944, SEQ. ID. NO: 9945, SEQ. ID. NO: 9946, SEQ. ID. NO: 9947, SEQ. ID. NO: 9948, SEQ. ID. NO: 9949, SEQ. ID. NO: 9950, SEQ. ID. NO: 9951, SEQ. ID. NO: 9952, SEQ. ID. NO: 9953, SEQ. ID. NO: 9955, SEQ. ID. NO: 9958, SEQ. ID. NO: 9963, SEQ. ID. NO: 9965, SEQ. ID. NO: 9967, SEQ. ID. NO: 9970, SEQ. ID. NO: 9971, SEQ. ID. NO: 9972, SEQ. ID. NO: 9974, SEQ. ID. NO: 9975, SEQ. ID. NO: 9976, SEQ. ID. NO: 9977, SEQ. ID. NO: 9979, SEQ. ID. NO: 9982, SEQ. ID. NO: 9984, SEQ. ID. NO: 9985, SEQ. ID. NO: 9986, SEQ. ID. NO: 9987, SEQ. ID. NO: 9989, SEQ. ID. NO: 9991, SEQ. ID. NO: 9992, SEQ. ID. NO: 9993, SEQ. ID. NO: 9994, SEQ. ID. NO: 9997, SEQ. ID. NO: 9998, SEQ. ID. NO: 9999, SEQ. ID. NO: 10000, SEQ. ID. NO: 10001, SEQ. ID. NO: 10003, SEQ. ID. NO: 10006, SEQ. ID. NO: 10007, SEQ. ID. NO: 10010, SEQ. ID. NO: 10011, SEQ. ID. NO: 10018, SEQ. ID. NO: 10019, SEQ. ID. NO: 10020, SEQ. ID. NO: 10021, SEQ. ID. NO: 10023, SEQ. ID. NO: 10024, SEQ. ID. NO: 10025, SEQ. ID. NO: 10026, SEQ. ID. NO: 10028, SEQ. ID. NO: 10029, SEQ. ID. NO: 10031, SEQ. ID. NO: 10032, SEQ. ID. NO: 10033, SEQ. ID. NO: 10036, SEQ. ID. NO: 10037, SEQ. ID. NO: 10039, SEQ. ID. NO: 10040, SEQ. ID. NO: 10041, SEQ. ID. NO: 10044, SEQ. ID. NO: 10045, SEQ. ID. NO: 10046, SEQ. ID. NO: 10047, SEQ. ID. NO: 10048, SEQ. ID. NO: 10050, SEQ. ID. NO: 10051, SEQ. ID. NO: 10052, SEQ. ID. NO: 10053, SEQ. ID. NO: 10054, SEQ. ID. NO: 10056, SEQ. ID. NO: 10062, SEQ. ID. NO: 10071, SEQ. ID. NO: 10072, SEQ. ID. NO: 10073, SEQ. ID. NO: 10076, SEQ. ID. NO: 10077, SEQ. ID. NO: 10078.

FIG. 5: A collection of nucleic acid molecules.

SEQ. ID. NO: 913, SEQ. ID. NO: 918, SEQ. ID. NO: 938, SEQ. ID. NO: 946, SEQ. ID. NO: 948, SEQ. ID. NO: 949, SEQ. ID. NO: 956, SEQ. ID. NO: 968, SEQ. ID. NO: 972, SEQ. ID. NO: 982, SEQ. ID. NO: 997, SEQ. ID. NO: 1011, SEQ. ID. NO: 1025, SEQ. ID. NO: 1043, SEQ. ID. NO: 1059, SEQ. ID. NO: 1073, SEQ. ID. NO: 1086, SEQ. ID. NO: 1110, SEQ. ID. NO: 1112, SEQ. ID. NO: 1113, SEQ. ID. NO: 1116, SEQ. ID. NO: 1117, SEQ. ID. NO: 1119, SEQ. ID. NO: 1120, SEQ. ID. NO: 1123, SEQ. ID. NO: 1124, SEQ. ID. NO: 1125, SEQ. ID. NO: 1126, SEQ. ID. NO: 1127, SEQ. ID. NO: 1129, SEQ. ID. NO: 1131, SEQ. ID. NO: 1132, SEQ. ID. NO: 1133, SEQ. ID. NO: 1134, SEQ. ID. NO: 1136, SEQ. ID. NO: 1137, SEQ. ID. NO: 1139, SEQ. ID. NO: 1140, SEQ. ID. NO: 1142, SEQ. ID. NO: 1144, SEQ. ID. NO: 1145, SEQ. ID. NO: 1146, SEQ. ID. NO: 1147, SEQ. ID. NO: 1148, SEQ. ID. NO: 1149, SEQ. ID. NO: 1150, SEQ. ID. NO: 1151, SEQ. ID. NO: 1153, SEQ. ID. NO: 1155, SEQ. ID. NO: 1157, SEQ. ID. NO: 1158, SEQ. ID. NO: 1159, SEQ. ID. NO: 1160, SEQ. ID. NO: 1161, SEQ. ID. NO: 1162, SEQ. ID. NO: 1163, SEQ. ID. NO: 1166, SEQ. ID. NO: 1167, SEQ. ID. NO: 1168, SEQ. ID. NO: 1171, SEQ. ID. NO: 1172, SEQ. ID. NO: 1173, SEQ. ID. NO: 1174, SEQ. ID. NO: 1175, SEQ. ID. NO: 1176, SEQ. ID. NO: 1178, SEQ. ID. NO: 1180, SEQ. ID. NO: 1181, SEQ. ID. NO: 1182, SEQ. ID. NO: 1183, SEQ. ID. NO: 1185, SEQ. ID. NO: 1186, SEQ. ID. NO: 1188, SEQ. ID. NO: 1189, SEQ. ID. NO: 1191, SEQ. ID. NO: 1193, SEQ. ID. NO: 1197, SEQ. ID. NO: 1199, SEQ. ID. NO: 1201, SEQ. ID. NO: 1202, SEQ. ID. NO: 1204, SEQ. ID. NO: 1205, SEQ. ID. NO: 1206, SEQ. ID. NO: 1207, SEQ. ID. NO: 1208, SEQ. ID. NO: 1209, SEQ. ID. NO: 1212, SEQ. ID. NO: 1215, SEQ. ID. NO: 1216, SEQ. ID. NO: 1217, SEQ. ID. NO: 1218, SEQ. ID. NO: 1219, SEQ. ID. NO: 1220, SEQ. ID. NO: 1222, SEQ. ID. NO: 1223, SEQ. ID. NO: 1224, SEQ. ID. NO: 1226, SEQ. ID. NO: 1228, SEQ. ID. NO: 1229, SEQ. ID. NO: 1230, SEQ. ID. NO: 1231, SEQ. ID. NO: 1232, SEQ. ID. NO: 1233, SEQ. ID. NO: 1235, SEQ. ID. NO: 1236, SEQ. ID. NO: 1238, SEQ. ID. NO: 1239, SEQ. ID. NO: 1242, SEQ. ID. NO: 1244, SEQ. ID. NO: 1246, SEQ. ID. NO: 1248, SEQ. ID. NO: 1249, SEQ. ID. NO: 1250, SEQ. ID. NO: 1251, SEQ. ID. NO: 1255, SEQ. ID. NO: 1259, SEQ. ID. NO: 1260, SEQ. ID. NO: 1261, SEQ. ID. NO: 1262, SEQ. ID. NO: 1264, SEQ. ID. NO: 1265, SEQ. ID. NO: 1267, SEQ. ID. NO: 1268, SEQ. ID. NO: 1269, SEQ. ID. NO: 1272, SEQ. ID. NO: 1273, SEQ. ID. NO: 1274, SEQ. ID. NO: 1276, SEQ. ID. NO: 1277, SEQ. ID. NO: 1278, SEQ. ID. NO: 1279, SEQ. ID. NO: 1283, SEQ. ID. NO: 1284, SEQ. ID. NO: 1285, SEQ. ID. NO: 1287, SEQ. ID. NO: 1292, SEQ. ID. NO: 1293, SEQ. ID. NO: 1294, SEQ. ID. NO: 1297, SEQ. ID. NO: 1298, SEQ. ID. NO: 1299, SEQ. ID. NO: 1300, SEQ. ID. NO: 1301, SEQ. ID. NO: 1302, SEQ. ID. NO: 1303, SEQ. ID. NO: 1304, SEQ. ID. NO: 1308, SEQ. ID. NO: 1309, SEQ. ID. NO: 1310, SEQ. ID. NO: 1311, SEQ. ID. NO: 1313, SEQ. ID. NO: 1314, SEQ. ID. NO: 1315, SEQ. ID. NO: 1318, SEQ. ID. NO: 1320, SEQ. ID. NO: 1322, SEQ. ID. NO: 1323, SEQ. ID. NO: 1324, SEQ. ID. NO: 1325, SEQ. ID. NO: 1327, SEQ. ID. NO: 1328, SEQ. ID. NO: 1329, SEQ. ID. NO: 1330, SEQ. ID. NO: 1331, SEQ. ID. NO: 1333, SEQ. ID. NO: 1334, SEQ. ID. NO: 1336, SEQ. ID. NO: 1337, SEQ. ID. NO: 1338, SEQ. ID. NO: 1340, SEQ. ID. NO: 1341, SEQ. ID. NO: 1345, SEQ. ID. NO: 1346, SEQ. ID. NO: 1348, SEQ. ID. NO: 1350, SEQ. ID. NO: 1352, SEQ. ID. NO: 1353, SEQ. ID. NO: 1355, SEQ. ID. NO: 1356, SEQ. ID. NO: 1358, SEQ. ID. NO: 1359, SEQ. ID. NO: 1360, SEQ. ID. NO: 1363, SEQ. ID. NO: 1364, SEQ. ID. NO: 1365, SEQ. ID. NO: 1366, SEQ. ID. NO: 1368, SEQ. ID. NO: 1369, SEQ. ID. NO: 1372, SEQ. ID. NO: 1373, SEQ. ID. NO: 1374, SEQ. ID. NO: 1376, SEQ. ID. NO: 1377, SEQ. ID. NO: 1378, SEQ. ID. NO: 1379, SEQ. ID. NO: 1380, SEQ. ID. NO: 1381, SEQ. ID. NO: 1382, SEQ. ID. NO: 1383, SEQ. ID. NO: 1385, SEQ. ID. NO: 1386, SEQ. ID. NO: 1389, SEQ. ID. NO: 1391, SEQ. ID. NO: 1394, SEQ. ID. NO: 1396, SEQ. ID. NO: 1398, SEQ. ID. NO: 1399, SEQ. ID. NO: 1400, SEQ. ID. NO: 1403, SEQ. ID. NO: 1406, SEQ. ID. NO: 1407, SEQ. ID. NO: 1408, SEQ. ID. NO: 1409, SEQ. ID. NO: 1410, SEQ. ID. NO: 1412, SEQ. ID. NO: 1413, SEQ. ID. NO: 1415, SEQ. ID. NO: 1416, SEQ. ID. NO: 1417, SEQ. ID. NO: 1418, SEQ. ID. NO: 1420, SEQ. ID. NO: 1421, SEQ. ID. NO: 1424, SEQ. ID. NO: 1428, SEQ. ID. NO: 1429, SEQ. ID. NO: 1430, SEQ. ID. NO: 1433, SEQ. ID. NO: 1435, SEQ. ID. NO: 1437, SEQ. ID. NO: 1438, SEQ. ID. NO: 1439, SEQ. ID. NO: 1440, SEQ. ID. NO: 1441, SEQ. ID. NO: 1443, SEQ. ID. NO: 1444, SEQ. ID. NO: 1446, SEQ. ID. NO: 1447, SEQ. ID. NO: 1449, SEQ. ID. NO: 1452, SEQ. ID. NO: 1453, SEQ. ID. NO: 1457, SEQ. ID. NO: 1458, SEQ. ID. NO: 1461, SEQ. ID. NO: 1462, SEQ. ID. NO: 1463, SEQ. ID. NO: 1464, SEQ. ID. NO: 1467, SEQ. ID. NO: 1468, SEQ. ID. NO: 1470, SEQ. ID. NO: 1471, SEQ. ID. NO: 1473, SEQ. ID. NO: 1474, SEQ. ID. NO: 1476, SEQ. ID. NO: 1478, SEQ. ID. NO: 1480, SEQ. ID. NO: 1482, SEQ. ID. NO: 1486, SEQ. ID. NO: 1488, SEQ. ID. NO: 1490, SEQ. ID. NO: 1492, SEQ. ID. NO: 1495, SEQ. ID. NO: 1496, SEQ. ID. NO: 1498, SEQ. ID. NO: 1499, SEQ. ID. NO: 1501, SEQ. ID. NO: 1502, SEQ. ID. NO: 1503, SEQ. ID. NO: 1504, SEQ. ID. NO: 1507, SEQ. ID. NO: 1509, SEQ. ID. NO: 1510, SEQ. ID. NO: 1512, SEQ. ID. NO: 1514, SEQ. ID. NO: 1515, SEQ. ID. NO: 1516, SEQ. ID. NO: 1518, SEQ. ID. NO: 1519, SEQ. ID. NO: 1521, SEQ. ID. NO: 1522, SEQ. ID. NO: 1525, SEQ. ID. NO: 1527, SEQ. ID. NO: 1529, SEQ. ID. NO: 1531, SEQ. ID. NO: 1532, SEQ. ID. NO: 1533, SEQ. ID. NO: 1534, SEQ. ID. NO: 1536, SEQ. ID. NO: 1538, SEQ. ID. NO: 1540, SEQ. ID. NO: 1542, SEQ. ID. NO: 1543, SEQ. ID. NO: 1544, SEQ. ID. NO: 1546, SEQ. ID. NO: 1547, SEQ. ID. NO: 1549, SEQ. ID. NO: 1550, SEQ. ID. NO: 1551, SEQ. ID. NO: 1552, SEQ. ID. NO: 1556, SEQ. ID. NO: 1557, SEQ. ID. NO: 1558, SEQ. ID. NO: 1559, SEQ. ID. NO: 1562, SEQ. ID. NO: 1566, SEQ. ID. NO: 1570, SEQ. ID. NO: 1571, SEQ. ID. NO: 1572, SEQ. ID. NO: 1573, SEQ. ID. NO: 1574, SEQ. ID. NO: 1575, SEQ. ID. NO: 1576, SEQ. ID. NO: 1577, SEQ. ID. NO: 1578, SEQ. ID. NO: 1580, SEQ. ID. NO: 1581, SEQ. ID. NO: 1583, SEQ. ID. NO: 1585, SEQ. ID. NO: 1586, SEQ. ID. NO: 1587, SEQ. ID. NO: 1589, SEQ. ID. NO: 1590, SEQ. ID. NO: 1592, SEQ. ID. NO: 1594, SEQ. ID. NO: 1595, SEQ. ID. NO: 1596,

FIG. 5 Con't.

SEQ. ID. NO: 1597, SEQ. ID. NO: 1598, SEQ. ID. NO: 1599, SEQ. ID. NO: 1600, SEQ. ID. NO: 1602, SEQ. ID. NO: 1604, SEQ. ID. NO: 1606, SEQ. ID. NO: 1607, SEQ. ID. NO: 1609, SEQ. ID. NO: 1616, SEQ. ID. NO: 1617, SEQ. ID. NO: 1619, SEQ. ID. NO: 1621, SEQ. ID. NO: 1624, SEQ. ID. NO: 1626, SEQ. ID. NO: 1627, SEQ. ID. NO: 1629, SEQ. ID. NO: 1630, SEQ. ID. NO: 1631, SEQ. ID. NO: 1633, SEQ. ID. NO: 1636, SEQ. ID. NO: 1641, SEQ. ID. NO: 1644, SEQ. ID. NO: 1646, SEQ. ID. NO: 1647, SEQ. ID. NO: 1648, SEQ. ID. NO: 1649, SEQ. ID. NO: 1650, SEQ. ID. NO: 1653, SEQ. ID. NO: 1654, SEQ. ID. NO: 1657, SEQ. ID. NO: 1658, SEQ. ID. NO: 1659, SEQ. ID. NO: 1663, SEQ. ID. NO: 1664, SEQ. ID. NO: 1666, SEQ. ID. NO: 1667, SEQ. ID. NO: 1672, SEQ. ID. NO: 1674, SEQ. ID. NO: 1675, SEQ. ID. NO: 1676, SEQ. ID. NO: 1681, SEQ. ID. NO: 1683, SEQ. ID. NO: 1684, SEQ. ID. NO: 1685, SEQ. ID. NO: 10079, SEQ. ID. NO: 10080, SEQ. ID. NO: 10081, SEQ. ID. NO: 10082, SEQ. ID. NO: 10083, SEQ. ID. NO: 10084, SEQ. ID. NO: 10085, SEQ. ID. NO: 10086, SEQ. ID. NO: 10087, SEQ. ID. NO: 10088, SEQ. ID. NO: 10089, SEQ. ID. NO: 10090, SEQ. ID. NO: 10091, SEQ. ID. NO: 10092, SEQ. ID. NO: 10094, SEQ. ID. NO: 10097, SEQ. ID. NO: 10099, SEQ. ID. NO: 10101, SEQ. ID. NO: 10102, SEQ. ID. NO: 10103, SEQ. ID. NO: 10104, SEQ. ID. NO: 10105, SEQ. ID. NO: 10106.

FIG. 6: A collection of nucleic acid molecules.

SEQ. ID. NO: 938, SEQ. ID. NO: 948, SEQ. ID. NO: 949, SEQ. ID. NO: 952, SEQ. ID. NO: 956, SEQ. ID. NO: 967, SEQ. ID. NO: 970, SEQ. ID. NO: 972, SEQ. ID. NO: 982, SEQ. ID. NO: 996, SEQ. ID. NO: 1024, SEQ. ID. NO: 1040, SEQ. ID. NO: 1086, SEQ. ID. NO: 8972, SEQ. ID. NO: 9080.

FIG. 7: A collection of nucleic acid molecules.

SEQ. ID. NO: 938, SEQ. ID. NO: 948, SEQ. ID. NO: 949, SEQ. ID. NO: 956, SEQ. ID. NO: 968, SEQ. ID. NO: 972, SEQ. ID. NO: 982, SEQ. ID. NO: 997, SEQ. ID. NO: 1025, SEQ. ID. NO: 1043, SEQ. ID. NO: 1086, SEQ. ID. NO: 1110, SEQ. ID. NO: 1112, SEQ. ID. NO: 1116, SEQ. ID. NO: 1117, SEQ. ID. NO: 1119, SEQ. ID. NO: 1120, SEQ. ID. NO: 1123, SEQ. ID. NO: 1126, SEQ. ID. NO: 1127, SEQ. ID. NO: 1129, SEQ. ID. NO: 1131, SEQ. ID. NO: 1133, SEQ. ID. NO: 1139, SEQ. ID. NO: 1142, SEQ. ID. NO: 1144, SEQ. ID. NO: 1145, SEQ. ID. NO: 1146, SEQ. ID. NO: 1147, SEQ. ID. NO: 1148, SEQ. ID. NO: 1149, SEQ. ID. NO: 1150, SEQ. ID. NO: 1151, SEQ. ID. NO: 1153, SEQ. ID. NO: 1155, SEQ. ID. NO: 1157, SEQ. ID. NO: 1158, SEQ. ID. NO: 1160, SEQ. ID. NO: 1161, SEQ. ID. NO: 1162, SEQ. ID. NO: 1166, SEQ. ID. NO: 1167, SEQ. ID. NO: 1168, SEQ. ID. NO: 1171, SEQ. ID. NO: 1172, SEQ. ID. NO: 1173, SEQ. ID. NO: 1174, SEQ. ID. NO: 1175, SEQ. ID. NO: 1176, SEQ. ID. NO: 1180, SEQ. ID. NO: 1181, SEQ. ID. NO: 1183, SEQ. ID. NO: 1186, SEQ. ID. NO: 1189, SEQ. ID. NO: 1191, SEQ. ID. NO: 1197, SEQ. ID. NO: 1199, SEQ. ID. NO: 1201, SEQ. ID. NO: 1202, SEQ. ID. NO: 1204, SEQ. ID. NO: 1205, SEQ. ID. NO: 1206, SEQ. ID. NO: 1207, SEQ. ID. NO: 1208, SEQ. ID. NO: 1209, SEQ. ID. NO: 1212, SEQ. ID. NO: 1215, SEQ. ID. NO: 1216, SEQ. ID. NO: 1217, SEQ. ID. NO: 1218, SEQ. ID. NO: 1219, SEQ. ID. NO: 1220, SEQ. ID. NO: 1222, SEQ. ID. NO: 1223, SEQ. ID. NO: 1224, SEQ. ID. NO: 1228, SEQ. ID. NO: 1229, SEQ. ID. NO: 1230, SEQ. ID. NO: 1232, SEQ. ID. NO: 1236, SEQ. ID. NO: 1238, SEQ. ID. NO: 1239, SEQ. ID. NO: 1242, SEQ. ID. NO: 1246, SEQ. ID. NO: 1248, SEQ. ID. NO: 1251, SEQ. ID. NO: 1255, SEQ. ID. NO: 1259, SEQ. ID. NO: 1260, SEQ. ID. NO: 1261, SEQ. ID. NO: 1264, SEQ. ID. NO: 1265, SEQ. ID. NO: 1267, SEQ. ID. NO: 1268, SEQ. ID. NO: 1272, SEQ. ID. NO: 1277, SEQ. ID. NO: 1278, SEQ. ID. NO: 1279, SEQ. ID. NO: 1283, SEQ. ID. NO: 1284, SEQ. ID. NO: 1285, SEQ. ID. NO: 1287, SEQ. ID. NO: 1292, SEQ. ID. NO: 1293, SEQ. ID. NO: 1294, SEQ. ID. NO: 1297, SEQ. ID. NO: 1298, SEQ. ID. NO: 1299, SEQ. ID. NO: 1300, SEQ. ID. NO: 1301, SEQ. ID. NO: 1304, SEQ. ID. NO: 1308, SEQ. ID. NO: 1309, SEQ. ID. NO: 1310, SEQ. ID. NO: 1314, SEQ. ID. NO: 1318, SEQ. ID. NO: 1322, SEQ. ID. NO: 1323, SEQ. ID. NO: 1324, SEQ. ID. NO: 1327, SEQ. ID. NO: 1329, SEQ. ID. NO: 1330, SEQ. ID. NO: 1334, SEQ. ID. NO: 1336, SEQ. ID. NO: 1337, SEQ. ID. NO: 1340, SEQ. ID. NO: 1341, SEQ. ID. NO: 1345, SEQ. ID. NO: 1346, SEQ. ID. NO: 1348, SEQ. ID. NO: 1352, SEQ. ID. NO: 1353, SEQ. ID. NO: 1355, SEQ. ID. NO: 1356, SEQ. ID. NO: 1358, SEQ. ID. NO: 1359, SEQ. ID. NO: 1360, SEQ. ID. NO: 1364, SEQ. ID. NO: 1365, SEQ. ID. NO: 1368, SEQ. ID. NO: 1369, SEQ. ID. NO: 1372, SEQ. ID. NO: 1377, SEQ. ID. NO: 1378, SEQ. ID. NO: 1379, SEQ. ID. NO: 1380, SEQ. ID. NO: 1381, SEQ. ID. NO: 1382, SEQ. ID. NO: 1383, SEQ. ID. NO: 1385, SEQ. ID. NO: 1386, SEQ. ID. NO: 1389, SEQ. ID. NO: 1394, SEQ. ID. NO: 1396, SEQ. ID. NO: 1399, SEQ. ID. NO: 1400, SEQ. ID. NO: 1406, SEQ. ID. NO: 1407, SEQ. ID. NO: 1408, SEQ. ID. NO: 1409, SEQ. ID. NO: 1410, SEQ. ID. NO: 1412, SEQ. ID. NO: 1413, SEQ. ID. NO: 1415, SEQ. ID. NO: 1416, SEQ. ID. NO: 1417, SEQ. ID. NO: 1418, SEQ. ID. NO: 1420, SEQ. ID. NO: 1421, SEQ. ID. NO: 1424, SEQ. ID. NO: 1428, SEQ. ID. NO: 1429, SEQ. ID. NO: 1430, SEQ. ID. NO: 1438, SEQ. ID. NO: 1444, SEQ. ID. NO: 1447, SEQ. ID. NO: 1452, SEQ. ID. NO: 1457, SEQ. ID. NO: 1458, SEQ. ID. NO: 1468, SEQ. ID. NO: 1470, SEQ. ID. NO: 1471, SEQ. ID. NO: 1486, SEQ. ID. NO: 1488, SEQ. ID. NO: 1490, SEQ. ID. NO: 1492, SEQ. ID. NO: 1496, SEQ. ID. NO: 1498, SEQ. ID. NO: 1499, SEQ. ID. NO: 1502, SEQ. ID. NO: 1503, SEQ. ID. NO: 1509, SEQ. ID. NO: 1510, SEQ. ID. NO: 1512, SEQ. ID. NO: 1519, SEQ. ID. NO: 1532, SEQ. ID. NO: 1536, SEQ. ID. NO: 1540, SEQ. ID. NO: 1543, SEQ. ID. NO: 1544, SEQ. ID. NO: 1546, SEQ. ID. NO: 1547, SEQ. ID. NO: 1549, SEQ. ID. NO: 1550, SEQ. ID. NO: 1556, SEQ. ID. NO: 1557, SEQ. ID. NO: 1558, SEQ. ID. NO: 1562, SEQ. ID. NO: 1566, SEQ. ID. NO: 1570, SEQ. ID. NO: 1571, SEQ. ID. NO: 1572, SEQ. ID. NO: 1576, SEQ. ID. NO: 1583, SEQ. ID. NO: 1594, SEQ. ID. NO: 1595, SEQ. ID. NO: 1597, SEQ. ID. NO: 1604, SEQ. ID. NO: 1606, SEQ. ID. NO: 1616, SEQ. ID. NO: 1617, SEQ. ID. NO: 1619, SEQ. ID. NO: 1621, SEQ. ID. NO: 1626, SEQ. ID. NO: 1627, SEQ. ID. NO: 1631, SEQ. ID. NO: 1633, SEQ. ID. NO: 1644, SEQ. ID. NO: 1647, SEQ. ID. NO: 1649, SEQ. ID. NO: 1653, SEQ. ID. NO: 1659, SEQ. ID. NO: 1674, SEQ. ID. NO: 1683, SEQ. ID. NO: 1684, SEQ. ID. NO: 10080, SEQ. ID. NO: 10081, SEQ. ID. NO: 10082, SEQ. ID. NO: 10084, SEQ. ID. NO: 10090, SEQ. ID. NO: 10091, SEQ. ID. NO: 10092, SEQ. ID. NO: 10099, SEQ. ID. NO: 10105.

FIG. 8: A collection of nucleic acid molecules.

SEQ. ID. NO: 13, SEQ. ID. NO: 118, SEQ. ID. NO: 119, SEQ. ID. NO: 122, SEQ. ID. NO: 127, SEQ. ID. NO: 129, SEQ. ID. NO: 134, SEQ. ID. NO: 142, SEQ. ID. NO: 165, SEQ. ID. NO: 169, SEQ. ID. NO: 172, SEQ. ID. NO: 174, SEQ. ID. NO: 177, SEQ. ID. NO: 180, SEQ. ID. NO: 185, SEQ. ID. NO: 189, SEQ. ID. NO: 197, SEQ. ID. NO: 216, SEQ. ID. NO: 221, SEQ. ID. NO: 223, SEQ. ID. NO: 225, SEQ. ID. NO: 236, SEQ. ID. NO: 240, SEQ. ID. NO: 278, SEQ. ID. NO: 282, SEQ. ID. NO: 283, SEQ. ID. NO: 285, SEQ. ID. NO: 287, SEQ. ID. NO: 295, SEQ. ID. NO: 297, SEQ. ID. NO: 306, SEQ. ID. NO: 309, SEQ. ID. NO: 310, SEQ. ID. NO: 317, SEQ. ID. NO: 320, SEQ. ID. NO: 322, SEQ. ID. NO: 325, SEQ. ID. NO: 328, SEQ. ID. NO: 334, SEQ. ID. NO: 349, SEQ. ID. NO: 353, SEQ. ID. NO: 354, SEQ. ID. NO: 358, SEQ. ID. NO: 384, SEQ. ID. NO: 386, SEQ. ID. NO: 390.

FIG. 9: A collection of nucleic acid molecules.

SEQ. ID. NO: 118, SEQ. ID. NO: 129, SEQ. ID. NO: 134, SEQ. ID. NO: 172, SEQ. ID. NO: 287, SEQ. ID. NO: 297, SEQ. ID. NO: 334, SEQ. ID. NO: 349, SEQ. ID. NO: 384, SEQ. ID. NO: 390

Dual color image of part of the raw microarray expression results for normal lung tissue (red) compared to adenoma tumor material (green). microRNAs that are upregulated or downregulated in tumor material show up as green and red, SEQ. ID. NO: respectively. microRNAs that do not change expression are yellow and non-expressed microRNAs appear black.

FIG. 11 differential expressed microRNAs between glioblastoma and normal control brain tissue

| | cand_id | human_hairpin | mouse_hairpin | intensity | log2(tumor / normal) | fold-change | Human patent_id | Mouse patent_id |
|---|---|---|---|---|---|---|---|---|
| 1 | mmHP1417069 | N/D | N/D | 9 | -2.88 | -7.4 | - | - |
| 2 | mmHP1417070 | mmu-mir-26a-2 | mmu-mir-26a-2 | 8.9 | -2.67 | -6.4 | - | - |
| 3 | cand706 | N/D | N/D | 10.5 | -2.58 | -6.0 | - | - |
| 4 | cand74 | mmu-mir-181a-1 | mmu-mir-181a-1 | 9 | -2.49 | -5.6 | - | - |
| 5 | mmu-mir-103-2 | mmu-mir-103-2 | mmu-mir-103-2 | 8.5 | -2.24 | -4.7 | - | - |
| 6 | cand943 | mmu-mir-128b | mmu-mir-128b | 7.5 | -2.19 | -4.6 | - | - |
| 7 | cand104 | N/D | N/D | 7.7 | -2.14 | -4.4 | - | - |
| 8 | cand225 | Hsd_from_Mmd_215 | Mmd_215 | 13.4 | -2.1 | -4.3 | 172 | 519 |
| 9 | cand284 | N/D | N/D | 7.9 | -2.08 | -4.2 | - | - |
| 10 | cand8 | Hsd_from_Mmd_416 | Mmd_416 | 7.7 | -2.08 | -4.2 | 287 | 732 |
| 11 | cand106 | mmu-let-7d | mmu-let-7d | 8.1 | -2.05 | -4.1 | - | - |
| 12 | cand578 | Hsd_from_Mmd_120 | Mmd_120 | 14.1 | -2.04 | -4.1 | 118 | 415 |
| 13 | cand226 | mmu-let-7e | mmu-let-7e | 8.1 | -2.03 | -4.1 | - | - |
| 14 | cand137 | mmu-mir-30e | mmu-mir-30e | 7.7 | -1.89 | -3.7 | - | - |
| 15 | cand277 | mmu-mir-103-1 | mmu-mir-103-1 | 9.1 | -1.83 | -3.6 | - | - |
| 16 | cand928 | N/D | N/D | 7.9 | -1.78 | -3.4 | - | - |
| 17 | cand358 | mmu-mir-107 | mmu-mir-107 | 9 | -1.69 | -3.2 | - | - |
| 18 | cand482 | Hsd_from_Mmd_98 | Mmd_98 | 7.7 | -1.64 | -3.1 | 390 | 903 |
| 19 | cand315 | N/D | N/D | 8.2 | -1.61 | -3.1 | - | - |
| 20 | cand369 | N/D | N/D | 7.2 | -1.56 | -2.9 | - | - |
| 21 | cand683 | Hsd_from_Mmd_511 | Mmd_511 | 9.3 | -1.55 | -2.9 | 349 | 833 |
| 22 | cand94 | mmu-mir-185 | mmu-mir-185 | 7.4 | -1.53 | -2.9 | - | - |
| 23 | cand306 | mmu-mir-320 | mmu-mir-320 | 7.8 | -1.51 | -2.8 | - | - |
| 24 | cand566 | N/D | Mmd_36 | 9.9 | -1.42 | -2.7 | - | 671 |
| 25 | mmHP2810075 | N/D | Mmd_434 | 8.4 | -1.38 | -2.6 | - | 752 |
| 26 | cand732 | Hsd_from_Mmd_49 | Mmd_49 | 11.2 | -1.26 | -2.4 | 334 | 809 |
| 27 | cand98 | Hsd_from_Mmd_41 | Mmd_41 | 9 | -1.25 | -2.4 | 282 | 725 |
| 28 | cand135 | N/D | N/D | 7.6 | -1.23 | -2.3 | - | - |
| 29 | cand192 | Hsd_from_Mmd_433 | Mmd_433 | 10 | -1.16 | -2.2 | 297 | 751 |
| 30 | cand629 | Hsd_from_Mmd_91 | Mmd_91 | 8.4 | -1.12 | -2.2 | 384 | 896 |
| 31 | cand341 | mmu-mir-19b-2 | mmu-mir-19b-2 | 7.7 | -1.1 | -2.1 | - | - |
| 32 | mmHP1181578 | N/D | N/D | 7.2 | -1.09 | -2.1 | - | - |
| 33 | cand674 | Hsd_from_Mmd_155 | Mmd_155 | 10 | -1.07 | -2.1 | 134 | 453 |
| 34 | cand497 | N/D | N/D | 7.1 | -1.06 | -2.1 | - | - |
| 35 | cand852 | N/D | Mmd_312 | 7.7 | -1.02 | -2.0 | - | 620 |
| 36 | mmu-mir-19b-1 | mmu-mir-19b-1 | mmu-mir-19b-1 | 7.8 | -1.02 | -2.0 | - | - |
| 37 | mmHP1778980 | N/D | Mmd_463 | 11.9 | 1.08 | 2.1 | - | 772 |
| 38 | cand160 | N/D | N/D | 9.9 | 1.11 | 2.2 | - | - |
| 39 | mmu-mir-329 | mmu-mir-329 | mmu-mir-329 | 11.4 | 1.12 | 2.2 | - | - |
| 40 | mmHP1170304 | N/D | Mmd_242 | 11.8 | 1.13 | 2.2 | - | 546 |
| 41 | cand356 | Hsd_from_Mmd_147 | Mmd_147 | 11.8 | 1.14 | 2.2 | 129 | 444 |
| 42 | cand913 | N/D | Mmd_121 | 15.7 | 1.36 | 2.6 | - | 416 |
| 43 | cand631 | N/D | Mmd_351 | 13.6 | 1.47 | 2.8 | - | 662 |
| 44 | cand189 | mmu-mir-21 | mmu-mir-21 | 8.4 | 2.82 | 7.1 | - | - |
| 45 | cand403 | N/D | Mmd_342 | 9 | 3.97 | 15.7 | - | 652 |

Total RNA was isolated from human tumor material and normal control brain tissue using a Trizol-based method. Samples were labelled using Kreatech ULS microRNA reagents and hybridized to custom-spotted Codelink microarrays that contained 847 different microRNA probes (DNA backbone), including about 150 known microRNAs. Each probe was represented 8 times on every slide. Microarray images were processed with FeatureExtractor software and the data was analyzed using limma package (Bioconductor). N/D not determined.

FIG. 12 differential expressed microRNAs between adenoma and normal control lung tissue

| # | cand_id | human_hairpin | mouse_hairpin | intensity log2 | log2 (tumor / normal) | fold-change | Human patent_id | Mouse patent_id |
|---|---|---|---|---|---|---|---|---|
| 1 | cand631 | N/D | Mmd_351 | 8.6 | -4.87 | -29.2 | - | 662 |
| 2 | mmHP1778980 | N/D | Mmd_453 | 8.3 | -3.77 | -13.6 | - | 772 |
| 3 | cand578 | Hsd_from_Mmd_120 | Mmd_120 | 11.8 | -3.25 | -9.5 | 118 | 415 |
| 4 | cand225 | Hsd_from_Mmd_215 | Mmd_215 | 9.9 | -2.95 | -7.7 | 173 | 519 |
| 5 | mmHP1170304 | N/D | Mmd_242 | 7.8 | -2.85 | -7.2 | - | 546 |
| 6 | cand326 | Hsd_from_Mmd_410 | Mmd_410 | 7.8 | -2.83 | -7.1 | 383 | 726 |
| 7 | cand706 | N/D | N/D | 12 | -2.69 | -6.5 | - | - |
| 8 | cand356 | Hsd_from_Mmd_147 | Mmd_147 | 8 | -2.36 | -5.1 | 139 | 444 |
| 9 | cand370 | mmu-mir-326 | mmu-mir-326 | 7.5 | -2.32 | -5.0 | - | - |
| 10 | cand445 | Hsd_from_Mmd_301 | Mmd_301 | 7.7 | -2.15 | -4.4 | 225 | 609 |
| 11 | cand192 | Hsd_from_Mmd_433 | Mmd_433 | 8.4 | -2.07 | -4.2 | 297 | 751 |
| 12 | mmu-mir-329 | mmu-mir-329 | mmu-mir-329 | 7.6 | -2.02 | -4.1 | - | - |
| 13 | cand884a | mmu-mir-125b-1 | mmu-mir-125b-1 | 7.5 | -1.89 | -3.7 | - | - |
| 14 | cand856 | mmu-mir-184 | mmu-mir-184 | 8.3 | -1.83 | -3.6 | - | - |
| 15 | cand674 | Hsd_from_Mmd_155 | Mmd_155 | 8.8 | -1.81 | -3.5 | 134 | 453 |
| 16 | cand540 | Hsd_from_Mmd_45 | Mmd_45 | 7.3 | -1.78 | -3.4 | 306 | 768 |
| 17 | cand418 | N/D | Mmd_218 | 7.6 | -1.77 | -3.4 | - | 522 |
| 18 | cand711 | Hsd_from_Mmd_167 | Mmd_167 | 7.5 | -1.76 | -3.4 | 142 | 466 |
| 19 | cand141 | Hsd_from_Mmd_472 | Mmd_472 | 7.4 | -1.75 | -3.4 | 320 | 791 |
| 20 | mmu-mir-370 | mmu-mir-370 | mmu-mir-370 | 7.5 | -1.72 | -3.3 | - | - |
| 21 | cand87 | Hsd_from_Mmd_245 | Mmd_245 | 7.5 | -1.69 | -3.2 | 189 | 549 |
| 22 | cand170 | mmu-mir-19a | mmu-mir-19a | 8.1 | -1.65 | -3.1 | - | - |
| 23 | mmHP291564 | N/D | Mmd_136 | 7.3 | -1.59 | -3.0 | - | 431 |
| 24 | cand224 | Hsd_from_Mmd_324 | Mmd_324 | 7.3 | -1.51 | -2.8 | 236 | 632 |
| 25 | mmu-mir-350 | mmu-mir-350 | mmu-mir-350 | 7.7 | -1.47 | -2.8 | - | - |
| 26 | mmu-mir-150 | mmu-mir-150 | mmu-mir-150 | 7.2 | -1.46 | -2.8 | - | - |
| 27 | cand162 | Hsd_from_Mmd_33 | Mmd_33 | 8.8 | -1.38 | -2.6 | 240 | 638 |
| 28 | cand447 | Hsd_from_Mmd_123 | Mmd_123 | 7.2 | -1.31 | -2.5 | 119 | 418 |
| 29 | cand254 | Hsd_11 | Mmd_11 | 7.1 | -1.24 | -2.4 | 13 | 403 |
| 30 | cand8 | Hsd_from_Mmd_416 | Mmd_416 | 10.7 | -1.23 | -2.3 | 267 | 732 |
| 31 | cand784a | N/D | MM_129 | 7.9 | -1.21 | -2.3 | - | 4264 |
| 32 | cand647 | mmu-mir-182 | mmu-mir-182 | 7.1 | -1.19 | -2.3 | - | - |
| 33 | cand510 | mmu-mir-145 | mmu-mir-145 | 7.2 | -1.18 | -2.3 | - | - |
| 34 | cand678 | N/D | Mmd_153 | 7.4 | -1.18 | -2.3 | - | 451 |
| 35 | mmu-mir-339 | mmu-mir-339 | mmu-mir-339 | 7.1 | -1.18 | -2.3 | - | - |
| 36 | cand291 | mmu-mir-196b | mmu-mir-196b | 7.1 | -1.11 | -2.2 | - | - |
| 37 | cand516 | N/D | Mmd_400 | 9.8 | -1.11 | -2.2 | - | 715 |
| 38 | cand963 | Hsd_from_Mmd_480 | Mmd_480 | 7.6 | 1 | 2.0 | 325 | 799 |
| 39 | cand342 | mmu-mir-92-2 | mmu-mir-92-2 | 7.4 | 1.01 | 2.0 | - | - |
| 40 | cand620 | Hsd_from_Mmd_141 | Mmd_141 | 6.2 | 1.03 | 2.0 | 137 | 438 |
| 41 | mmHP855413 | N/D | Mmd_216 | 6.7 | 1.13 | 2.2 | - | 520 |
| 42 | cand683 | Hsd_from_Mmd_511 | Mmd_511 | 7.5 | 1.15 | 2.2 | 349 | 833 |
| 43 | cand541 | Hsd_from_Mmd_228 | Mmd_228 | 7.2 | 1.16 | 2.2 | 180 | 180 |
| 44 | cand466 | Hsd_from_Mmd_235 | Mmd_235 | 8.4 | 1.19 | 2.3 | 165 | 539 |
| 45 | cand239 | Hsd_from_Mmd_456 | Mmd_456 | 7.2 | 1.23 | 2.3 | 310 | 775 |
| 46 | cand331 | Hsd_from_Mmd_93 | Mmd_93 | 10 | 1.25 | 2.4 | 386 | 898 |
| 47 | mmHP874966 | N/D | Mmd_309 | 8.2 | 1.27 | 2.4 | - | 616 |
| 48 | mmHP2052148 | N/D | Mmd_83 | 6.7 | 1.31 | 2.5 | - | 887 |
| 49 | mmHP901055 | N/D | N/D | 6.3 | 1.31 | 2.5 | - | - |
| 50 | cand190 | Hsd_from_Mmd_455 | Mmd_455 | 7.1 | 1.33 | 2.5 | 309 | 774 |
| 51 | cand852 | N/D | Mmd_312 | 7.2 | 1.46 | 2.8 | - | 820 |
| 52 | cand271 | Hsd_from_Mmd_483 | Mmd_483 | 8.1 | 1.47 | 2.8 | 328 | 802 |
| 53 | mmu-mir-296 | mmu-mir-296 | mmu-mir-296 | 7.4 | 1.53 | 2.9 | - | - |

FIG. 12 Con't.

differential expressed microRNAs between adenoma and normal control lung tissue

| | cand_id | human_hairpin | mouse_hairpin | intensity log2 | fold-change | Human patent_id | Mouse patent_id |
|---|---|---|---|---|---|---|---|
| | | | | (tumor / normal) | | | |
| 54 | cand478 | Hsd_from_Mmd_219 | Mmd_219 | 6.6 | 1.55 | 2.9 | 174 | 523 |
| 55 | cand667 | N/D | N/D | 9.8 | 1.57 | 3.0 | - | - |
| 56 | cand629 | Hsd_from_Mmd_91 | Mmd_91 | 9.9 | 1.61 | 3.1 | 384 | 896 |
| 57 | mmHP633267 | N/D | Mmd_21 | 6.9 | 1.62 | 3.1 | - | 513 |
| 58 | cand607 | Hsd_from_Mmd_430 | Mmd_430 | 8.8 | 1.63 | 3.1 | 295 | 748 |
| 59 | cand676 | Hsd_from_Mmd_519 | Mmd_519 | 6.9 | 1.67 | 3.2 | 354 | 839 |
| 60 | mmu-mir-134 | mmu-mir-134 | mmu-mir-134 | 6.8 | 1.72 | 3.3 | - | - |
| 61 | cand189 | mmu-mir-21 | mmu-mir-21 | 15.2 | 1.8 | 3.5 | - | - |
| 62 | cand460 | N/D | Mmd_331 | 8.4 | 1.84 | 3.6 | - | 640 |
| 63 | cand690 | N/D | Mmd_349 | 6.5 | 1.84 | 3.6 | - | 659 |
| 64 | cand458 | Hsd_from_Mmd_225 | Mmd_225 | 6.4 | 1.86 | 3.6 | 177 | 177 |
| 65 | mmHP2682003 | N/D | Mmd_104 | 8.3 | 1.88 | 3.7 | - | 397 |
| 66 | cand658 | N/D | Mmd_164 | 7.2 | 1.9 | 3.7 | - | 463 |
| 67 | cand223 | mmu-mir-203 | mmu-mir-203 | 7.1 | 1.91 | 3.8 | - | - |
| 68 | cand380 | mmu-mir-200b | mmu-mir-200b | 6.7 | 1.91 | 3.8 | - | - |
| 69 | mmu-mir-188 | mmu-mir-188 | mmu-mir-188 | 7.4 | 1.93 | 3.8 | - | - |
| 70 | cand482 | Hsd_from_Mmd_98 | Mmd_98 | 11.4 | 2.05 | 4.1 | 390 | 803 |
| 71 | cand617 | Hsd_from_Mmd_129 | Mmd_129 | 7.2 | 2.06 | 4.2 | 122 | 424 |
| 72 | cand300 | mmu-mir-93 | mmu-mir-93 | 6.7 | 2.13 | 4.4 | - | - |
| 73 | cand790 | Hsd_from_Mmd_518 | Mmd_518 | 6.7 | 2.15 | 4.4 | 353 | 838 |
| 74 | cand686 | Hsd_from_Mmd_299 | Mmd_299 | 7.1 | 2.17 | 4.5 | 223 | 605 |
| 75 | mmHP453167 | Hsd_from_Mmd_412 | Mmd_412 | 6.6 | 2.18 | 4.5 | 285 | 728 |
| 76 | cand498 | Hsd_from_Mmd_291 | Mmd_291 | 8.5 | 2.23 | 4.7 | 216 | 597 |
| 77 | cand521 | N/D | N/D | 6.5 | 2.25 | 4.8 | - | - |
| 78 | cand246 | N/D | Mmd_337 | 7.8 | 2.27 | 4.8 | - | 646 |
| 79 | mmHP254944S | N/D | Mmd_134 | 6.5 | 2.3 | 4.9 | - | 430 |
| 80 | cand368 | Hsd_from_Mmd_47 | Mmd_47 | 7.4 | 2.33 | 5.0 | 317 | 788 |
| 81 | cand978 | N/D | Mmd_403 | 9.2 | 2.41 | 5.3 | - | 718 |
| 82 | mmHP1181578 | N/D | N/D | 8.7 | 2.41 | 5.3 | - | - |
| 83 | mmHP157519 | N/D | Mmd_127 | 9.6 | 2.49 | 5.6 | - | 422 |
| 84 | cand415 | Hsd_from_Mmd_477 | Mmd_477 | 7.3 | 2.56 | 5.9 | 322 | 795 |
| 85 | cand713 | Hsd_from_Mmd_258 | Mmd_258 | 8.1 | 2.76 | 6.8 | 197 | 562 |
| 86 | cand308 | mmu-mir-320 | mmu-mir-320 | 7 | 2.79 | 6.9 | - | - |
| 87 | cand732 | Hsd_from_Mmd_49 | Mmd_49 | 9.2 | 2.9 | 7.5 | 334 | 809 |
| 88 | cand595 | Hsd_from_Mmd_198 | Mmd_198 | 11.7 | 2.98 | 7.9 | 185 | 499 |
| 89 | cand708 | mmu-mir-365-1 | mmu-mir-365-1 | 7.1 | 3.07 | 8.4 | - | - |
| 90 | cand593 | Hsd_from_Mmd_526 | Mmd_526 | 11 | 3.14 | 8.8 | 358 | 844 |
| 91 | mmHP1181586 | N/D | Mmd_132 | 7.3 | 3.14 | 8.8 | - | 428 |
| 92 | cand152 | N/D | N/D | 7.4 | 3.43 | 10.8 | - | - |
| 93 | cand519 | Hsd_from_Mmd_40 | Mmd_40 | 7.1 | 3.52 | 11.5 | 278 | 714 |
| 94 | cand592 | N/D | N/D | 13 | 3.67 | 12.7 | - | - |
| 95 | mmHP432573 | N/D | Mmd_214 | 8.3 | 3.69 | 12.9 | - | 518 |
| 96 | cand461 | Hsd_from_Mmd_297 | Mmd_297 | 9.9 | 3.77 | 13.6 | 221 | 603 |
| 97 | mmHP3140720 | N/D | Mmd_46 | 10.1 | 3.77 | 13.6 | - | 779 |
| 98 | cand540 | Hsd_from_Mmd_208 | Mmd_208 | 9.5 | 3.79 | 13.8 | 169 | 511 |
| 99 | mmu-mir-30c-1 | mmu-mir-30c-1 | mmu-mir-30c-1 | 10.3 | 3.85 | 14.4 | - | - |
| 100 | mmu-mir-494 | mmu-mir-494 | mmu-mir-494 | 11.9 | 3.94 | 15.3 | - | - |

Total RNA was isolated from human tumor material and normal control tissue using a Trizol-based method. Samples were labeled using Kreatech ULS microRNA reagents and hybridized to custom-spotted Codelink microarrays that contained 847 different microRNA probes (DNA backbone), including about 150 known microRNAs. Each probe was represented 8 times on every slide. Microarray images were processed with FeatureExtractor software and the data was analyzed using limma package (Bioconductor). N/D not determined.

derRNA, der stands for Drosha excised RNA. Although derRNAs are excised from RNA transcripts by Drosha, analogous larger precursor RNA species can be identified that are processed by other enzymes. Likewise, the invention provides novel siRNA sequences and precursors and complements thereof.

NUCLEIC ACID MOLECULES AND COLLECTIONS THEREOF, THEIR APPLICATION AND MODIFICATION

This application is a divisional application of U.S. application Ser. No. 12/087,649, filed Jul. 23, 2009, issued as U.S. Pat. No. 8,362,230 on Jan. 29, 2013 which is a 371 of PCT/NL2007/000012 filed Jan. 10, 2007, which claims priority to PCT/NL2006/000010filed Jan. 10, 2006 and PCT/NL2006/000491, filed Sep. 29, 2006, each of which is incorporated by reference in their entirety herein.

The invention relates to nucleic acid molecules and collections thereof. The invention further relates to the use of nucleic acid molecules in therapeutic and diagnostic applications. The invention furthermore relates to a method for identifying a miRNA molecule or a precursor molecule thereof.

MicroRNAs (miRNAs) are non-coding RNAs that regulate the expression of genes at the post-transcriptional level (reviewed in Bartel, 2004). Although only recently discovered, they have been found to play key roles in a wide variety of biological processes, including cell fate specification, cell death, proliferation, and fat storage (Brennecke, 2003, Poy et al., 2004, reviewed in Ambros, 2004). About 200 different miRNAs have now been described for mouse and human (Griffiths-Jones, 2004). The molecular requirements and mechanism by which miRNAs regulate gene expression are currently being clarified (Bartel, 2004), but individual biological functions remain largely unknown. Temporal and spatial expression of miRNAs may be key features driving cellular specificity.

MiRNAs, like siRNAs, are known in the context of RNA interference (RNAi). RNAi is the silencing of gene expression by the administration of double-stranded RNA (dsRNA). Endogenous RNAi seems to be a primitive sort of immune system, aimed at the defense of genomes against molecular parasites like viruses and transposons. During the process of RNAi, the dsRNA is converted into a shorter form: the siRNAs. siRNA is shorthand for "short interfering RNA", and synthetic versions of these 21 nucleotide long molecules are widely used to induce RNAi in mammalian cell systems because they circumvent the aspecific interferon response of these cells to dsRNA. The miRNAs are another species of small RNA molecules. MiRNAs, however, are always encoded by the genome itself, as hairpin structures, whereas siRNAs can both be artificial as well as endogenous (Hamilton & Baulcombe 1999; Aravin et al, 2001; Reinhart & Bartel 2002; Ambros et al, 2003). Both molecules feed largely into one and the same process that can either lead to mRNA degradation or to the inhibition of protein synthesis. As a rule, siRNAs cause mRNA destruction, whereas miRNAs can do both: in plants the majority of miRNAs direct cleavage, whereas miRNAs in animals most often induce translation inhibition; however, examples of translation inhibition in plants and cleavage in animals have been found (Chen 2004; Yekta et al, 2004).

MiRNA genes are transcribed by RNA polymerase II and transcripts are subsequently capped and poly-adenylated (Cai et al., 2004). Therefore, expression patterns of miRNAs in C. elegans can be easily determined by fusing green fluorescent protein (GFP) to upstream sequences (Johnson et al, 2003; Johnston & Hobert 2003). The nascent transcript of the miRNA is named pri-miRNA (primary miRNA) and can contain more than one miRNA. The individual miRNA-containing hairpin precursor (or pre-miRNA) is excised from this pri-miRNA by the enzyme Drosha (Lee et al, 2003) in the nucleus, and is assisted by a dsRNA-binding protein, gripper (G. Hannon, Cold Spring Harbor, N.Y., USA). Drosha is an animal-specific RNaseIII enzyme, and is essential for the production of miRNA precursor structures that can be exported from the nucleus. In plants, this role appears to be taken by one of the Dicer homologues (DCL1; Park et al, 2002; Reinhart et al, 2002; Xie et al, 2004).

The pre-miRNA is then exported to the cytosol (Yi et al, 2003; Bohnsack et al, 2004; Lund et al, 2004), where it is further processed by Dicer (Grishok et al, 2001; Hutvagner et al, 2001; Ketting et al, 2001). This enzyme basically can take any dsRNA and convert it to si/miRNAs (Bernstein et al, 2001) and there have been many models for how this is achieved. However, now it seems clear that the human Dicer enzyme does so by binding, as a monomer, to one end of the dsRNA through the PAZ (=Piwi-Argonaute-Zwille) domain (Lingel et al, 2003; Song et al, 2003; Yan et al, 2003), which seems to specifically recognize dsRNA ends produced by RNaseIII enzymes (Ma et al, 2004). This positions the two RNaseIII domains of the Dicer monomer such that they form one active site approximately 21 basepairs away (Zhang et al, 2004). In the case of miRNAs, this mode of action usually leads to the production of only one miRNA of specific sequence, as only the paired end of the pre-miRNA hairpin can be recognized. The mode of action of production of miRNAs from pre-miRNAs is unpredictable in that specific miRNAs cannot be predicted on the basis of the nucleic acid sequence of the pre-miRNA.

The complex that is ultimately responsible for silencing has been named the RNA-induced silencing complex (RISC), which incorporates both si- and miRNAs. Only single-stranded RNA is incorporated, however, and which of the two strands makes it into RISC is determined by the thermodynamically asymmetric nature of the siRNA: the strand with the most loosely basepaired 5' end is in most cases incorporated (Khvorova et al, 2003; Schwarz et al, 2003). P. Zamore (Worcester, Mass., USA) reported that this asymmetry is sensed by Dicer in complex with the dsRNA-binding protein R2D2, which literally takes this strand to the RISC complex (Lee et al, 2004; Pham et al, 2004; Tomari et al, 2004). What happens next is determined by a combination of factors: the origin of the small RNA (that is, whether it has been processed by Drosha and/or Dicer), associated proteins and the extent of basepairing between the target mRNA and the si/miRNA.

One of the outcomes is cleavage of the mRNA. The protein that executes this cleavage ("Slicer") remains elusive, but it is known what chemistry this enzyme should use: a 3' hydroxyl and a 5' phosphate group characterize the cleavage product (Martinez & Tuschl 2004; Schwarz et al, 2004). Also, RISC behaves like a true enzyme, so it catalyses many rounds of cleavage. The other outcome, translation inhibition, is not completely elucidated either. The step of translation that is actually inhibited could be initiation and/or elongation. Alternatively the process of translation could not be inhibited at all. One way of translational silencing might involve nascent chain degradation.

Currently, about 200 different mammalian miRNAs are known. A published estimate of the total number of miRNA genes in the human genome has been that the human genome contains at most 255 miRNA genes (Lim et al., 2003). The invention surprisingly found that there are many more different miRNA expressed in mammalian cells. At least ~1000 putative miRNAs in the human genome are conserved in at least some other vertebrates, and there are also a substantial number of species-specific miRNAs.

The invention provides novel miRNA sequences and precursors and complements thereof. The larger RNA species from which miRNA are excised have various names such as pre-miRNA, pri-miRNA and as used in the invention hairpin RNA. The invention provides many different miRNA and at least some of the larger RNA species from which they are derived. The miRNA and hairpin RNA provided by the invention are listed in FIG. 1. This figure contains a substantial amount of information on the miRNA, the cloning source, the hairpin RNA structure, mammalian homologues thereof, and extracted data from experimental results of FIG. 2, etc. The various elements of FIG. 1 are detailed in FIG. 1A. Different cell types were analysed for the presence of the respective miRNAs. In cases where a miRNA was produced by a cell, the structure and nucleotide sequence of the miRNA was determined. The invention thus further provides a method for analysing a sample comprising nucleic acid from a cell by determining the presence therein of a particular miRNA or hairpin RNA of FIG. 1. Correlation of the detected miRNAs with the pre-miRNAs revealed that accurate prediction of miRNA directly on the basis of the nucleic acid sequence of a pre-miRNA is not possible. The results found by the modified RAKE-approach, as detailed in FIG. 2A, for example in, one instance, showed a resulting miRNA from one strand of a predicted miRNA precursor, in another instance from two strands of a precursor. Moreover there was a significant variability of the position of the miRNA in the predicted precursor, the amount and sequence of nucleotides at either end of a strand.

It was found that miRNAs and hairpin RNAs of the invention are differentially expressed in cells of various origins. A probe specific for an individual miRNA or hairpin RNA can thus be used to differentiated samples on the basis of the expression of the respective miRNA or hairpin RNA. The invention therefore provides a method for characterising a sample comprising nucleic acid derived from a cell, said method comprising determining whether said sample comprises at least a minimal sequence of at least one miRNA (miRNA) of the invention or a mammalian homologue thereof and/or whether said sample comprises a precursor of said miRNA (hairpin RNA) of the invention or mammalian homologue thereof and characterizing said sample on the basis of the presence, relative abundance, or absence of said miRNA or hairpin RNA.

FIG. 1 depicts miRNA and precursors thereof (further referred to herein as hairpin RNA) of the invention. The hairpin RNA provided in FIG. 1 is typically shorter than the actual precursor RNA found in the cell. It contains the sequences that form the stem-loop structure from which miRNA are excised.

MiRNA were detected in various biological sources, depending on the miRNA and the biological source. Analysis of the structure of the miRNA revealed that miRNA produced from hairpin RNA are a heterologous group wherein the individual miRNA share a typically central, sequence. The individual miRNA produced from a pre-miRNA differ from each other at the 5' end, the 3' end, or both ends. A minimal sequence of a miRNA of the invention is a sequence that is shared by all identified miRNA variants from one half of the pre-miRNA or hairpin RNA. The half may be the half having the 5' of the pre-miRNA or hairpin RNA or the half having the 3' end of the pre-miRNA or hairpin RNA. A minimal sequence of a miRNA containing an uneven number of nucleotides is typically a sequence of at least 10 nucleotides comprising the central nucleotide of the miRNA and at least the 4 nucleotides next to the central nucleotide at either the 5' or the 3' side of the central nucleotide. For a miRNA containing an even number of nucleotides, a minimal sequence is typically a sequence of 10 nucleotides comprising the two central nucleotide of the miRNA and at least the 4 nucleotides next to the central nucleotides at either the 5' or the 3' side of the two central nucleotides. In another embodiment a minimal sequence of a miRNA of FIG. 1, comprises at least the "seed" sequence of said miRNA, i.e. nucleotides 2-8 of a miRNA of FIG. 1.

As different miRNA are differently expressed in various cell types or tissues, a method of the invention can be used to characterized the source of the sample. For instance, a probe specific for a miRNA that is expressed in heart tissue but not in embryonic cells can be used to classify a sample as either not containing RNA from the heart or vice versa, not containing nucleic acid derived from embryonic cells. For miRNA expressed in other tissues or cells similar characterisations are possible.

Nucleic acid obtained from a natural source can be either DNA or RNA. In the present invention it is preferred that said nucleic acid comprises RNA. The nucleic acid is preferably directly derived from a cell. However, the nucleic acid can also have undergone one or more processing steps such as but not limited to chemical modification. A miRNA or pre-miRNA of the invention, or complement thereof can also be used to analyse DNA samples, for instance, by analysing a sequence of an obtained (pre-) miRNA it is possible to determine the species that the cell belonged to that provided the nucleic acid for the analysis.

Characterisation of a sample on the basis of the presence, relative abundance, or absence of a particular miRNA and/or hairpin RNA can be used as an indicator for the presence or absence of disease, such as cancer. For instance, when a sample from a tissue comprises a different expression pattern of miRNA and/or hairpin RNA when compared to a comparable tissue from a normal individual, or when compared to a comparable tissue from an unsuspected part of said tissue from the same individual. A difference in the presence of one miRNA and/or hairpin RNA provides an indication in this type of analysis. However, the accuracy (i.e. predictive value) of the analysis typically increases with increasing numbers of different miRNA and/or hairpin RNA that are analysed. Thus a method for the characterisation of a sample of the invention preferably comprises determining whether said sample comprises at the least minimal sequence of 5 different miRNA or hairpin RNA of FIG. 1 or a mammalian homologue thereof. Preferably, at the least minimal sequence of 10, preferably at least 20 more preferably at least 60 different miRNA and/or hairpin RNA of FIG. 1 or a mammalian homologue thereof. A method of the invention may of course further include detection of miRNA and/or hairpin RNA of the art. It is preferred that the presence or absence of at least a minimal sequence of a miRNA of FIG. 1 is determined in a method of the invention. It is typically the miRNA that exerts an expression regulating function in a cell. The presence of pre-miRNA and/or hairpin RNA in a sample is of course indicative for the presence of at least the minimal sequence of the corresponding miRNA in said sample, although this does not always have to be true. Preferably, a method of the invention, further comprises determining whether said sample comprises at least a minimal sequence of at least five miRNA (miRNA) of FIG. 1, or a mammalian homologue thereof wherein said at least five miRNA are derived from at least five different hairpin RNA and characterizing said sample on the basis of the presence or absence of said miRNA.

A sample can comprise cells. Typically, however, a sample has undergone some type of manipulation prior to analysing the presence or absence therein of a miRNA and/or hairpin RNA according to the invention. Such manipulation, typically, though not necessarily comprises isolation of at least (part of) the nucleic acid of the cells. The nucleic acid in a sample may also have undergone some type of amplification and/or conversion prior to analysis with a method of the invention. miRNA can be detected directly via complementary probe specific for said miRNA or indirectly. Indirect forms include, but are not limited to conversion into DNA or protein and subsequent specific detection of the product of the conversion. Conversion can also involve several conversions. For instance, RNA can be converted into DNA and subsequently into RNA which in turn can be translated into protein. Of course such conversions may involve adding the appropriate signal sequences such as promoters, translation initiation sites and the like. Other non-limiting examples include amplification, with or without conversion of said miRNA in said sample for instance by means of PCR or NASBA or other nucleic acid amplification method. All these indirect methods have in common that the converted product retains at least some of the specificity information of the original miRNA and/or hairpin RNA, for instance in the nucleic acid sequence or in the amino acid sequence or other sequence. Indirect methods can further comprise that nucleotides or amino acids other than occurring in nature are incorporated into the converted and/or amplified product. Such products are of course also within the scope of the invention as long as they comprise at least some of the specificity information of the original miRNA and/or hairpin RNA. By at least some of the specificity information of the original miRNA and/or hairpin RNA is meant that the converted product (or an essential part thereof) is characteristic for the miRNA and/or hairpin RNA of which the presence or absence is to be determined.

The cell comprising said nucleic acid can be any type of cell. As mentioned above, it can be an embryonic cell, a foetal cell or other pre-birth cell, or it can be a cell of an individual after birth, for instance a juvenile or an adult. It can also be a cell from a particular part of a body or tissue of a mammal. Preferably, said cell is an aberrant cell, preferably a cell with an aberrant proliferation phenotype such as a tumour cell or a tissue culture cell. Preferably a cancer cell, or a cell suspected of being a cancer cell. In a preferred embodiment said cancer cell is a glioma cell. In another preferred embodiment said cancer cell is a lung cancer cell. In another preferred embodiment said cell is an adenoma cell, preferably a lung adenoma cell. In another preferred embodiment said cell is a cell that is infected with a pathogen. Preferably said pathogen is a virus or a (myco)bacterium. A method of the invention is particularly suited for determining the stage of said aberrant cell. For instance, tumorigenic cells can have varying degrees of malignancy. While progressing through the various degrees of malignancy the pattern of expression of (pre-) miRNA changes and can be detected. Such a pattern can thus be correlated with the degree of malignancy. A method of the invention can thus be used for determining a prognosis for the individual suffering from said cancer.

The cell is preferably a lung cell, a skin cell, a brain cell, a liver cell, an embryonic cell, a heart cell, an embryonic cell line or an aberrant cell derived there from.

Changes in expression are better detected when a test sample is compared with a reference. Thus in one aspect the invention provides a method for determining whether a cell in a sample is different from a reference cell, comprising determining whether expression of at least one at least one miRNA of FIG. 1 or a mammalian homologue thereof or at least one hairpin RNA of FIG. 1 or a mammalian homologue thereof, in said cell is different when compared to said reference cell. Preferably it is determined whether the expression of at least 5 miRNA or hairpin RNA is different in said cell in said sample when compared to a reference cell. Expression is different when there is at least a factor of two difference in the level of expression. Preferably, the difference is a difference between detectable miRNA expression and not detectable. Preferably said at least 5 miRNA or pre-miRNA are of FIG. 1. Expression levels can be compared by comparing steady state levels or by comparing synthesis rates.

A cell as used herein is a cell of a mammal, preferably a mouse, a rat, a primate or a human. A sample is for example characterized for the presence or absence of a disease, for belonging or not belonging to a certain species, or for being in a specific stage of development. In many instances however, a sample is best characterized by determining the presence, relative abundance, or absence therein of a collection of miRNAs and/or hairpin RNAs of the invention, as a sample of an organism usually displays a natural and/or pathological variation in diverse parameters.

Another reason why a sample is preferably characterized on the basis of a collection of miRNAs and/or hairpin RNAs, is that a disorder manifests itself in variable manners in different individuals. These two causes of variability can however, be calculated in through providing detection information of a collection of miRNAs and/or hairpin RNAs. For example, a characteristic expression profile of a disease is composed of a collection of miRNAs and/or hairpin RNAs. By comparing an expression profile of said collection in a sample to a reference expression profile of said collection that is characteristic of said disease, an individual from whom this sample is taken, is thus tested for presence or absence of said disease. The process of determining whether a sample matches an expression profile of a disease or a species depends on multiple factors. A miRNA itself has more or less distinctive power within, for example, a disorder or a species. Further a miRNA as part of a collection represents a percentage of a total collection. Characterizing a sample thus preferably comprises, apart from determining the absence or presence of one miRNA, determining the absence or presence of more miRNAs. Absence or presence of a miRNA is for example a positive or a negative indicator for a disease or a species. A collection or an expression profile preferably comprises one or more positive and/or negative indicators. Said positive and/or negative indicators are for example expressed as a percentage of a total number of miRNAs or as an absolute number of miRNAs. When expressing indicators in percentages, a weight is optionally attributed to an indicator. An indicator with a higher distinctive power is herein preferably given a higher weight than an indicator with a low distinctive power.

In one embodiment the invention provides a method according to the invention, comprising determining whether said sample comprises at least a minimal sequence of at least two, preferably at least three, more preferably at least four, most preferably at least five miRNAs of FIG. 1 or a mammalian homologue thereof wherein said miRNA are preferably derived from different precursor miRNA (pre-miRNA) and characterizing said sample on the basis of the presence or absence of said miRNA. The presence on a different hairpin RNA as depicted in FIG. 1, or on different mammalian homologs thereof is indicative for the presence on different precursor miRNA. In a preferred embodiment said characterization of said sample is a test for a disease. In many instances a test comprising more miRNAs has a higher diagnostic value, however, this need not always be the case. In another preferred embodiment of the invention one or more miRNAs according to the invention are determined in a sample, in combination with one or more other miRNAs. In a further preferred embodiment at least one miRNA according to the invention is determined in a sample in combination with one or more other miRNAs, resulting in determining a total of at least 10, preferably at least 15, more preferably at least 20 or most preferably at least 25 miRNAs. In a preferred embodiment said other miRNAs determined in a sample are involved in the same type of disorder as said miRNA according to the invention that is determined in said sample. Alternatively, a test is composed of miRNAs with indicative values of two or more diseases or two or more species.

Said sample preferably comprises nucleic acid of a differentiated cell. Differentiated as used herein is either cellular differentiated or evolutionary differentiated. Preferably differentiated is cellular differentiated. A differentiated cell is derived from any part of an organism. Said cell is preferably derived from a part of an organism that is associated with a disease. For example, when characterizing a sample for cancer, said cell is preferably derived from a tumour. In another preferred embodiment said sample comprises nucleic acid of an embryonic cell. An embryonic cell can be derived from any organism but is preferably derived from a mammal. A sample comprising nucleic acid derived from an embryonic cell, is for example taken for early diagnosis of a disease in an organism. A embryonic cell is in one embodiment an embryonic stem cell. In a further preferred embodiment said sample comprises nucleic acid of a cell with an aberrant proliferation phenotype. An aberrant proliferation phenotype indicates that a proliferation process has somehow been disturbed. The disturbance is either caused by internal factors or by external factors or by a combination thereof. An aberrant proliferation phenotype is for example found in hepatitis, a bowel disease or a cancer. Preferably a cell with an aberrant proliferation phenotype is a tumour cell and/or cell line cell. A tumour cell is for example a leukemic cell, such as a leukemic B-cell. Said tumour cell line cell is for example obtained from a cell line that is cultured from a cell derived from a tumour of an organism, preferably a mammal. Alternatively said tumour cell line cell is obtained from a cell line that is cultured from a cell wherein tumour characteristics have been induced artificially, for example with a chemical substance. In a preferred embodiment the invention provides a method for characterizing a sample comprising nucleic acid derived from a cell according to the invention, wherein said cell is a lung cell, a skin cell, a brain cell, a liver cell, an embryonic cell, a heart cell, or an embryonic cell line.

In one embodiment the invention provides a method for determining whether a cell in a sample is modified when compared to a reference cell, comprising determining whether expression of at least one at least one miRNA of FIG. 1 or a mammalian homologue thereof and/or a hairpin RNA of FIG. 1 or a mammalian homologue thereof in said cell is altered when compared to said reference cell. A reference cell as used herein is for example a healthy or pathological counterpart of respectively a pathological or healthy cell. A reference cell is for example another cell of the same cell type of the same organism wherefrom said sample is taken but preferably from another organism. The other organism is preferably comparable in species and/or constitution and/or development and/or age. In a preferred embodiment said cell is a differentiated cell. In another preferred embodiment is an embryonic cell. In a further embodiment said cell is a cell with an aberrant proliferation phenotype. Preferably said cell with an aberrant proliferation phenotype is a tumour cell and/or cell line cell. In one embodiment the invention provides a method for determining whether a cell in a sample is modified when compared to a reference cell according to the invention, wherein said cell is a lung cell, a skin cell, a brain cell, a liver cell, an embryonic cell, a heart cell, or an embryonic cell line.

A mammalian homologue of a hairpin RNA as depicted in FIG. 1 is a sequence that comprises at least 70% sequence identity with a hairpin RNA of FIG. 1 that can fold in a similar stem loop (hairpin) structure as the corresponding hairpin RNA of FIG. 1 (graphically depicted in FIG. 3). A mammalian homologue of a miRNA as depicted in FIG. 1 is a sequence that exhibits 90% sequence identity with at least 20, preferably consecutive, nucleotides of the corresponding miRNA of FIG. 1 (graphically depicted in FIG. 3). Preferably, said mammalian homologue of a miRNA of FIG. 1 is present in a mammalian homologue of the corresponding hairpin RNA. Preferably, said miRNA homologue is present in a part of said hairpin homologue that can form a stem structure.

The presence, relative abundance or absence of a miRNA of FIG. 1 or a mammalian homologue thereof and/or a hairpin RNA of FIG. 1 or a mammalian homologue thereof in a sample, can be determined by using a detection method. Typically a method for the specific detection of nucleic acid is used. Currently there are many methods for the specific detection a nucleic acids. Typically, though not necessarily these use a probe that specifically recognizes at least part of the nucleic acid to be tested. Such probe is often nucleic acid, but can also be an analogue thereof. For instance, various nucleotide analogues are presently available that mimic at least some of the base pairing characteristics of the "standard" nucleotides A, C, G, T and U. Alternatively, nucleotide analogues such as inosine can be incorporated into such probes. Other types for analogues include LNA, PNA, morpholino and the like. Further methods for the specific detection of nucleic acid include but are not limited to specific nucleic acid amplification methods such as polymerase chain reaction (PCR) and NASBA. Such amplification methods typically use one or more specific primers. A primer or probe preferably comprises at least 12 nucleotides having at least 90% sequence identity to a sequence as depicted in FIG. 1, or the complement thereof.

The present invention provides an isolated nucleic acid molecule comprising:
  a) a nucleotide sequence as shown in FIG. 1, and/or
  b) a nucleotide sequence which is a complement of a), and/or
  c) a nucleotide sequence which has an identity of at least 80% to a sequence of a) or b) and/or
  d) a nucleotide sequence which hybridizes under stringent conditions to a sequence of a), b) or c).

A complement of a nucleic acid sequence as used herein is a sequence wherein most, but not necessarily all bases are replaced by their complementary base: adenine (A) by thymidine (T) or uracil (U), cytosine (C) by guanine (G), and vice versa. Identity of sequence in percentage is preferably determined by dividing the number of identical nucleotides between a given and a comparative sequence by the length of the comparative sequence. In a preferred embodiment the invention provides a nucleic acid molecule according to the invention, wherein the identity of sequence c) to a sequence of a) or b) is at least 90%. In a more preferred embodiment said identity of sequence c) to a sequence of a) or b) is at least 95%. Preferably, said sequence identity to a miRNA of FIG. 1 or its complement is 90% in a stretch of preferably 20 nucleotides of said miRNA. Nucleotides A, C, G and U as used in the invention, are either ribonucleotides, deoxyribonucleotides and/or other nucleotide analogues, such as synthetic nucleotide analogues. A nucleotide analogue as used in the invention is, for example, a peptide nucleic acid (PNA), a locked nucleic acid (LNA), or alternatively a backbone- or sugar-modified ribonucleotide or deoxyribonucleotide. Furthermore the nucleotides are optionally substituted by corresponding nucleotides that are capable of forming analogous H-bonds to a complementary nucleic acid sequence. An example of such a substitution is the substitution of U by T. Stringent conditions under which a nucleotide sequence hybridizes to a sequence according to the invention are highly controlled conditions. Stringent laboratory hybridization conditions are known to a person skilled in the art.

In a preferred embodiment the invention provides a nucleic acid molecule according to the invention, which is a miRNA molecule or an analogue thereof. A further preferred embodiment of the invention provides a hairpin RNA molecule and a DNA molecule encoding miRNA or hairpin molecule. In another embodiment the invention provides an miRNA homologue of FIG. 1 or a mammalian homologue of a miRNA of FIG. 1. A homologue as used herein is a sequence, preferably a gene or a product of this gene that has evolved from a common ancestor in two or more species.

An isolated nucleic acid according to the invention preferably has a length of from 18 to 100 nucleotides, more preferably from 18 to 80 nucleotides. Mature miRNA usually has a length of from 18 to 26 nucleotides, mostly approximately 22 nucleotides. In a preferred embodiment the invention thus provides a nucleic acid molecule according to the invention having a length of from 18 to 26 nucleotides, preferably of from 19-24 nucleotides, most preferably 20, 21, 22 or 23 nucleotides. MiRNAs are also provided by the invention as precursor molecules. The invention thus further provides a nucleic acid molecule according to the invention which is a pre-miRNA, a hairpin RNA as depicted in FIG. 1 or a DNA molecule coding therefore. Precursor or hairpin molecules usually have a length of from 50-90 nucleotides. The invention provides a nucleic acid molecule according to the invention, having a length of 50-90 nucleotides of a hairpin RNA of FIG. 1. In a preferred embodiment the invention thus provides a nucleic acid molecule according to the invention, which is a pre-miRNA or a DNA molecule coding therefore, having a length of 60-110 nucleotides. The invention further provides a nucleic acid molecule according to the invention which has a length of more than 110 nucleotides, as a precursor miRNA is for example produced by processing a primary transcript. In a preferred embodiment the invention provides a nucleic acid molecule according to the invention, wherein said pre-miRNA is a pre-miRNA of FIG. 1 or a mammalian homologue or ortholog thereof.

As mentioned above, single-stranded miRNA is incorporated in a RISC. A miRNA precursor molecule is often partially double-stranded. Usually a miRNA precursor molecule is at least partially self-complementary and forms double-stranded parts such as loop- and stem-structures. The invention in one embodiment provides a nucleic acid molecule according to the invention, which is single-stranded. In another embodiment the invention provides a nucleic acid molecule according to the invention, which is at least partially double-stranded. In one embodiment of the invention a nucleic acid molecule according to the invention is selected from RNA, DNA, or nucleic acid analogue molecules or a combination thereof. In another embodiment of the invention aforementioned nucleic acid molecule is a molecule containing at least one modified nucleotide analogue. In a further embodiment the invention provides use of said nucleic acid molecule according to the invention in a therapeutic and/or diagnostic application.

A nucleic acid molecule according to the invention is in one embodiment part of a collection of nucleic acid molecules. Such a collection is preferably, but not exclusively, used in a test. A collection of nucleic acid molecules is for example used in a test as described above, for instance to determine absence or presence of a disease in an individual by testing a sample taken from this individual. A collection of nucleic acid molecules usually has a higher predictive value in any experimental setting when the number of nucleic acid molecules provided herein is larger. Thus, in one embodiment, the invention provides a collection of nucleic acid molecules, comprising at least 5, preferably at least 10, more preferably at least 20 nucleic acid molecules comprising a nucleotide sequence as shown in FIG. 1. A collection of nucleic acid molecules according to the invention, is in one embodiment used for the diagnosis of diseases such as cancer, heart disease, viral infections or disease susceptibility.

Further provided is a collection of nucleic acid molecules, comprising at least 5, preferably at least 10, more preferably at least 20 nucleic acid molecules that are complementary to miRNAs shown in FIG. 1, or that have nucleotide sequences which hybridize under stringent conditions to miRNAs shown in FIG. 1. A collection of nucleic acid molecules are preferably used in the diagnosis of cancer, heart disease, viral infections and other diseases.

A nucleic acid molecule according to the invention can be obtained by any method. Non-limiting examples are chemical synthesis methods or recombinant methods. A nucleic acid molecule according to the invention is in one embodiment modified. Said modification is for example a nucleotide replacement. Said modification is for example performed in order to modify a target specificity for a target in a cell, for instance a specificity for an oncogene. Said modified nucleic acid molecule preferably has an identity of at least 80% to the original miRNA, more preferably of at least 85%, most preferred of at least 90%. In another embodiment a nucleic acid molecule according to the invention is modified to form a siRNA molecule. For example, a miRNA molecule is processed in a symmetrical form and subsequently generated as a double-stranded siRNA. In a preferred embodiment the invention provides a nucleic acid molecule according to the invention, which is selected from RNA, DNA or nucleic acid analogue molecules which preferably further comprises at least one nucleotide analogue. In one embodiment a nucleic acid molecule of the invention is present in a recombinant expression vector. A recombinant expression vector according to the invention for example comprises a recombinant nucleic acid operatively linked to an expression control sequence. Said vector is any vector capable of establishing nucleic acid expression in an organism, preferably a mammal. Said vector is preferably a viral vector or a plasmid. In a preferred embodiment introduction of said vector in an organism establishes transcription of said nucleic acid. In a preferred embodiment after said transcription the transcript is processed to result in a pre-miRNA molecule and/or a hairpin molecule and subsequently in a miRNA molecule.

Nucleic acids according to the invention are in one embodiment provided as a probe. Many different kinds of probes are presently known in the art. Probes are often nucleic acids, however, alternatives having the same binding specificity in kind, not necessarily in amount are available to the person skilled in the art, such alternatives include but are not limited to nucleotide analogues. In one embodiment the invention provides a set of probes comprising at least one nucleic acid molecule according to the invention. In a preferred embodiment the invention provides a set of probes according to the invention, wherein said nucleic acid molecule is a miRNA molecule of FIG. 1 or a functional part, derivative and/or analogue thereof. In a further preferred embodiment the invention provides a set of probes according to the invention, wherein said nucleic acid molecule is a complement of a miRNA molecule or a functional part, derivative and/or analogue thereof. In a further preferred embodiment the invention provides a set of probes comprising a collection of nucleic acid molecules according to the invention. A collection in this embodiment preferably is a collection of nucleic acid molecules, comprising at least 5, preferably at least 10, more preferably at least 20 nucleic acid molecules comprising a nucleotide sequence as shown in FIG. 1 or a mammalian homologue thereof, or is a collection of nucleic acid molecules, comprising at least 5, preferably at least 10, more preferably at least 20 nucleic acid molecules with a nucleotide sequence which is a complement of a nucleotide sequence as shown in FIG. 1, or with a nucleotide sequence which hybridizes under stringent conditions to a nucleotide sequence as shown in FIG. 1, or is a combination thereof.

Further provided is an array comprising one or more nucleic acids of the invention. An array is used to analyze one or more samples at the same time. Preferably said array comprises at least two probes, wherein at least one probe comprises a nucleic acid molecule according to the invention. In a preferred embodiment said array comprises a set of probes comprising a collection of nucleic acid molecules according to the invention, or a combination of collections of nucleic acid molecules according to the invention. In one embodiment an array of the invention is a microarray. Said microarray preferably comprises oligonucleotides. A set of probes or an array or microarray according to the invention is in a preferred embodiment used in a diagnostic test.

A diagnostic test as used in the invention, is a test wherein a nucleic acid molecule according to the invention is used to subject a sample of an organism to a diagnostic procedure. Said organism preferably is a mammal, more preferably a human being. A sample as used in the invention preferably is a biological sample. A biological sample is for example a bodily fluid. A preferred biological sample is a tissue sample. A tissue sample is, for instance, used to determine a stage of differentiation or development of a cell. Alternatively a cell type or tissue type is classified as corresponding with a disorder. Said disorder is, for example, characterized by a typical expression level of a miRNA molecule or a typical expression pattern of miRNA molecules. The invention provides a nucleic acid molecule according to the invention for diagnostic applications as well as for therapeutic applications. A diagnostic of therapeutic application according to the invention relates to a disorder, for example a viral infection or cancer. Recently miRNAs have been described to be an important causal factor in cancer (Lu et al., 2005; He et al., 2005; O'Donnell et al., 2005; Alvarez-Garcia and Miska 2005) or a powerful indicator for prognosis and progression of cancer (Calm et al., 2005). A cancer is for example leukemia.

In one embodiment the invention provides a pharmaceutical composition, comprising as an active agent at least one nucleic acid molecule according to the invention, and optionally a pharmaceutically acceptable carrier. A pharmaceutical composition according to the invention further optionally comprises another additive. Such another additive can for example be a preservative or a colorant. Alternatively an additive is a known pharmaceutically active compound. A carrier is any suitable pharmaceutical carrier. A preferred carrier is a compound that is capable of increasing the efficacy of a nucleic acid molecule to enter a target-cell. Examples of such compounds are liposomes, particularly cationic liposomes. A composition is for example a tablet, an ointment or a cream. Preferably a composition is an injectable solution or an injectable suspension. In one embodiment the invention provides a pharmaceutical composition according to the invention for diagnostic applications. In another embodiment the invention provides a pharmaceutical composition according to the invention for therapeutic applications. In a preferred embodiment the invention provides a pharmaceutical composition according to the invention, as a modulator for a developmental or pathogenic disorder. In a preferred embodiment said developmental or pathogenic disorder is cancer. A miRNA molecule for example functions as a suppressor gene or as a regulator of translation of a gene.

A nucleic acid molecule according to the invention is administered by any suitable known method. The mode of administration of a pharmaceutical composition of course depends on its form. In a preferred embodiment a solution is injected in a tissue. A nucleic acid molecule according to the invention is introduced in a target cell by any known method in vitro or in vivo. Said introduction is for example established by a gene transfer technique known to the person skilled in the art, such as electroporation, microinjection, DEAE-dextran, calcium phosphate, cationic liposomes or viral methods.

A nucleic acid molecule according to the invention is in one embodiment used as a marker of a gene. A marker identifies a gene, for example a gene involved in cancer or another developmental disorder. A marker is, for instance, a miRNA that is typically differentially expressed in a disorder or is a set of two or more miRNAs that display a typical expression pattern in a disorder. A nucleic acid molecule is alternatively for example labelled with a fluorescent or a radioactive label. A nucleic acid molecule according to the invention is, in another embodiment, a target for a diagnostic or therapeutic application. For example, a miRNA molecule according to the invention is inhibited or activated and the effect of the inhibition or activation is determined by measuring differentiation of a cell type. In another embodiment, a nucleic acid according to the invention is not a target itself, but alternatively used to address a target in a cell. A target in a cell is preferably a gene. Preferably said gene is at least partially complementary to said nucleic acid molecule. For example, a miRNA according to the invention is used to find a gene in a cell that has a sequence that is at least partially complementary to the sequence of said miRNA. In a preferred embodiment the invention provides a pharmaceutical composition as a marker or modulator of expression of a gene. In another preferred embodiment the invention provides a pharmaceutical composition according to the invention, wherein said gene is at least partially complementary to said nucleic acid molecule. A modulator of expression of a gene is for example a miRNA. A miRNA that functions as a tumour-suppressor is for instance provided and expressed in and/or delivered to a tumour cell thus suppressing the development of a tumour. In a preferred embodiment the invention provides a use of a nucleic acid molecule according to the invention, for down regulating expression of a gene. Down regulating expression of a gene is for example important in cancer. In an alternative embodiment a miRNA is introduced and/or expressed in a cell of a tissue that does not express said miRNA. As a result said cell of said tissue for example shows a different differentiation type. Such a procedure is for example used as a tissue reprogramming procedure.

At present, there are essentially two approaches for identification of novel miRNA genes: cloning of size-fractionated (18-25 nt) RNAs and computational prediction based on different structural features of miRNAs followed by experimental verification. Cloning of size-fractioned RNAs is a laborious procedure and has resulted in a restricted amount of identified miRNAs. Established methods for validation of predicted miRNA genes rely on construction of size-fractionated cDNA libraries. This is a technically challenging procedure that does not scale well. Moreover it requires testing many tissues and developmental time points. Established methods of experimental validation of predicted miRNAs thus do not scale for the analysis of thousands of candidates regions. The invention surprisingly found a high-throughput approach for testing candidate miRNA regions. The invention provides a modified RAKE assay for high-throughput expression studies of candidate miRNA regions. The provided assay allows exact mapping of 3' ends of mature miRNAs, thus providing information on both structure and expression profiles of novel miRNA genes. Different microarray technologies, including RAKE assay, have been applied for expression profiling of known miRNAs. However, microarrays were not previously used for detection of novel, computationally predicted miRNAs. The unique method of combining a computational method with a modified RAKE assay, provided by the invention, has led to the discovery of numerous new miRNAs. Furthermore the provided method offers an opportunity to discover further miRNAs.

Cross-species sequence comparison is a powerful approach to identify functional genomic elements, but its sensitivity decreases with increasing phylogenetic distance, especially for short sequences. In addition, taxon-specific elements may be missed. To overcome the limitations of classical phylogenetic footprinting methods, the invention applied the phylogenetic shadowing approach (Boffelli et al., 2003), allowing unambiguous sequence alignments and accurate conservation determination at single nucleotide resolution level. This approach is based on the alignment of phylogenetically closely related species; since these show only few sequence differences, many different (but related) genomes need to be aligned to identify invariant (conserved) positions. In the invention 700 bp regions surrounding 122 miRNAs in 10 different primate species were sequenced, including orangutan, gorilla, 2 chimpanzee and 2 macaque species, tamarin, spider monkey, wooly monkey and lemur. Besides the region spanning the pre-miRNA, no additional conserved regions common to different miRNAs could be found, suggesting that, in contrast to *C. elegans* (Ohler et al., 2004), no common cis-acting elements can be immediately recognized in mammalian miRNAs. In the invention it was surprisingly found that there is a prominent drop of conservation immediately flanking pre-miRNA regions. This characteristic conservation pattern can also be recognized in pairwise alignments between more diverged species like human and mouse and was used to identify novel miRNA genes by screening mouse-human and rat-human whole-genome sequence alignments for this typical conservation profile. Additional stringent filtering for the ability of candidate regions to fold into a thermodynamically favorable stable hairpin, as calculated by Randfold software (Bonnet et al., 2004), resulted in the identification of 976 candidate miRNAs, containing 83% of all known human miRNAs (158 out of 189, based on miRNA registry v.3.1).

Screening for homologues in additional vertebrate genomes (zebrafish, chicken, opossum, cow and dog) revealed that 678 candidates are conserved in at least one other species besides rodents. A substantial part of the predictions consists of miRNAs unique to mammals. Both the genomic distribution and the extent of supportive data for expression are comparable for the mammalian-specific subset and the set of candidates that are also conserved in at least one non-mammalian species. Even though the degree of genome coverage varies for the species used in the comparisons, this data suggests that there are a significant number of lineage-specific miRNAs and indicates that both rapidly and slowly evolving miRNAs exist (let-7 being a typical example of a slow evolver).

Fourteen novel candidates share homology with known miRNAs and an additional 60 share homology with at least one other candidate, making up novel subfamilies. In addition to the established clustering behavior of miRNAs (Bartel 2004, Rodriguez et al, 2004), the ratio between the number of miRNA genes in inter- and intragenic regions is similar for both known and novel miRNAs. Although a fair proportion of candidates are predicted on the strand opposite to annotated transcripts, the disproportionate presence of miRNA genes in introns is intriguing and may reflect expression mechanisms by co-transcription with the host gene and processing of spliced introns. 171 of the predicted novel miRNAs reside in genomic regions that are annotated as exons. In experimental approaches, such candidates are often discarded as potential cloning artifacts, but these regions can be processed into mature miRNAs. Work by Cullen and co-workers (Cal et al, 2004) demonstrated that a transcript harbouring simultaneously a miRNA and an ORF is efficiently used for both miRNA and protein production. About 25% (44) of the exonic candidates reside in non-coding parts and although 127 candidates overlap with annotated protein coding sequences, 75 are predicted on the opposite strand.

Support for the expression of candidate miRNAs is provided through various sources. Three candidates are present in the FANTOM2 database of expressed sequences and 11 candidates reside in gene clusters containing one or more known miRNAs. These miRNAs are likely to be co-expressed from the same primary transcript (Bartel, 2004, Rodriguez et al., 2004). Systematic human transcriptome analysis using high-density oligonucleotide tiling arrays (Kapranov et al., 2002) is in progress and in the invention it was found that the genomic regions encoding 64 known and 214 novel miRNAs has now been covered. From this set, 13 known (20%) and 72 novel (34%) miRNAs are expressed in the SK-N-AS cell line, for which data is publicly available. Although poly (A)+RNA was used for these experiments and properties of miRNA-containing transcripts remain largely to be elucidated, both intergenic and intronic miRNAs were detected. Various lines of research support the finding that at least some miRNAs are processed from poly-adenylated RNA (Cai et al., 2004, Lee et al., 2004).

To provide experimental support for the predicted miRNAs, in the invention Northern blotting experiments were performed for 69 candidates, confirming the expression of 16 mature miRNAs (23%). Although these verification rates are lower than previously published rates using cloning- and PCR-based approaches (38 out of 93; Lim et al., 2003), they may be an under-representation as a result of a bias in the set of already known miRNAs for highly expressed and thus most easily detectable miRNAs, the sensitivity of the detection method, and spatio-temporal limitations of the RNA samples used. Therefore, we developed another potentially more sensitive strategy for candidate miRNA validation based on the RAKE (RNA-primed Array-based Klenow Extension, Nelson et al., 2004) assay.

This assay is based on the ability of an RNA molecule to function as a primer for Klenow polymerase extension when fully base-paired with a single stranded DNA molecule. As the exact 3'-end of the miRNA should be known for successful extension and computational predictions are not optimal for predicting the correct start and end of the mature miRNA, we designed a tiling path of probes complementary to both known and predicted miRNA precursors. Such a tiling path RAKE assay is less prone to false positives than standard hybridization assays, as it depends on the presence of a fully matching 3'-end of the miRNA and hence distinguishes between miRNA family members that differ in their 3' sequences. Flanking tiling path probes function as negative controls. Although some rules have been put forward to determine which strand of the stem is preferentially loaded as mature miRNA in the RISC complex (Khvorova et al., 2003; Schwarz et al., 2003), such computational predictions can only be done when the precise ends of the processed miRNA duplex are known. In addition, due to the nature of the hairpin sequence it is often difficult to predict which strand of the genomic DNA encodes a precursor. To take a fully unbiased approach, we designed tiling paths of 11 probes covering each arm of the stem-loop structure, for the sense as well as the anti-sense genomic sequence, resulting in sets of 44 probes per candidate miRNA gene. Due to G-U pairing allowed in RNA folding and different nucleotide composition of the complementary DNA strand, anti-sense transcripts do not necessarily fold into stable stem-loop structures and for such candidates only 22 probes were included. The central position in the tiling path was determined by predicting the most likely Dicer/Drosha processing sites from secondary structure hairpin information. We designed a custom validation microarray with 44,000 features, covering 271 known mouse miRNAs and 676 of the predicted miRNAs that are conserved between mouse and human, and filled up the array with 199 additional candidates based on stringent randfold criteria (Bonnet et al., 2004) and mouse and rat genome conservation. These arrays were probed with 4 different sources of small RNAs: mouse embryos at embryonic days 8.5 and 16.5, adult mouse brain and embryonic stem (ES) cells (FIG. 2). Mature miRNAs were semi-manually annotated after pre-processing the raw microarray output data using custom scripts. A redundant set of 221 of the known miRNAs (82%), 429 of the candidate conserved miRNAs (63%), and 126 of the extra set (63%) were found positive (FIG. 2). As different genomic loci can produce an identical mature miRNA from a different hairpin (e.g. miR-1-1 and miR-1-2), the total number of non-redundant mature miRNAs is lower. Interestingly, for more than half of the known miRNAs, the most prominent 3' end observed in the RAKE assay differed from the annotated form, including 8 mature miRNAs residing in the other arm of the hairpin, suggesting that originally the star-sequence was annotated. In addition, for various candidate and known miRNAs, multiple subsequent probes (2 or 3) resulted in a positive signal, indicating that 3' end processing of miRNAs is not a completely accurate process at the single nucleotide level. These findings are in line with the observed variation in ends of cloned miRNAs (Aravin and Tuschl, 2005).

The second approach we pursued to experimentally confirm novel miRNAs is deep sequencing of size-fractionated small RNA libraries of isolated human and mouse tissues. Although it was suggested previously that such efforts had reached near saturation (Lim et al., 2003), only limited numbers of library clones from a selected set of vertebrate tissues have been sequenced (Lagos-Quintana et al., 2001, Lim et al., 2003, Bentwich et al., 2005). Moreover, our computational predictions and microarray(RAKE)-based confirmations suggested many novel miRNAs to be discovered. Therefore, we generated seven high-titer non-concatemerized libraries of size-fractioned small RNA's from mouse brain and various human fetal tissues (brain, skin, heart, lung, and mixed tissues) and sequenced 83,040 clones. After vector and quality trimming 51,044 inserts longer than 17 bases were recovered that represent 8,768 and 7,306 non-redundant mouse and human sequences, respectively. We established a computational pipeline for automated annotation of the cloned sequences, taking into account unique chromosomal position, location in repetitive elements or rRNA, tRNA, snoRNA genes, conservation data from 9 vertebrate genomes (human, mouse, rat, dog, cow, chicken, opossum, zebrafish, and fugu), and secondary structure information using randfold (Bonnet et al., 2004). This analysis was applied to the mouse and human cloned fragments, as well as to all known human and mouse miRNAs and the positive candidates identified using the RAKE assay. 214 out of 238 mouse (90%) and 306 out of 319 human (96%) miRNAs, as deposited in miRBase (Griffiths-Jones, 2004), passed the automated filtering and annotation, showing that the false negative rate is low for the known miRNAs. For the sequenced small RNAs, 21,537 mouse (69%) and 13,120 human (66%) clones passed this filtering. Known abundant miRNA sequences dominate this set, but interestingly about 2% of the reads represent 115 novel mouse and 111 novel human miRNA genes (FIG. 1).

Taken together, we identified 535 novel mouse (RAKE and cloning) and 111 novel human (cloning only) miRNA genes. Although only 17 miRNAs were cloned from both human and mouse samples, the majority of the novel mouse miRNAs has a clear human homologue (over 90% identity for the mature miRNA and 70% for the pre-miRNA), adding up to 401 and 542 of newly discovered miRNA genes in the human and mouse genomes, respectively.

As the majority of novel miRNAs were cloned only once and our cloning efforts identified only about ⅔ of all known miRNAs, we reasoned that the cloning efforts were not exhausted. Therefore, we generated another 32 size-fractionated small RNA libraries from human, chimpanzee, and macaque brain samples. These libraries were not cloned in bacteria, but amplified clonally in an emulsion PCR, followed by massively parallel pyrosequencing (Margulies et al., 2005). A total of more than 1.6 million sequencing reads were evaluated using the bioinformatics analysis pipeline mentioned above. As more vertebrate genomes were available at the time of this analysis, we used an alternative approach for the identification of homologous miRNA genes in other species for this set of miRNAs. The human, chimpanzee, and macaque experiments resulted in the identification of 878, 227, and 1973 novel miRNAs respectively (FIG. 1C). Homology analysis resulted in a set of 2384 novel human microRNAs. 65 microRNAs were found to be human-specific, whereas 17 and 519 were restricted to the chimpanzee and macaque genome, respectively In one embodiment the invention provides a method of identifying a human miRNA or a mouse miRNA. In a further embodiment a method according to the invention comprises an additional step. Said step comprises determining an ortholog or a homologue of a gene. An ortholog or a homologue is determined by comparison of sequences. A human homologue or ortholog is for example determined of a mouse sequence or vice versa, a mouse ortholog is determined of a human sequence. A homologue of a miRNA of FIG. 1 is preferably a mammalian homologue. Mammalian homologues of a miRNA of FIG. 1, comprise at least 90% sequence identity in a stretch of at least 20 consecutive nucleotides of a miRNA of FIG. 1, and are preferably situated in a larger RNA that comprises 70% sequence identity with the corresponding hairpin RNA of said miRNA, wherein said larger RNA is preferably capable of forming a stem loop structure as predicted by an appropriate computer model, and wherein said homologue is preferably situated in a predicted stem region in said larger RNA.

MiRNAs are single strand products derived of longer stem-loop precursors; they can base-pair to messenger RNAs, and thus prevent their expression. Animal genomes contain hundreds of miRNA genes and thousands of genes that axe targeted by them. miRNAs often have striking organ-specific expression and can thus be used to discriminate between different cell types.

Historically miRNAs were discovered as freak regulators in weird worms: mutants defective in the timing of cell division in the larvae of the nematode *C. elegans* were found to be defective in a gene lin-4, which encoded a small RNA that was shown to bind to and silence translation of the lin-14 mRNA (Lee et al., 1993). The general relevance of this landmark discovery became clearer when a second small RNA, let-7, was found to be strongly conserved from worms to flies and human (Reinhart et al., 2000), and when subsequently additional miRNAs were discovered. The current picture is that the human genome contains probably at least 500 miRNA genes (Bartel 2004, Berezikov et al., 2005), which are likely to regulate thousands of target genes (Lim et al., 2005, Lewis et al., 2005). Only the 7 base seed sequence (position 2-8 from the 5' end) seems required for miRNA action in animal cells; why then is the entire miRNA so strongly conserved? Surely other positions contribute small but nevertheless significant effects to miRNA action, but additional explanations may be that the other sequences within the miRNA are required for processing of the precursors, so before the miRNA is mature, and one can not rule out that miRNAs serve other unknown functions in the cell, for which these other sequences are required.

Independent of the discovery of miRNAs, gene silencing by siRNAs was discovered: RNA interference (Fire et al., 1997). The similarity was not immediately recognized, but the central agents in RNAi were RNA molecules of the same size as miRNAs, and since the RNase that makes siRNAs out of longer double stranded RNA had been discovered (Bernstein et al., 2001), it did not—as the phrase is since the 1953 double helix paper—escape anybody's notice that perhaps Dicer might also be responsible for making miRNAs (which was indeed confirmed by a series of parallel papers that showed Dicer mutants are defective in miRNA synthesis). Since then an impressive body of genetic and biochemical analysis has lead to the conclusion that the complexes that silence a mRNA and are guided by a small RNA (RISC, for RNA induced silencing complex) may differ from organism to organism, from tissue to tissue, and there may even be parallel pathways within one cell, but in essence miRNAs and siRNAs act via a fairly similar complex, which always contains at least one member of the family of Argonaut proteins.

The precise mechanism by which miRNAs silence mRNAs is unclear, with several issues that need to be resolved. The original discovery of the first miRNA lin-4 indicated that the target mRNA was left intact and not changed in stead-state levels (Lee et al., 1993); the miRNA was thought to silence but not degrade its target. Since then it has been found that miRNA silencing is actually accompanied by a drop of the levels of the target mRNAs; the drop is often modest, a factor of 2-3 is common, which seems insufficient to fully explain the drop in protein levels, suggesting that also intact mRNAs are silenced (Bagga et al., 2005). The discrepancy with earlier data may be explained because the original study measured RNA levels by RNase protection rather than Northern blots, a technique that is not so sensitive to partial degradation of RNA. A second point that needs to be clarified is whether the translation-suppressing effect of miRNAs is on initiation or elongation of translation, with a recent study showing that introduction of an IRES (Internal Ribosome Entry Site) over-rules miRNA repression, suggesting the action is on initiation (Pillai et al., 2005).

What is the function of miRNAs? The virtual lack of miRNA mutants discovered in forward mutant hunts in genetic systems such as *Drosophila* or *C. elegans* may partly be attributed to the small size of the miRNAs as targets of mutagenesis; in addition the miRNAs seem fairly tolerant of a single base change as long as it does not affect the "seed sequence" of 7 nucleotides. Furthermore researchers trying to map a mutation to a protein coding region may have chosen to ignore mutations in non-coding miRNA sequences. However, probably the most important explanation that the miRNAs have been missed in mutant screens is that their knock-out has often no phenotype. In a recent study miRNAs in the nematode genome were knocked out, and the result was that single mutants did not while multiple mutants did have a phenotype (Abbott et al., 2005). We also see this with knock-down of miRNAs in zebrafish embryos using morpholinos. The conclusion is that there is much redundancy; possibly the very high levels of miRNAs in a cell (often more than 50,000 copies) is best achieved by a set of related miRNA encoding genes, and the loss of one of them leads to a modest reduction of levels that is not immediately resulting in a strong visible phenotype. As so often in biology, this raises the question why so many miRNA genes have been strongly conserved if there seems so little selective pressure, and as so often the answer needs to lay in subtle effects that are not recognized under laboratory conditions.

As the seed sequence seems to determine the target specificity of the miRNA the present invention further provides a nucleic acid sequence comprising at least nucleotides 2-8 of a miRNA as depicted in FIG. 1, or the seed sequence of a mammalian homologue of a miRNA as depicted in FIG. 1. In a preferred embodiment said nucleic acid sequence comprising at least nucleotides 2-8 of a miRNA of FIG. 1 comprises between about 18 and 26 nucleotides. Preferably, between about 20-24 nucleotides, more preferably about 22 nucleotides.

As described, knock out mutants of single miRNAs give few hints about the function of miRNAs. One indication of function comes from the study of the expression pattern of miRNAs: our laboratory showed recently that many miRNAs have striking organ specific expression, or even expression restricted to single tissue layers within one organ. This indicates that they play no general housekeeping role in cell metabolism, but most likely a role in an aspect of the difference between differentiated cells (Wienholds et al., 2005). An example of such expression patterns is miR-206 in muscle and miR-34A in the cerebellum. A second hint comes from the crudest miRNA knock out experiment possible: the knock out of all miRNAs (plus siRNAs), by disruption of the Dicer gene, which encodes the nuclease that make miRNAs. (Wienholds et al., 2003). As perhaps expected, this mutation is lethal. In mouse Dicer function is even required for stem cell formation. In zebrafish, however, it is not. Thus one can cross two Dicer heterozygous fish, and analyze the homozygous progeny: it develops normally until approximately a week of age, at which time growth stops and the animals eventually die. The fish embryos have formed most of their organs by 24-48 hour, and after a week swim around, eat and behave as real little beasts, all of this without Dicer. Analysis of miRNA levels show part of the explanation: maternal rescue. In the first days of development even Dicer mutant embryos form new zygotic miRNAs, and this must be done by maternal Dicer function (Dicer mRNA and/or protein in the oocyte). Still it is noteworthy that—with the exception of a few miRNAs—in the first 24-48 hours of development only low levels are seen, also in the wildtype (Wienholds et al., 2005). Thus the temporal pattern of miRNA expression is that they appear long after most cells have differentiated and tissues have been formed. The slow rise of levels must be the result of accumulation over time: many miRNA genes are embedded in introns of protein coding genes, and are initially transcribed together with their "host" mRNA, and therefore presumably equimolar to the mRNAs; while the mRNA levels remain modest, the miRNA levels build up over time, because the miRNAs are much less turned over than their host mRNAs. An elegant experiment (Giraldez et al., 2005) further drove down the point that miRNAs play no great role in early development: the maternal expression of Dicer can be removed by transplanting germ cells from Dicer mutant embryos into wildtype embryos of the same age: when the fish grow up they are fertile, but their germ line is genetically Dicer mutant. In this situation the fish do not have maternal Dicer, and indeed the animals now arrest earlier in development, but they still form several tissues. The conclusion of these experiments is that miRNAs are required for full development, have an expression patterns suggestive of developmental roles, but are not required for initial tissue differentiation. The abovementioned studies can be further refined with the discovery of the miRNAs of FIG. 1 as new targets for expression of miRNAs in development have now become available.

Some recent studies describe how miRNAs can tune gene expression in development. One study describes the role of mir-61 in determining the fate of one cell in vulval development of the nematode via a feedback loop: cell fate is determined by mutually exclusive expression of one gene or another, and one protein turns on the expression of a miRNA, which tunes down the expression of the second protein (Yoo and Greenwald, 2005). Another recent study describes how miR-196 acts upstream of Hox genes (Hornstein et al., 2005). Genes in the Notch signaling cascade are regulated by a set of miRNAs (Lai et al., 2005). All of these cases can be referred to as programmed miRNA action: the action of miRNAs is an integral part of a developmental event. The logical consequence is that the action is under positive evolutionary pressure, and indeed the Notch-pathway study could exploit the evolutionary conservation of the target sites among insect species to recognize them in 3' UTRs of genes.

A prerequisite for such developmental switches is that at some moment in time the miRNA and its target mRNA are expressed in the same tissue, so that the miRNA can exert its action and silence the expression of its target. Intuitively this is what one might expect to be the rule: if a mRNA is a "genuine target" of a miRNA, the two need to be co-expressed. In other words: a naïve approach to discover biologically relevant miRNA/target pairs would be the following: screen the sequence of the crucial seven base pair "seed" sequence of each miRNA against the 3'UTR of all known genes; take the sets of miRNA/mRNA pairs that result, then filter the entire set by only accepting the pairs where miRNA and target mRNA are expressed in the same tissue. This would seem logical, since how could the two interact if they are not expressed in the same cells? Interestingly two recent studies show the situation is more complex than that. One study was done in *Drosophila* (Stark et al., 2005), the other in mammals (Farh et al., 2005), and in essence the conclusion are largely the same. The first striking result is this. If one takes miRNAs known to be expressed in a certain type of tissue (say muscle), and looks at the expression levels of genes whose 3'UTR contain a (potential) target-site of such a miRNA (defined operationally as a perfect match to the 7 base seed sequence), then genes with a target site are expressed at higher levels in tissues that do not express the miRNA than in tissues that do! So real partners (miRNAs plus targets) are not necessarily co-expressed. Is this effect cause or consequence? Both of these studies compare miRNA levels to mRNA transcript levels, and since miRNAs can reduce transcript levels (see above) the cause/consequence relation is not entirely clear in all cases. Thus saying that mRNAs and miRNAs avoid co-expression may be an overstatement, since the reduction of a mRNA may also be the consequence of the action of the miRNA, not a consequence of avoidance at the transcriptional level. Bartel and coworkers addressed this point in an elegant fashion: they looked at genes in mouse that do not have a miRNA target, while the human ortholog does. These mouse genes are nevertheless still significantly avoiding expression in the tissues that express the miRNA. This suggests the avoidance is really at the transcriptional level, and is not absence as a result of miRNA action (because the mouse version of the gene sees no miRNA action in that tissue).

Then there is a second effect. Both papers find evidence for "anti-targets": there is selective avoidance of target sites in genes that are expressed at high levels in tissues where the miRNAs are expressed. Since gene expression is reduced by miRNAs, the acquisition of new miRNA target sites for miRNAs expressed in that tissue (probably not an infrequent event in evolution, since the crucial seed sequence is only 7 nucleotides long) is bad news and will be selected against if it results in an undesired knock down of that gene.

So how do the examples of programmed miRNA action, serving as developmental switches, relate to the notion of avoidance of co-expression? If the miRNA relates to its target as vacuum cleaner to dust, how can the two be seen as finetuned partners in a subtle developmental switch? The answer is provided by a beautiful distinction made in the study by Bartel and colleagues (Farh et al., 2005): targets of miRNAs fall into two classes: conserved and non-conserved. This is here operationally defined as those targets which are or are not conserved in the 3'UTRs of human versus orthologous mouse genes. The majority is not conserved, a minority is. Now here is the discovery: the conserved targets are in genes that do not avoid co-expression with their miRNAs, the non-conserved do avoid it.

The class of conserved targets is explained by the essential role the miRNA plays in developmental switches, such as those discussed above in the vulva and the Notch pathways, and we can refer to those cases as programmed miRNA silencing. A second type of conserved targets are those where gene expression is required in one phase of development, but after cell fate determination the miRNAs survey cells to wipe out the remaining traces of expression of these mRNAs that are not meant to be expressed in that tissue. The miRNA system is a vacuum cleaner removing the last speckle of undesired transcripts. Alternatively the system may serve to tune down but deliberately not shut off their targets. Together with the late onset and perseverance of expression of many miRNAs and the differentiation of tissues in embryos of fish devoid of all miRNAs, this indicates that the primary function of many miRNAs may not be to switch cell fate, but rather to dampen the expression of undesired genes, to remind a cell of the fate it has chosen previously: remember you are a muscle cell, do not have the nerve to highly express other genes!

The non-conserved majority has a completely different explanation: apparently 3'UTRs of genes are full of sequences to which miRNAs can bind; this is not surprising if the only truly essential feature is homology to the 7 nucleotide seed sequence: with a 3'UTR of one or two thousand base pairs, and with hundreds of different miRNAs, there will often be matches. In evolution such new "miRNA" recognition sequences pop up all of the time, and there is nothing wrong with them per se. The problem appears only if the target is in a gene that needs to be expressed at a significant level precisely in the tissue in which the corresponding miRNA is present at high levels, ready to silence any miRNA that matches its seed sequence. For these genes the match to this miRNA may be a nuisance, with negative fitness as result, and thus these matches are counter selected. Newly appearing miRNA target sequences (of no function, and thus under no evolutionary pressure to remain conserved) will not be selected against, and have essentially neutral fitness effects if the miRNA that could bind to them is not expressed in the same tissue. These target sequences have no physiological relevance, and thus are therefore ignored by evolution, neither selected for nor against, as long as they are not expressed in the tissues that express the miRNAs. These 7 base pair sequences are to the organism like EcoRI restriction sites in DNA (GAATTC): of no concern or interest (as long as there is no EcoRI around in the cell).

The combinations between miRNAs and their target can thus be classified in at least three groups: positively selected, neutral and negatively selected.

1. The positively selected or programmed interactions can be genuine cell fate switches, such as the switch of the 2nd vulval cell fate by miR-61 in worms, where at a crucial phase in time a cell needs to make a choice. A second type of programmed targets are those where after cell fate determination all traces of mRNAs that were required in a previous developmental stage need to be removed, or levels of genes need to remain tuned down significantly. Such interactions may be expected to be conserved, since they contribute positively to stable establishment or maintenance of cell fate.
2. The second class of combinations is neutral. There are two possibilities. The first one is trivial: miRNAs and targets are not expressed in the same tissue. If a gene is expressed uniquely in gut epithelium, the presence of a target for a muscle miRNA is irrelevant. A second class of pairs is real, meaning the miRNA and its target do interact in real life, but the effect is evolutionarily neutral. A gene may be tuned down a bit, or it may not, and the organism does not care. Note that these interactions are neutral in an evolutionary sense, no selective effect, but not in a biochemical sense, since the miRNAs do down-regulate (and experimental knock out of the miRNA would therefore result in an upward effect on target gene expression). The class of neutral but active miRNA-target interactions may turn out to be very large. While the first class (programmed interactions) will be conserved among species, the second class is not.
3. The third class of miRNA-target interactions are those where the miRNA is expressed in the same tissue as the mRNA, shutting off genes that need to be expressed. The avoidance data suggest that there is selective pressure against such co-expression, and they have been referred to as anti-targets. There is inevitably a steady state level of recently appeared target sites in anti-target genes, but these will be filtered out eventually by selective pressure.

Given these distinctions, there are several ways that mutation of miRNA-target interactions may cause disease. A miRNA may mutate and lose function; there is in many cases some level of redundancy, but this is at a gross level (visible in the laboratory), while loss of even one miRNA gene may have subtle negative disease-causing effects. Also a programmed miRNA target site may mutate, releasing the gene from miRNA-control. Finally a gene may acquire a novel and undesired miRNA target sequence: there are numerous sequences that are only one mutation away from becoming a target for one of the miRNAs expressed in the same tissue. Some of these mutations will result in undesired reduction of gene activity, and may cause disease. So the three possible causes of disease are: 1. mutation of a miRNA gene 2. mutation of a programmed miRNA target site 3. mutation that creates a new target-site in an anti-target gene.

On a more positive note: given complex combinatorial effects of regulation of genes by often more than one miRNA, each of which has a subtle effect on gene expression, polymorphisms in miRNA targets may be the ideal substrate for the type of small variations in development that natural selection can act upon in evolution. Protein coding changes may often either fully disrupt protein function altogether, which rarely contributes positively to fitness, they may leave the protein unaltered, or reduce the activity of the encoded protein. On the other hand miRNA target changes may sculpture expression patterns with great finesse. The many gradual differences that add up to make a mouse embryo out of a mouse zygote and a fish out of a fish zygote are certainly mostly differences in timing and levels of expression of factors that perform essentially identical biochemical actions, rather than differences in protein action. Therefore fine tuning of gene expression by gain or loss of miRNA target sequences may be expected to be a major mechanism in evolution and disease processes.

Where in the present invention the expression of a miRNA of FIG. 1 is measured in a method of the invention, or a collection of miRNA of FIG. 1 is provided or a complement thereof or a sequence which hybridizes under stringent conditions thereto, or the complement thereof, or a (micro-)array comprising a miRNA of FIG. 1 is provided, or of a complement thereof or a sequence which hybridizes under stringent conditions thereto, or the complement thereof, it is preferred that the expression, collection or array is measured of or comprises at least 5 miRNA of FIG. 1 or a complement thereof or a sequence which hybridizes under stringent conditions thereto, or the complement thereof. More preferably, the expression, collection or array is measured of or comprises at least 10 miRNA of FIG. 1 or a complement thereof or a sequence which hybridizes under stringent conditions thereto, or the complement thereof. More preferably, the expression, collection or array is measured of or comprises at least 20 miRNA of FIG. 1 or a complement thereof or a sequence which hybridizes under stringent conditions thereto, or the complement thereof. More preferably, the expression, collection or array is measured of or comprises at least 40 miRNA of FIG. 1 or a complement thereof or a sequence which hybridizes under stringent conditions thereto, or the complement thereof. More preferably, the expression, collection or array is measured of or comprises at least 60 miRNA of FIG. 1 or a complement thereof or a sequence which hybridizes under stringent conditions thereto, or the complement thereof. More preferably, the expression, collection or array is measured of or comprises at least 100 miRNA of FIG. 1 or a complement thereof or a sequence which hybridizes under stringent conditions thereto, or the complement thereof. More preferably, the expression, collection or array is measured of or comprises at least 200 miRNA of FIG. 1 or a complement thereof or a sequence which hybridizes under stringent conditions thereto, or the complement thereof. More preferably, the expression, collection or array is measured of or comprises at least 400 miRNA of FIG. 1 or a complement thereof or a sequence which hybridizes under stringent conditions thereto, or the complement thereof. More preferably, the expression, collection or array is measured of or comprises at least 600 miRNA of FIG. 1 or a complement thereof or a sequence which hybridizes under stringent conditions thereto, or the complement thereof.

Where in the present invention the expression of a hairpin RNA of FIG. 1 is measured in a method of the invention, or a collection of hairpin RNA of FIG. 1 is provided or a complement thereof or a sequence which hybridizes under stringent conditions thereto, or the complement thereof, or a (micro-) array comprising a hairpin RNA of FIG. 1 is provided, or a complement thereof or a sequence which hybridizes under stringent conditions thereto, or the complement thereof, it is preferred that the expression, collection or array is measured of or comprises at least 5 hairpin RNA of FIG. 1 or a complement thereof or a sequence which hybridizes under stringent conditions thereto, or the complement thereof. More preferably, the expression, collection or array is measured of or comprises at least 10 hairpin RNA of FIG. 1 or a complement thereof or a sequence which hybridizes under stringent conditions thereto, or the complement thereof. More preferably, the expression, collection or array is measured of or comprises at least 20 hairpin RNA of FIG. 1 or a complement thereof or a sequence which hybridizes under stringent conditions thereto, or the complement thereof. More preferably, the expression, collection or array is measured of or comprises at least 40 hairpin RNA of FIG. 1 or a complement thereof or a sequence which hybridizes under stringent conditions thereto, or the complement thereof. More preferably, the expression, collection or array is measured of or comprises at least 60 hairpin RNA of FIG. 1 or a complement thereof or a sequence which hybridizes under stringent conditions thereto, or the complement thereof. More preferably, the expression, collection or array is measured of or comprises at least 100 hairpin RNA of FIG. 1 or a complement thereof or a sequence which hybridizes under stringent conditions thereto, or the complement thereof. More preferably, the expression, collection or array is measured of or comprises at least 200 hairpin RNA of FIG. 1 or a complement thereof or a sequence which hybridizes under stringent conditions thereto, or the complement thereof. More preferably, the expression, collection or array is measured of or comprises at least 400 hairpin RNA of FIG. 1 or a complement thereof or a sequence which hybridizes under stringent conditions thereto, or the complement thereof. More preferably, the expression, collection or array is measured of or comprises at least 600 hairpin RNA of FIG. 1 or a complement thereof or a sequence which hybridizes under stringent conditions thereto, or the complement thereof. Expression is preferably measured through determining whether a cell comprises said miRNA or hairpin RNA. This is also used for characterizing a cell or a sample.

In a preferred embodiment expression or the presence of a human miRNA or hairpin RNA is measured or characterized in a cell or sample using a method of the invention. Thus in a preferred embodiment said collection and or (micro-)array comprises at least one, preferably at least 5, more preferably at least 10, more preferably at least 20, more preferably at least 40, more preferably at least 60, more preferably at least 100, more preferably at least 200, more preferably at least 200, more preferably at least 400, more preferably at least 600 human miRNA and/or human hairpin RNA of FIG. 1, or a complement thereof or a sequence which hybridizes under stringent conditions thereto, or the complement thereof.

In a preferred embodiment expression or the presence of a primate miRNA or hairpin RNA is measured or characterized in a cell or sample using a method of the invention. Thus in a preferred embodiment said collection and or (micro-)array comprises at least one, preferably at least 5, more preferably at least 10, more preferably at least 20, more preferably at least 40, more preferably at least 60, more preferably at least 100, more preferably at least 200, more preferably at least 200, more preferably at least 400, more preferably at least 600 primate miRNA and/or primate hairpin RNA of FIG. 1, or a complement thereof or a sequence which hybridizes under stringent conditions thereto, or the complement thereof. In a preferred embodiment said primate is a human. In another preferred embodiment said primate is a chimpanzee or a macaque.

Where in the present invention a nucleic acid molecule is provided comprising a nucleotide sequence as shown in FIG. 1, and/or a nucleotide sequence which is the complement thereof, and/or a nucleotide sequence which has an identity of at least 80% to said nucleotide sequence or complement thereof, and/or a nucleotide sequence which hybridizes under stringent conditions to such a nucleotide sequence it is preferred at least 5 different nucleic acid molecules comprising a nucleotide sequence as shown in FIG. 1, and/or a nucleotide sequence which is the complement thereof, and/or a nucleotide sequence which has an identity of at least 80% to said nucleotide sequence or complement thereof, and/or a nucleotide sequence which hybridizes under stringent conditions to such a nucleotide sequence, are provided. Preferably at least 10, more preferably at least 20, more preferably at least 40, more preferably at least 60, more preferably at least 100, more preferably at least 200 and more preferably at least 600 different nucleic acid molecules comprising a nucleotide sequence as shown in FIG. 1, and/or a nucleotide sequence which is the complement thereof, and/or a nucleotide sequence which has an identity of at least 80% to said nucleotide sequence or complement thereof, and/or a nucleotide sequence which hybridizes under stringent conditions to such a nucleotide sequence, are provided. In a preferred aspect of this embodiment, said sequence of FIG. 1 is a miRNA sequence, preferably a human miRNA sequence. In a further preferred aspect of this embodiment, said sequence of FIG. 1 is a hairpin RNA sequence, preferably a primate hairpin sequence, more preferably a human sequence. In another preferred embodiment said hairpin RNA sequence is a chimpanzee sequence or macaque sequence.

The invention further provides a collection of oligonucleotides or oligonucleotide analogues selected from the group consisting of set A, set B and set C, wherein;
   set A is a set of oligonucleotides or oligonucleotide analogues comprising complementary sequences to all of the sequences identified in FIG. 9,
   set B is a set of oligonucleotides or oligonucleotide analogues comprising complementary sequences to all of the sequences of set A and
   set C is the set of oligonucleotides identified in FIG. 9.

These collections are especially suited to determine the differentiation state of a cell. A sample comprising RNA of said cell can be scrutinized for the presence of the microRNAs identified in FIG. 9. These microRNAs are differentially expressed in primitive versus differentiated cells. Cells that have undergone one or more modification on the way to tumorigenesis, or tumour cells themselves are often dedifferentiated when compared to the cell type they originated from. The sets A, B or C are therefore very well suited to determine whether a sample of cells comprises dedifferentiated cells, preferably tumour cells. The miRNA referred to is often under expressed in the dedifferentiated tissue. In a preferred embodiment the invention provides a collection of oligonucleotides or oligonucleotide analogues selected from the group consisting of set A, set B and set C, wherein;
   set A is a set of oligonucleotides or oligonucleotide analogues comprising complementary sequences to at least the minimal sequence and/or seed sequence of all of the miRNA sequences identified in FIG. 9, set B is a set of oligonucleotides or oligonucleotide analogues comprising complementary sequences to at least the minimal sequence and/or seed sequence of all of the miRNA sequences of set A and set C is the set of oligonucleotides comprising at least the minimal sequence and/or seed sequence of the miRNAs identified in FIG. 9.

Set A is a set of oligonucleotides or oligonucleotide analogues comprising complementary sequences to all of the sequences identified in FIG. 9. The set A therefore preferably comprises the same number of oligonucleotides are oligonucleotide analogues as specified in FIG. 9. Similarly, set B is a set of oligonucleotides or oligonucleotide analogues comprising complementary sequences to at least the minimal sequence and/or seed sequence of all of the miRNA sequences of set A. Thus set B therefore preferably comprises the same number of oligonucleotides are oligonucleotide analogues as specified in FIG. 9. An oligonucleotide analogue is a nucleic acid analogue having a sequence that corresponds to the sequence of an oligonucleotide. A set of oligonucleotides of the invention preferably comprises oligonucleotides or nucleic acid analogues thereof, having or corresponding to a sequence length of a nucleic acid of the invention, preferably a miRNA of the invention. Thus an oligonucleotide is defined herein as a nucleic acid molecule according to the invention having a length of from 18 to 26 nucleotides, preferably of from 19-24 nucleotides, most preferably 20, 21, 22 or 23 nucleotides. Currently many different types of nucleic acid modifications and alternative structures are generated that mimic the sequence of a nucleic acid but are themselves sometime not referred to as nucleic acid. Non-limiting examples of such nucleic acid analogues are analogues containing one or more nucleotide analogues that mimic the base pairing characteristics of the nucleotide they replace. Nucleic acid molecules that include such nucleotide analogues are considered to be a nucleic acid analogue of a nucleic acid molecule of the invention if they contain the same hybridisation characteristics or base pairing characteristics in kind not necessarily in amount as said nucleic acid molecule of the invention. Other non-limiting examples of nucleic acid molecule analogues are locked nucleic acid (LNA), peptide nucleic acid (PNA) or morpholino. Yet other nor-limiting examples of nucleic acid molecule analogues of the invention are modifications of the sugar backbone that alter the stability of the molecule, such modifications typically do not alter the kind of base pairing characteristics. A non-limiting example of such a modification is the 2-O-methyl modification often used for oligonucleotides.

In a preferred, embodiment the invention provides a collection of oligonucleotides or nucleic acid analogues thereof selected from the group consisting of set A, set B and set C, wherein;

set A is a set of oligonucleotides or nucleic acid analogues thereof comprising complementary sequences to all of the sequences identified in FIG. 9, set B is a set of oligonucleotides or nucleic acid analogues thereof comprising complementary sequences to all of the sequences of set A and set C is the set of oligonucleotides identified in FIG. 9.

The invention further provides a collection of oligonucleotides or nucleic acid analogues thereof selected from the group consisting of sets D-R, wherein;

set D is the set of oligonucleotides identified in FIG. 4,
set E is the set of oligonucleotides identified in FIG. 5,
set F is the set of oligonucleotides identified in FIG. 6,
set G is the set of oligonucleotides identified in FIG. 7,
set H is the set of oligonucleotides identified in FIG. 8, set I is a set of oligonucleotides or nucleic acid analogues thereof comprising complementary sequences to all of the sequences identified in FIG. 4, set J is a set of oligonucleotides or nucleic acid analogues thereof comprising complementary sequences to all of the sequences identified in FIG. 5, set K is a set of oligonucleotides or nucleic acid analogues thereof comprising complementary sequences to all of the sequences identified in FIG. 6, set L is a set of oligonucleotides or nucleic acid analogues thereof comprising complementary sequences to all of the sequences identified in FIG. 7, set M is a set of oligonucleotides or nucleic acid analogues thereof comprising complementary sequences to all of the sequences identified in FIG. 8, and oligonucleotide sets N, O, P, Q and R or nucleic acid analogues thereof, that comprise complementary sequences to all of the sequences of respectively sets I, J, K, L and M. Set N thus corresponds to set I, set O to set J, set P to set K, set Q to set L and set R to set M.

The invention further provides a collection of oligonucleotides or nucleic acid analogues thereof selected from the group consisting of sets D-R, wherein;

set D is the set of oligonucleotides comprising at least the minimal sequence and/or seed sequence of the microRNAs identified in FIG. 4, set E is the set of oligonucleotides comprising at least the minimal sequence and/or seed sequence of the microRNAs identified in FIG. 5, set F is the set of oligonucleotides comprising at least the minimal sequence and/or seed sequence of the microRNAs identified in FIG. 6, set G is the set of oligonucleotides comprising at least the minimal sequence and/or seed sequence of the microRNAs identified in FIG. 7, set H is the set of oligonucleotides comprising at least the minimal sequence and/or seed sequence of the microRNAs identified in FIG. 8, set I is a set of oligonucleotides or nucleic acid analogues thereof comprising complementary sequences to at least the minimal sequence and/or seed sequence of all of the microRNAs identified in FIG. 4, set J is a set of oligonucleotides or nucleic acid analogues thereof comprising complementary sequences to at least the minimal sequence and/or seed sequence of all of the microRNAs identified in FIG. 5, set K is a set of oligonucleotides or nucleic acid analogues thereof comprising complementary sequences to at least the minimal sequence and/or seed sequence of all of the microRNAs identified in FIG. 6, set L is a set of oligonucleotides or nucleic acid analogues thereof comprising complementary sequences to at least the minimal sequence and/or seed sequence of all of the microRNAs identified in FIG. 7, set M is a set of oligonucleotides or nucleic acid analogues thereof comprising complementary sequences to at least the minimal sequence and/or seed sequence of all of the microRNAs identified in FIG. 8, and oligonucleotide sets N, O, P, Q and R or nucleic acid analogues thereof, that comprise complementary sequences to all of the sequences of respectively sets I, J, K, L and M. Set N thus corresponds to set I, set O to set J, set P to set K, set Q to set L and set R to set M.

BRIEF DESCRIPTION OF THE DRAWINGS

FIG. 1*a* contains an explanation of the format.

FIG. 2

Modified RAKE microarray results. Hybridization results for a single positive tissue (mouse 8.5 dpc embryo, 16.5 dpc embryo, brain or embryonic stem (ES) cells) doe all probes in a tiling path are shown for every novel miRNA. Hairpin sequences are shown where numbers indicate the most '3 end of the respective probe on the RARE microarray. The small images show the raw results for the respective probes. Annotation (cand*** probe %%) refers to the positive probe and matches experimental evidence annotation for the mature miRNAs in FIG. 1.

FIG. 3

Schematic representation of mature miRNA nad the corresponding hairpin RNA. The miRNA is depicted as a light box and the remainder of the hairpin as a dark (box/line). The scheme is not to scale.

FIG. 4

List of sequence ID numbers of the sequence listing for the most abundant or longest human mature sequence as determined by cloning.

FIG. 5

List of sequence ID numbers of the sequence listing for the most abundant or longest mouse mature sequence as determined by cloning.

FIG. 6

List of sequence ID numbers of the sequence listing from the human mature sequences from FIG. 2 for which the mouse orthologs have evidence for differential expression in RAKE experiments (mouse embryo 8.5 dpc, mouse embryo 16.5 dpc, mouse brain, mouse ES cells). Only mature sequences that were cloned in human are included here.

FIG. 7

Figure 1A:
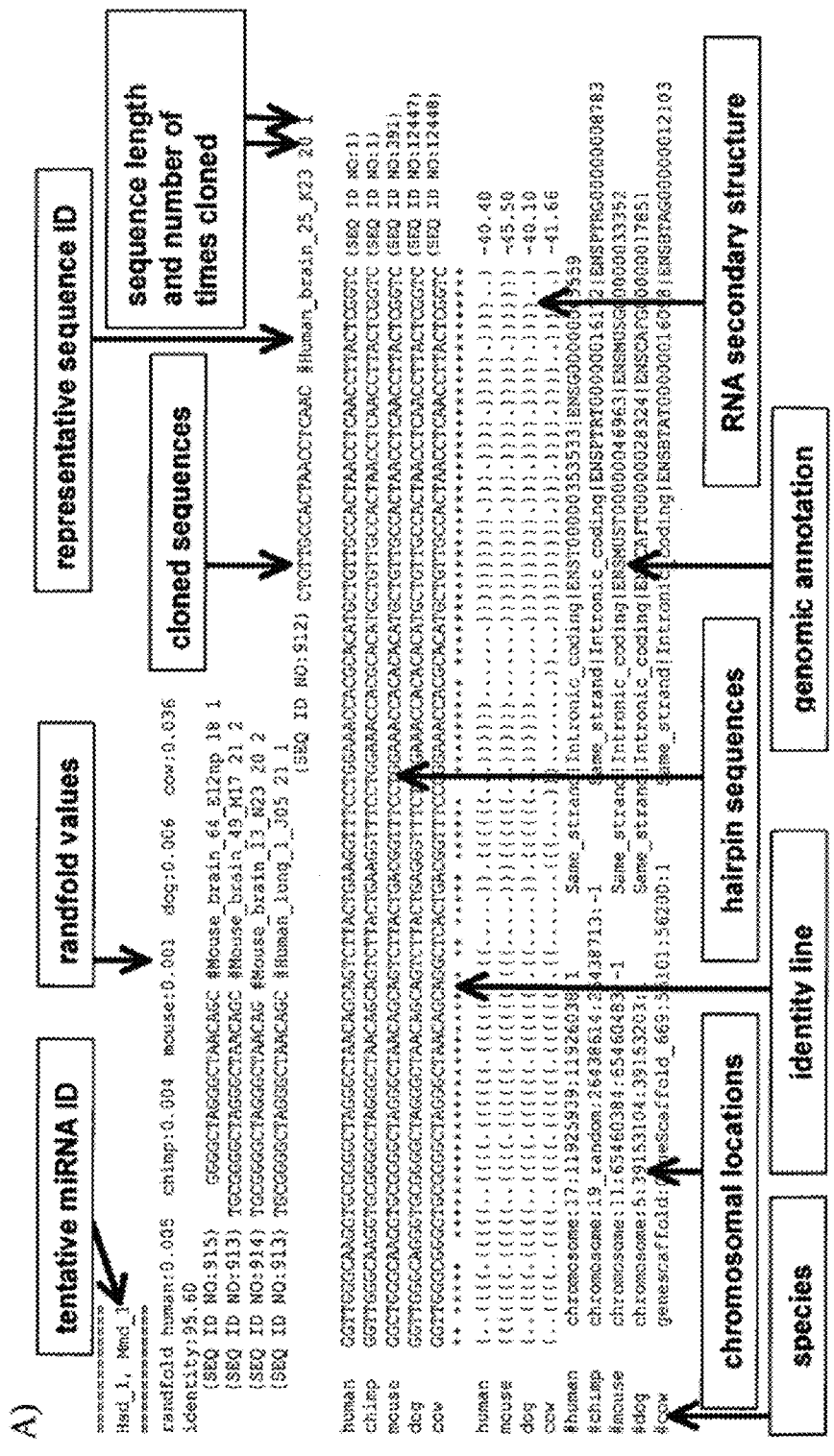
FIG. 1A, FIG. 1B and FIG. 1C are directed to Compilation of miRNA and hairpin RNA and expression thereof.
Figure 1B:
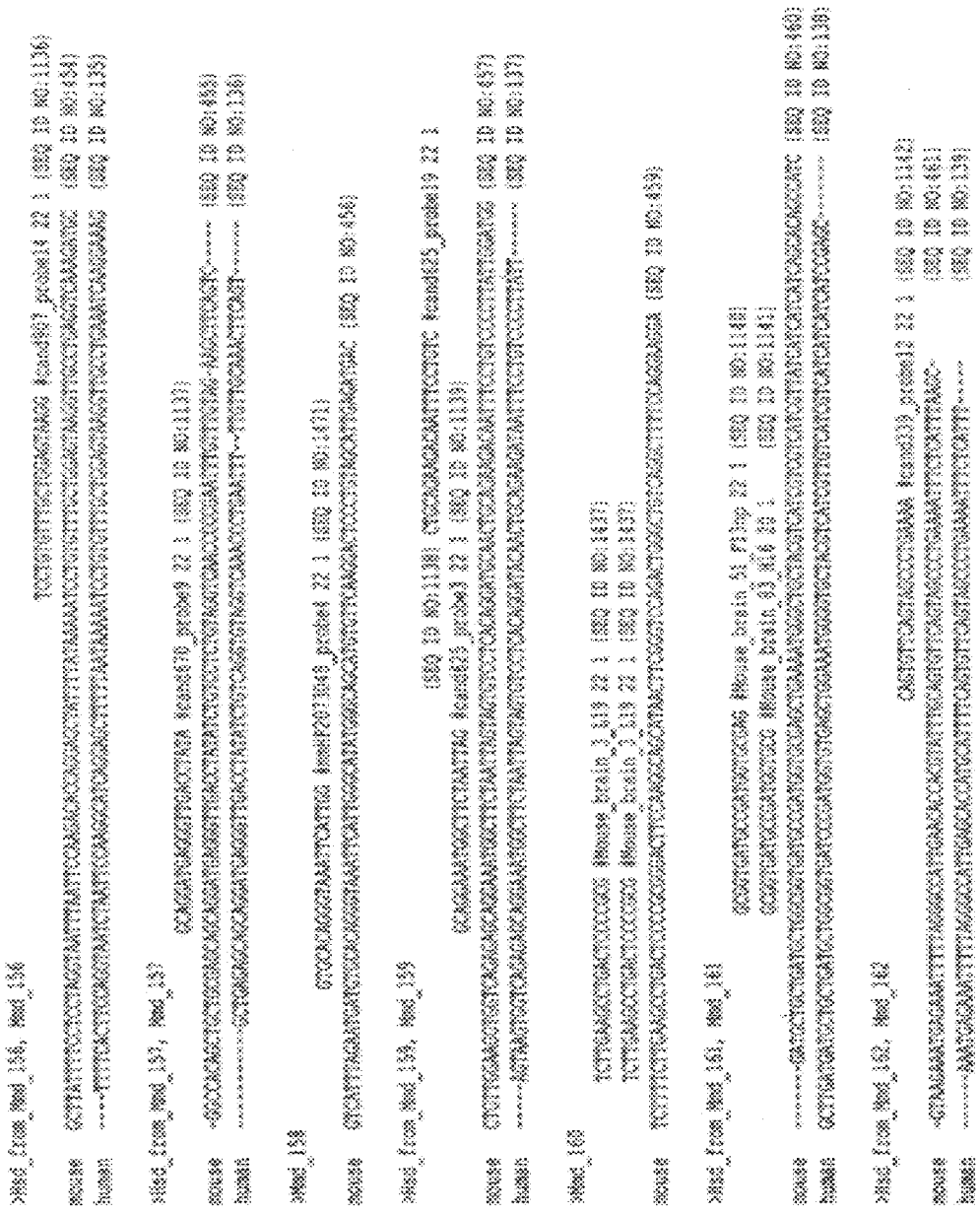
Figure 1C:
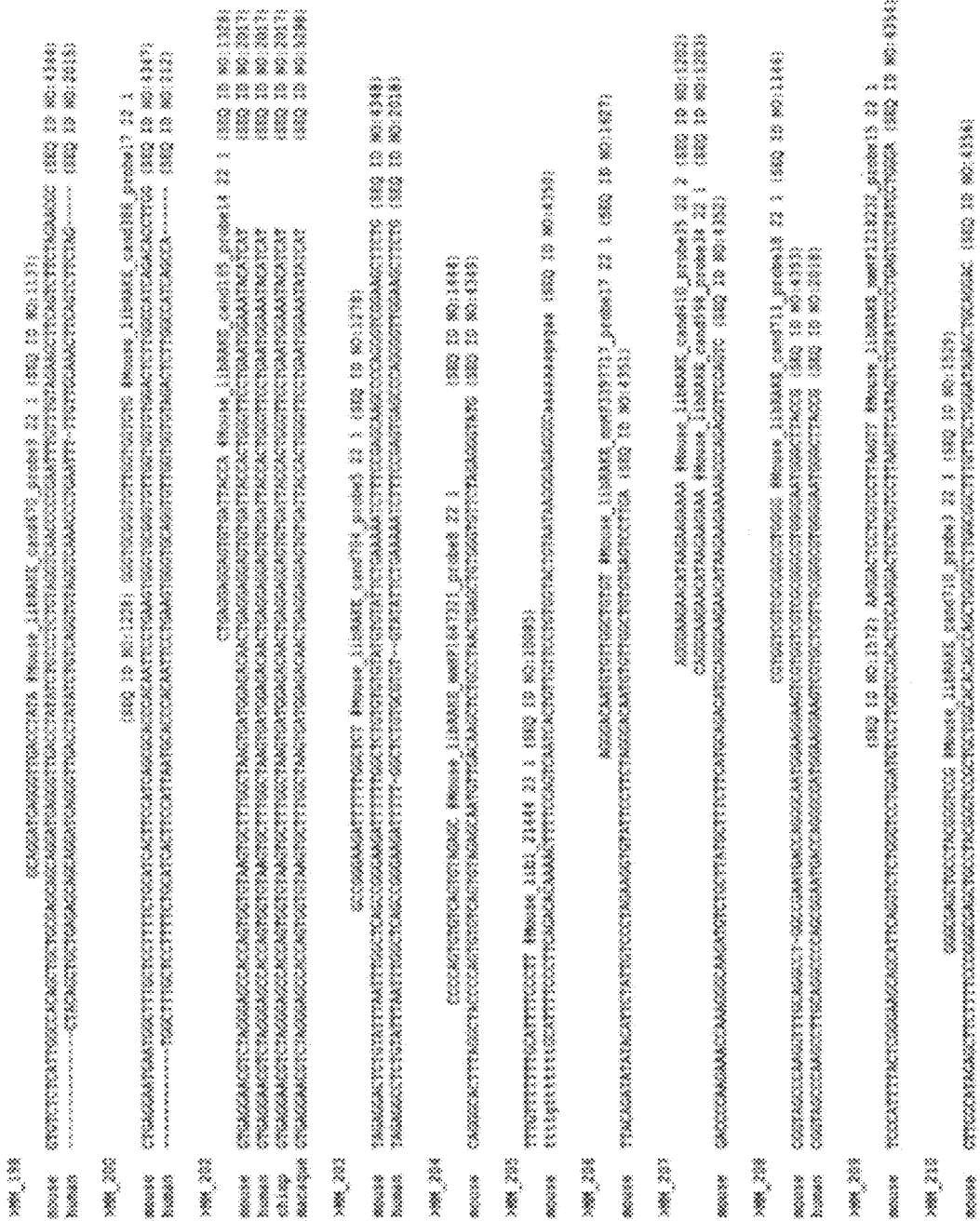
Figure 1C:
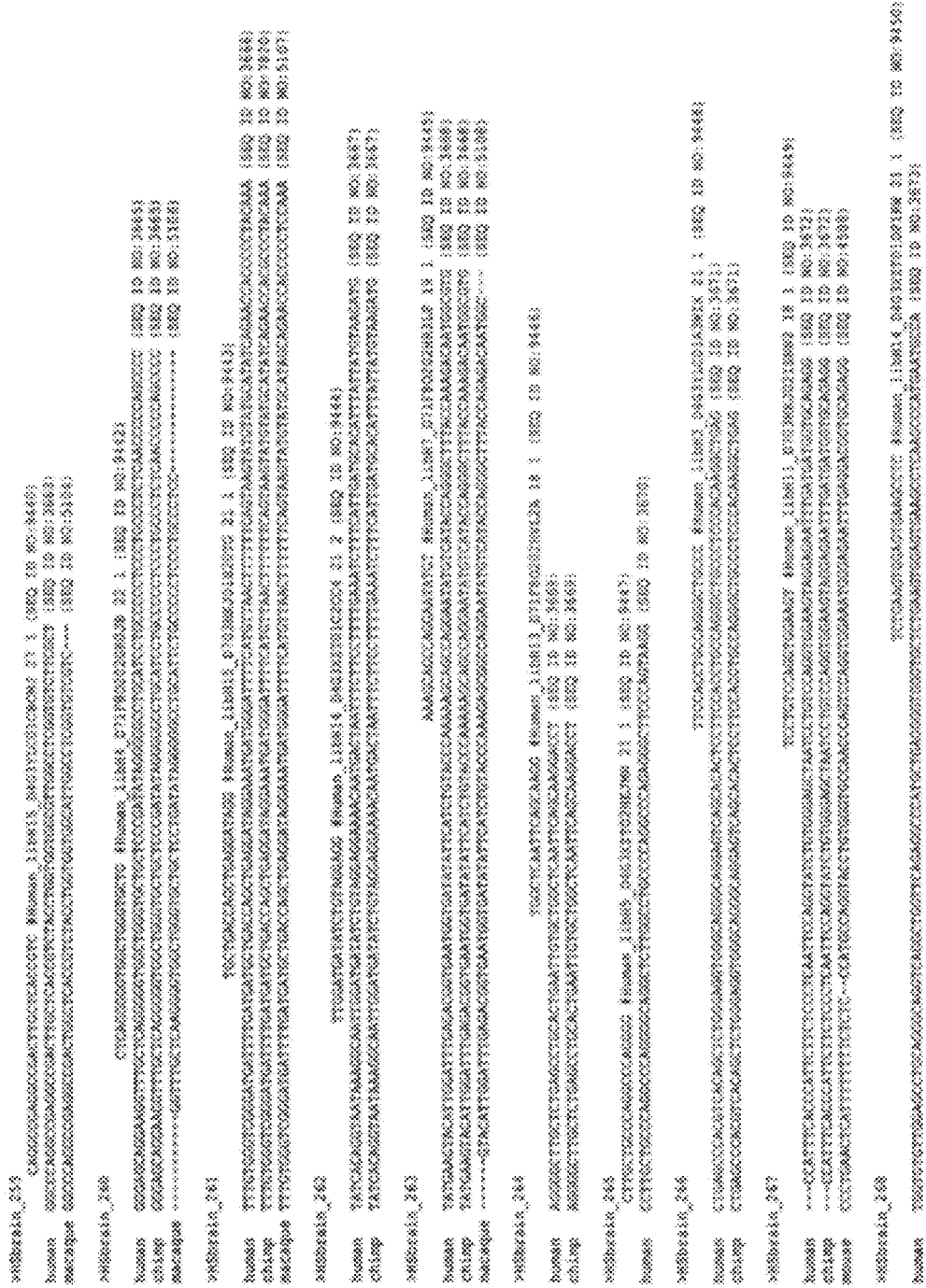
Figure 1C:
Figure 1C:
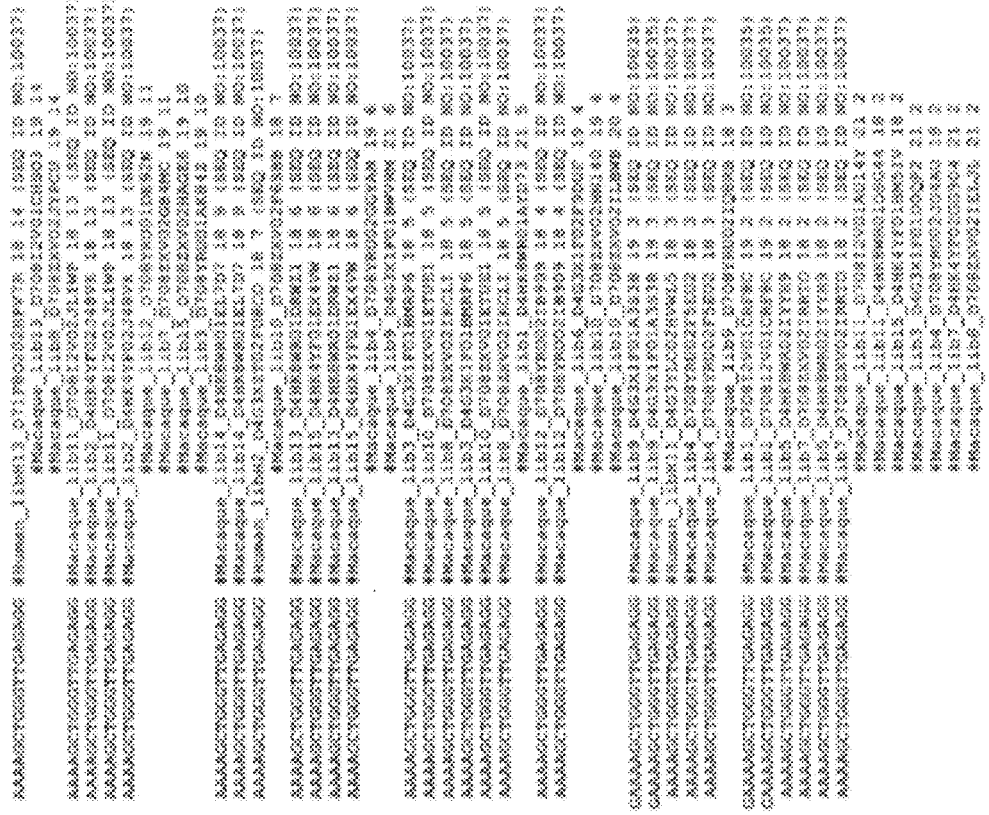
Figure 1C:
Figure 1C:
Figure 1C:
Figure 1C:
Figure 1C:
Figure 1C:
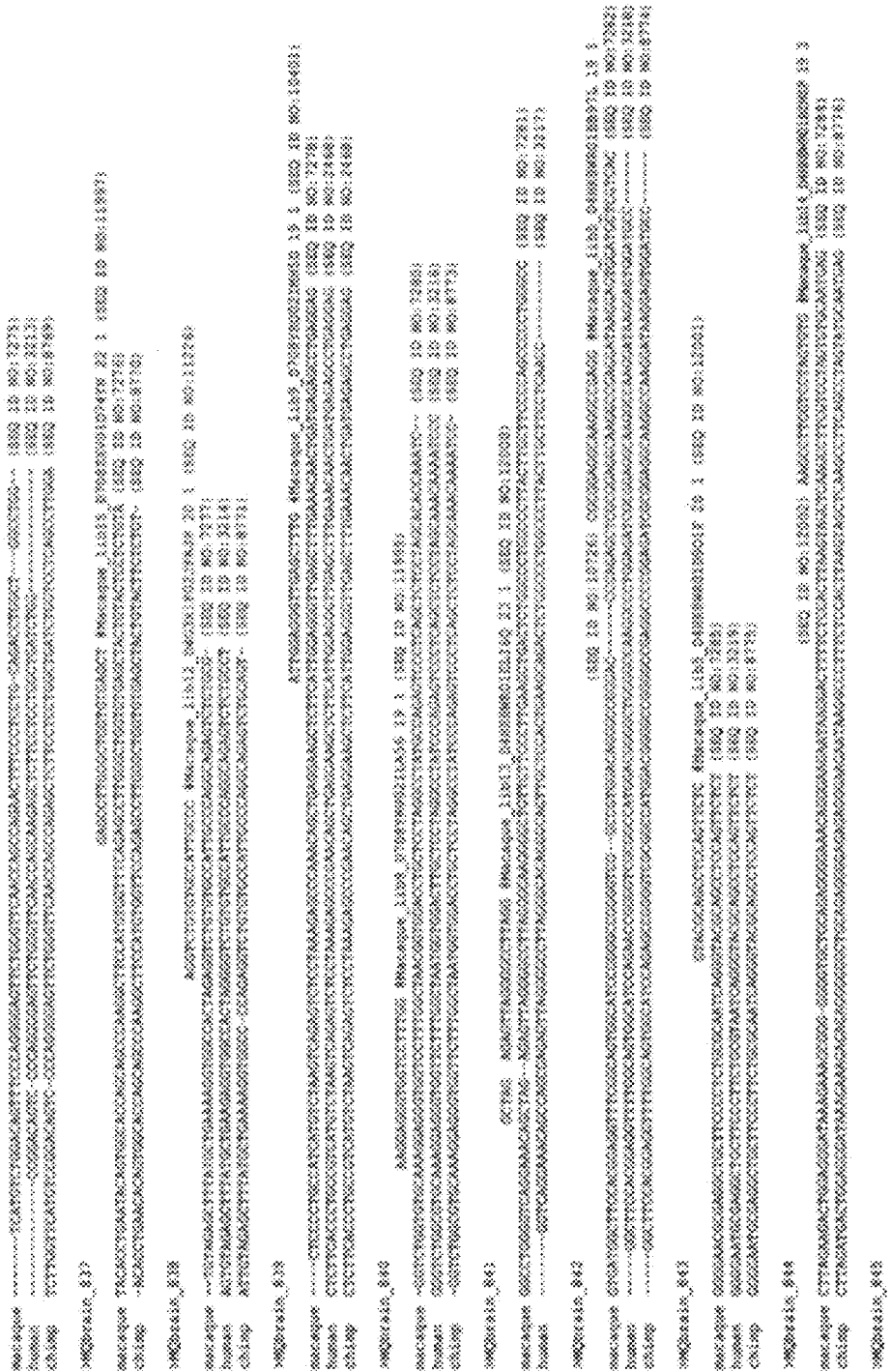
Figure 1C:
Figure 1C:
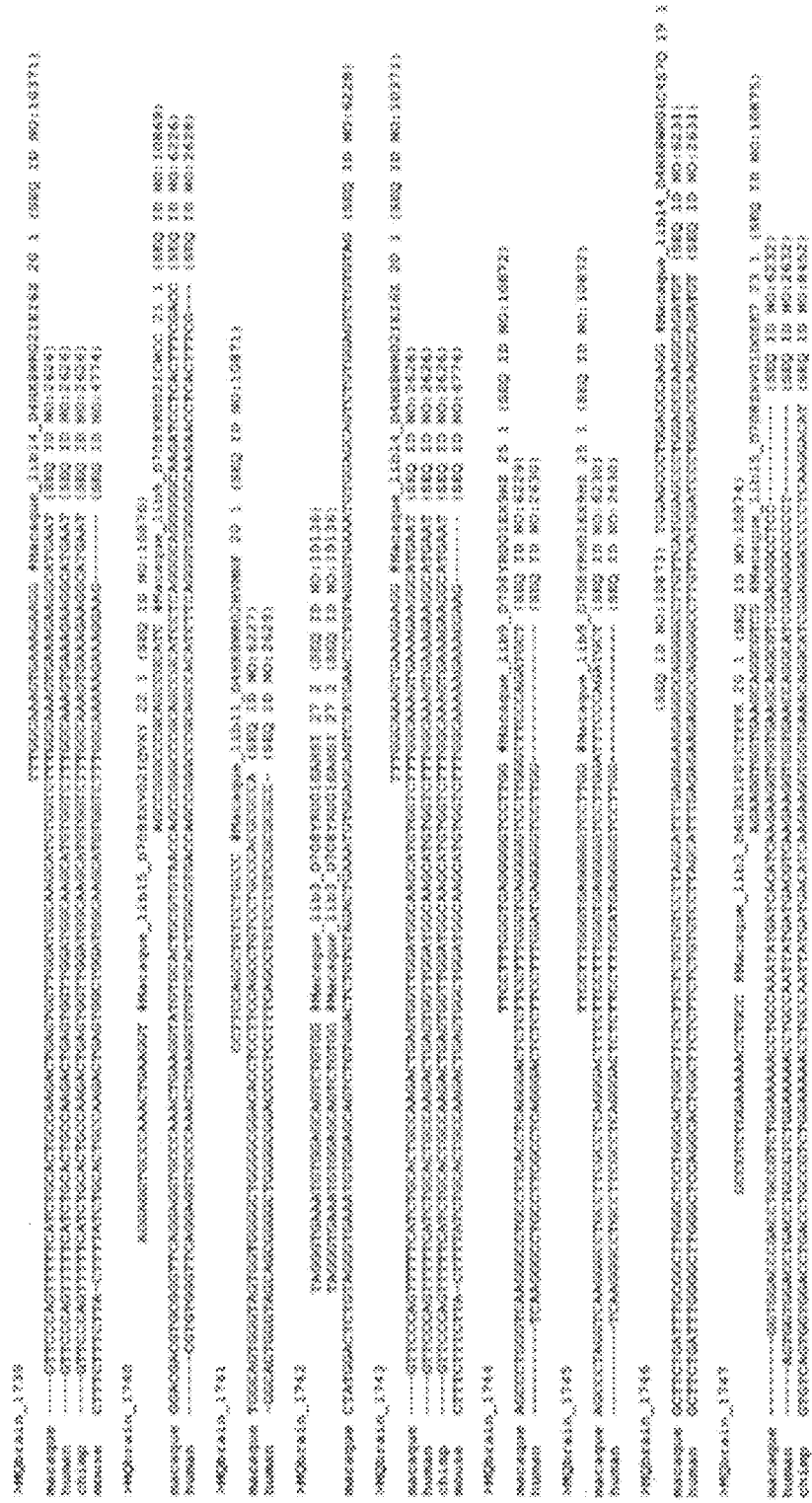
Figure 1C:
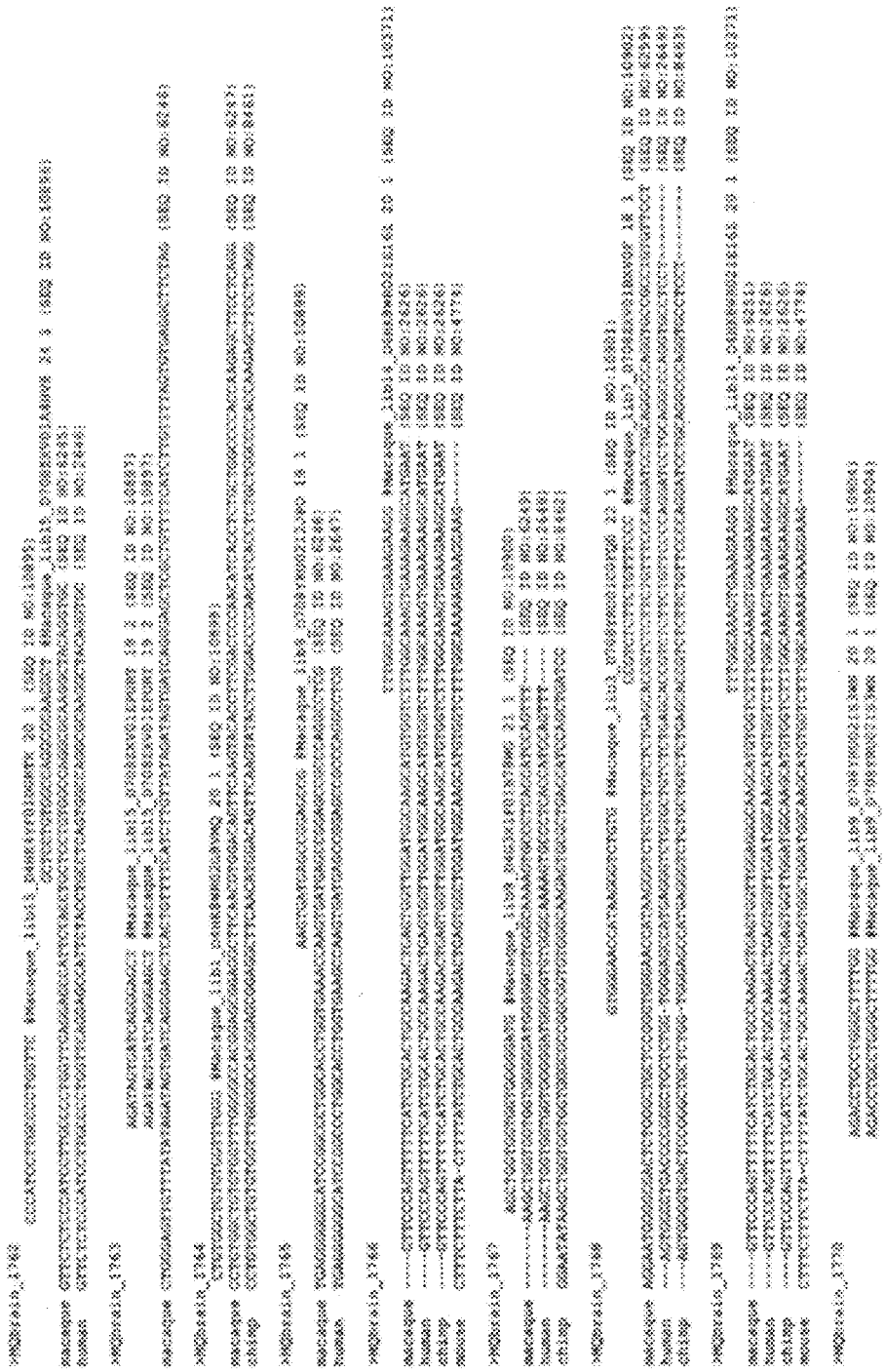
Figure 1C:
Figure 1C:
Figure 1C:
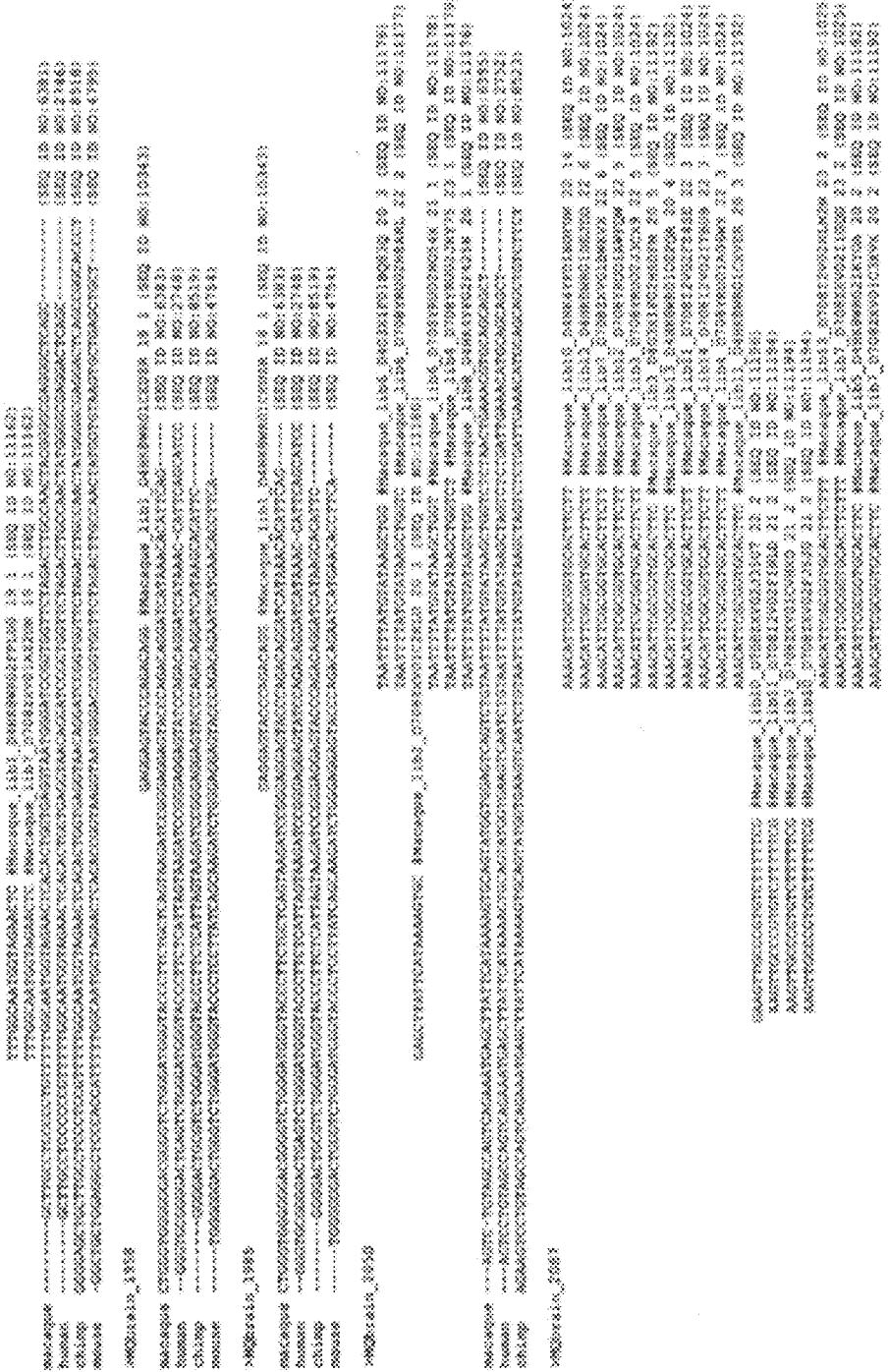
Figure 3:
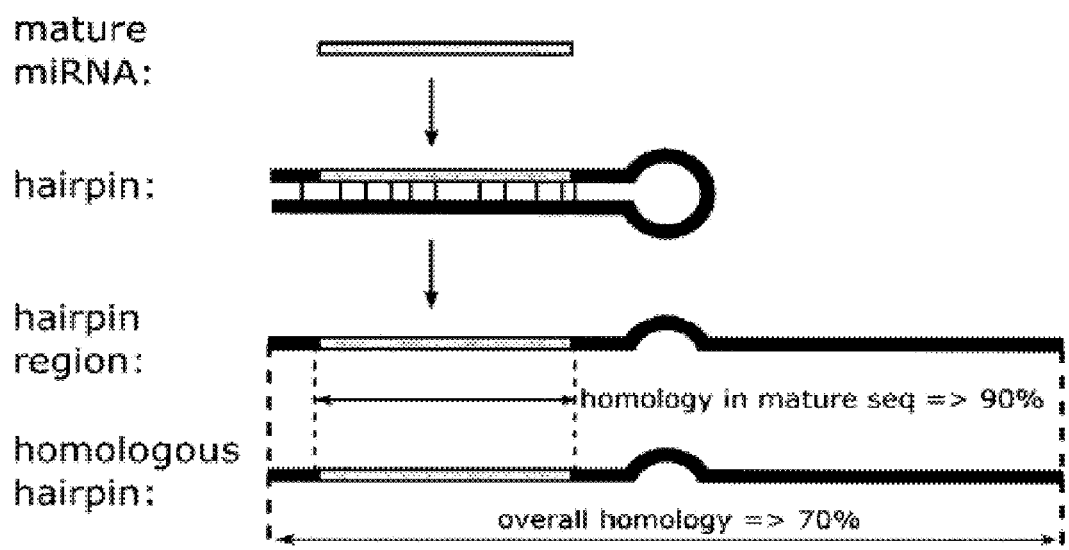
Figure 10:
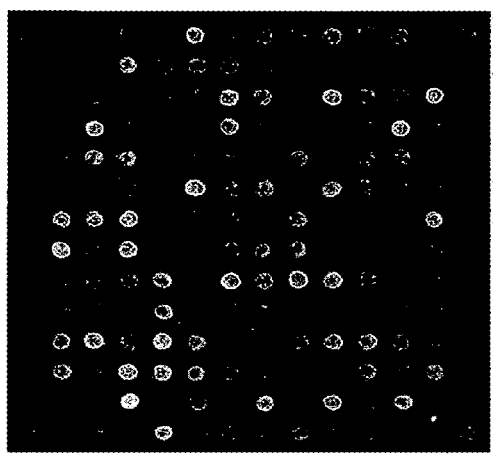

List of sequence ID numbers of the sequence listing the mouse mature sequences from FIG. 3 that have evidence for differential expression in RAKE experiments (mouse embryo 8.5 dpc, mouse embryo 16.5 dpc, mouse brain, mouse ES cells). Probe sequences that were not necessarily cloned in mouse are included.

FIG. 8

List of sequence ID numbers of the sequence listing human mature microRNA sequences that are differentially expressed (more than 2-fold up or down) in either glioblastoma versus normal brain tissue or adenoma versus normal lung tissue or in both (from FIGS. 11 and 12).

FIG. 9

List of sequence ID numbers of the sequence listing of human mature microRNA sequences that are differentially expressed (more than 2-fold up or down) in both glioblastoma versus normal brain tissue and adenoma versus normal lung tissue (from FIGS. 11 and 12).

FIG. 10

Dual color image of part of the raw microarray expression results for normal lung tissue (red) compared to adenoma tumor material (green). microRNAs that are upregulated or downregulated in tumor material show up as green and red, respectively. microRNAs that do not change expression are yellow and non-expressed microRNAs appear black.

FIG. 11

Differential expressed microRNAs between glioblastoma and normal control brain tissue.

FIG. 12

Differential expressed microRNAs between adenoma and normal control lung tissue.

EXAMPLES

Material and Methods
Sequencing and Analysis of miRNA Regions in Primates.

Nested primer sets for PCR amplification of ~700 bp regions for 144 known miRNA genes were designed using custom interface to primer3 software (http://primers.niob.knaw.nI). Primer selection was based solely on human sequences. Genomic DNAs of 10 primate species (NIA Aging Cell Repository DNA Panel PRP00001) were purchased from Coriell Cell Repositories (Camden, N.J.). All PCR reactions were carried out in a total volume of 10 μl with 0.5 Units Taq Polymerase (Invitrogen, Carlsbad Calif.) according to the manufacturer's conditions and universal cycling conditions (60 seconds 94° C., followed by 30 cycles of 94° C. for 20 seconds, 58° C. for 20 seconds and 72° C. for 60 seconds). PCR products were sequenced from both ends using an ABI3700 capillary sequencer (Applied Biosystems, Foster City Calif.). Sequences were quality trimmed and assembled using phred/phrap software (Ewing et al., 1998, Gordon et al., 1998) and aligned using POA (Lee et al., 2002).

Computational Prediction of miRNA Genes

All the analyses were performed using in-house developed software (Pen) when not stated otherwise. Whole-genome alignments (WGA) for human (July 2003 assembly), mouse (October 2003 assembly) and rat (June 2003 assembly) were downloaded from the UCSC Genome Bioinformatics site (http://genome.uscsc.edu). We first screened WGAs for blocks that fit miRNA-like conservation profile, i.e. have a conserved stem-loop region of ~100 nt and non-conserved flanks of ~50 nt. Technically, for every position we first calculated the percentage of conservation over a sliding window of 15 nt and assigned a value from 0 to 9 and 'o', where 'o' represents 100% identity, 9 between 90 and 100%, etcetera. Next, the resulting conservation string was searched by the following regular expression to define the conservation profile: /([0-8]{50,60})([o98]{53,260})([0-8]{50,60})/. At the next step we used RNAfold software (Hofacker, 2003) to evaluate the potential of conserved regions to form fold-back structures. The secondary structures matching the following regular expression were accepted: /((\((?:\.*\( ){24,})(\.{2,17}|\.*\({1,8}\.*\){1,8}\.*\({1,8}\.*\){1,8}\.*)(\)(?:\.*\) ){50,}))/x (detailed scripts are available from the authors upon request). This step resulted in 12,958 candidate regions from human/mouse alignments and 12,530 candidate regions from human/rat alignments, which included 167 and 154 known human miRNAs, respectively. The original human/mouse and human/rat WGAs contained 187 and 172 annotated human miRNAs (miRNA registry v.3.1), respectively. Thus, the combined sensitivity of conservation profiling and fold-back structure selection steps is almost 90%. We did not calculate directly the contribution of the first, conservation-profiling, step to the filtering of candidate miRNA regions. It was reported previously, however, that about 800,000 stem-loops could be identified in conserved human/mouse non-coding regions (Lim et al., 2003). Therefore, we can estimate that conservation profiling is a very efficient filter that removes more than 98% of all potential fold-back structures while retaining 90% of real miRNAs. In cases where overlapping candidate regions were predicted on different DNA strands, the candidate with lower free folding energy was selected. This 'naïve' approach correctly identified the orientation of 144 known miRNAs out of 165 tested (87%).

As the third filtering step we used a recently discovered property of miRNAs to have lower folding free energies than random sequences with the same nucleotide content (Bonnet et al., 2004). Application of the Randfold program (filtering for regions with p<=0.005) further reduced the number of candidates 18-fold, to 716 for human/mouse and 639 for human/rat datasets. The sensitivity of this filtering step, when using p<=0.005 cutoff for randfold value, is about 85% (143 of 167 known miRNAs retained in human/mouse—, and 134 of 154—in human/rat dataset). The cutoff value of 0.005 is very stringent but provides an optimal sensitivity/specificity ratio for filtering.

Next, we intersected human/mouse and human/rat predictions using human genomic coordinates and orientation. It appeared that only 379 candidate regions that included 119 known miRNAs, were predicted in both datasets, and a substantial fraction of the predictions was set-specific, i.e. 337 candidates that include 24 known miRNAs, were found in human/mouse but not in human/rat WGA, whereas 260 candidates (including 15 known miRNAs) were found in human/rat but not human/mouse datasets. The detailed analysis of non-overlapping predictions revealed that about two thirds of them actually could be mapped to the corresponding genomic regions in the second rodent species (mouse predictions to the rat genome and vice versa) but failed to satisfy either conservation profiling or randfold criteria (for rodent sequences) or were simply not present in the initial WGA and hence were not picked up by our computational pipeline in a particular dataset. This analysis illustrates the value of combining data from two rodent species rather than concentrating on one, e.g. human/mouse, dataset.

In total, we have identified 976 candidate miRNA regions that satisfy the following criteria: (1) have characteristic miRNA-like conservation profiles in human/mouse or human/rat alignments; (2) form fold-back structures, and (3) have randfold value p<=0.005 for both human and rodent sequences. These 976 candidate regions included 158 known miRNAs (based on data from miRNA registry v.3.1). The initial whole-genome human/murine alignments, then combined, covered 189 known miRNAs. Therefore, the sensitivity of our analysis, based on this dataset, is 83% (158/189). At the same time, the specificity of the predictions ideally should be inferred from experimental verifications of all predictions. It is possible, however, to use conservation of candidate regions in additional genomes as an indirect measure of robustness of predictions. We have used zebrafish, chicken, opossum, cow and dog genomes to search for orthologs of our predicted candidates. Since opossum and cow genomes were not assembled at the time of analysis, we utilized Genotrace software (Berezikov et al., 2002) to make partial assemblies of regions of interest from trace data. The region from a genome was considered as orthologous to the candidate region if it (1) had at least 16 identical matches to the candidate sequence in at least 18 bp long hit, (2) was folded into a hairpin and (3) passed the randfold free energy criterion. It appeared that 678 out of 976 candidates (~70%) are conserved in at least one more species besides rodents.

To produce additional candidate microRNA genes, the mouse genome was scanned for potential hairpins with a sliding window of 100 nt, and randfold values were calculated for resulting hairpins (mononucleotide shuffling, 1000 iterations). From a large set of hairpins that have low randfold values but are not necessarily conserved in other species, a subset of 199 was randomly selected.

Characterization of Candidate miRNA Regions

To put the predicted miRNA candidates into genomic context, we used the Ensembl (version 24) annotation of the human genome. We have searched our candidates against the ncRNA subset of the FANTOM database (Okazaki et al., 2002) and found that 3 regions (cand428, cand523 and cand420) overlap with or reside next to non-coding RNAs.

Data for Affymetrix high-resolution tiling arrays (Kapranov et al., 2002) were downloaded from the UCSC Genome web site (http://hgdownload.cse.ucsc.edu/goldenPath/10april2003/database/affyTranscription.txt.gz and affyTransfrags.txt.gz), remapped to the July 2003 human genome assembly and intersected with candidate region predictions. Candidate regions that overlapped or resided within 50 bp from an annotated Transfrag region were associated with a given Transfrag fragment.

Northern Blot Analysis of Predicted miRNA Regions

We performed Northern blot analysis of 69 candidates representing different subgroups of candidates, such as broadly (zebrafish) or narrowly (rodents only) conserved, clustered or in families, located in introns, exons or intergenic. We limited our analysis to testing the expression of miRNAs in 3 mouse embryonic stages (8.5, 12.5 and 16.5 dpc), mouse ES cells, and mouse brain. Since we cannot predict the exact position of the mature miRNA in a stem, we used 35 nt-long probes that cover most of the hairpin arm. The arm containing a mature miRNA sequence was predicted on the basis of conservation level. For some candidate regions both arms of the hairpin were tested. For the candidates conserved in zebrafish, we also performed Northern blot analysis on RNA from zebrafish embryos (7, 14, 21 and 28 days) and a Dicer mutant (Wienholds et al., 2003).

RNA was isolated using mirVana miRNA isolation kit (Arabion, Austin Tex.), separated on 12% denaturing polyacrylamide gels alongside RNA Decadeä marker (Ambion, Austin Tex.), transferred by electroblotting to positively charged nylone membranes (Roche, Basel). Blots were hybridized overnight at 37° C. with radioactively (32P) labeled DNA oligo probes in modified Church and Gilbert buffer, washed three times with 2×SSC, 0.1% SDS at 37° C., and visualized using phosphoimaging (Typhoon, Amersham, UK). In some cases (cand181 and cand707), mature bands were detected only after a weeklong exposure of a blot, indicating the sensitivity limits of Northern blot analysis.

RAKE Microarray Design and Analysis

The microarray for verification of candidate microRNAs using the RAKE assay was designed as a 44K custom microarray (Agilent Technologies, Palo Alto Calif, USA). 60-mer probes that are attached to the glass surface with their 3'-end were designed to include a fully matching probe sequence of 25 nucleotides complementary to the predicted microRNA with universal spacers on each side 5'-spacer: CGATCTTT (SEQ ID NO:12413), sequence of 21 nt complementary to the microRNA candidate region (tiling path), 3'-spacer: TAGGGTCCGATAAGGGTCAGT-GCTCGCTCTA (SEQ ID NO:12414), 3'-end attached to glass surface). The three T40 s in the 5'-spacer function as a template for Klenow-mediated microRNA extension using biotin-dATP. A tiling path of 11 nucleotides was designed to cover the most likely Dicer/Drosha cleavage site determined at 22 nt upstream and downstream from the terminal loop extended to contain at least 11 unpaired nucleotides. For all cases, probes were designed for both arms of the hairpin sequence and for 648 candidates an additional set of 2.times.11 probes was designed as the transcript originating from the antisense genomic sequence can also efficiently fold into a stable hairpin structure. All 22/44 probes for a candidate microRNA were located in clusters on the array to exclude regional background effects. 10 different hybridization controls complementary to plant microRNAs (miR-402, UUCGAGGCCUAUUAAACCUCUG (SEQ ID NO:12415); miR-418, UAAUGUGAUGAUGAACUGACCU (SEQ ID NO:12416); miR-167, UGAAGCUGCCAGCAUGAT-CUGG (SEQ ID NO:12417); miR-416, GGUUCGUACGUACACUGUUCAU (SEQ ID NO:12418); miR-173, UUCGCUUGCAGAGAGAAAUCAC (SEQ ID NO:12419); miR-417, GAAGGUAGUGAAUUUGUUC-GAC (SEQ ID NO:12420); miR-163, GAAGAGGACUUG-GAACUUCGAU (SEQ ID NO:12421); miR-419, UUAUGAAUGCUGAGGAUGUUGU (SEQ ID NO:12422); miR-405, GAGUUGGGUCUAAC-CCAUAACU (SEQ ID NO:12423); miR-420, UAAAC-UAAUCACGGAAAUGCAC (SEQ ID NO:12424)) were represented 10 times randomly distributed on the array. Microarrays were scanned on an Agilent scanner model G2565B at 10 μm resolution and spot identification and intensity determination was done using Agilent Feature Extraction software (Image Analysis version A.7.5.1) with standard settings. To permit manual inspection and annotation of mature microRNA sequences, the raw images and spot intensity data were processed using custom scripts and visualized together with tiling path sequence information. Web-based interfaces were designed for annotation of single experiments and for summarizing all experiments. After manual inspection, all novel mature microRNA sequences that were positive were fed into the bioinformatic analysis pipeline set up for the evaluation of the cloned small RNAs, to filter out signal originating from repetitive elements and structural RNAs and to find homologous miRNAs in other species.

Modified RAKE Assay

The original RAKE assay (Nelson et al., 2004) was modified for use with high-density custom-printed microarrays in the Agilent platform. Most importantly, in contrast to most custom-spotted micro-arrays, custom-printed probes are attached with their 3'-end to the glass surface. This excludes the need for the exonuclease that was included in the original protocol to reduce background signal from fold-backs of the free 3-ends of the probes that result in double-stranded DNA structures that can function as a template for the Klenow extension, resulting in aspecific background signal. Furthermore, hybridization, washing, and incubation conditions were adapted. All hybridization and wash buffers were made fresh from autoclaved stock solutions using DEPC-treated water, filter-sterilized and pre-heated. Microarray slides and coverslips were pre-washed two times for 2 minutes at 37° C. with preheated wash buffer (2×SSPE, 0.025% N-lauroylsarcosine), followed by 5 minute incubation with pre-hybridization buffer (5×SSPE, 40% formamide, 0.025% N-lauroylsarcosine). Next, the Agilent hybridization chamber was completely filled with hybridization mix, leaving no air-bubbles, as the usual air-bubble for mixing does not move around at low temperature and with the hybridization mix used. The hybridization mix (750 μl total per slide) consists of 500 μl 1.5× hybridization buffer (7.5×SSPE, 60% formamide, 0.0375% N-lauroylsarcosine), 10 μl spike-in RNA (control plant microRNAs stock: miR-402, $1 \times 10^{-6}$ M; miR-418, $3.3 \times 10^{-7}$ M; miR-167, $1 \times 10^{-7}$ M; miR-416, $3.3 \times 10^{-8}$ M; miR-173, $1 \times 10^{-8}$ M; miR-417, $3.3 \times 10^{-9}$ M; miR-163, $1 \times 10^{-9}$ M; miR-419, $3.3 \times 10^{-10}$ M; miR-405, $1 \times 10^{-10}$ M; miR-420, $3.3 \times 10^{-11}$ M), and 20 μg small RNA sample (8.5 dpc and 16.5 dpc mouse embryo, mouse embryonic stem (ES) cells and total brain), isolated using the MirVana microRNA isolation kit (Ambion, Austin Tex., USA) and supplemented with DEPC-treated water up to 240 μl. The hybridization mix was heated to 75° C. for 5 minutes and cooled on ice before application to the array. The array was incubated overnight at 37° C., followed by 4 washes of 2 minutes in wash buffer and 1 wash for 2 minutes in 1× Klenow buffer (10 mM Tris pH7.9, 50 mM NaCl, 10 mM $MgCl_2$, 1 mM DTT, 0.025% N-lauroylsarcosine). For the Klenow extension, an enzyme mix (750 μl total per slide) containing 375 μl 2× Klenow buffer, 365 μl DEPC-treated water, 2.5 μl Klenow Exo- (50,000 U/μl, NEB, Ipswich Mass., USA), and 7.5 μl biotin-14-dATP (4 μM stock, Perkin Elmer, Wellesley Mass., USA) was applied to the array in a clean incubation chamber and incubated for 1 hour at 37° C. Next, the array was washed four times for 2 minutes with wash buffer and once for 2 minutes with 1× Klenow buffer. Next, the dye conjugation mix (total volume 750 μl) consisting of 375 μl 2× Klenow buffer, 368 μl DEPC-treated water and 20 μl streptavidin-conjugated Alexa fluor-647 (2 mg/ml stock, Invitrogen, Carlsbad Calif., USA) was applied in a new incubation chamber for 30 minutes at 37° C., followed by four washes of 2 minutes at 37° C. with wash buffer and 5 brief dips in DEPC water to remove salts. Slides were dried by centrifugation in a 50 ml tube by spinning for 5 minutes at 1000 rpm (180×g).

Small RNA Library Construction by Bacterial Cloning and Dideoxy Sequencing of Inserts.

Seven high-titer small RNA libraries were made. Briefly, the small RNA fraction from adult mouse brain (12 weeks) and various human fetal tissues (17 weeks of development: brain; heart; skin; lung; mix 1: multiple fetal tissues; mix 2: liver, stomach, bowel) was isolated using the mirVana microRNA isolation kit (Ambion), followed by an additional enrichment by excision of the 15 to 30 nt fraction from a polyacrylamide gel. For cDNA synthesis the RNA molecules in this fraction were first poly A-tailed using yeast poly(A) polymerase followed by ligation of a RNA linker oligo to the 5' phosphate of the miRNAs. First strand cDNA synthesis was then performed using an oligo(dT)-linker primer and M-MLV-RNase H-reverse transcriptase. The resulting cDNA was then PCR amplified for 15 to 22 cycles (depending on the start material quality and quantity), followed by restriction nuclease treatment, gel purification of the 95-110 by fraction, and cloning in the EcoRI and BamHI sites of the pBSII SK+plasmid vector. Ligations were electroporated into T1 Phage resistant TransforMaxTMEC100™ electrocompetent cells (Epicentre), resulting in titers between 1.2 and $3.3 \times 10^6$ recombinant clones per library. A total of 83,328 colonies were automatically picked into 384-well plates (Genetix QPix2,New Milton Hampshire, UK) containing 75 μl LB-Amp and grown overnight at 37° C. with continuous shaking. All following pipetting steps were performed using liquid handling robots (Tecan (Mannedorf, Switzerland) Genesis RSP200 with integrated TeMo96 and Velocity11(Menlo Park Calif, USA) Vprep with BenchCell 4× 5 μl of culture was transferred to a 384-well PCR plate (Greiner, Mannheim, Germany) containing 20 μl water, and cells were lysed by heating for 15 minutes at 95 ° C. in a PCR machine. 1 μl of lysed suspension was transferred to a fresh 384-wells plate containing 4μl PCR mix (final concentrations: 0.2 μM M13 forward, TGTAAAACGACGGCCAGT (SEQ ID NO:12425); 0.2 μM M 13reverse, AGGAAACAGCTAT-GACCAT (SEQ ID NO:12426), 400 μM of each dNTP, 25 mM tricine, 7.0% glycerol (w/v), 1.6% DMSO (w/v), 2 mM $MgCl2$, 85 mM ammonium acetate pH 8.7 and 0.2 U Taq Polymerase in a total volume of 10 μl) and the insert was amplified by 35 cycles of 20" 94° C., 10" 58° C., 30" 72° C. After adding 30 μl water, 1 μl of PCR product was directly used for dideoxy sequencing by transferring to a new 384-well PCR plate containing 4 μl sequencing mix (0.027 μl BigDye terminator mix v3.1 (Applied Biosystems, Foster City, Calif, USA), 1.96μl 2.5x dilution buffer (Applied Biosystems), 0.01 μl sequencing oligo (100 μM stock T7, GTAATACGACTCACTATAGGGC (SEQ ID NO:12427)), and 2 μl water). Thermocycling was performed for 35 cycles of 10" 94° C., 10" 50° C., 20" 60° C. and final products were purified by ethanol precipitation in 384-well plates as recommended by the manufacturer (Applied Biosystems) and analyzed on ABI3730XL sequencers with a modified protocol for generating approximately 100 nt sequencing reads.

Library Construction for Massively Parallel Sequencing

High-titer small RNA libraries were made by Vertis Biotechnology AG (Freising-Weihenstephan, Germany) from human male fetal brain and juvenile male chimpanzee brain (7 years). For human fetal tissue, individual permission using standard informed consent procedures and prior approval of the ethics committee of the University Medical Center Utrecht were obtained. Chimpanzee material was obtained from a cryopreserved resource (BPRC). Briefly, the small RNA fraction from adult chimpanzee brain sections (temporal, frontal, and oxcipital lobes and brain stem) and from human fetal brain (mixed composition) was isolated using the mirVana microRNA isolation kit (Ambion), followed by an additional enrichment by excision of the 15 to 30 nt fraction from a polyacrylamide gel. For cDNA synthesis the RNA molecules in this fraction were first poly A-tailed using poly(A)polymerase followed by ligation of synthetic RNA adapter to the 5' phosphate of the miRNAs. First strand cDNA synthesis was then performed using an oligo(dT)-linker primer and M-MLV-RNase H-reverse transcriptase. cDNA was FOR-amplified with adapter-specific primers and used in single-molecule sequencing. Massively parallel sequencing was performed by 454 Life Sciences (Branford, USA) using the Genome Sequencer 20 system.

Computational Analysis of Cloned Small RNAs Sequencing Reads

Base calling and quality trimming of sequence chromatograms was done by phred software (Ewing et al., 1998). After masking of vector and adapter sequences, and removing redundancy, inserts of length 18 bases and longer were mapped to genomes (ncbi35 assembly for human and ncbim34 assembly for mouse) using megablast software (found at the ftp site at ncbi.nlm.nih.gov/blast). Not all inserts matched perfectly to a genome, and detailed analysis of non-matching sequences indicated that many of them represent known microRNAs with several additional nucleotides added to one of the ends. These non-genomic sequences may be artifacts of the cloning procedure or a result of non-templated modification of mature microRNAs (Aravin et al., 2005). Such sequences were corrected according to the best blast hit to a genome. Next, for every genomic locus matching to an insert, repeat annotations were retrieved from the Ensembl database (At Worldwide web URL ensembl.org) and repetitive regions were discarded from further analysis, with the exception of the following repeats: MIR, MER, L2, MARNA, MON, Arthur and trf, since these repeat annotations overlap with some known microRNAs. Genomic regions containing inserts with 100 nt flanks were retrieved from Ensembl and a sliding window of 100 nt was used to calculate RNA secondary structures by RNAfold (Hofacker, 2003). Only regions that folded into hairpins and contained an insert in one of the hairpin arms, we used in further analysis. Since every non-redundant insert produced independent hits at this stage, hairpins with overlapping genomic coordinates were merged into one region, tracing locations of matching inserts. In cases when several inserts overlapped, the complete region covered by overlapping inserts was used in downstream calculations as a mature sequence. Next, gene and repeat annotations for hairpin genomic regions were retrieved from Ensembl, and repetitive regions (with above mentioned exceptions) as well as ribosomal RNAs, tRNAs and snoRNAs were discarded. To find homologous hairpins in other genomes, mature regions were blasted against human, mouse, rat, dog, cow, opossum, chicken, zebrafish and fugu genomes. Hits with length of at least 20 nt and identity of at least 70% were extracted from genomes along with flanking sequences of length similar to that observed in original hairpins to which a certain mature query sequence belonged. Extracted sequences were checked for hairpin structures using RNAfold, and positive hairpins were aligned with the original hairpin using clustalw (Thompson et al., 1994). Only homologs with at least 70% overall identity and 90% identity within mature sequence were considered. In cases were several homologous hairpins in a species were identified, the best clustalw-scoring hairpin was retained. Next, homologs from different organisms were aligned with the original hairpin by clustalw to produce a final multiple alignment of the hairpin region. Chromosomal location of homologous sequences were used to retrieve gene and repeat annotations from respective species Ensembl databases. Hairpins that contained repeat/RNA annotations in one of the species, as well as hairpins containing mature regions longer that 25 nt or with GC-content higher than 85% were discarded. For remaining hairpins, randfold values were calculated for every sequence in an alignment using mononucleotide shuffling and 1000 iterations. The cut-off of 0.01 was used for randfold and only regions that contained a hairpin below this cut-off for at least one species in an alignment, were considered as microRNA genes. Finally, positive hairpins were split into known and novel microRNAs according annotations. To facilitate these annotations and also to track performance of the pipeline, mature sequences of known microRNAs from miRBase (Griffiths-Jones, 2004) were included into the analysis.

The sequences obtained by massively parallel pyrosequencing were analyzed with the same computational pipeline, but homologs in other genomes were identified slightly differently, although similar parameters were used. Homologous hairpins in other genomes were identified by comparing mature miRNA regions using BLAST against human, chimpanzee, macaque, mouse, rat, dog, cow, opossum, chicken, zebrafish, fugu, tetraodon, $xenopus$, anopheles, $drosophila$, bee and ciona genomes. Where available, BLASTZ_NET aligned regions were also retrieved from Ensembl. All hits matching to at least 7 continuous nucleotides strafing from $1^{st}$, $2^{nd}$ or $3^{rd}$ nucleotide of the mature sequence were extracted and folded using the RNAshapes program (Steffen et al., 2005; sliding windows of 80, 100 and 120 nt). Only regions that 1) folded into hairpins with the abstract shape '☐', 2) had a probability of folding greater than 0.8, and 3) contained a homologous sequence in one of the hairpin arms, were used in further analysis. Next, similarity between all potential homologous hairpins and the original hairpin was calculated using RNAforester software (http://bibiserv.techfak.uni-bielefeld.de/rnaforester). If a BLASTZ_NET aligned region folded into a hairpin and had an RNAforetsre score above 0.3, it was assigned as an orthologous hairpin in a particular species; otherwise, the highest scoring hairpin above score of 0.3 was defined as an ortholog. Next, homologs from different organisms were aligned with the original hairpin by clustalw (Thompson et al., 1994) to produce a final multiple alignment of the hairpin region. Chromosomal locations of homologous sequences were used to retrieve gene and repeat annotations from the respective species in the Ensembl database. Hairpins that contained repeat/RNA annotations in one of the species, as well as hairpins containing mature regions longer that 25 nt or with GC-content higher than 85% were discarded. For remaining hairpins, randfold values were calculated for every sequence in an alignment using mononucleotide shuffling and 1000 iterations (Bonnet at al., 2004). The cut-off of 0.005 was used for randfold and only regions that contained a hairpin below this cut-off for at least one species in an alignment were considered as microRNA genes. Finally, positive hairpins were split into known and novel microRNAs according to annotations. To facilitate these annotations and also to track performance of the pipeline, mature sequences of known microRNAs from miRBase v.8.0 (Griffiths-Jones et al, 2006) were included into the analysis.

Expression of miRNA in Tissue Samples

Custom microarrays (Amersham CodeLink) were made by spotting 3'-aminolinked oligonucleotides (60-mers, as described above for the custom Agilent microarrays) for detection of all known and novel mature microRNAs. At this point, no tiling path is needed anymore, resulting in a slide with about 15,000 spots that represent the full human, mouse and rat miRNA reportoire in 8-fold. These slides were hybridized with small RNA from mouse heart and mouse thymus (isolated using the Ambion MirVana small RNA isolation kit) as described above for the custom Agilent microarrays. In the table below, normalized intensities (arbitrary values, average of 8 spots, normalized by assuming a constant total amount of microRNA molecules per sample) for thymus and heart are shown for the those miRNAs that are more than two-fold differentially expressed. It should be noted that low values may indicate background signal and absence of this particular miRNA in a sample. Clearly, eight out of the 24 miRNAs that are differentially expressed between thymus and heart and hence provide a characteristic signature of the respective tissues, are novel miRNAs as described in FIG. 1.

TABLE expression of miRNAs as detected by microarray analysis

| rank | miRNA | signal intensity | | fold difference |
|---|---|---|---|---|
| | | thymus | heart | |
| 1 | mmu-mir-133b | 0.2767 | 5.3531 | 19.3 |
| 2 | novel Mmd_532 | 3.5050 | 0.2970 | −11.8 |
| 3 | mmu-mir-125b | 1.3814 | 11.9810 | 8.7 |
| 4 | mmu-mir-99a | 0.8470 | 6.1479 | 7.3 |
| 5 | novel Mmd_524 | 0.0117 | 0.0527 | 4.5 |
| 6 | novel Mmd_124 | 0.0094 | 0.0412 | 4.4 |
| 7 | mmu-mir-126 | 4.2831 | 16.3321 | 3.8 |
| 8 | mmu-mir-145 | 1.1160 | 4.1833 | 3.7 |
| 9 | mmu-mir-30a | 2.1039 | 7.3289 | 3.5 |
| 10 | mmu-mir-150 | 4.5540 | 1.4430 | −3.2 |
| 11 | mmu-mir-106a | 0.6968 | 0.2245 | −3.1 |
| 12 | mmu-mir-30e | 2.6240 | 7.6983 | 2.9 |
| 13 | novel Mmd_297 | 0.2878 | 0.8431 | 2.9 |
| 14 | mmu-mir-145 | 0.5578 | 1.5293 | 2.7 |
| 15 | mmu-mir-21 | 4.1493 | 1.5676 | −2.6 |
| 16 | novel Mmd_254 | 0.0178 | 0.0461 | 2.6 |
| 17 | novel Mmd_120 | 0.3228 | 0.1308 | −2.5 |
| 18 | mmu-mir-26a | 2.4855 | 5.9199 | 2.4 |
| 19 | mmu-let-7e | 1.1802 | 2.7889 | 2.4 |
| 20 | novel Mmd_45 | 0.3750 | 0.1599 | −2.3 |
| 21 | novel Mmd_93 | 0.0239 | 0.0558 | 2.3 |
| 22 | mmu-mir-185 | 0.6790 | 1.5214 | 2.2 |
| 23 | mmu-mir-149 | 0.1115 | 0.2333 | 2.1 |
| 24 | mmu-mir-18 | 1.9616 | 0.9721 | −2.0 |

References

Abbott, A. L., Alvarez-Saavedra, E., Miska, E. A., Lau, N. C., Bartel, D. P., Horvitz, H. R., Ambros, V. (2005). The let-7 microRNA family members mir-48, mir-84 and mir-241 function together to regulate developmental timing in Caenorhabditis elegans. Dev. Cell 9, 403-414.

Alvarez-Garcia, I. & Miska; E. A. MicroRNA functions in animal development and human disease. Development 132, 4653-62 (2005).

Ambros, V. (2004). The functions of animal microRNAs. Nature 431, 350-355.

Ambros, V., Lee, R. C., Lavanway, A., Williams, P. T. and Jewell, D. (2003). MicroRNAs and Other Tiny Endogenous RNAs in C. elegans Curr Biol 13: 807-18.

Aravin, A. & Tuschl, T. Identification and characterization of small RNAs involved in RNA silencing. FEBS Lett 579, 5830-40 (2005).

Aravin, A. A., Naumova, N. M., Tulin, A. V., Vagin, V. V., Rozovsky, Y. M. and Gvozdev, V. A. (2001). Double-stranded RNA-mediated silencing of genomic tandem repeats and transposable elements in the D. melanogaster germline Curr Biol 11: 1017-27.

Bagga, S., Bracht, J., Hunter, S., Massirer, K, Holtz, J., Eachus, R., Pasquinelli, A. E. (2005). Regulation by let-7 and lin-4 miRNAs results in target mRNA degradation. Cell 122, 553-563.

Bartel, D. P. (2004). MicroRNAs: genomics, biogenesis, mechanism, and function. Cell 116, 281-297.

Bentwich I, Avniel A, Karov Y, Aharonov R, Gilad S, Barad O, Barzilai A, Einat P, Einav U, Meiri E, Sharon E, Spector Y, Bentwich Z. (2005) Identification of hundreds of conserved and nonconserved human microRNAs. Nature Genet. 37, 766-770.

Berezikov, E., Plasterk, R. H. and Cuppen, E. (2002). GENOTRACE: cDNA-based local GENOme assembly from TRACE archives. Bioinformatics 18, 1396-1397.

Berezikov, E., Guryev, V., van de Belt, J., Wienholds, E., Plasterk, R. H., Cuppen, E. (2005). Phylogenetic shadowing and computational identification of human microRNA genes. Cell 120, 21-24.

Bernstein, E., Caudy, A. A., Hammond, S. M. and Hannon, G. J. (2001). Role for a bidentate ribonuclease in the initiation step of RNA interference. Nature 409: 363-6.

Boffelli, D., McAuliffe, J., Ovcharenko, D., Lewis, K. D., Ovcharenko, I., Pachter, L. and Rubin, E. M. (2003). Phylogenetic shadowing of primate sequences to find functional regions of the human genome. Science 299, 1391-1394.

Bohnsack, M. T., Czaplinski, K. and Gorlich, D. (2004). Exportin 5 is a RanGTP-dependent dsRNA-binding protein that mediates nuclear export of pre-miRNAs. Rna 10: 185-91.

Bonnet, E., Wuyts, J., Rouze, P. and Van De, P.e.Y. (2004). Evidence that microRNA precursors, unlike other non-coding RNAs; have lower folding free energies than random sequences. Bioinformatics 20, 2911-2917.

Brennecke, J., Hipfner, D. R., Stark, A, Russell, R. B. and Cohen. S. M. (2003). bantam encodes a developmentally regulated microRNA that controls cell proliferation and regulates the proapoptotic gene hid in Drosophila. Cell 113: 25-36.

Cai, X., Hagedorn, C. H. and Cullen, B. R. (2004). Human microRNAs are processed from capped, polyadenylated transcripts that can also function as mRNAs. RNA 10, 1957-1966.

Calin, G. A. et al. A MicroRNA signature associated with prognosis and progression in chronic lymphocytic leukemia. N Engl J Med 353, 1793-801 (2005).

Chen, X. (2004). A microRNA as a translational repressor of APETALA2 in Arabidopsis flower development. Science 303: 2022-5.

Ewing, B., Hillier, L., Wendl, M. C. & Green, P. Base-calling of automated sequencer traces using phred. I. Accuracy assessment. Genome Res 8, 175-85 (1998).

Farh, K. K., Grimson, A., Jan, C., Lewis, B. P., Johnston, W. K., Lim, L. P., Burge, C. B., Bartel, D. P. (2005). The widespread impact of mammalian microRNAs on mRNA repression and evolution. Science 310, 1817-1821.

Fire, A., Xu, S., Montgomery, M. K., Kostas, S. A., Driver, S. E. and Mello, C. C. (1998). Potent and specific genetic interference by double-stranded RNA in *Caenorhabditis elegans*. Nature 391: 806-11.

Giraldez, A. J., Cinalli, R. M., Glasner, M. E., Enright, A. J., Thomson, J. M., Baskerville, S., Hammond, S. M., Bartel, D. P., Schier, A. F. (2005). MicroRNAs regulate brain morphogenesis in zebrafish. Science 308, 833-838.

Gordon, D., Abajian, C. and Green, P. (1998). Consed: a graphical tool for sequence finishing. Genome Res 8, 195-202.

Griffiths-Jones, S. (2004). The microRNA Registry. Nucleic Acids Res 32 Database issue, D109-11.

Griffiths-Jones, S., Grocock, R. J., van Dongen, S., Bateman, A. & Enright, A. J. miRBase: microRNA sequences, targets and gene nomenclature. 2006. Nucleic Acids Res 34, D140-4.

Grishok, A., Pasquinelli, A. E., Conte, D., Li, N., Parrish, S., Ha, I., Baillie, D. L., Fire, A., Ruvkun, G. and Mello, C. C. (2001). Genes and mechanisms related to RNA interference regulate expression of the small temporal RNAs that control *C. elegans* developmental timing. Cell 106: 23-34.

Hamilton, A. J. and Baulcombe, D. C. (1999). A species of small antisense RNA in posttranscriptional gene silencing in plants. Science 286: 950-2.

Hammond, S. M. MicroRNAs as oncogenes. Curr Opin Genet Dev (2005).

He L, Thomson J M, Hemann M T, Hernando-Mange E, Mu D, Goodson S, Powers S, Cordon-Cardo C, Lowe S W, Hannon G J, Hammond S M (2005) A microRNA polycistron as a potential human oncogene. Nature 435, 828-33.

Hofacker, I. L. Vienna RNA secondary structure server. Nucleic Acids Res 31, 3429-31 (2003).

Hornstein, E., Mansfield, J. H., Yekta, S., Kuang-Hsien Hu, J., Harfe, B. D., McManus, M. T., Baskerville, S., Bartel, D. P., Tabin, C. J. (2005). The microRNA miR-196 acts upstream of Hoxb8 and Shh in limb development. Nature 438, 671-674.

Hutvagner, G., McIachlan, J., Pasquinelli, A. E., Balint, E., Tuschl, T. and Zamore, P. D. (2001). A cellular function for the RNA-interference enzyme Dicer in the maturation of the let-7 small temporal RNA. Science 293: 834-8.

Johnson, S. M., Lin, S. Y. and Slack, F. J. (2003). The time of appearance of the *C. elegans* let-7 microRNA is transcriptionally controlled utilizing a temporal regulatory element in its promoter. Dev Biol 259: 364-79.

Johnston, R. J. and Hobert, O. (2003). A microRNA controlling left/right neuronal asymmetry in *Caenorhabditis elegans*. Nature 426: 845-9.

Kapranov, P., Cawley, S. E., Drenkow, J., Bekiranov, S., Strausberg. R. L., Fodor, S. P. and Gingeras, T. R. (2002). Large-scale transcriptional activity in chromosomes 21 and 22. Science 296, 916-919.

Ketting, R. F., Fischer, S. E., Bernstein, E., Sijen, T., Hannon, G. J. and Plasterk, R. H. (2001). Dicer functions in RNA interference and in synthesis of small RNA involved in developmental timing in *C. elegans*. Genes Dev. 15: 2654-9.

Khvorova, A., Reynolds, A. and Jayasena, S. D. (2003). Functional siRNAs and miRNAs exhibit strand bias. Cell 115: 209-16.

Lagos-Quintana, M., Rauhut, R., Lendeckel, W. & Tuscbl, T. Identification of novel genes coding for small expressed RNAs. Science 294, 853-8 (2001).

Lai, E. C., Tam, B., Rubin, G. M. (2005). Pervasive regulation of *Drosophila* Notch target genes by GY-box-, Brd-Box-, and K-box-class microRNAs. Genes Dev. 19, 1067-1080.

Lee, R. C., Feinbaum, R. L., Ambros, V. (1993). The *C. elegans* heterochronic gene lin-4 encodes small RNAs with antisense complementarity to lin-14. Cell 75, 843-854.

Lee, C. Grasso, C. and Sharlow, M. F. (2002). Multiple sequence alignment using partial order graphs. Bioinformatics 18, 452-464.

Lee, Y., Ahn, C., Han, J., Choi, H., Kim, J., Yim, J., Lee, J., Provost, P., Radmark, O., Kim, S. and Kim, V. N. (2003). The nuclear RNase III Drosha initiates microRNA processing. Nature 425: 415-9.

Lee, Y., Kim, M., Han, J., Yeom, K. H., Lee, S., Baek, S. H. and Kim, V. N. (2004). MicroRNA genes are transcribed by RNA polymerase II. EMBO J 23, 4051-4060.

Lee, Y. S., Nakahara, K., Pham, J. W., Kim, K., He, Z., Sontheimer, E. J. and Carthew, R. W. (2004). Distinct roles for *Drosophila* Dicer-1 and Dicer-2 in the siRNA/miRNA silencing pathways. Cell 117: 69-81.

Lewis, B. P., Burge, C. B., Bartel, D. P. (2005). Conserved seed pairing, often flanked by adenosines, indicates that thousands of human genes are microRNA targets. Cell 120, 15-20.

Lim, L. P., Glasner, M. E., Yekta, S., Burge, C. B. and Bartel, D. P. (2003). Vertebrate microRNA genes. Science 299, 1540.

Lim, L. P., Lau, N. C., Garrett-Engele, P., Grimson, A., Schelter, J. M., Castle, J., Bartel, D. P., Linsley, P. S., Johnson, J. M. (2005). Microarray analysis shows that some microRNAs downregulate large numbers of target mRNAs. Nature 433, 769-773.

Lingel, A., Simon, B., Izaurralde, E. and Sattler, M. (2003). Structure and nucleic-acid binding of the *Drosophila* Argonaute 2 PAZ domain. Nature 426: 465-9.

Lu, J. et al. MicroRNA expression profiles classify human cancers. Nature 435, 834-8 (2005).

Lund, E., Guttinger, S., Calado, A., Dahlberg, J. E. and Kutay, U. (2004). Nuclear export of microRNA precursors. Science 303: 95-8.

Ma, J., Ye, K. and Patel, D. (2004). Structural basis for overhang-specific small interfering RNA recognition by the PAZ domain. Nature in press.

Margulies, M. Eghold, M. et al. Genome sequencing in microfabricated high-density picolitre reactors. Nature. 2005 Sep. 15; 437(7057):326-7.

Martinez, J. and Tuschl, T. (2004). RISC is a 5' phosphomonoester-producing RNA endonuclease. Genes Dev.

Nelson, P. T. et al. Microarray-based, high-throughput gene expression profiling of microRNAs. Nat Methods 1, 155-61 (2004).

O'Donnell K A, Wentzel E A, Zeller K I, Dang C V, Mendell J T. (2005) c-Myc-regulated microRNAs modulate E2F1 expression. Nature 435:839-43

Ohler, U., Yekta, S., Lim, L. P., Bartel, D. P. and Burge, C. B. (2004). Patterns of flanking sequence conservation and a characteristic upstream motif for microRNA gene identification. RNA 10, 1309-1322.

Okazaki, Y., Furuno, M., Kasukawa, T., Adachi, J., Bono, H., Kondo, S., Nikaido, I., Osato, N., Saito, R., Suzuki, H., Yamanaka, I., Kiyosawa, H., Yagi, K., Tomaru, Y., Hasegawa, Y., Nogami, A., Schonbach, C., Gojobori, T., Baldarelli, R. and Hill, D. P. (2002). Analysis of the mouse transcriptome based on functional annotation of 60,770 full-length cDNAs. Nature 420, 563-573.

Park, W., Li, J., Song, R., Messing, J. and Chen, X. (2002). CARPEL FACTORY, a Dicer homolog, and HEN1, a novel protein, act in microRNA metabolism in *Arabidopsis thaliana*. Curr Biol 12: 1484-95.

Pham, J. W., Pellino, J. L., Lee, Y. S., Carthew, R. W. and Sontheimer, E. J. (2004). A Dicer-2-dependent 80s complex cleaves targeted mRNAs during RNAi in *Drosophila*. Cell 117: 83-94.

Pillai, R. S., Bhattacharyya, S. N., Artus, C. G., Zoller, T., Cougot, N., Basyuk, E., Bertrand, E., Filipowicz, W. (2005). Inhibition of translational initiation by let-7 microRNA in human cells. Science 309, 1573-1576.

Poy, M. N., Eliasson, L., Krutzfeldt, J., Kuwajima, S., Ma, X., Macdonald, P. E., Pfeffer, S., Tuschl, T., Rajewsky, N., Rorsman, P. and Stoffel, M. (2004). A pancreatic islet-specific microRNA regulates insulin secretion. Nature 432, 226-230.

Reinhart, B. J. and Bartel, D. P. (2002) Small RNAs correspond to centromere heterochromatic repeats. Science 297: 1831.

Reinhart, B. J., Slack, F. J., Basson, M., Pasquinelli, A. E., Bettinger, J. C., Rougvie, A. E., Horvitz, H. R., Ruvkun, G. (2000). The 21-nucleotide let-7 RNA regulates developmental timing in *Caenorhabditis elegans*. Nature 403, 901-906.

Reinhart, B. J., Weinstein, E. G., Rhoades, M. W., Bartel, B. and Bartel, D. P. (2002). MicroRNAs in plants. Genes Dev 16: 1616-26.

Rodriguez, A., Griffiths-Jones, S., Ashurst, J. L. and Bradley, A. (2004). Identification of Mammalian microRNA Host Genes and Transcription Units. Genome Res 14, 1902-1910.

Schwarz, D. S., Hutvagner, G., Du, T., Xu, Z., Aronin, N. and Zamore, P. D. (2003). Asymmetry in the assembly of the RNAi enzyme complex. Cell 115: 199-208.

Schwarz, D. S., Tomari, Y. and Zamore, P. D. (2004). The RNA-Induced Silencing Complex Is a Mg(2+)-Dependent Endonuclease. Curr Biol 14: 787-91.

Song, J. J., Liu, J., Tolia, N. H., Schneiderman, J., Smith, S. K., Martienssen, R. A., Hannon, G. J. and Joshua-Tor, L. (2003). The crystal structure of the Argonaute2 PAZ domain reveals an RNA binding motif in RNAi effector complexes. Nat Struct Biol 10: 1026-1032.

Stark, A., Brennecke, J., Bushati, N., Russell, R. B., Cohen, S. M. (2005). Animal microRNAs confer robustness to gene expression and have a significant impact on 3'-UTR evolution. Cell 123, 1133-1146.

Steffen, P., Voss, B., Rehmsmeier, M., Reeder, J., Giegerich, R. 2006. RNAshapes: an integrated RNA analysis package based on abstract shapes. Bioinformatics 22:500-3.

Thompson, J. D., Higgins, D. G. & Gibson, T. J. CLUSTAL W: improving the sensitivity of progressive multiple sequence alignment through sequence weighting, position-specific gap penalties and weight matrix choice. Nucleic Acids Res 22, 4673-80 (1994).

Tomari, Y., Du, T., Haley, B., Schwarz, D. S., Bennett, R., Cook, H. A., Koppetsch, B. S., Theurkauf, W. E. and Zamore, P. D. (2004). RISC assembly defects in the *Drosophila* RNAi mutant armitage. Cell 116: 831-41.

Wienholds, E., Kloosterman, W. P., Miska, E., Alvarez-Saavedra, E., Berezikov, E., de Bruijn, E., Horvitz, H. R., Kauppinen, S., Plasterk, R. H. (2005). MicroRNA expression in zebrafish embryonic development. Science 309, 310-311.

Wienholds, E., Koudijs, M. J., van Eeden, F. J., Cuppen, E., Plasterk, R. H. (2003). The microRNA-producing enzyme Dicer1 is essential for zebrafish development. Nat. Genet. 35, 217-218.

Xie, Z., Johansen, L. K., Gustafson, A. M., Kasschau, K. D., Lellis, A. D., Zilberman, D., Jacobsen, S. E. and Carrington, J. C. (2004). Genetic and Functional Diversification of Small RNA Pathways in Plants. PLoS Biol 2: E104.

Yan, K. S., Yan, S., Farooq, A., Han, A., Zeng, L. and Zhou, M. M. (2003). Structure and conserved RNA binding of the PAZ domain. Nature 426: 468-74.

Yekta, S., Shih, I. H. and Bartel, D. P. (2004). MicroRNA-directed cleavage of HOXB8 mRNA. Science 304: 594-6.

Yi, R., Qin, Y., Macara, I. G. and Cullen, B. R. (2003). Exportin-5 mediates the nuclear export of pre-microRNAs and short hairpin RNAs. Genes Dev 17: 3011-6.

Yoo, A. S., Greenwald, I. (2005). Lin-12/Notch activation leads to microRNA-mediated down-regulation of Vav in *C. elegans*. Science 310, 1330-1333.

Zhang, H., Kolb, F. A., Jaakiewisz, L., Westhof, E. and Filipowicz, W. (2004). Single processing center models for human Dicer and bacterial RNase III. Cell in press.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08895720B2). An electronic copy of the "Sequence Listing" will also be available from the USPTO upon request and payment of the fee set forth in 37 CFR 1.19(b)(3).

We claim:

1. An isolated nucleic acid molecule, wherein said nucleic acid molecule is a miRNA, a pre-miRNA or a DNA molecule encoding said pre-miRNA, which has a length of 18-26 nucleotides in the case of miRNA, wherein:
   (a) the sequence of the nucleic acid molecule comprises SEQ ID NO:11390 or its corresponding ribonucleotide sequence, or
   (b) the sequence of the nucleic acid molecule has at least 90% identity over 20 consecutive nucleotides with the miRNA sequence of (a),
wherein said sequence comprises at least one modification selected from the group consisting of: a nucleotide analogue, a peptide nucleic acid a locked nucleic acid a backbone modified ribonucleotide or deoxyribonucleotide and a sugar modified ribonucleotide or deoxyribonucleotide.

2. The nucleic acid molecule of claim 1 which is a miRNA molecule.

3. The nucleic acid molecule of claim 2, the length of which is from 18 to 26 nucleotides.

4. The nucleic acid molecule of claim 1, wherein the nucleic acid molecule is the pre-miRNA or the DNA molecule coding therefore.

5. The nucleic acid molecule of claim 1, that is single-stranded.

6. The nucleic acid molecule of claim 1, that is at least partially double-stranded.

7. The nucleic acid molecule claim 1, that is RNA, DNA, or a combination thereof.

8. A composition comprising as an active agent, a nucleic acid molecule according to claim 1.

9. The nucleic acid molecule of claim 1, that comprises SEQ ID NO:11390.

* * * * *

UNITED STATES PATENT AND TRADEMARK OFFICE
CERTIFICATE OF CORRECTION

| | | |
|---|---|---|
| PATENT NO. | : 8,895,720 B2 | Page 1 of 1 |
| APPLICATION NO. | : 13/722643 | |
| DATED | : November 25, 2014 | |
| INVENTOR(S) | : Ronald H. A. Plasterk et al. | |

It is certified that error appears in the above-identified patent and that said Letters Patent is hereby corrected as shown below:

On the Title Page

Insert -- (30) Foreign Application Priority Data:

Jan. 10, 2006   (WO) ...................... PCT/NL2006/000010

Sep. 29, 2006   (WO) ...................... PCT/NL2006/000491 --

Signed and Sealed this
Twenty-ninth Day of September, 2015

Michelle K. Lee
*Director of the United States Patent and Trademark Office*